US008637313B2

(12) United States Patent
Chamberlain et al.

(10) Patent No.: US 8,637,313 B2
(45) **Date of Patent: *Jan. 28, 2014**

(54) PRODUCTION OF VIRAL VECTORS

(75) Inventors: Jeffrey S. Chamberlain, Seattle, WA (US); Dennis J. Hartigan-O'Connor, S Lake Tahoe, CA (US)

(73) Assignee: The Regents of the University of Michigan, Ann Arbor, MI (US)

( * ) Notice: Subject to any disclaimer, the term of this patent is extended or adjusted under 35 U.S.C. 154(b) by 112 days.

This patent is subject to a terminal disclaimer.

(21) Appl. No.: 12/884,027

(22) Filed: Sep. 16, 2010

(65) Prior Publication Data

US 2011/0033926 A1 Feb. 10, 2011

Related U.S. Application Data

(63) Continuation of application No. 10/381,153, filed as application No. PCT/US01/29496 on Sep. 21, 2001, now Pat. No. 7,820,441.

(60) Provisional application No. 60/235,060, filed on Sep. 25, 2000.

(51) Int. Cl.

| | |
|---|---|
| *C12P 15/00* | (2006.01) |
| *C12N 15/36* | (2006.01) |
| *C12N 7/01* | (2006.01) |
| *C12N 7/00* | (2006.01) |
| *C12N 5/00* | (2006.01) |

(52) U.S. Cl.
USPC .... 435/457; 424/93.2; 424/93.21; 424/199.1; 424/233.1; 435/325; 435/320.1

(58) Field of Classification Search
None
See application file for complete search history.

(56) References Cited

U.S. PATENT DOCUMENTS

| | | | | |
|---|---|---|---|---|
| 5,811,238 | A | 9/1998 | Stemmer et al. | 435/6 |
| 5,824,544 | A | 10/1998 | Armentano et al. | 435/320.1 |
| 5,919,676 | A | 7/1999 | Graham et al. | |
| 5,932,210 | A | 8/1999 | Gregory et al. | 424/93.2 |
| 6,083,750 | A | 7/2000 | Chamberlain et al. | 435/369 |
| 6,630,346 | B1 | 10/2003 | Morsy et al. | |
| 7,820,441 | B2 * | 10/2010 | Chamberlain et al. | 435/457 |

FOREIGN PATENT DOCUMENTS

| | | | |
|---|---|---|---|
| EP | 1 016 724 | | 7/2000 |
| WO | WO 97/25446 | | 1/1997 |
| WO | WO 97/25446 | * | 7/1997 |
| WO | WO 98 13510 | | 4/1998 |
| WO | WO 00 18939 | | 4/2000 |
| WO | WO 00 46360 | | 8/2000 |

OTHER PUBLICATIONS

Hartigan-O'Connor et al, Improved Production of Gutted Adenovirus in Cells Expressing Adenovirus Preterminal Protein and DNA Polymerase, Journal of Virology, Sep. 1999, p. 7835-7841.*

Amalfitano et al., in Lucy J, and Brown S. (eds): Dystrophin: Gene, Protein, and Cell Biology (Cambridge University Press, 1997), Chpt. 1, 1-26.

Chaltberg MD., Rawlins Dr.,"Template requirements for the initiation of adenovirus DNA replication," *P.N.A.S.*, 81(1):100-4 (1984).

Graham, F.L.,"Covalently closed circles of human adenovirus DNA are infectious," *The EMBO J.*, 3:2917-2922 (1984).

Hanahan, D.,"Studies on transformation of *Escherichia coli* with plasmids," *J. Mol. Biol.*, 166:557-580 (1983).

Hirt, B.,"Selective extraction of polyoma DNA from infected mouse cell cultures," *J. Mol. Biol.* 26:365-369 (1967).

Pronk et al.,"The adenovirus terminal protein influences binding of replication proteins and changes the origin structure," *Nucleic Acids Research*, 25(10):2293-2300 ( 1993).

Wright, E. et al., "Dual-origin plasmids containing an amplifiable ColEl*ori*; temperature-controlled expression of cloned genes," *Gene* 49(3):311-321 (1986).

* cited by examiner

*Primary Examiner* — Maria Marvich
(74) *Attorney, Agent, or Firm* — Medlen & Carroll, LLP

(57) ABSTRACT

The present invention relates to methods and compositions for the production of viral vectors. In particular, the present invention provides methods and compositions for faster, higher titer and higher purity production of viral vectors (e.g. adenoviral vectors). In some embodiments, the present invention provides gutted and helper viruses with identical or similar termini. In other embodiments, the present invention provides terminal protein linked adenoviral DNA. In certain embodiments, the present invention provides template extended adenoviral DNA.

11 Claims, 49 Drawing Sheets

A.

| Origin | Structure |
| --- | --- |
| Natural or TP-primer-modified | CATCATCAATAA<br>GTAGTAGTTATT |
| Deproteinized or Hirt prep | Serine<br>CATCATCAATAA<br>GTAGTAGTTATT |
| PacI | TAACATCATCAATAA<br>TAATTGTAGTAGTTATT |
| FseI | CCATCATCAATAA<br>GGCCGGTAGTAGTTATT |

B.

| | 12587 | | | 17756 | |
| --- | --- | --- | --- | --- | --- |
| Wild-type: | GACGA GGCCGGCC TGGTC | ... | GGCAT | GGCCGGCC ACGGC | |
| ΔFseI.4: | GACGA AGCCGGCC TGGTC | ... | GGCAT | GGCCGGCT ACGGC | |

C.

FIGURE 4
A.
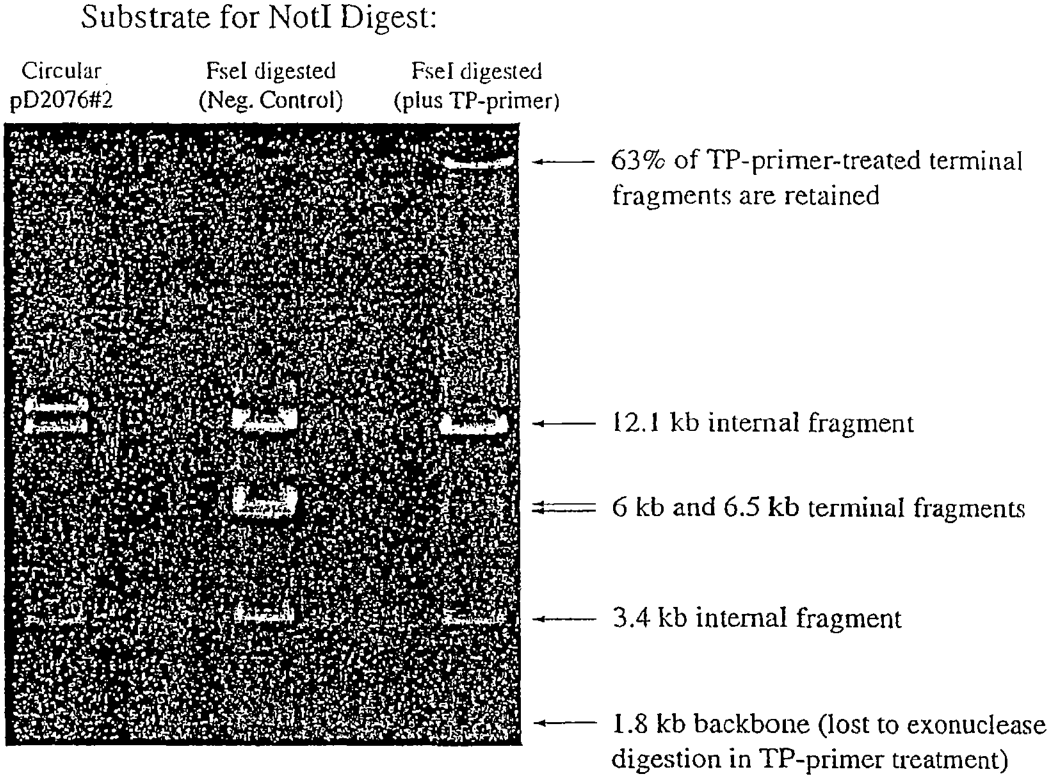
B.
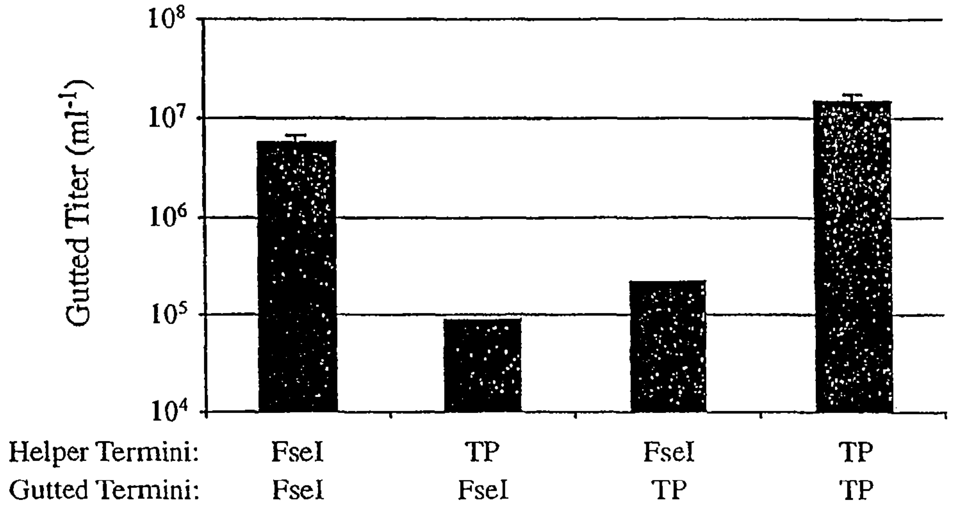

FIGURE 8 (SEQ ID NO:1) (+)lox(+)pol helper virus

CATCATCAATAATATACCTTATTTTGGATTGAAGCCAATATGATAATGAGGGGGTGGAGTTTGTGACGTGGCGCGG
GGCGTGGGAACGGGGCGGGTGACGTAGTAGTGTGGCGGAAGTGTGATGTTGCAAGTGTGGCGGAACACATGTATAA
CTTCGTATAATGTATGCTATACGAAGTTATACATGTAAGCGACGGATGTGGCAAAAGTGACGTTTTTGGTGTGCGC
CGGTGTACACAGGAAGTGACAATTTTCGCGCGGTTTTAGGCGGATGTTGTAGTAAATTTGGGCGTAACCGAGTAAG
ATTTGGCCATTTTCGCGGGAAAACTGAATAAGAGGAAGTGAAATCTGAATAATTTTGTGTTACTCATAGCGCGTAA
TATTTGTCTAGGGAGATCTATAACTTCGTATAATGTATGCTATACGAAGTTATTACCGAAGAAATGGCTCGAGATC
TGGAAGGTGCTGAGGTACGATGAGACCCGCACCAGGTGCAGACCCTGCGAGTGTGGCGGTAAACATATTAGGAACC
AGCCTGTGATGCTGGATGTGACCGAGGAGCTGAGGCCCGATCACTTGGTGCTGGCCTGCACCCGCGCTGAGTTTGG
CTCTAGCGATGAAGATACAGATTGAGGTACTGAAATGTGTGGGCGTGGCTTAAGGGTGGGAAAGAATATATAAGGT
GGGGGTCTTATGTAGTTTTGTATCTGTTTTGCAGCAGCCGCCGCCGCCATGAGCACCAACTCGTTTGATGGAAGCA
TTGTGAGCTCATATTTGACAACGCGCATGCCCCCATGGGCCGGGGTGCGTCAGAATGTGATGGGCTCCAGCATTGA
TGGTCGCCCCGTCCTGCCCGCAAACTCTACTACCTTGACCTACGAGACCGTGTCTGGAACGCCGTTGGAGACTGCA
GCCTCCGCCGCCGCTTCAGCCGCTGCAGCCACCGCCCGCGGGATTGTGACTGACTTTGCTTTCCTGAGCCCGCTTG
CAAGCAGTGCAGCTTCCCGTTCATCCGCCCGCGATGACAAGTTGACGGCTCTTTTGGCACAATTGGATTCTTTGAC
CCGGGAACTTAATGTCGTTTCTCAGCAGCTGTTGGATCTGCGCCAGCAGGTTTCTGCCCTGAAGGCTTCCTCCCCT
CCCAATGCGGTTTAAAACATAAATAAAAAACCAGACTCTGTTTGGATTTGGATCAAGCAAGTGTCTTGCTGTCTTT
ATTTAGGGGTTTTGCGCGCGCGGTAGGCCCGGGACCAGCGGTCTCGGTCGTTGAGGGTCCTGTGTATTTTTTCCAG
GACGTGGTAAAGGTGACTCTGGATGTTCAGATACATGGGCATAAGCCCGTCTCTGGGGTGGAGGTAGCACCACTGC
AGAGCTTCATGCTGCGGGGTGGTGTTGTAGATGATCCAGTCGTAGCAGGAGCGCTGGGCGTGGTGCCTAAAAATGT
CTTTCAGTAGCAAGCTGATTGCCAGGGGCAGGCCCTTGGTGTAAGTGTTTACAAAGCGGTTAAGCTGGGATGGGTG
CATACGTGGGGATATGAGATGCATCTTGGACTGTATTTTTAGGTTGGCTATGTTCCCAGCCATATCCCTCCGGGGA
TTCATGTTGTGCAGAACCACCAGCACAGTGTATCCGGTGCACTTGGGAAATTTGTCATGTAGCTTAGAAGGAAATG
CGTGGAAGAACTTGGAGACGCCCTTGTGACCTCCAAGATTTTCCATGCATTCGTCCATAATGATGGCAATGGGCCC
ACGGGCGGCGGCCTGGGCGAAGATATTTCTGGGATCACTAACGTCATAGTTGTGTTCCAGGATGAGATCGTCATAG
GCCATTTTTACAAAGCGCGGGCGGAGGGTGCCAGACTGCGGTATAATGGTTCCATCCGGCCCAGGGGCGTAGTTAC
CCTCACAGATTTGCATTTCCCACGCTTTGAGTTCAGATGGGGGGATCATGTCTACCTGCGGGGCGATGAAGAAAAC
GGTTTCCGGGGTAGGGGAGATCAGCTGGGAAGAAAGCAGGTTCCTGAGCAGCTGCGACTTACCGCAGCCGGTGGGC
CCGTAAATCACACCTATTACCGGGTGCAACTGGTAGTTAAGAGAGCTGCAGCTGCCGTCATCCCTGAGCAGGGGGG
CCACTTCGTTAAGCATGTCCCTGACTCGCATGTTTTCCCTGACCAAATCCGCCAGAAGGCGCTCGCCGCCCAGCGA
TAGCAGTTCTTGCAAGGAAGCAAAGTTTTTCAACGGTTTGAGACCGTCCGCCGTAGGCATGCTTTTGAGCGTTTGA
CCAAGCAGTTCCAGGCGGTCCCACAGCTCGGTCACCTGCTCTACGGCATCTCGATCCAGCATATCTCCTCGTTTCG
CGGGTTGGGGCGGCTTTCGCTGTACGGCAGTAGTCGGTGCTCGTCCAGACGGGCCAGGGTCATGTCTTTCCACGGG
CGCAGGGTCCTCGTCAGCGTAGTCTGGGTCACGGTGAAGGGGTGCGCTCCGGGCTGCGCGCTGGCCAGGGTGCGCT
TGAGGCTGGTCCTGCTGGTGCTGAAGCGCTGCCGGTCTTCGCCCTGCGCGTCGGCCAGGTAGCATTTGACCATGGT
GTCATAGTCCAGCCCCTCCGCGGCGTGGCCCTTGGCGCGCAGCTTGCCCTTGGAGGAGGCGCCGCACGAGGGGCAG
TGCAGACTTTTGAGGGCGTAGAGCTTGGGCGCGAGAAATACCGATTCCGGGGAGTAGGCATCCGCGCCGCAGGCCC
CGCAGACGGTCTCGCATTCCACGAGCCAGGTGAGCTCTGGCCGTTCGGGGTCAAAAACCAGGTTTCCCCCATGCTT
TTTGATGCGTTTCTTACCTCTGGTTTCCATGAGCCGGTGTCCACGCTCGGTGACGAAAAGGCTGTCCGTGTCCCCG
TATACAGACTTGAGAGGCCTGTCCTCGAGCGGTGTTCCGCGGTCCTCCTCGTATAGAAACTCGGACCACTCTGAGA
CAAAGGCTCGCGTCCAGGCCAGCACGAAGGAGGCTAAGTGGGAGGGGTAGCGGTCGTTGTCCACTAGGGGGTCCAC
TCGCTCCAGGGTGTGAAGACACATGTCGCCCTCTTCGGCATCAAGGAAGGTGATTGGTTTGTAGGTGTAGGCCACG
TGACCGGGTGTTCCTGAAGGGGGGCTATAAAAGGGGGTGGGGGCGCGTTCGTCCTCACTCTCTTCCGCATCGCTGT
CTGCGAGGGCCAGCTGTTGGGGTGAGTACTCCCTCTGAAAAGCGGGCATGACTTCTGCGCTAAGATTGTCAGTTTC
CAAAAACGAGGAGGATTTGATATTCACCTGGCCCGCGGTGATGCCTTTGAGGGTGGCCGCATCCATCTGGTCAGAA
AAGACAATCTTTTTGTTGTCAAGCTTGGTGGCAAACGACCCGTAGAGGGCGTTGGACAGCAACTTGGCGATGGAGC
GCAGGGTTTGGTTTTTGTCGCGATCGGCGCGCTCCTTGGCCGCGATGTTTAGCTGCACGTATTCGCGCGCAACGCA
CCGCCATTCGGGAAAGACGGTGGTGCGCTCGTCGGGCACCAGGTGCACGCGCCAACCGCGGTTGTGCAGGGTGACA
AGGTCAACGCTGGTGGCTACCTCTCCGCGTAGGCGCTCGTTGGTCCAGCAGAGGCGGCCGCCCTTGCGCGAGCAGA
ATGGCGGTAGGGGGTCTAGCTGCGTCTCGTCCGGGGGGTCTGCGTCCACGGTAAAGACCCCGGGCAGCAGGCGCGC
GTCGAAGTAGTCTATCTTGCATCCTTGCAAGTCTAGCGCCTGCTGCCATGCGCGGGCGGCAAGCGCGCGCTCGTAT
GGGTTGAGTGGGGGACCCCATGGCATGGGGTGGGTGAGCGCGGAGGCGTACATGCCGCAAATGTCGTAAACGTAGA
GGGGCTCTCTGAGTATTCCAAGATATGTAGGGTAGCATCTTCCACCGCGGATGCTGGCGCGCACGTAATCGTATAG
TTCGTGCGAGGGAGCGAGGAGGTCGGGACCGAGGTTGCTACGGGCGGGCTGCTCTGCTCGGAAGACTATCTGCCTG
AAGATGGCATGTGAGTTGGATGATATGGTTGGACGCTGGAAGACGTTGAAGCTGGCGTCTGTGAGACCTACCGCGT
CACGCACGAAGGAGGCGTAGGAGTCGCGCAGCTTGTTGACCAGCTCGGCGGTGACCTGCACGTCTAGGGCGCAGTA
GTCCAGGGTTTCCTTGATGATGTCATACTTATCCTGTCCCTTTTTTTTCCACAGCTCGCGGTTGAGGACAAACTCT
TCGCGGTCTTTCCAGTACTCTTGGATCGGAAACCCGTCGGCCTCCGAACGGTAAGAGCCTAGCATGTAGAACTGGT
TGACGGCCTGGTAGGCGCAGCATCCCTTTTCTACGGGTAGCGCGTATGCCTGCGCGGCCTTCCGGAGCGAGGTGTG
GGTGAGCGCAAAGGTGTCCCTGACCATGACTTTGAGGTACTGGTATTTGAAGTCAGTGTCGTCGCATCCGCCCTGC
TCCCAGAGCAAAAAGTCCGTGCGCTTTTTGGAACGCGGATTTGGCAGGGCGAAGGTGACATCGTTGAAGAGTATCT
TTCCCGCGCGAGGCATAAAGTTGCGTGTGATGCGGAAGGGTCCCGGCACCTCGGAACGGTTGTTAATTACCTGGGC

FIGURE 8 (cont.)

GGCGAGCACGATCTCGTCAAAGCCGTTGATGTTGTGGCCCACAATGTAAAGTTCCAAGAAGCGCGGATGCCCTTG
ATGGAAGGCAATTTTTTAAGTTCCTCGTAGGTGAGCTCTTCAGGGGAGCTGAGCCCGTGCTCTGAAAGGGCCCAGT
CTGCAAGATGAGGGTTGGAAGCGACGAATGAGCTCCACAGGTCACGGGCCATTAGCATTTGCAGGTGGTCGCGAAA
GGTCCTAAACTGGCGACCTATGGCCATTTTTTCTGGGGTGATGCAGTAGAAGGTAAGCGGGTCTTGTTCCCAGCGG
TCCCATCCAAGGTTCGCGGCTAGGTCTCGCGCGGCAGTCACTAGAGGCTCATCTCCGCCGAACTTCATGACCAGCA
TGAAGGGCACGAGCTGCTTCCCAAAGGCCCCCATCCAAGTATAGGTCTCTACATCGTAGGTGACAAAGAGACGCTC
GGTGCGAGGATGCGAGCCGATCGGGAAGAACTGGATCTCCCGCCACCAATTGGAGGAGTGGCTATTGATGTGGTGA
AAGTAGAAGTCCCTGCGACGGGCCGAACACTCGTGCTGGCTTTTGTAAAAACGTGCGCAGTACTGGCAGCGGTGCA
CGGGCTGTACATCCTGCACGAGGTTGACCTGACGACCGCGCACAAGGAAGCAGAGTGGGAATTTGAGCCCCTCGCC
TGGCGGGTTTGGCTGGTGGTCTTCTACTTCGGCTGCTTGTCCTTGACCGTCTGGCTGCTCGAGGGGAGTTACGGTG
GATCGGACCACCACGCCGCGCGAGCCCAAAGTCCAGATGTCCGCGCGCGGCGGTCGGAGCTTGATGACAACATCGC
GCAGATGGGAGCTGTCCATGGTCTGGAGCTCCCGCGGCGTCAGGTCAGGCGGGAGCTCCTGCAGGTTTACCTCGCA
TAGACGGGTCAGGGCGCGGGCTAGATCCAGGTGATACCTAATTTCCAGGGGCTGGTTGGTGGCGGCGTCGATGGCT
TGCAAGAGGCCGCATCCCCGCGGCGCGACTACGGTACCGCGCGGCGGGCGGTGGGCCGCGGGGGTGTCCTTGGATG
ATGCATCTAAAAGCGGTGACGCGGGCGAGCCCCCGGAGGTAGGGGGGGCTCCGGACCCGCCGGGAGAGGGGGCAGG
GGCACGTCGGCGCCGCGCGCGGGCAGGAGCTGGTGCTGCGCGCGTAGGTTGCTGGCGAACGCGACGACGCGGCGGT
TGATCTCCTGAATCTGGCGCCTCTGCGTGAAGACGACGGGCCCGGTGAGCTTGAGCCTGAAAGAGAGTTCGACAGA
ATCAATTTCGGTGTCGTTGACGGCGGCCTGGCGCAAAATCTCCTGCACGTCTCCTGAGTTGTCTTGATAGGCGATC
TCGGCCATGAACTGCTCGATCTCTTCCTCCTGGAGATCTCCGCGTCCGGCTCGCTCCACGGTGGCGGCGAGGTCGT
TGGAAATGCGGGCCATGAGCTGCGAGAAGGCGTTGAGGCCTCCCTCGTTCCAGACGCGGCTGTAGACCACGCCCCC
TTCGGCATCGCGGGCGCGCATGACCACCTGCGCGAGATTGAGCTCCACGTGCCGGGCGAAGACGGCGTAGTTTCGC
AGGCGCTGAAAGAGGTAGTTGAGGGTGGTGGCGGTGTGTTCTGCCACGAAGAAGTACATAACCCAGCGTCGCAACG
TGGATTCGTTGATATCCCCCAAGGCCTCAAGGCGCTCCATGGCCTCGTAGAAGTCCACGGCGAAGTTGAAAAACTG
GGAGTTGCGCGCCGACACGGTTAACTCCTCCTCCAGAAGACGGATGAGCTCGGCGACAGTGTCGCGCACCTCGCGC
TCAAAGGCTACAGGGGCCTCTTCTTCTTCTTCAATCTCCTCTTCCATAAGGGCCTCCCCTTCTTCTTCTTCTGGCG
GCGGTGGGGGAGGGGGGACACGGCGGCGACGACGGCGCACCGGGAGGCGGTCGACAAAGCGCTCGATCATCTCCCC
GCGGCGACGGCGCATGGTCTCGGTGACGGCGCGGCCGTTCTCGCGGGGGCGCAGTTGGAAGACGCCGCCCGTCATG
TCCCGGTTATGGGTTGGCGGGGGGCTGCCATGCGGCAGGGATACGGCGCTAACGATGCATCTCAACAATTGTTGTG
TAGGTACTCCGCCGCCGAGGGACCTGAGCGAGTCCGCATCGACCGGATCGGAAAACCTCTCGAGAAAGGCGTCTAA
CCAGTCACAGTCGCAAGGTAGGCTGAGCACCGTGGCGGGCGGCAGCGGGCGGCGGTCGGGGTTGTTTCTGGCGGAG
GTGCTGCTGATGATGTAATTAAAGTAGGCGGTCTTGAGACGGCGGATGGTCGACAGAAGCACCATGTCCTTGGGTC
CGGCCTGCTGAATGCGCAGGCGGTCGGCCATGCCCCAGGCTTCGTTTTGACATCGGCGCAGGTCTTTGTAGTAGTC
TTGCATGAGCCTTTCTACCGGCACTTCTTCTTCTCCTTCCTCTTGTCCTGCATCTCTTGCATCTATCGCTGCGGCG
GCGGCGGAGTTTGGCCGTAGGTGGCGCCCTCTTCCTCCCATGCGTGTGACCCCGAAGCCCCTCATCGGCTGAAGCA
GGGCTAGGTCGGCGACAACGCGCTCGGCTAATATGGCCTGCTGCACCTGCGTGAGGGTAGACTGGAAGTCATCCAT
GTCCACAAAGCGGTGGTATGCGCCCGTGTTGATGGTGTAAGTGCAGTTGGCCATAACGGACCAGTTAACGGTCTGG
TGACCCGGCTGCGAGAGCTCGGTGTACCTGAGACGCGAGTAAGCCCTCGAGTCAAATACGTAGTCGTTGCAAGTCC
GCACCAGGTACTGGTATCCCACCAAAAAGTGCGGCGGCGGCTGGCGGTAGAGGGGCCAGCGTAGGGTGGCCGGGGC
TCCGGGGGCGAGATCTTCCAACATAAGGCGATGATATCCGTAGATGTACCTGGACATCCAGGTGATGCCGGCGGCG
GTGGTGGAGGCGCGCGGAAAGTCGCGGACGCGGTTCCAGATGTTGCGCAGCGGCAAAAAGTGCTCCATGGTCGGGA
CGCTCTGGCCGGTCAGGCGCGCGCAATCGTTGACGCTCTACCGTGCAAAAGGAGAGCCTGTAAGCGGGCACTCTTC
CGTGGTCTGGTGGATAAATTCGCAAGGGTATCATGGCGGACGACCGGGGTTCGAGCCCCGTATCCGGCCGTCCGCC
GTGATCCATGCGGTTACCGCCCGCGTGTCGAACCCAGGTGTGCGACGTCAGACAACGGGGGAGTGCTCCTTTTGGC
TTCCTTCCAGGCGCGGCGGCTGCTGCGCTAGCTTTTTTGGCCACTGGCCGCGCGCAGCGTAAGCGGTTAGGCTGGA
AAGCGAAAGCATTAAGTGGCTCGCTCCCTGTAGCCGGAGGGTTATTTTCCAAGGGTTGAGTCGCGGGACCCCCGGT
TCGAGTCTCGGACCGGCCGGACTGCGGCGAACGGGGGTTTGCCTCCCCGTCATGCAAGACCCCGCTTGCAAATTCC
TCCGGAAACAGGGACGAGCCCCTTTTTTGCTTTTCCCAGATGCATCCGGTGCTGCGGCAGATGCGCCCCCCTCCTC
AGCAGCGGCAAGAGCAAGAGCAGCGGCAGACATGCAGGGCACCCTCCCCTCCTCCTACCGCGTCAGGAGGGGCGAC
ATCCGCGGTTGACGCGGCAGCAGATGGTGATTACGAACCCCCGCGGCGCCGGGCCCGGCACTACCTGGACTTGGAG
GAGGGCGAGGGCCTGGCGCGGCTAGGAGCGCCCTCTCCTGAGCGGTACCCAAGGGTGCAGCTGAAGCGTGATACGC
GTGAGGCGTACGTGCCGCGGCAGAACCTGTTTCGCGACCGCGAGGGAGAGGAGCCCGAGGAGATGCGGGATCGAAA
GTTCCACGCAGGGCGCGAGCTGCGGCATGGCCTGAATCGCGAGCGGTTGCTGCGCGAGGAGGACTTTGAGCCCGAC
GCGCGAACCGGGATTAGTCCCGCGCGCGCACACGTGGCGGCCGCCGACCTGGTAACCGCATACGAGCAGACGGTGA
ACCAGGAGATTAACTTTCAAAAAAGCTTTAACAACCACGTGCGTACGCTTGTGGCGCGCGAGGAGGTGGCTATAGG
ACTGATGCATCTGTGGGACTTTGTAAGCGCGCTGGAGCAAAACCCAAATAGCAAGCCGCTCATGGCGCAGCTGTTC
CTTATAGTGCAGCACAGCAGGGACAACGAGGCATTCAGGGATGCGCTGCTAAACATAGTAGAGCCCGAGGGCCGCT
GGCTGCTCGATTTGATAAACATCCTGCAGAGCATAGTGGTGCAGGAGCGCAGCTTGAGCCTGGCTGACAAGGTGGC
CGCCATCAACTATTCCATGCTTAGCCTGGGCAAGTTTTACGCCCGCAAGATATACCATACCCCTTACGTTCCCATA
GACAAGGAGGTAAAGATCGAGGGGTTCTACATGCGCATGGCGCTGAAGGTGCTTACCTTGAGCGACGACCTGGGCG
TTTATCGCAACGAGCGCATCCACAAGGCCGTGAGCGTGAGCCGGCGGCGCGAGCTCAGCGACCGCGAGCTGATGCA
CAGCCTGCAAAGGGCCCTGGCTGGCACGGGCAGCGGCGATAGAGAGGCCGAGTCCTACTTTGACGCGGGCGCTGAC

FIGURE 8 (cont.)

CTGCGCTGGGCCCCAAGCCGACGCGCCCTGGAGGCAGCTGGGGCCGGACCTGGGCTGGCGGTGGCACCCGCGCGCG
CTGGCAACGTCGGCGGCGTGGAGGAATATGACGAGGACGATGAGTACGAGCCAGAGGACGGCGAGTACTAAGCGGT
GATGTTTCTGATCAGATGATGCAAGACGCAACGGACCCGGCGGTGCGGGCGGCGCTGCAGAGCCAGCCGTCCGGCC
TTAACTCCACGGACGACTGGCGCCAGGTCATGGACCGCATCATGTCGCTGACTGCGCGCAATCCTGACGCGTTCCG
GCAGCAGCCGCAGGCCAACCGGCTCTCCGCAATTCTGGAAGCGGTGGTCCCGGCGCGCGCAAACCCCACGCACGAG
AAGGTGCTGGCGATCGTAAACGCGCTGGCCGAAAACAGGGCCATCCGGCCCGACGAGGCCGGCCTGGTCTACGACG
CGCTGCTTCAGCGCGTGGCTCGTTACAACAGCGGCAACGTGCAGACCAACCTGGACCGGCTGGTGGGGGATGTGCG
CGAGGCCGTGGCGCAGCGTGAGCGCGCGCAGCAGCAGGGCAACCTGGGCTCCATGGTTGCACTAAACGCCTTCCTG
AGTACACAGCCCGCCAACGTGCCGCGGGGACAGGAGGACTACACCAACTTTGTGAGCGCACTGCGGCTAATGGTGA
CTGAGACACCGCAAAGTGAGGTGTACCAGTCTGGGCCAGACTATTTTTTCCAGACCAGTAGACAAGGCCTGCAGAC
CGTAAACCTGAGCCAGGCTTTCAAAAACTTGCAGGGGCTGTGGGGGGTGCGGGCTCCCACAGGCGACCGCGCGACC
GTGTCTAGCTTGCTGACGCCCAACTCGCGCCTGTTGCTGCTGCTAATAGCGCCCTTCACGGACAGTGGCAGCGTGT
CCCGGGACACATACCTAGGTCACTTGCTGACACTGTACCGCGAGGCCATAGGTCAGGCGCATGTGGACGAGCATAC
TTTCCAGGAGATTACAAGTGTCAGCCGCGCGCTGGGGCAGGAGGACACGGGCAGCCTGGAGGCAACCCTAAACTAC
CTGCTGACCAACCGGCGGCAGAAGATCCCCTCGTTGCACAGTTTAAACAGCGAGGAGGAGCGCATTTTGCGCTACG
TGCAGCAGAGCGTGAGCCTTAACCTGATGCGCGACGGGGTAACGCCCAGCGTGGCGCTGGACATGACCGCGCGCAA
CATGGAACCGGGCATGTATGCCTCAAACCGGCCGTTTATCAACCGCCTAATGGACTACTTGCATCGCGCGGCCGCC
GTGAACCCCGAGTATTTCACCAATGCCATCTTGAACCCGCACTGGCTACCGCCCCCTGGTTTCTACACCGGGGGAT
TCGAGGTGCCCGAGGGTAACGATGGATTCCTCTGGGACGACATAGACGACAGCGTGTTTTCCCCGCAACCGCAGAC
CCTGCTAGAGTTGCAACAGCGCGAGCAGGCAGAGGCGGCGCTGCGAAAGGAAAGCTTCCGCAGGCCAAGCAGCTTG
TCCGATCTAGGCGCTGCGGCCCCGCGGTCAGATGCTAGTAGCCCATTTCCAAGCTTGATAGGGTCTCTTACCAGCA
CTCGCACCACCCGCCCGCGCCTGCTGGGCGAGGAGGAGTACCTAAACAACTCGCTGCTGCAGCCGCAGCGCGAAAA
AAACCTGCCTCCGGCATTTCCCAACAACGGGATAGAGAGCCTAGTGGACAAGATGAGTAGATGGAAGACGTACGCG
CAGGAGCACAGGGACGTGCCAGGCCCGCGCCCGCCCACCCGTCGTCAAAGGCACGACCGTCAGCGGGGTCTGGTGT
GGGAGGACGATGACTCGGCAGACGACAGCAGCGTCCTGGATTTGGGAGGGAGTGGCAACCCGTTTGCGCACCTTCG
CCCCAGGCTGGGGAGAATGTTTTAAAAAAAAAAAAGCATGATGCAAAATAAAAAACTCACCAAGGCCATGGCACCG
AGCGTTGGTTTTCTTGTATTCCCCTTAGTATGCGGCGCGCGGCGATGTATGAGGAAGGTCCTCCTCCCTCCTACGA
GAGTGTGGTGAGCGCGGCGCCAGTGGCGGCGGCGCTGGGTTCTCCCTTCGATGCTCCCCTGGACCCGCCGTTTGTG
CCTCCGCGGTACCTGCGGCCTACCGGGGGGAGAAACAGCATCCGTTACTCTGAGTTGGCACCCCTATTCGACACCA
CCCGTGTGTACCTGGTGGACAACAAGTCAACGGATGTGGCATCCCTGAACTACCAGAACGACCACAGCAACTTTCT
GACCACGGTCATTCAAAACAATGACTACAGCCCGGGGGAGGCAAGCACACAGACCATCAATCTTGACGACCGGTCG
CACTGGGGCGGCGACCTGAAAACCATCCTGCATACCAACATGCCAAATGTGAACGAGTTCATGTTTACCAATAAGT
TTAAGGCGCGGGTGATGGTGTCGCGCTTGCCTACTAAGGACAATCAGGTGGAGCTGAAATACGAGTGGGTGGAGTT
CACGCTGCCCGAGGGCAACTACTCCGAGACCATGACCATAGACCTTATGAACAACGCGATCGTGGAGCACTACTTG
AAAGTGGGCAGACAGAACGGGGTTCTGGAAAGCGACATCGGGGTAAAGTTTGACACCCGCAACTTCAGACTGGGGT
TTGACCCCGTCACTGGTCTTGTCATGCCTGGGGTATATACAAACGAAGCCTTCCATCCAGACATCATTTTGCTGCC
AGGATGCGGGGTGGACTTCACCCACAGCCGCCTGAGCAACTTGTTGGGCATCCGCAAGCGGCAACCCTTCCAGGAG
GGCTTTAGGATCACCTACGATGATCTGGAGGGTGGTAACATTCCCGCACTGTTGGATGTGGACGCCTACCAGGCGA
GCTTGAAAGATGACACCGAACAGGGCGGGGGTGGCGCAGGCGGCAGCAACAGCAGTGGCAGCGGCGCGGAAGAGAA
CTCCAACGCGGCAGCCGCGGCAATGCAGCCGGTGGAGGACATGAACGATCATGCCATTCGCGGCGACACCTTTGCC
ACACGGGCTGAGGAGAAGCGCGCTGAGGCCGAAGCAGCGGCCGAAGCTGCCGCCCCCGCTGCGCAACCCGAGGTCG
AGAAGCCTCAGAAGAAACCGGTGATCAAACCCCTGACAGAGGACAGCAAGAAACGCAGTTACAACCTAATAAGCAA
TGACAGCACCTTCACCCAGTACCGCAGCTGGTACCTTGCATACAACTACGGCGACCCTCAGACCGGAATCCGCTCA
TGGACCCTGCTTTGCACTCCTGACGTAACCTGCGGCTCGGAGCAGGTCTACTGGTCGTTGCCAGACATGATGCAAG
ACCCCGTGACCTTCCGCTCCACGCGCCAGATCAGCAACTTTCCGGTGGTGGGCGCCGAGCTGTTGCCCGTGCACTC
CAAGAGCTTCTACAACGACCAGGCCGTCTACTCCCAACTCATCCGCCAGTTTACCTCTCTGACCCACGTGTTCAAT
CGCTTTCCCGAGAACCAGATTTTGGCGCGCCCGCCAGCCCCCACCATCACCACCGTCAGTGAAAACGTTCCTGCTC
TCACAGATCACGGGACGCTACCGCTGCGCAACAGCATCGGAGGAGTCCAGCGAGTGACCATTACTGACGCCAGACG
CCGCACCTGCCCCTACGTTTACAAGGCCCTGGGCATAGTCTCGCCGCGCGTCCTATCGAGCCGCACTTTTTGAGCA
AGCATGTCCATCCTTATATCGCCCAGCAATAACACAGGCTGGGGCCTGCGCTTCCCAAGCAAGATGTTTGGCGGGG
CCAAGAAGCGCTCCGACCAACACCCAGTGCGCGTGCGCGGGCACTACCGCGCGCCCTGGGGCGCGCACAAACGCGG
CCGCACTGGGCGCACCACCGTCGATGACGCCATCGACGCGGTGGTGGAGGAGGCGCGCAACTACACGCCCACGCCG
CCACCAGTGTCCACAGTGGACGCGGCCATTCAGACCGTGGTGCGCGGAGCCCGGCGCTATGCTAAAATGAAGAGAC
GGCGGAGGCGCGTAGCACGTCGCCACCGCCGCCGACCCGGCACTGCCGCCCAACGCGCGGCGGCGGCCCTGCTTAA
CCGCGCACGTCGCACCGGCCGACGGGCGGCCATGCGGGCCGCTCGAAGGCTGGCCGCGGGTATTGTCACTGTGCCC
CCCAGGTCCAGGCGACGAGCGGCCGCCGCAGCAGCCGCGGCCATTAGTGCTATGACTCAGGGTCGCAGGGGCAACG
TGTATTGGGTGCGCGACTCGGTTAGCGGCCTGCGCGTGCCCGTGCGCACCCGCCCCCCGCGCAACTAGATTGCAAG
AAAAAACTACTTAGACTCGTACTGTTGTATGTATCCAGCGGCGGCGGCGCGCAACGAAGCTATGTCCAAGCGCAAA
ATCAAAGAAGAGATGCTCCAGGTCATCGCGCCGGAGATCTATGGCCCCCCGAAGAAGGAAGAGCAGGATTACAAGC
CCCGAAAGCTAAAGCGGGTCAAAAAGAAAAAGAAAGATGATGATGATGAACTTGACGACGAGGTGGAACTGCTGCA
CGCTACCGCGCCCAGGCGACGGGTACAGTGGAAAGGTCGACGCGTAAAACGTGTTTTGCGACCCGGCACCACCGTA

FIGURE 8 (cont.)

GTCTTTACGCCCGGTGAGCGCTCCACCCGCACCTACAAGCGCGTGTATGATGAGGTGTACGGCGACGAGGACCTGC
TTGAGCAGGCCAACGAGCGCCTCGGGGAGTTTGCCTACGGAAAGCGGCATAAGGACATGCTGGCGTTGCCGCTGGA
CGAGGGCAACCCAACACCTAGCCTAAAGCCCGTAACACTGCAGCAGGTGCTGCCCGCGCTTGCACCGTCCGAAGAA
AAGCGCGGCCTAAAGCGCGAGTCTGGTGACTTGGCACCCACCGTGCAGCTGATGGTACCCAAGCGCCAGCGACTGG
AAGATGTCTTGGAAAAAATGACCGTGGAACCTGGGCTGGAGCCCGAGGTCCGCGTGCGGCCAATCAAGCAGGTGGC
GCCGGGACTGGGCGTGCAGACCGTGGACGTTCAGATACCCACTACCAGTAGCACCAGTATTGCCACCGCCACAGAG
GGCATGGAGACACAAACGTCCCCGGTTGCCTCAGCGGTGGCGGATGCCGCGGTGCAGGCGGTCGCTGCGGCCGCGT
CCAAGACCTCTACGGAGGTGCAAACGGACCCGTGGATGTTTCGCGTTTCAGCCCCCCGGCGCCCGCGCGGTTCGAG
GAAGTACGGCGCCGCCAGCGCGCTACTGCCCGAATATGCCCTACATCCTTCCATTGCGCCTACCCCCGGCTATCGT
GGCTACACCTACCGCCCCAGAAGACGAGCAACTACCCGACGCCGAACCACCACTGGAACCCGCCGCCGCCGTCGCC
GTCGCCAGCCCGTGCTGGCCCCGATTTCCGTGCGCAGGGTGGCTCGCGAAGGAGGCAGGACCCTGGTGCTGCCAAC
AGCGCGCTACCACCCCAGCATCGTTTAAAAGCCGGTCTTTGTGGTTCTTGCAGATATGGCCCTCACCTGCCGCCTC
CGTTTCCCGGTGCCGGGATTCCGAGGAAGAATGCACCGTAGGAGGGGCATGGCCGGCCACGGCCTGACGGGCGGCA
TGCGTCGTGCGCACCACCGGCGGCGGCGCGCGTCGCACCGTCGCATGCGCGGCGGTATCCTGCCCCTCCTTATTCC
ACTGATCGCCGCGGCGATTGGCGCCGTGCCCGGAATTGCATCCGTGGCCTTGCAGGCGCAGAGACACTGATTAAAA
ACAAGTTGCATGTGGAAAAATCAAAATAAAAAGTCTGGACTCTCACGCTCGCTTGGTCCTGTAACTATTTTGTAGA
ATGGAAGACATCAACTTTGCGTCTCTGGCCCCGCGACACGGCTCGCGCCCGTTCATGGGAAACTGGCAAGATATCG
GCACCAGCAATATGAGCGGTGGCGCCTTCAGCTGGGGCTCGCTGTGGAGCGGCATTAAAAATTTCGGTTCCACCGT
TAAGAACTATGGCAGCAAGGCCTGGAACAGCAGCACAGGCCAGATGCTGAGGGATAAGTTGAAAGAGCAAAATTTC
CAACAAAAGGTGGTAGATGGCCTGGCCTCTGGCATTAGCGGGGTGGTGGACCTGGCCAACCAGGCAGTGCAAAATA
AGATTAACAGTAAGCTTGATCCCCGCCCTCCCGTAGAGGAGCCTCCACCGGCCGTGGAGACAGTGTCTCCAGAGGG
GCGTGGCGAAAAGCGTCCGCGCCCCGACAGGGAAGAAACTCTGGTGACGCAAATAGACGAGCCTCCCTCGTACGAG
GAGGCACTAAAGCAAGGCCTGCCCACCACCCGTCCCATCGCGCCCATGGCTACCGGAGTGCTGGGCCAGCACACAC
CCGTAACGCTGGACCTGCCTCCCCCCGCCGACACCCAGCAGAAACCTGTGCTGCCAGGCCCGACCGCCGTTGTTGT
AACCCGTCCTAGCCGCGCGTCCCTGCGCCGCGCCGCCAGCGGTCCGCGATCGTTGCGGCCCGTAGCCAGTGGCAAC
TGGCAAAGCACACTGAACAGCATCGTGGGTCTGGGGGTGCAATCCCTGAAGCGCCGACGATGCTTCTGAATAGCTA
ACGTGTCGTATGTGTGTCATGTATGCGTCCATGTCGCCGCCAGAGGAGCTGCTGAGCCGCCGCGCGCCCGCTTTCC
AAGATGGCTACCCCTTCGATGATGCCGCAGTGGTCTTACATGCACATCTCGGGCCAGGACGCCTCGGAGTACCTGA
GCCCCGGGCTGGTGCAGTTTGCCCGCGCCACCGAGACGTACTTCAGCCTGAATAACAAGTTTAGAAACCCCACGGT
GGCGCCTACGCACGACGTGACCACAGACCGGTCCCAGCGTTTGACGCTGCGGTTCATCCCTGTGGACCGTGAGGAT
ACTGCGTACTCGTACAAGGCGCGGTTCACCCTAGCTGTGGGTGATAACCGTGTGCTGGACATGGCTTCCACGTACT
TTGACATCCGCGGCGTGCTGGACAGGGGCCCTACTTTTAAGCCCTACTCTGGCACTGCCTACAACGCCCTGGCTCC
CAAGGGTGCCCCAAATCCTTGCGAATGGGATGAAGCTGCTACTGCTCTTGAAATAAACCTAGAAGAAGAGGACGAT
GACAACGAAGACGAAGTAGACGAGCAAGCTGAGCAGCAAAAAACTCACGTATTTGGGCAGGCGCCTTATTCTGGTA
TAAATATTACAAAGGAGGGTATTCAAATAGGTGTCGAAGGTCAAACACCTAAATATGCCGATAAAACATTTCAACC
TGAACCTCAAATAGGAGAATCTCAGTGGTACGAAACTGAAATTAATCATGCAGCTGGGAGAGTCCTTAAAAAGACT
ACCCCAATGAAACCATGTTACGGTTCATATGCAAAACCCACAAATGAAAATGGAGGGCAAGGCATTCTTGTAAAGC
AACAAAATGGAAAGCTAGAAAGTCAAGTGGAAATGCAATTTTTCTCAACTACTGAGGCGACCGCAGGCAATGGTGA
TAACTTGACTCCTAAAGTGGTATTGTACAGTGAAGATGTAGATATAGAAACCCCAGACACTCATATTTCTTACATG
CCCACTATTAAGGAAGGTAACTCACGAGAACTAATGGGCCAACAATCTATGCCCAACAGGCCTAATTACATTGCTT
TTAGGGACAATTTTATTGGTCTAATGTATTACAACAGCACGGGTAATATGGGTGTTCTGGCGGGCCAAGCATCGCA
GTTGAATGCTGTTGTAGATTTGCAAGACAGAAACACAGAGCTTTCATACCAGCTTTTGCTTGATTCCATTGGTGAT
AGAACCAGGTACTTTTCTATGTGGAATCAGGCTGTTGACAGCTATGATCCAGATGTTAGAATTATTGAAAATCATG
GAACTGAAGATGAACTTCCAAATTACTGCTTTCCACTGGGAGGTGTGATTAATACAGAGACTCTTACCAAGGTAAA
ACCTAAAACAGGTCAGGAAAATGGATGGGAAAAAGATGCTACAGAATTTTCAGATAAAAATGAAATAAGAGTTGGA
AATAATTTTGCCATGGAAATCAATCTAAATGCCAACCTGTGGAGAAATTTCCTGTACTCCAACATAGCGCTGTATT
TGCCCGACAAGCTAAAGTACAGTCCTTCCAACGTAAAAATTTCTGATAACCCAAACACCTACGACTACATGAACAA
GCGAGTGGTGGCTCCCGGGTTAGTGGACTGCTACATTAACCTTGGAGCACGCTGGTCCCTTGACTATATGGACAAC
GTCAACCCATTTAACCACCACCGCAATGCTGGCCTGCGCTACCGCTCAATGTTGCTGGGCAATGGTCGCTATGTGC
CCTTCCACATCCAGGTGCCTCAGAAGTTCTTTGCCATTAAAAACCTCCTTCTCCTGCCGGGCTCATACACCTACGA
GTGGAACTTCAGGAAGGATGTTAACATGGTTCTGCAGAGCTCCCTAGGAAATGACCTAAGGGTTGACGGAGCCAGC
ATTAAGTTTGATAGCATTTGCCTTTACGCCACCTTCTTCCCCATGGCCCACAACACCGCCTCCACGCTTGAGGCCA
TGCTTAGAAACGACACCAACGACCAGTCCTTTAACGACTATCTCTCCGCCGCCAACATGCTCTACCCTATACCCGC
CAACGCTACCAACGTGCCCATATCCATCCCCTCCCGCAACTGGGCGGCTTTCCGCGGCTGGGCCTTCACGCGCCTT
AAGACTAAGGAAACCCCATCACTGGGCTCGGGCTACGACCCTTATTACACCTACTCTGGCTCTATACCCTACCTAG
ATGGAACCTTTTACCTCAACCACACCTTTAAGAAGGTGGCCATTACCTTTGACTCTTCTGTCAGCTGGCCTGGCAA
TGACCGCCTGCTTACCCCCAACGAGTTTGAAATTAAGCGCTCAGTTGACGGGGAGGGTTACAACGTTGCCCAGTGT
AACATGACCAAAGACTGGTTCCTGGTACAAATGCTAGCTAACTACAACATTGGCTACCAGGGCTTCTATATCCCAG
AGAGCTACAAGGACCGCATGTACTCCTTCTTTAGAAACTTCCAGCCCATGAGCCGTCAGGTGGTGGATGATACTAA
ATACAAGGACTACCAACAGGTGGGCATCCTACACCAACACAACAACTCTGGATTTGTTGGCTACCTTGCCCCCACC
ATGCGCGAAGGACAGGCCTACCCTGCTAACTTCCCCTATCCGCTTATAGGCAAGACCGCAGTTGACAGCATTACCC

FIGURE 8 (cont.)

AGAAAAAGTTTCTTTGCGATCGCACCCTTTGGCGCATCCCATTCTCCAGTAACTTTATGTCCATGGGCGCACTCAC
AGACCTGGGCCAAAACCTTCTCTACGCCAACTCCGCCCACGCGCTAGACATGACTTTTGAGGTGGATCCCATGGAC
GAGCCCACCCTTCTTTATGTTTTGTTTGAAGTCTTTGACGTGGTCCGTGTGCACCGGCCGCACCGCGGCGTCATCG
AAACCGTGTACCTGCGCACGCCCTTCTCGGCCGGCAACGCCACAACATAAAGAAGCAAGCAACATCAACAACAGCT
GCCGCCATGGGCTCCAGTGAGCAGGAACTGAAAGCCATTGTCAAAGATCTTGGTTGTGGGCCATATTTTTTGGGCA
CCTATGACAAGCGCTTTCCAGGCTTTGTTTCTCCACACAAGCTCGCCTGCGCCATAGTCAATACGGCCGGTCGCGA
GACTGGGGGCGTACACTGGATGGCCTTTGCCTGGAACCCGCACTCAAAAACATGCTACCTCTTTGAGCCCTTTGGC
TTTTCTGACCAGCGACTCAAGCAGGTTTACCAGTTTGAGTACGAGTCACTCCTGCGCCGTAGCGCCATTGCTTCTT
CCCCCGACCGCTGTATAACGCTGGAAAAGTCCACCCAAAGCGTACAGGGGCCCAACTCGGCCGCCTGTGGACTATT
CTGCTGCATGTTTCTCCACGCCTTTGCCAACTGGCCCCAAACTCCCATGGATCACAACCCCACCATGAACCTTATT
ACCGGGGTACCCAACTCCATGCTCAACAGTCCCCAGGTACAGCCCACCCTGCGTCGCAACCAGGAACAGCTCTACA
GCTTCCTGGAGCGCCACTCGCCCTACTTCCGCAGCCACAGTGCGCAGATTAGGAGCGCCACTTCTTTTTGTCACTT
GAAAAACATGTAAAAATAATGTACTAGAGACACTTTCAATAAAGGCAAATGCTTTTATTTGTACACTCTCGGGTGA
TTATTTACCCCCACCCTTGCCGTCTGCGCCGTTTAAAAATCAAAGGGGTTCTGCCGCGCATCGCTATGCGCCACTG
GCAGGGACACGTTGCGATACTGGTGTTTAGTGCTCCACTTAAACTCAGGCACAACCATCCGCGGCAGCTCGGTGAA
GTTTTCACTCCACAGGCTGCGCACCATCACCAACGCGTTTAGCAGGTCGGGCGCCGATATCTTGAAGTCGCAGTTG
GGGCCTCCGCCCTGCGCGCGCGAGTTGCGATACACAGGGTTGCAGCACTGGAACACTATCAGCGCCGGGTGGTGCA
CGCTGGCCAGCACGCTCTTGTCGGAGATCAGATCCGCGTCCAGGTCCTCCGCGTTGCTCAGGGCGAACGGAGTCAA
CTTTGGTAGCTGCCTTCCCAAAAAGGGCGCGTGCCCAGGCTTTGAGTTGCACTCGCACCGTAGTGGCATCAAAAGG
TGACCGTGCCCGGTCTGGGCGTTAGGATACAGCGCCTGCATAAAAGCCTTGATCTGCTTAAAAGCCACCTGAGCCT
TTGCGCCTTCAGAGAAGAACATGCCGCAAGACTTGCCGGAAAACTGATTGGCCGGACAGGCCGCGTCGTGCACGCA
GCACCTTGCGTCGGTGTTGGAGATCTGCACCACATTTCGGCCCCACCGGTTCTTCACGATCTTGGCCTTGCTAGAC
TGCTCCTTCAGCGCGCGCTGCCCGTTTTCGCTCGTCACATCCATTTCAATCACGTGCTCCTTATTTATCATAATGC
TTCCGTGTAGACACTTAAGCTCGCCTTCGATCTCAGCGCAGCGGTGCAGCCACAACGCGCAGCCCGTGGGCTCGTG
ATGCTTGTAGGTCACCTCTGCAAACGACTGCAGGTACGCCTGCAGGAATCGCCCCATCATCGTCACAAAGGTCTTG
TTGCTGGTGAAGGTCAGCTGCAACCCGCGGTGCTCCTCGTTCAGCCAGGTCTTGCATACGGCCGCCAGAGCTTCCA
CTTGGTCAGGCAGTAGTTTGAAGTTCGCCTTTAGATCGTTATCCACGTGGTACTTGTCCATCAGCGCGCGCGCAGC
CTCCATGCCCTTCTCCCACGCAGACACGATCGGCACACTCAGCGGGTTCATCACCGTAATTTCACTTTCCGCTTCG
CTGGGCTCTTCCTCTTCCTCTTGCGTCCGCATACCACGCGCCACTGGGTCGTCTTCATTCAGCCGCCGCACTGTGC
GCTTACCTCCTTTGCCATGCTTGATTAGCACCGGTGGGTTGCTGAAACCCACCATTTGTAGCGCCACATCTTCTCT
TTCTTCCTCGCTGTCCACGATTACCTCTGGTGATGGCGGGCGCTCGGGCTTGGGAGAAGGGCGCTTCTTTTTCTTC
TTGGGCGCAATGGCCAAATCCGCCGCCGAGGTCGATGGCCGCGGGCTGGGTGTGCGCGGCACCAGCGCGTCTTGTG
ATGAGTCTTCCTCGTCCTCGGACTCGATACGCCGCCTCATCCGCTTTTTTGGGGGCGCCCGGGGAGGCGGCGGCGA
CGGGGACGGGGACGACACGTCCTCCATGGTTGGGGGACGTCGCGCCGCACCGCGTCCGCGCTCGGGGGTGGTTTCG
CGCTGCTCCTCTTCCCGACTGGCCATTTCCTTCTCCTATAGGCAGAAAAAGATCATGGAGTCAGTCGAGAAGAAGG
ACAGCCTAACCGCCCCCTCTGAGTTCGCCACCACCGCCTCCACCGATGCCGCCAACGCGCCTACCACCTTCCCCGT
CGAGGCACCCCCGCTTGAGGAGGAGGAAGTGATTATCGAGCAGGACCCAGGTTTTGTAAGCGAAGACGACGAGGAC
CGCTCAGTACCAACAGAGGATAAAAAGCAAGACCAGGACAACGCAGAGGCAAACGAGGAACAAGTCGGGCGGGGGG
ACGAAAGGCATGGCGACTACCTAGATGTGGGAGACGACGTGCTGTTGAAGCATCTGCAGCGCCAGTGCGCCATTAT
CTGCGACGCGTTGCAAGAGCGCAGCGATGTGCCCCTCGCCATAGCGGATGTCAGCCTTGCCTACGAACGCCACCTA
TTCTCACCGCGCGTACCCCCCAAACGCCAAGAAAACGGCACATGCGAGCCCAACCCGCGCCTCAACTTCTACCCCG
TATTTGCCGTGCCAGAGGTGCTTGCCACCTATCACATCTTTTTCCAAAACTGCAAGATACCCCTATCCTGCCGTGC
CAACCGCAGCCGAGCGGACAAGCAGCTGGCCTTGCGGCAGGGCGCTGTCATACCTGATATCGCCTCGCTCAACGAA
GTGCCAAAAATCTTTGAGGGTCTTGGACGCGACGAGAAGCGCGCGGCAAACGCTCTGCAACAGGAAAACAGCGAAA
ATGAAAGTCACTCTGGAGTGTTGGTGGAACTCGAGGGTGACAACGCGCGCCTAGCCGTACTAAAACGCAGCATCGA
GGTCACCCACTTTGCCTACCCGGCACTTAACCTACCCCCCAAGGTCATGAGCACAGTCATGAGTGAGCTGATCGTG
CGCCGTGCGCAGCCCCTGGAGAGGGATGCAAATTTGCAAGAACAAACAGAGGAGGGCCTACCCGCAGTTGGCGACG
AGCAGCTAGCGCGCTGGCTTCAAACGCGCGAGCCTGCCGACTTGGAGGAGCGACGCAAACTAATGATGGCCGCAGT
GCTCGTTACCGTGGAGCTTGAGTGCATGCAGCGGTTCTTTGCTGACCCGGAGATGCAGCGCAAGCTAGAGGAAACA
TTGCACTACACCTTTCGACAGGGCTACGTACGCCAGGCCTGCAAGATCTCCAACGTGGAGCTCTGCAACCTGGTCT
CCTACCTTGGAATTTTGCACGAAAACCGCCTTGGGCAAAACGTGCTTCATTCCACGCTCAAGGGCGAGGCGCGCCG
CGACTACGTCCGCGACTGCGTTTACTTATTTCTATGCTACACCTGGCAGACGGCCATGGGCGTTTGGCAGCAGTGC
TTGGAGGAGTGCAACCTCAAGGAGCTGCAGAAACTGCTAAAGCAAAACTTGAAGGACCTATGGACGGCCTTCAACG
AGCGCTCCGTGGCCGCGCACCTGGCGGACATCATTTTCCCCGAACGCCTGCTTAAAACCCTGCAACAGGGTCTGCC
AGACTTCACCAGTCAAAGCATGTTGCAGAACTTTAGGAACTTTATCCTAGAGCGCTCAGGAATCTTGCCCGCCACC
TGCTGTGCACTTCCTAGCGACTTTGTGCCCATTAAGTACCGCGAATGCCCTCCGCCGCTTTGGGGCCACTGCTACC
TTCTGCAGCTAGCCAACTACCTTGCCTACCACTCTGACATAATGGAAGACGTGAGCGGTGACGGTCTACTGGAGTG
TCACTGTCGCTGCAACCTATGCACCCCGCACCGCTCCCTGGTTTGCAATTCGCAGCTGCTTAACGAAAGTCAAATT
ATCGGTACCTTTGAGCTGCAGGGTCCCTCGCCTGACGAAAAGTCCGCGGCTCCGGGGTTGAAACTCACTCCGGGGC
TGTGGACGTCGGCTTACCTTCGCAAATTTGTACCTGAGGACTACCACGCCCACGAGATTAGGTTCTACGAAGACCA
ATCCCGCCCGCCAAATGCGGAGCTTACCGCCTGCGTCATTACCCAGGGCCACATTCTTGGCCAATTGCAAGCCATC

FIGURE 8 (cont.)

AACAAAGCCCGCCAAGAGTTTCTGCTACGAAAGGGACGGGGGGTTTACTTGGACCCCCAGTCCGGCGAGGAGCTCA
ACCCAATCCCCCCGCCGCCGCAGCCCTATCAGCAGCAGCCGCGGGCCCTTGCTTCCCAGGATGGCACCCAAAAAGA
AGCTGCAGCTGCCGCCGCCACCCACGGACGAGGAGGAATACTGGGACAGTCAGGCAGAGGAGGTTTTGGACGAGGA
GGAGGAGGACATGATGGAAGACTGGGAGAGCCTAGACGAGGAAGCTTCCGAGGTCGAAGAGGTGTCAGACGAAACA
CCGTCACCCTCGGTCGCATTCCCCTCGCCGGCGCCCCAGAAATCGGCAACCGGTTCCAGCATGGCTACAACCTCCG
CTCCTCAGGCGCCGCCGGCACTGCCCGTTCGCCGACCCAACCGTAGATGGGACACCACTGGAACCAGGGCCGGTAA
GTCCAAGCAGCCGCCGCCGTTAGCCCAAGAGCAACAACAGCGCCAAGGCTACCGCTCATGGCGCGGGCACAAGAAC
GCCATAGTTGCTTGCTTGCAAGACTGTGGGGGCAACATCTCCTTCGCCCGCCGCTTTCTTCTCTACCATCACGGCG
TGGCCTTCCCCCGTAACATCCTGCATTACTACCGTCATCTCTACAGCCCATACTGCACCGGCGGCAGCGGCAGCGG
CAGCAACAGCAGCGGCCACACAGAAGCAAAGGCGACCGGATAGCAAGACTCTGACAAAGCCCAAGAAATCCACAGC
GGCGGCAGCAGCAGGAGGAGGAGCGCTGCGTCTGGCGCCCAACGAACCCGTATCGACCCGCGAGCTTAGAAACAGG
ATTTTTCCCACTCTGTATGCTATATTTCAACAGAGCAGGGGCCAAGAACAAGAGCTGAAAATAAAAAACAGGTCTC
TGCGATCCCTCACCCGCAGCTGCCTGTATCACAAAAGCGAAGATCAGCTTCGGCGCACGCTGGAAGACGCGGAGGC
TCTCTTCAGTAAATACTGCGCGCTGACTCTTAAGGACTAGTTTCGCGCCCTTTCTCAAATTTAAGCGCGAAAACTA
CGTCATCTCCAGCGGCCACACCCGGCGCCAGCACCTGTCGTCAGCGCCATTATGAGCAAGGAAATTCCCACGCCCT
ACATGTGGAGTTACCAGCCACAAATGGGACTTGCGGCTGGAGCTGCCCAAGACTACTCAACCCGAATAAACTACAT
GAGCGCGGGACCCCACATGATATCCCGGGTCAACGGAATCCGCGCCCACCGAAACCGAATTCTCTTGGAACAGGCG
GCTATTACCACCACACCTCGTAATAACCTTAATCCCCGTAGTTGGCCCGCTGCCCTGGTGTACCAGGAAAGTCCCG
CTCCCACCACTGTGGTACTTCCCAGAGACGCCCAGGCCGAAGTTCAGATGACTAACTCAGGGGCGCAGCTTGCGGG
CGGCTTTCGTCACAGGGTGCGGTCGCCCGGGCAGGGTATAACTCACCTGACAATCAGAGGGCGAGGTATTCAGCTC
AACGACGAGTCGGTGAGCTCCTCGCTTGGTCTCCGTCCGGACGGGACATTTCAGATCGGCGGCGCCGGCCGTCCTT
CATTCACGCCTCGTCAGGCAATCCTAACTCTGCAGACCTCGTCCTCTGAGCCGCGCTCTGGAGGCATTGGAACTCT
GCAATTTATTGAGGAGTTTGTGCCATCGGTCTACTTTAACCCCTTCTCGGGACCTCCCGGCCACTATCCGGATCAA
TTTATTCCTAACTTTGACGCGGTAAAGGACTCGGCGGACGGCTACGACTGAATGTTAAGTGGAGAGGCAGAGCAAC
TGCGCCTGAAACACCTGGTCCACTGTCGCCGCCACAAGTGCTTTGCCCGCGACTCCGGTGAGTTTTGCTACTTTGA
ATTGCCCGAGGATCATATCGAGGGCCCGGCGCACGGCGTCCGGCTTACCGCCCAGGGAGAGCTTGCCCGTAGCCTG
ATTCGGGAGTTTACCCAGCGCCCCCTGCTAGTTGAGCGGGACAGGGGACCCTGTGTTCTCACTGTGATTTGCAACT
GTCCTAACCTTGGATTACATCAAGATCCTCTAGTTAATTAACAGCTTGCATGCCTGCAGGTCGACGGATCGGGAGA
TCTCGGCCGCATATTAAGTGCATTGTTCTCGATACCGCTAAGTGCATTGTTCTCGTTAGCTCGATGGACAAGTGCA
TTGTTCTCTTGCTGAAAGCTCGATGGACAAGTGCATTGTTCTCTTGCTGAAAGCTCGATGGACAAGTGCATTGTTC
TCTTGCTGAAAGCTCAGTACCCGGGAGTACCCTCGACCGCCGGAGTATAAATAGAGGCGCTTCGTCTACGGAGCGA
CAATTCAATTCAAACAAGCAAAGTGAACACGTCGCTAAGCGAAAGCTAAGCAAATAAACAAGCGCAGCTGAACAAG
CTAAACAATCTGCAGTAAAGTGCAAGTTAAAGTGAATCAATTAAAAGTAACCAGCAACCAAGTAAATCAACTGCAA
CTACTGAAATCTGCCAAGAAGTAATTATTGAATACAAGAAGAGAACTCTGAATACTTTCAACAAGTTACCGAGAAA
GAAGAACTCACACACAGCTAGCGTTTAAACTTAAGCTTCACCATGGTGGGGCCCTGCATGCTGCTGCTGCTGCTGC
TGCTGGGCCTGAGGCTACAGCTCTCCCTGGGCATCATCCTAGTTGAGGAGGAGAACCCGGACTTCTGGAACCGCGA
GGCAGCCGAGGCCCTGGGTGCCGCCAAGAAGCTGCAGCCTGCACAGACAGCCGCCAAGAACCTCATCATCTTCCTG
GGCGATGGGGTGGGGGTGTCTACGGTGACAGCTGCCAGGATCCTAAAAGGGCAGAAGAAGGACAAACTGGGGCCTG
AGATACCCCTGGCCATGGACCGCTTCCCATATGTGGCTCTGTCCAAGACATACAATGTAGACAAACATGTGCCAGA
CAGTGGAGCCACAGCCACGGCCTACCTGTGCGGGGTCAAGGGCAACTTCCAGACCATTGGCTTGAGTGCAGCCGCC
CGCTTTAACCAGTGCAACACGACACGCGGCAACGAGGTCATCTCCGTGATGAATCGGGCCAAGAAAGCAGGGAAGT
CAGTGGGAGTGGTAACCACCACACGAGTGCAGCACGCCTCGCCAGCCGGCACCTACGCCCACACGGTGAACCGCAA
CTGGTACTCGGACGCCGACGTGCCTGCCTCGGCCCGCCAGGAGGGGTGCCAGGACATCGCTACGCAGCTCATCTCC
AACATGGACATTGACGTGATCCTAGGTGGGGGCCGAAAGTACATGTTTCGCATGGGAACCCCAGACCCTGAGTACC
CAGATGACTACAGCCAAGGTGGGACCAGGCTGGACGGGAAGAATCTGGTGCAGGAATGGCTGGCGAAGCACCAGGG
TGCCCGGTACGTGTGGAACCGCACTGAGCTCATGCGGGCTTCCCTGGACCCGTCTGTGGCCCATCTCATGGGTCTC
TTTGAGCCTGGAGACATGAAATACGAGATCCACCGAGACTCCACACTGGACCCCTCCCTGATGGAGATGACAGAGG
CTGCCCTGCGCCTGCTGAGCAGGAACCCCCGCGGCTTCTTCCTCTTCGTGGAGGGTGGTCGCATCGACCATGGTCA
TCATGAAAGCAGGGCTTACCGGGCACTGACTGAGACGATCATGTTCGACGACGCCATTGAGAGGGCGGGCCAGCTC
ACCAGCGAGGAGGACACGCTGAGCCTCGTCACTGCCGACCACTCCCACGTCTTCTCCTTCGGAGGCTGCCCCCTGC
GAGGGGGCTCCATCTTCGGGCTGGCCCCTGGCAAGGCCCGGGACAGGAAGGCCTACACGGTCCTCCTATACGGAAA
CGGTCCAGGCTATGTGCTCAAGGACGGCGCCCGGCCGGATGTTACCGAGAGCGAGAGCGGGAGCCCCGAGTATCGG
CAGCAGTCAGCAGTGCCCCTGGACGAAGAGACCCACGCAGGCGAGGACGTGGCGGTGTTCGCGCGCGGCCCGCAGG
CGCACCTGGTTCACGGCGTGCAGGAGCAGACCTTCATAGCGCACGTCATGGCCTTCGCCGCCTGCCTGGAGCCCTA
CACCGCCTGCGACCTGGCGCCCCCCGCCGGCACCACCGACGCCGCGCACCCGGGGCGGTCCGTGGTCCCCGCGTTG
CTTCCTCTGCTGGCCGGGACCCTGCTGCTGCTGGAGACGGCCACTGCTCCCTGAGTGTCCCGTCCCTGGGGCTCCT
GCTTCCCCATCCCGGAGTTCTCCTGCTCCCCGCCTCCTGTCGTCCTGCCTGGCCTCCAGCCCGAGTCGTCATCCCC
GGAGTCCCTATACAGAGGTCCTGCCATGGAACCTTCCCCTCCCCGTGCGCTCTGGGGACTGAGCCCATGACACCAA
ACCTGCCCCTTGGCTGCTCTCGGACTCCCTACCCCAACCCCAGGGACAGATCTGGCCAGATTTGTAAAACAAATAG
ATTTTAGGCCCAAAGATTATTTAAAGCATTGCCTGGAACGCAGTGAGTTTTTGTTAGAAAAGAGAATAATTCAAAG
TGGCATTGCTTTGCTTCTTATGTTAATTTGGTACAGACCTGTGGCTGAGTTTGCTCAAAGTATTCAGAGCAGAATT

FIGURE 8 (cont.)

GTGGAGTGGAAAGAGAGATTGGACAAAGAGTTTAGTTTGTCAGTGTATCAAAAAATGAAGTTTAATGTGGCTATGG
GAATTGGAGTTTTAGATTGGCTAAGAAACAGTGATGATGATGATGAAGACAGCCAGGAAAATGCTGATAAAAATGA
AGATGGTGGGAGAAGAACATGGAAGACTCAGGGCATGAAACAGGCATTGATTCACAGTCCCAAGGCTCATTTCAG
GCCCCTCAGTCCTCACAGTCTGTTCATGATCATAATCAGCCATACCACATTTGTAGAGGTTTTACTTGCTTTAAAA
AACCTCCCACACCTCCCCCTGAACCTGAAACATAAAATGAATGCAATTGTTGTTGTTAACTTGTTTATTGCAGCTT
ATAATGGTTACAAATAAAGCAATAGCATCACAAATTTCACAAATAAAGCATTTTTTTCACTGCATTCTAGTTGTGG
TTTGTCCAAACTCATCAATGTATCTTATCATGTCTGGATCCCCAGGAAGCTCCTCTGTGTCCTCATAAACCCTAAC
CTCCTCTACTTGAGAGGACATTCCAATCATAGGCTGCCCATCCACCCTCTGTGTCCTCCTGTTAATTAGGTCACTT
AACAAAAAGGAAATTGGGTAGGGGTTTTTCACAGACCGCTTTCTAAGGGTAATTTTAAAATATCTGGGAAGTCCCT
TCCACTGCTGTGTTCCAGAAGTGTTGGTAAACAGCCCACAAATGTCAACAGCAGAAACATACAAGCTGTCAGCTTT
GCACAAGGGCCCAACACCCTGCTCATCAAGAAGCACTGTGGTTGCTGTGTTAGTAATGTGCAAAACAGGAGGCACA
TTTTCCCCACCTGTGTAGGTTCCAAAATATCTAGTGTTTTCATTTTTACTTGGATCAGGAACCCAGCACTCCACTG
GATAAGCATTATCCTTATCCAAAACAGCCTTGTGGTCAGTGTTCATCTGCTGACTGTCAACTGTAGCATTTTTTGG
GGTTACAGTTTGAGCAGGATATTTGGTCCTGTAGTTTGCTAACACACCCTGCAGCTCCAAAGGTTCCCCACCAACA
GCAAAAAAATGAAAATTTGACCCTTGAATGGGTTTTCCAGCACCATTTTCATGAGTTTTTTGTGTCCCTGAATGCA
AGTTTAACATAGCAGTTACCCCAATAACCTCAGTTTTAACAGTAACAGCTTCCCACATCAAAATATTTCCACAGGT
TAAGTCCTCATTTAAATTAGGCAAAGGAATTCCACTTCCCACTGCCTTGCTTCCGTCTCCCATTCAAACTTTTATC
AACTGACATTATTCTAAGTAAAATCCTCTTCATTATGTTGTCAGCAATCCATTGCTTGAAGGCCTGGCTCCCCAGA
ACCCCTCGACTGGTATGTCTTCTCCTAGAATACTCCAGAAGAAAAGGAGTGTATGAAGATAGTGACTGCACATTAA
AATGACTGAAACCATAGTAAATTAGGATGAGATTCTGGGCAGATAAACAGACAGCTGGCTAGGATCATTTTTTTAT
GCCTTGGACTTCTTTGGCAATCTGTTGAAGCCTGACATTCCTCAGAATAATGTTTTAAAGCCCAACAATAAGACCC
TGTAGCACATATAATAAGTACTGCAGTTTTGAAGTAGTGATAAGCATAAATGATATTTTGATATATTTATTATAAC
TGTAATGAGATGTGTACATATCTGTGACTTCATAGGTACTGATTGTACTACTGTGATTTTTTTGCCTACTTTCAAA
ATGAAAAGGAATGCTTAATTTCAGTTAGAGGTTAGTAAAGACAAATAGGTAATTTTCTTCTCCAGTGAAGAGCATG
GCGCCCCTTGCTATTCATGGACGCTTGCTTAAAGACTTGTACACAGGCTTGCTTTGTATCAACCTATGACTTCCCC
TTACAGCCGATGATAGGTTTTTATTTGCACCTCCTTCGTGTACAAAGACAGTTTTGGTGGCTACGCCATCATTAAA
CTCATTATTATCATGCTTAAGCCTATAGATGTATCCAGTTCTTCTGTTACATAATTGAAGCTGTAGTGAATTGTCT
ATCTTAAACTGCATCGCTAACTGACTACATTTCACACTTCATTTGCTTCCAACATAGACTAACCTTCTTGGATGTC
CACTATTATTTGAACTTTTGAGATTTTTTTTCCTATTTCTAATATCTTAAAATTTCAGAAGACTTAAAGTTTTGCA
ACTACAGGGCTCCATATAGACATCTAGCTTGAATTTATACACTTTCTTTCATTGATGTCCCTGGACTAAAAAATGT
TAAATATTTCTAACCGCTGTACTTAAAGTCCATTACAAACGAAGACTACTGTTGTTAAGTTGAATAGGCATCTTAT
ATATTTTTCACCGGTGCAATAAATAACTTCTATTCCCTTCTAACATCTGCTTGCGTTGCACTGAGAGTACACTATT
GATTAGCAATAGGTTCGTGATTACAGCCCTTCTATAATTAATTGTTAGGTTAACATATTATTCATAAAATATTATT
TTATTAATTTTTACTTGATTTGCTACTGGATGCTTAGAAATAGCTATGAGTATATTGGTAGAACCAGTACTTATAT
TTTATTACATTTTTACATTTCATAAAATTTAAGTGATATAAAAATCCTGAGGAAGTATGCCACAAAAGTGGTCTCA
GTGGAAATTTAAATATGTTAACATTTATTTTTAAAATGTAGCGTGAAATAGACAACTTTAAAAGCTCAGCTTAAAA
AAAAAACTCAAGGAAGCTGAACTTGACTTTTTAAAGCACTGAAGTGCAATATTTAATGTAGGTCAACATGTTTAAA
TGGGAAAATTTTTTTCCTAATTACAGCCAAATCCCTAGCTGTAATTAACTTAAAATTTGTATACTATTTCACAACA
GAGTCAGCATATACCACTTTCTTATAAAATTAGAAAGATCTAAAATTTTAGAGCTTATTTGGTGAAACAGGCATAT
TGCTACATCTTTGTTTATAAATTATAATGTGCCTTTAGAGCCCAATAACAGATAACAAGATTTTGAAAATTCAGGT
GAATTAGAGTTATCAGAGGGAATGTTAATACACTCTATTCAAATACTATATGAGTAAGACATTTAAAATAGGAAAC
AATACTTTATATATTAAAAAAAATTAATCTTCCAGTCGATTTAATCCACTTTATGAATTCATTTAAATCGATTTAA
ATTCGAATTAATTAACTAGAGTACCCGGGGATCTTATTCCCTTTAACTAATAAAAAAAAATAATAAAGCATCACTT
ACTTAAAATCAGTTAGCAAATTTCTGTCCAGTTTATTCAGCAGCACCTCCTTGCCCTCCTCCCAGCTCTGGTATTG
CAGCTTCCTCCTGGCTGCAAACTTTCTCCACAATCTAAATGGAATGTCAGTTTCCTCCTGTTCCTGTCCATCCGCA
CCCACTATCTTCATGTTGTTGCAGATGAAGCGCGCAAGACCGTCTGAAGATACCTTCAACCCCGTGTATCCATATG
ACACGGAAACCGGTCCTCCAACTGTGCCTTTTCTTACTCCTCCCTTTGTATCCCCCAATGGGTTTCAAGAGAGTCC
CCCTGGGGTACTCTCTTTGCGCCTATCCGAACCTCTAGTTACCTCCAATGGCATGCTTGCGCTCAAAATGGGCAAC
GGCCTCTCTCTGGACGAGGCCGGCAACCTTACCTCCCAAAATGTAACCACTGTGAGCCCACCTCTCAAAAAAACCA
AGTCAAACATAAACCTGGAAATATCTGCACCCCTCACAGTTACCTCAGAAGCCCTAACTGTGGCTGCCGCCGCACC
TCTAATGGTCGCGGGCAACACACTCACCATGCAATCACAGGCCCCGCTAACCGTGCACGACTCCAAACTTAGCATT
GCCACCCAAGGACCCCTCACAGTGTCAGAAGGAAAGCTAGCCCTGCAAACATCAGGCCCCCTCACCACCACCGATA
GCAGTACCCTTACTATCACTGCCTCACCCCCTCTAACTACTGCCACTGGTAGCTTGGGCATTGACTTGAAAGAGCC
CATTTATACACAAAATGGAAAACTAGGACTAAAGTACGGGGCTCCTTTGCATGTAACAGACGACCTAAACACTTTG
ACCGTAGCAACTGGTCCAGGTGTGACTATTAATAATACTTCCTTGCAAACTAAAGTTACTGGAGCCTTGGGTTTTG
ATTCACAAGGCAATATGCAACTTAATGTAGCAGGAGGACTAAGGATTGATTCTCAAAACAGACGCCTTATACTTGA
TGTTAGTTATCCGTTTGATGCTCAAAACCAACTAAATCTAAGACTAGGACAGGGCCCTCTTTTTATAAACTCAGCC
CACAACTTGGATATTAACTACAACAAAGGCCTTTACTTGTTTACAGCTTCAAACAATTCCAAAAAGCTTGAGGTTA
ACCTAAGCACTGCCAAGGGGTTGATGTTTGACGCTACAGCCATAGCCATTAATGCAGGAGATGGGCTTGAATTTGG
TTCACCTAATGCACCAAACACAAATCCCCTCAAAACAAAAATTGGCCATGGCCTAGAATTTGATTCAAACAAGGCT
ATGGTTCCTAAACTAGGAACTGGCCTTAGTTTTGACAGCACAGGTGCCATTACAGTAGGAAACAAAAATAATGATA

FIGURE 8 (cont.)

AGCTAACTTTGTGGACCACACCAGCTCCATCTCCTAACTGTAGACTAAATGCAGAGAAAGATGCTAAACTCACTTT
GGTCTTAACAAAATGTGGCAGTCAAATACTTGCTACAGTTTCAGTTTTGGCTGTTAAAGGCAGTTTGGCTCCAATA
TCTGGAACAGTTCAAAGTGCTCATCTTATTATAAGATTTGACGAAAATGGAGTGCTACTAAACAATTCCTTCCTGG
ACCCAGAATATTGGAACTTTAGAAATGGAGATCTTACTGAAGGCACAGCCTATACAAACGCTGTTGGATTTATGCC
TAACCTATCAGCTTATCCAAAATCTCACGGTAAAACTGCCAAAAGTAACATTGTCAGTCAAGTTTACTTAAACGGA
GACAAAACTAAACCTGTAACACTAACCATTACACTAAACGGTACACAGGAAACAGGAGACACAACTCCAAGTGCAT
ACTCTATGTCATTTTCATGGGACTGGTCTGGCCACAACTACATTAATGAAATATTTGCCACATCCTCTTACACTTT
TTCATACATTGCCCAAGAATAAAGAATCGTTTGTGTTATGTTTCAACGTGTTTATTTTTCAATTGCAGAAAATTTC
AAGTCATTTTTCATTCAGTAGTATAGCCCCACCACCACATAGCTTATACAGATCACCGTACCTTAATCAAACTCAC
AGAACCCTAGTATTCAACCTGCCACCTCCCTCCCAACACACAGAGTACACAGTCCTTTCTCCCCGGCTGGCCTTAA
AAAGCATCATATCATGGGTAACAGACATATTCTTAGGTGTTATATTCCACACGGTTTCCTGTCGAGCCAAACGCTC
ATCAGTGATATTAATAAACTCCCCGGGCAGCTCACTTAAGTTCATGTCGCTGTCCAGCTGCTGAGCCACAGGCTGC
TGTCCAACTTGCGGTTGCTTAACGGGCGGCGAAGGAGAAGTCCACGCCTACATGGGGGTAGAGTCATAATCGTGCA
TCAGGATAGGGCGGTGGTGCTGCAGCAGCGCGCGAATAAACTGCTGCCGCCGCCGCTCCGTCCTGCAGGAATACAA
CATGGCAGTGGTCTCCTCAGCGATGATTCGCACCGCCCGCAGCATAAGGCGCCTTGTCCTCCGGGCACAGCAGCGC
ACCCTGATCTCACTTAAATCAGCACAGTAACTGCAGCACAGCACCACAATATTGTTCAAAATCCCACAGTGCAAGG
CGCTGTATCCAAAGCTCATGGCGGGGACCACAGAACCCACGTGGCCATCATACCACAAGCGCAGGTAGATTAAGTG
GCGACCCCTCATAAACACGCTGGACATAAACATTACCTCTTTTGGCATGTTGTAATTCACCACCTCCCGGTACCAT
ATAAACCTCTGATTAAACATGGCGCCATCCACCACCATCCTAAACCAGCTGGCCAAAACCTGCCCGCCGGCTATAC
ACTGCAGGGAACCGGGACTGGAACAATGACAGTGGAGAGCCCAGGACTCGTAACCATGGATCATCATGCTCGTCAT
GATATCAATGTTGGCACAACACAGGCACACGTGCATACACTTCCTCAGGATTACAAGCTCCTCCCGCGTTAGAACC
ATATCCCAGGGAACAACCCATTCCTGAATCAGCGTAAATCCCACACTGCAGGGAAGACCTCGCACGTAACTCACGT
TGTGCATTGTCAAAGTGTTACATTCGGGCAGCAGCGGATGATCCTCCAGTATGGTAGCGCGGGTTTCTGTCTCAAA
AGGAGGTAGACGATCCCTACTGTACGGAGTGCGCCGAGACAACCGAGATCGTGTTGGTCGTAGTGTCATGCCAAAT
GGAACGCCGGACGTAGTCATATTTCCTGAAGCAAAACCAGGTGCGGGCGTGACAAACAGATCTGCGTCTCCGGTCT
CGCCGCTTAGATCGCTCTGTGTAGTAGTTGTAGTATATCCACTCTCTCAAAGCATCCAGGCGCCCCCTGGCTTCGG
GTTCTATGTAAACTCCTTCATGCGCCGCTGCCCTGATAACATCCACCACCGCAGAATAAGCCACACCCAGCCAACC
TACACATTCGTTCTGCGAGTCACACACGGGAGGAGCGGGAAGAGCTGGAAGAACCATGTTTTTTTTTTATTCCAA
AAGATTATCCAAAACCTCAAAATGAAGATCTATTAAGTGAACGCGCTCCCCTCCGGTGGCGTGGTCAAACTCTACA
GCCAAAGAACAGATAATGGCATTTGTAAGATGTTGCACAATGGCTTCCAAAAGGCAAACGGCCCTCACGTCCAAGT
GGACGTAAAGGCTAAACCCTTCAGGGTGAATCTCCTCTATAAACATTCCAGCACCTTCAACCATGCCCAAATAATT
CTCATCTCGCCACCTTCTCAATATATCTCTAAGCAAATCCCGAATATTAAGTCCGGCCATTGTAAAAATCTGCTCC
AGAGCGCCCTCCACCTTCAGCCTCAAGCAGCGAATCATGATTGCAAAAATTCAGGTTCCTCACAGACCTGTATAAG
ATTCAAAAGCGGAACATTAACAAAAATACCGCGATCCCGTAGGTCCCTTCGCAGGGCCAGCTGAACATAATCGTGC
AGGTCTGCACGGACCAGCGCGGCCACTTCCCCGCCAGGAACCTTGACAAAAGAACCCACACTGATTATGACACGCA
TACTCGGAGCTATGCTAACCAGCGTAGCCCCGATGTAAGCTTTGTTGCATGGGCGGCGATATAAAATGCAAGGTGC
TGCTCAAAAAATCAGGCAAAGCCTCGCGCAAAAAAGAAAGCACATCGTAGTCATGCTCATGCAGATAAAGGCAGGT
AAGCTCCGGAACCACCACAGAAAAAGACACCATTTTTCTCTCAAACATGTCTGCGGGTTTCTGCATAAACACAAAA
TAAAATAACAAAAAAACATTTAAACATTAGAAGCCTGTCTTACAACAGGAAAAACAACCCTTATAAGCATAAGACG
GACTACGGCCATGCCGGCGTGACCGTAAAAAAACTGGTCACCGTGATTAAAAAGCACCACCGACAGCTCCTCGGTC
ATGTCCGGAGTCATAATGTAAGACTCGGTAAACACATCAGGTTGATTCATCGGTCAGTGCTAAAAAGCGACCGAAA
TAGCCCGGGGGAATACATACCCGCAGGCGTAGAGACAACATTACAGCCCCCATAGGAGGTATAACAAAATTAATAG
GAGAGAAAAACACATAAACACCTGAAAAACCCTCCTGCCTAGGCAAAATAGCACCCTCCCGCTCCAGAACAACATA
CAGCGCTTCACAGCGGCAGCCTAACAGTCAGCCTTACCAGTAAAAAAGAAAACCTATTAAAAAAACACCACTCGAC
ACGGCACCAGCTCAATCAGTCACAGTGTAAAAAAGGGCCAAGTGCAGAGCGAGTATATATAGGACTAAAAAATGAC
GTAACGGTTAAAGTCCACAAAAAACACCCAGAAAACCGCACGCGAACCTACGCCCAGAAACGAAAGCCAAAAAACC
CACAACTTCCTCAAATCGTCACTTCCGTTTTCCCACGTTACGTCACTTCCCATTTTAAGAAAACTACAATTCCCAA
CACATACAAGTTACTCCGCCCTAAAACCTACGTCACCCGCCCCGTTCCCACGCCCCGCGCCACGTCACAAACTCCA
CCCCCTCATTATCATATTGGCTTCAATCCAAAATAAGGTATATTATTGATGATG

FIGURE 9 (pBSX sequence, SEQ ID NO:12)

CTAAATTGTAAGCGTTAATATTTTGTTAAAATTCGCGTTAAATTTTTGTTAAATCAGCTCATTTTTTAACCAATAG
GCCGAAATCGGCAAAATCCCTTATAAATCAAAAGAATAGACCGAGATAGGGTTGAGTGTTGTTCCAGTTTGGAACA
AGAGTCCACTATTAAAGAACGTGGACTCCAACGTCAAAGGGCGAAAAACCGTCTATCAGGGCGATGGCCCACTACG
TGAACCATCACCCTAATCAAGTTTTTTGGGGTCGAGGTGCCGTAAAGCACTAAATCGGAACCCTAAAGGGAGCCCC
CGATTTAGAGCTTGACGGGGAAAGCCGGCGAACGTGGCGAGAAAGGAAGGGAAGAAAGCGAAAGGAGCGGGCGCTA
GGGCGCTGGCAAGTGTAGCGGTCACGCTGCGCGTAACCACCACACCCGCCGCGCTTAATGCGCCGCTACAGGGCGC
GTCCCATTCGCCATTCAGGCTGCGCAACTGTTGGGAAGGGCGATCGGTGCGGGCCTCTTCGCTATTACGCCAGCTG
GCGAAAGGGGGATGTGCTGCAAGGCGATTAAGTTGGGTAACGCCAGGGTTTTCCCAGTCACGACGTTGTAAAACGA
CGGCCAGTGAGCGCGCGTAATACGACTCACTATAGGGCGAATTGGAGCTTACGTATTAATTAAGGCGCCGCGGTGG
CGGCCGCTCTAGAACTAGTGGATCCCCCGGGCTGCAGGAATTCGGCCGCCTAGGCCACGCGTAAGCTTATCGATAC
CGTCGACCTCGAGGGGGGGCCCGGTACCCAGCTTTTGTTCCCTTTAGTGAGGGTTAATTGCGCGCTTGGCGTAATC
ATGGTCATAGCTGTTTCCTGTGTGAAATTGTTATCCGCTCACAATTCCACACAACATACGAGCCGGAAGCATAAAG
TGTAAAGCCTGGGGTGCCTAATGAGTGAGCTAACTCACATTAATTGCGTTGCGCTCACTGCCCGCTTTCCAGTCGG
GAAACCTGTCGTGCCAGCTGCATTAATGAATCGGCCAACGCGCGGGGAGAGGCGGTTTGCGTATTGGGCGCTCTTC
CGCTTCCTCGCTCACTGACTCGCTGCGCTCGGTCGTTCGGCTGCGGCGAGCGGTATCAGCTCACTCAAAGGCGGTA
ATACGGTTATCCACAGAATCAGGGGATAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCTGACGAGCATCACAAAAATCGACGCTCAAG
TCAGAGGTGGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCATAGCTCAC
GCTGTAGGTATCTCAGTTCGGTGTAGGTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGACACGACTTATCGCCACTGGCAGCAGCC
ACTGGTAACAGGATTAGCAGAGCGAGGTATGTAGGCGGTGCTACAGAGTTCTTGAAGTGGTGGCCTAACTACGGCT
ACACTAGAAGGACAGTATTTGGTATCTGCGCTCTGCTGAAGCCAGTTACCTTCGGAAAAAGAGTTGGTAGCTCTTG
ATCCGGCAAACAAACCACCGCTGGTAGCGGTGGTTTTTTTGTTTGCAAGCAGCAGATTACGCGCAGAAAAAAAGGA
TCTCAAGAAGATCCTTTGATCTTTTCTACGGGGTCTGACGCTCAGTGGAACGAAAACTCACGTTAAGGGATTTTGG
TCATGAGATTATCAAAAAGGATCTTCACCTAGATCCTTTTAAATTAAAAATGAAGTTTTAAATCAATCTAAAGTAT
ATATGAGTAAACTTGGTCTGACAGTTACCAATGCTTAATCAGTGAGGCACCTATCTCAGCGATCTGTCTATTTCGT
TCATCCATAGTTGCCTGACTCCCCGTCGTGTAGATAACTACGATACGGGAGGGCTTACCATCTGGCCCCAGTGCTG
CAATGATACCGCGAGACCCACGCTCACCGGCTCCAGATTTATCAGCAATAAACCAGCCAGCCGGAAGGGCCGAGCG
CAGAAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGGCTT
CATTCAGCTCCGGTTCCCAACGATCAAGGCGAGTTACATGATCCCCCATGTTGTGCAAAAAAGCGGTTAGCTCCTT
CGGTCCTCCGATCGTTGTCAGAAGTAAGTTGGCCGCAGTGTTATCACTCATGGTTATGGCAGCACTGCATAATTCT
CTTACTGTCATGCCATCCGTAAGATGCTTTTCTGTGACTGGTGAGTACTCAACCAAGTCATTCTGAGAATAGTGTA
TGCGGCGACCGAGTTGCTCTTGCCCGGCGTCAATACGGGATAATACCGCGCCACATAGCAGAACTTTAAAAGTGCT
CATCATTGGAAAACGTTCTTCGGGGCGAAAACTCTCAAGGATCTTACCGCTGTTGAGATCCAGTTCGATGTAACCC
ACTCGTGCACCCAACTGATCTTCAGCATCTTTTACTTTCACCAGCGTTTCTGGGTGAGCAAAAACAGGAAGGCAAA
ATGCCGCAAAAAAGGGAATAAGGGCGACACGGAAATGTTGAATACTCATACTCTTCCTTTTTCAATATTATTGAAG
CATTTATCAGGGTTATTGTCTCATGAGCGGATACATATTTGAATGTATTTAGAAAAATAAACAAATAGGGGTTCCG
CGCACATTTCCCCGAAAAGTGCCAC

FIGURE 11 ΔFseI.4 (SEQ ID NO:9)

CATCATCAATAATATACCTTATTTTGGATTGAAGCCAATATGATAATGAGGGGGTGGAGTTTGTGACGTGGCGCGG
GGCGTGGGAACGGGGCGGGTGACGTAGTAGTGTGGCGGAAGTGTGATGTTGCAAGTGTGGCGGAACACATGTATAA
CTTCGTATAATGTATGCTATACGAAGTTATACATGTAAGCGACGGATGTGGCAAAAGTGACGTTTTTGGTGTGCGC
CGGTGTACACAGGAAGTGACAATTTTCGCGCGGTTTTAGGCGGATGTTGTAGTAAATTTGGGCGTAACCGAGTAAG
ATTTGGCCATTTTCGCGGGAAAACTGAATAAGAGGAAGTGAAATCTGAATAATTTTGTGTTACTCATAGCGCGTAA
TATTTGTCTAGGGAGATCTATAACTTCGTATAATGTATGCTATACGAAGTTATTACCGAAGAAATGGCTCGAGATC
TGGAAGGTGCTGAGGTACGATGAGACCCGCACCAGGTGCAGACCCTGCGAGTGTGGCGGTAAACATATTAGGAACC
AGCCTGTGATGCTGGATGTGACCGAGGAGCTGAGGCCCGATCACTTGGTGCTGGCCTGCACCCGCGCTGAGTTTGG
CTCTAGCGATGAAGATACAGATTGAGGTACTGAAATGTGTGGGCGTGGCTTAAGGGTGGGAAAGAATATATAAGGT
GGGGGTCTTATGTAGTTTTGTATCTGTTTTGCAGCAGCCGCCGCCGCCATGAGCACCAACTCGTTTGATGGAAGCA
TTGTGAGCTCATATTTGACAACGCGCATGCCCCCATGGGCCGGGGTGCGTCAGAATGTGATGGGCTCCAGCATTGA
TGGTCGCCCCGTCCTGCCCGCAAACTCTACTACCTTGACCTACGAGACCGTGTCTGGAACGCCGTTGGAGACTGCA
GCCTCCGCCGCCGCTTCAGCCGCTGCAGCCACCGCCCGCGGGATTGTGACTGACTTTGCTTTCCTGAGCCCGCTTG
CAAGCAGTGCAGCTTCCCGTTCATCCGCCCGCGATGACAAGTTGACGGCTCTTTTGGCACAATTGGATTCTTTGAC
CCGGGAACTTAATGTCGTTTCTCAGCAGCTGTTGGATCTGCGCCAGCAGGTTTCTGCCCTGAAGGCTTCCTCCCCT
CCCAATGCGGTTTAAAACATAAATAAAAAACCAGACTCTGTTTGGATTTGGATCAAGCAAGTGTCTTGCTGTCTTT
ATTTAGGGGTTTTGCGCGCGCGGTAGGCCCGGGACCAGCGGTCTCGGTCGTTGAGGGTCCTGTGTATTTTTTCCAG
GACGTGGTAAAGGTGACTCTGGATGTTCAGATACATGGGCATAAGCCCGTCTCTGGGGTGGAGGTAGCACCACTGC
AGAGCTTCATGCTGCGGGGTGGTGTTGTAGATGATCCAGTCGTAGCAGGAGCGCTGGGCGTGGTGCCTAAAAATGT
CTTTCAGTAGCAAGCTGATTGCCAGGGGCAGGCCCTTGGTGTAAGTGTTTACAAAGCGGTTAAGCTGGGATGGGTG
CATACGTGGGGATATGAGATGCATCTTGGACTGTATTTTTAGGTTGGCTATGTTCCCAGCCATATCCCTCCGGGGA
TTCATGTTGTGCAGAACCACCAGCACAGTGTATCCGGTGCACTTGGGAAATTTGTCATGTAGCTTAGAAGGAAATG
CGTGGAAGAACTTGGAGACGCCCTTGTGACCTCCAAGATTTTCCATGCATTCGTCCATAATGATGGCAATGGGCCC
ACGGGCGGCGGCCTGGGCGAAGATATTTCTGGGATCACTAACGTCATAGTTGTGTTCCAGGATGAGATCGTCATAG
GCCATTTTTACAAAGCGCGGGCGGAGGGTGCCAGACTGCGGTATAATGGTTCCATCCGGCCCAGGGGCGTAGTTAC
CCTCACAGATTTGCATTTCCCACGCTTTGAGTTCAGATGGGGGGATCATGTCTACCTGCGGGGCGATGAAGAAAAC
GGTTTCCGGGGTAGGGGAGATCAGCTGGGAAGAAAGCAGGTTCCTGAGCAGCTGCGACTTACCGCAGCCGGTGGGC
CCGTAAATCACACCTATTACCGGGTGCAACTGGTAGTTAAGAGAGCTGCAGCTGCCGTCATCCCTGAGCAGGGGGG
CCACTTCGTTAAGCATGTCCCTGACTCGCATGTTTTCCCTGACCAAATCCGCCAGAAGGCGCTCGCCGCCCAGCGA
TAGCAGTTCTTGCAAGGAAGCAAAGTTTTTCAACGGTTTGAGACCGTCCGCCGTAGGCATGCTTTTGAGCGTTTGA
CCAAGCAGTTCCAGGCGGTCCCACAGCTCGGTCACCTGCTCTACGGCATCTCGATCCAGCATATCTCCTCGTTTCG
CGGGTTGGGGCGGCTTTCGCTGTACGGCAGTAGTCGGTGCTCGTCCAGACGGGCCAGGGTCATGTCTTTCCACGGG
CGCAGGGTCCTCGTCAGCGTAGTCTGGGTCACGGTGAAGGGGTGCGCTCCGGGCTGCGCGCTGGCCAGGGTGCGCT
TGAGGCTGGTCCTGCTGGTGCTGAAGCGCTGCCGGTCTTCGCCCTGCGCGTCGGCCAGGTAGCATTTGACCATGGT
GTCATAGTCCAGCCCCTCCGCGGCGTGGCCCTTGGCGCGCAGCTTGCCCTTGGAGGAGGCGCCGCACGAGGGGCAG
TGCAGACTTTTGAGGGCGTAGAGCTTGGGCGCGAGAAATACCGATTCCGGGGAGTAGGCATCCGCGCCGCAGGCCC
CGCAGACGGTCTCGCATTCCACGAGCCAGGTGAGCTCTGGCCGTTCGGGGTCAAAAACCAGGTTTCCCCCATGCTT
TTTGATGCGTTTCTTACCTCTGGTTTCCATGAGCCGGTGTCCACGCTCGGTGACGAAAAGGCTGTCCGTGTCCCCG
TATACAGACTTGAGAGGCCTGTCCTCGAGCGGTGTTCCGCGGTCCTCCTCGTATAGAAACTCGGACCACTCTGAGA
CAAAGGCTCGCGTCCAGGCCAGCACGAAGGAGGCTAAGTGGGAGGGGTAGCGGTCGTTGTCCACTAGGGGGTCCAC
TCGCTCCAGGGTGTGAAGACACATGTCGCCCTCTTCGGCATCAAGGAAGGTGATTGGTTTGTAGGTGTAGGCCACG
TGACCGGGTGTTCCTGAAGGGGGGCTATAAAAGGGGGTGGGGGCGCGTTCGTCCTCACTCTCTTCCGCATCGCTGT
CTGCGAGGGCCAGCTGTTGGGGTGAGTACTCCCTCTGAAAAGCGGGCATGACTTCTGCGCTAAGATTGTCAGTTTC
CAAAAACGAGGAGGATTTGATATTCACCTGGCCCGCGGTGATGCCTTTGAGGGTGGCCGCATCCATCTGGTCAGAA
AAGACAATCTTTTTGTTGTCAAGCTTGGTGGCAAACGACCCGTAGAGGGCGTTGGACAGCAACTTGGCGATGGAGC
GCAGGGTTTGGTTTTTGTCGCGATCGGCGCGCTCCTTGGCCGCGATGTTTAGCTGCACGTATTCGCGCGCAACGCA
CCGCCATTCGGGAAAGACGGTGGTGCGCTCGTCGGGCACCAGGTGCACGCGCCAACCGCGGTTGTGCAGGGTGACA
AGGTCAACGCTGGTGGCTACCTCTCCGCGTAGGCGCTCGTTGGTCCAGCAGAGGCGGCCGCCCTTGCGCGAGCAGA
ATGGCGGTAGGGGGTCTAGCTGCGTCTCGTCCGGGGGGTCTGCGTCCACGGTAAAGACCCCGGGCAGCAGGCGCGC
GTCGAAGTAGTCTATCTTGCATCCTTGCAAGTCTAGCGCCTGCTGCCATGCGCGGGCGGCAAGCGCGCGCTCGTAT
GGGTTGAGTGGGGGACCCCATGGCATGGGGTGGGTGAGCGCGGAGGCGTACATGCCGCAAATGTCGTAAACGTAGA
GGGGCTCTCTGAGTATTCCAAGATATGTAGGGTAGCATCTTCCACCGCGGATGCTGGCGCGCACGTAATCGTATAG
TTCGTGCGAGGGAGCGAGGAGGTCGGGACCGAGGTTGCTACGGGCGGGCTGCTCTGCTCGGAAGACTATCTGCCTG
AAGATGGCATGTGAGTTGGATGATATGGTTGGACGCTGGAAGACGTTGAAGCTGGCGTCTGTGAGACCTACCGCGT
CACGCACGAAGGAGGCGTAGGAGTCGCGCAGCTTGTTGACCAGCTCGGCGGTGACCTGCACGTCTAGGGCGCAGTA
GTCCAGGGTTTCCTTGATGATGTCATACTTATCCTGTCCCTTTTTTTTCCACAGCTCGCGGTTGAGGACAAACTCT
TCGCGGTCTTTCCAGTACTCTTGGATCGGAAACCCGTCGGCCTCCGAACGGTAAGAGCCTAGCATGTAGAACTGGT
TGACGGCCTGGTAGGCGCAGCATCCCTTTTCTACGGGTAGCGCGTATGCCTGCGCGGCCTTCCGGAGCGAGGTGTG
GGTGAGCGCAAAGGTGTCCCTGACCATGACTTTGAGGTACTGGTATTTGAAGTCAGTGTCGTCGCATCCGCCCTGC
TCCCAGAGCAAAAAGTCCGTGCGCTTTTTGGAACGCGGATTTGGCAGGGCGAAGGTGACATCGTTGAAGAGTATCT
TTCCCGCGCGAGGCATAAAGTTGCGTGTGATGCGGAAGGGTCCCGGCACCTCGGAACGGTTGTTAATTACCTGGGC

FIGURE 11 (cont.)

GGCGAGCACGATCTCGTCAAAGCCGTTGATGTTGTGGCCCACAATGTAAAGTTCCAAGAAGCGCGGGATGCCCTTG
ATGGAAGGCAATTTTTTAAGTTCCTCGTAGGTGAGCTCTTCAGGGGAGCTGAGCCCGTGCTCTGAAAGGGCCCAGT
CTGCAAGATGAGGGTTGGAAGCGACGAATGAGCTCCACAGGTCACGGGCCATTAGCATTTGCAGGTGGTCGCGAAA
GGTCCTAAACTGGCGACCTATGGCCATTTTTTCTGGGGTGATGCAGTAGAAGGTAAGCGGGTCTTGTTCCCAGCGG
TCCCATCCAAGGTTCGCGGCTAGGTCTCGCGCGGCAGTCACTAGAGGCTCATCTCCGCCGAACTTCATGACCAGCA
TGAAGGGCACGAGCTGCTTCCCAAAGGCCCCCATCCAAGTATAGGTCTCTACATCGTAGGTGACAAAGAGACGCTC
GGTGCGAGGATGCGAGCCGATCGGGAAGAACTGGATCTCCCGCCACCAATTGGAGGAGTGGCTATTGATGTGGTGA
AAGTAGAAGTCCCTGCGACGGGCCGAACACTCGTGCTGGCTTTTGTAAAAACGTGCGCAGTACTGGCAGCGGTGCA
CGGGCTGTACATCCTGCACGAGGTTGACCTGACGACCGCGCACAAGGAAGCAGAGTGGGAATTTGAGCCCCTCGCC
TGGCGGGTTTGGCTGGTGGTCTTCTACTTCGGCTGCTTGTCCTTGACCGTCTGGCTGCTCGAGGGGAGTTACGGTG
GATCGGACCACCACGCCGCGCGAGCCCAAAGTCCAGATGTCCGCGCGCGGCGGTCGGAGCTTGATGACAACATCGC
GCAGATGGGAGCTGTCCATGGTCTGGAGCTCCCGCGGCGTCAGGTCAGGCGGGAGCTCCTGCAGGTTTACCTCGCA
TAGACGGGTCAGGGCGCGGGCTAGATCCAGGTGATACCTAATTTCCAGGGGCTGGTTGGTGGCGGCGTCGATGGCT
TGCAAGAGGCCGCATCCCCGCGGCGCGACTACGGTACCGCGCGGCGGGCGGTGGGCCGCGGGGGTGTCCTTGGATG
ATGCATCTAAAAGCGGTGACGCGGGCGAGCCCCCGGAGGTAGGGGGGGCTCCGGACCCGCCGGGAGAGGGGGCAGG
GGCACGTCGGCGCCGCGCGCGGGCAGGAGCTGGTGCTGCGCGCGTAGGTTGCTGGCGAACGCGACGACGCGGCGGT
TGATCTCCTGAATCTGGCGCCTCTGCGTGAAGACGACGGGCCCGGTGAGCTTGAGCCTGAAAGAGAGTTCGACAGA
ATCAATTTCGGTGTCGTTGACGGCGGCCTGGCGCAAAATCTCCTGCACGTCTCCTGAGTTGTCTTGATAGGCGATC
TCGGCCATGAACTGCTCGATCTCTTCCTCCTGGAGATCTCCGCGTCCGGCTCGCTCCACGGTGGCGGCGAGGTCGT
TGGAAATGCGGGCCATGAGCTGCGAGAAGGCGTTGAGGCCTCCCTCGTTCCAGACGCGGCTGTAGACCACGCCCCC
TTCGGCATCGCGGGCGCGCATGACCACCTGCGCGAGATTGAGCTCCACGTGCCGGGCGAAGACGGCGTAGTTTCGC
AGGCGCTGAAAGAGGTAGTTGAGGGTGGTGGCGGTGTGTTCTGCCACGAAGAAGTACATAACCCAGCGTCGCAACG
TGGATTCGTTGATATCCCCCAAGGCCTCAAGGCGCTCCATGGCCTCGTAGAAGTCCACGGCGAAGTTGAAAAACTG
GGAGTTGCGCGCCGACACGGTTAACTCCTCCTCCAGAAGACGGATGAGCTCGGCGACAGTGTCGCGCACCTCGCGC
TCAAAGGCTACAGGGGCCTCTTCTTCTTCTTCAATCTCCTCTTCCATAAGGGCCTCCCCTTCTTCTTCTTCTGGCG
GCGGTGGGGGAGGGGGGACACGGCGGCGACGACGGCGCACCGGGAGGCGGTCGACAAAGCGCTCGATCATCTCCCC
GCGGCGACGGCGCATGGTCTCGGTGACGGCGCGGCCGTTCTCGCGGGGGCGCAGTTGGAAGACGCCGCCCGTCATG
TCCCGGTTATGGGTTGGCGGGGGGCTGCCATGCGGCAGGGATACGGCGCTAACGATGCATCTCAACAATTGTTGTG
TAGGTACTCCGCCGCCGAGGGACCTGAGCGAGTCCGCATCGACCGGATCGGAAAACCTCTCGAGAAAGGCGTCTAA
CCAGTCACAGTCGCAAGGTAGGCTGAGCACCGTGGCGGGCGGCAGCGGGCGGCGGTCGGGGTTGTTTCTGGCGGAG
GTGCTGCTGATGATGTAATTAAAGTAGGCGGTCTTGAGACGGCGGATGGTCGACAGAAGCACCATGTCCTTGGGTC
CGGCCTGCTGAATGCGCAGGCGGTCGGCCATGCCCCAGGCTTCGTTTTGACATCGGCGCAGGTCTTTGTAGTAGTC
TTGCATGAGCCTTTCTACCGGCACTTCTTCTTCTCCTTCCTCTTGTCCTGCATCTCTTGCATCTATCGCTGCGGCG
GCGGCGGAGTTTGGCCGTAGGTGGCGCCCTCTTCCTCCCATGCGTGTGACCCCGAAGCCCCTCATCGGCTGAAGCA
GGGCTAGGTCGGCGACAACGCGCTCGGCTAATATGGCCTGCTGCACCTGCGTGAGGGTAGACTGGAAGTCATCCAT
GTCCACAAAGCGGTGGTATGCGCCCGTGTTGATGGTGTAAGTGCAGTTGGCCATAACGGACCAGTTAACGGTCTGG
TGACCCGGCTGCGAGAGCTCGGTGTACCTGAGACGCGAGTAAGCCCTCGAGTCAAATACGTAGTCGTTGCAAGTCC
GCACCAGGTACTGGTATCCCACCAAAAAGTGCGGCGGCGGCTGGCGGTAGAGGGGCCAGCGTAGGGTGGCCGGGGC
TCCGGGGGCGAGATCTTCCAACATAAGGCGATGATATCCGTAGATGTACCTGGACATCCAGGTGATGCCGGCGGCG
GTGGTGGAGGCGCGCGGAAAGTCGCGGACGCGGTTCCAGATGTTGCGCAGCGGCAAAAAGTGCTCCATGGTCGGGA
CGCTCTGGCCGGTCAGGCGCGCGCAATCGTTGACGCTCTACCGTGCAAAAGGAGAGCCTGTAAGCGGGCACTCTTC
CGTGGTCTGGTGGATAAATTCGCAAGGGTATCATGGCGGACGACCGGGGTTCGAGCCCCGTATCCGGCCGTCCGCC
GTGATCCATGCGGTTACCGCCCGCGTGTCGAACCCAGGTGTGCGACGTCAGACAACGGGGGAGTGCTCCTTTTGGC
TTCCTTCCAGGCGCGGCGGCTGCTGCGCTAGCTTTTTTGGCCACTGGCCGCGCGCAGCGTAAGCGGTTAGGCTGGA
AAGCGAAAGCATTAAGTGGCTCGCTCCCTGTAGCCGGAGGGTTATTTTCCAAGGGTTGAGTCGCGGGACCCCCGGT
TCGAGTCTCGGACCGGCCGGACTGCGGCGAACGGGGGTTTGCCTCCCCGTCATGCAAGACCCCGCTTGCAAATTCC
TCCGGAAACAGGGACGAGCCCCTTTTTTGCTTTTCCCAGATGCATCCGGTGCTGCGGCAGATGCGCCCCCCTCCTC
AGCAGCGGCAAGAGCAAGAGCAGCGGCAGACATGCAGGGCACCCTCCCCTCCTCCTACCGCGTCAGGAGGGGCGAC
ATCCGCGGTTGACGCGGCAGCAGATGGTGATTACGAACCCCCGCGGCGCCGGGCCCGGCACTACCTGGACTTGGAG
GAGGGCGAGGGCCTGGCGCGGCTAGGAGCGCCCTCTCCTGAGCGGTACCCAAGGGTGCAGCTGAAGCGTGATACGC
GTGAGGCGTACGTGCCGCGGCAGAACCTGTTTCGCGACCGCGAGGGAGAGGAGCCCGAGGAGATGCGGGATCGAAA
GTTCCACGCAGGGCGCGAGCTGCGGCATGGCCTGAATCGCGAGCGGTTGCTGCGCGAGGAGGACTTTGAGCCCGAC
GCGCGAACCGGGATTAGTCCCGCGCGCGCACACGTGGCGGCCGCCGACCTGGTAACCGCATACGAGCAGACGGTGA
ACCAGGAGATTAACTTTCAAAAAAGCTTTAACAACCACGTGCGTACGCTTGTGGCGCGCGAGGAGGTGGCTATAGG
ACTGATGCATCTGTGGGACTTTGTAAGCGCGCTGGAGCAAAACCCAAATAGCAAGCCGCTCATGGCGCAGCTGTTC
CTTATAGTGCAGCACAGCAGGGACAACGAGGCATTCAGGGATGCGCTGCTAAACATAGTAGAGCCCGAGGGCCGCT
GGCTGCTCGATTTGATAAACATCCTGCAGAGCATAGTGGTGCAGGAGCGCAGCTTGAGCCTGGCTGACAAGGTGGC
CGCCATCAACTATTCCATGCTTAGCCTGGGCAAGTTTTACGCCCGCAAGATATACCATACCCCTTACGTTCCCATA
GACAAGGAGGTAAAGATCGAGGGGTTCTACATGCGCATGGCGCTGAAGGTGCTTACCTTGAGCGACGACCTGGGCG
TTTATCGCAACGAGCGCATCCACAAGGCCGTGAGCGTGAGCCGGCGGCGCGAGCTCAGCGACCGCGAGCTGATGCA
CAGCCTGCAAAGGGCCCTGGCTGGCACGGGCAGCGGCGATAGAGAGGCCGAGTCCTACTTTGACGCGGGCGCTGAC

FIGURE 11 (cont.)

CTGCGCTGGGCCCCAAGCCGACGCGCCCTGGAGGCAGCTGGGGCCGGACCTGGGCTGGCGGTGGCACCCGCGCGCG
CTGGCAACGTCGGCGGCGTGGAGGAATATGACGAGGACGATGAGTACGAGCCAGAGGACGGCGAGTACTAAGCGGT
GATGTTTCTGATCAGATGATGCAAGACGCAACGGACCCGGCGGTGCGGGCGGCGCTGCAGAGCCAGCCGTCCGGCC
TTAACTCCACGGACGACTGGCGCCAGGTCATGGACCGCATCATGTCGCTGACTGCGCGCAATCCTGACGCGTTCCG
GCAGCAGCCGCAGGCCAACCGGCTCTCCGCAATTCTGGAAGCGGTGGTCCCGGCGCGCGCAAACCCCACGCACGAG
AAGGTGCTGGCGATCGTAAACGCGCTGGCCGAAAACAGGGCCATCCGGCCCGACGAAGCCGGCCTGGTCTACGACG
CGCTGCTTCAGCGCGTGGCTCGTTACAACAGCGGCAACGTGCAGACCAACCTGGACCGGCTGGTGGGGGATGTGCG
CGAGGCCGTGGCGCAGCGTGAGCGCGCGCAGCAGCAGGGCAACCTGGGCTCCATGGTTGCACTAAACGCCTTCCTG
AGTACACAGCCCGCCAACGTGCCGCGGGGACAGGAGGACTACACCAACTTTGTGAGCGCACTGCGGCTAATGGTGA
CTGAGACACCGCAAAGTGAGGTGTACCAGTCTGGGCCAGACTATTTTTTCCAGACCAGTAGACAAGGCCTGCAGAC
CGTAAACCTGAGCCAGGCTTTCAAAAACTTGCAGGGGCTGTGGGGGGTGCGGGCTCCCACAGGCGACCGCGCGACC
GTGTCTAGCTTGCTGACGCCCAACTCGCGCCTGTTGCTGCTGCTAATAGCGCCCTTCACGGACAGTGGCAGCGTGT
CCCGGGACACATACCTAGGTCACTTGCTGACACTGTACCGCGAGGCCATAGGTCAGGCGCATGTGGACGAGCATAC
TTTCCAGGAGATTACAAGTGTCAGCCGCGCGCTGGGGCAGGAGGACACGGGCAGCCTGGAGGCAACCCTAAACTAC
CTGCTGACCAACCGGCGGCAGAAGATCCCCTCGTTGCACAGTTTAAACAGCGAGGAGGAGCGCATTTTGCGCTACG
TGCAGCAGAGCGTGAGCCTTAACCTGATGCGCGACGGGGTAACGCCCAGCGTGGCGCTGGACATGACCGCGCGCAA
CATGGAACCGGGCATGTATGCCTCAAACCGGCCGTTTATCAACCGCCTAATGGACTACTTGCATCGCGCGGCCGCC
GTGAACCCCGAGTATTTCACCAATGCCATCTTGAACCCGCACTGGCTACCGCCCCCTGGTTTCTACACCGGGGGAT
TCGAGGTGCCCGAGGGTAACGATGGATTCCTCTGGGACGACATAGACGACAGCGTGTTTTCCCCGCAACCGCAGAC
CCTGCTAGAGTTGCAACAGCGCGAGCAGGCAGAGGCGGCGCTGCGAAAGGAAAGCTTCCGCAGGCCAAGCAGCTTG
TCCGATCTAGGCGCTGCGGCCCCGCGGTCAGATGCTAGTAGCCCATTTCCAAGCTTGATAGGGTCTCTTACCAGCA
CTCGCACCACCCGCCCGCGCCTGCTGGGCGAGGAGGAGTACCTAAACAACTCGCTGCTGCAGCCGCAGCGCGAAAA
AAACCTGCCTCCGGCATTTCCCAACAACGGGATAGAGAGCCTAGTGGACAAGATGAGTAGATGGAAGACGTACGCG
CAGGAGCACAGGGACGTGCCAGGCCCGCGCCCGCCCACCCGTCGTCAAAGGCACGACCGTCAGCGGGGTCTGGTGT
GGGAGGACGATGACTCGGCAGACGACAGCAGCGTCCTGGATTTGGGAGGGAGTGGCAACCCGTTTGCGCACCTTCG
CCCCAGGCTGGGGAGAATGTTTTAAAAAAAAAAAAGCATGATGCAAAATAAAAAACTCACCAAGGCCATGGCACCG
AGCGTTGGTTTTCTTGTATTCCCCTTAGTATGCGGCGCGCGGCGATGTATGAGGAAGGTCCTCCTCCCTCCTACGA
GAGTGTGGTGAGCGCGGCGCCAGTGGCGGCGGCGCTGGGTTCTCCCTTCGATGCTCCCCTGGACCCGCCGTTTGTG
CCTCCGCGGTACCTGCGGCCTACCGGGGGGAGAAACAGCATCCGTTACTCTGAGTTGGCACCCCTATTCGACACCA
CCCGTGTGTACCTGGTGGACAACAAGTCAACGGATGTGGCATCCCTGAACTACCAGAACGACCACAGCAACTTTCT
GACCACGGTCATTCAAAACAATGACTACAGCCCGGGGGAGGCAAGCACACAGACCATCAATCTTGACGACCGGTCG
CACTGGGGCGGCGACCTGAAAACCATCCTGCATACCAACATGCCAAATGTGAACGAGTTCATGTTTACCAATAAGT
TTAAGGCGCGGGTGATGGTGTCGCGCTTGCCTACTAAGGACAATCAGGTGGAGCTGAAATACGAGTGGGTGGAGTT
CACGCTGCCCGAGGGCAACTACTCCGAGACCATGACCATAGACCTTATGAACAACGCGATCGTGGAGCACTACTTG
AAAGTGGGCAGACAGAACGGGGTTCTGGAAAGCGACATCGGGGTAAAGTTTGACACCCGCAACTTCAGACTGGGGT
TTGACCCCGTCACTGGTCTTGTCATGCCTGGGGTATATACAAACGAAGCCTTCCATCCAGACATCATTTTGCTGCC
AGGATGCGGGGTGGACTTCACCCACAGCCGCCTGAGCAACTTGTTGGGCATCCGCAAGCGGCAACCCTTCCAGGAG
GGCTTTAGGATCACCTACGATGATCTGGAGGGTGGTAACATTCCCGCACTGTTGGATGTGGACGCCTACCAGGCGA
GCTTGAAAGATGACACCGAACAGGGCGGGGGTGGCGCAGGCGGCAGCAACAGCAGTGGCAGCGGCGCGGAAGAGAA
CTCCAACGCGGCAGCCGCGGCAATGCAGCCGGTGGAGGACATGAACGATCATGCCATTCGCGGCGACACCTTTGCC
ACACGGGCTGAGGAGAAGCGCGCTGAGGCCGAAGCAGCGGCCGAAGCTGCCGCCCCCGCTGCGCAACCCGAGGTCG
AGAAGCCTCAGAAGAAACCGGTGATCAAACCCCTGACAGAGGACAGCAAGAAACGCAGTTACAACCTAATAAGCAA
TGACAGCACCTTCACCCAGTACCGCAGCTGGTACCTTGCATACAACTACGGCGACCCTCAGACCGGAATCCGCTCA
TGGACCCTGCTTTGCACTCCTGACGTAACCTGCGGCTCGGAGCAGGTCTACTGGTCGTTGCCAGACATGATGCAAG
ACCCCGTGACCTTCCGCTCCACGCGCCAGATCAGCAACTTTCCGGTGGTGGGCGCCGAGCTGTTGCCCGTGCACTC
CAAGAGCTTCTACAACGACCAGGCCGTCTACTCCCAACTCATCCGCCAGTTTACCTCTCTGACCCACGTGTTCAAT
CGCTTTCCCGAGAACCAGATTTTGGCGCGCCCGCCAGCCCCCACCATCACCACCGTCAGTGAAAACGTTCCTGCTC
TCACAGATCACGGGACGCTACCGCTGCGCAACAGCATCGGAGGAGTCCAGCGAGTGACCATTACTGACGCCAGACG
CCGCACCTGCCCCTACGTTTACAAGGCCCTGGGCATAGTCTCGCCGCGCGTCCTATCGAGCCGCACTTTTTGAGCA
AGCATGTCCATCCTTATATCGCCCAGCAATAACACAGGCTGGGGCCTGCGCTTCCCAAGCAAGATGTTTGGCGGGG
CCAAGAAGCGCTCCGACCAACACCCAGTGCGCGTGCGCGGGCACTACCGCGCGCCCTGGGGCGCGCACAAACGCGG
CCGCACTGGGCGCACCACCGTCGATGACGCCATCGACGCGGTGGTGGAGGAGGCGCGCAACTACACGCCCACGCCG
CCACCAGTGTCCACAGTGGACGCGGCCATTCAGACCGTGGTGCGCGGAGCCCGGCGCTATGCTAAAATGAAGAGAC
GGCGGAGGCGCGTAGCACGTCGCCACCGCCGCCGACCCGGCACTGCCGCCCAACGCGCGGCGGCGGCCCTGCTTAA
CCGCGCACGTCGCACCGGCCGACGGGCGGCCATGCGGGCCGCTCGAAGGCTGGCCGCGGGTATTGTCACTGTGCCC
CCCAGGTCCAGGCGACGAGCGGCCGCCGCAGCAGCCGCGGCCATTAGTGCTATGACTCAGGGTCGCAGGGGCAACG
TGTATTGGGTGCGCGACTCGGTTAGCGGCCTGCGCGTGCCCGTGCGCACCCGCCCCCCGCGCAACTAGATTGCAAG
AAAAAACTACTTAGACTCGTACTGTTGTATGTATCCAGCGGCGGCGGCGCGCAACGAAGCTATGTCCAAGCGCAAA
ATCAAAGAAGAGATGCTCCAGGTCATCGCGCCGGAGATCTATGGCCCCCCGAAGAAGGAAGAGCAGGATTACAAGC
CCCGAAAGCTAAAGCGGGTCAAAAAGAAAAAGAAAGATGATGATGATGAACTTGACGACGAGGTGGAACTGCTGCA
CGCTACCGCGCCCAGGCGACGGGTACAGTGGAAAGGTCGACGCGTAAAACGTGTTTTGCGACCCGGCACCACCGTA

FIGURE 11 (cont.)

GTCTTTACGCCCGGTGAGCGCTCCACCCGCACCTACAAGCGCGTGTATGATGAGGTGTACGGCGACGAGGACCTGC
TTGAGCAGGCCAACGAGCGCCTCGGGGAGTTTGCCTACGGAAAGCGGCATAAGGACATGCTGGCGTTGCCGCTGGA
CGAGGGCAACCCAACACCTAGCCTAAAGCCCGTAACACTGCAGCAGGTGCTGCCCGCGCTTGCACCGTCCGAAGAA
AAGCGCGGCCTAAAGCGCGAGTCTGGTGACTTGGCACCCACCGTGCAGCTGATGGTACCCAAGCGCCAGCGACTGG
AAGATGTCTTGGAAAAAATGACCGTGGAACCTGGGCTGGAGCCCGAGGTCCGCGTGCGGCCAATCAAGCAGGTGGC
GCCGGGACTGGGCGTGCAGACCGTGGACGTTCAGATACCCACTACCAGTAGCACCAGTATTGCCACCGCCACAGAG
GGCATGGAGACACAAACGTCCCCGGTTGCCTCAGCGGTGGCGGATGCCGCGGTGCAGGCGGTCGCTGCGGCCGCGT
CCAAGACCTCTACGGAGGTGCAAACGGACCCGTGGATGTTTCGCGTTTCAGCCCCCCGGCGCCCGCGCGGTTCGAG
GAAGTACGGCGCCGCCAGCGCGCTACTGCCCGAATATGCCCTACATCCTTCCATTGCGCCTACCCCCGGCTATCGT
GGCTACACCTACCGCCCCAGAAGACGAGCAACTACCCGACGCCGAACCACCACTGGAACCCGCCGCCGCCGTCGCC
GTCGCCAGCCCGTGCTGGCCCCGATTTCCGTGCGCAGGGTGGCTCGCGAAGGAGGCAGGACCCTGGTGCTGCCAAC
AGCGCGCTACCACCCCAGCATCGTTTAAAAGCCGGTCTTTGTGGTTCTTGCAGATATGGCCCTCACCTGCCGCCTC
CGTTTCCCGGTGCCGGGATTCCGAGGAAGAATGCACCGTAGGAGGGGCATGGCCGGCTACGGCCTGACGGGCGGCA
TGCGTCGTGCGCACCACCGGCGGCGGCGCGCGTCGCACCGTCGCATGCGCGGCGGTATCCTGCCCCTCCTTATTCC
ACTGATCGCCGCGGCGATTGGCGCCGTGCCCGGAATTGCATCCGTGGCCTTGCAGGCGCAGAGACACTGATTAAAA
ACAAGTTGCATGTGGAAAAATCAAAATAAAAAGTCTGGACTCTCACGCTCGCTTGGTCCTGTAACTATTTTGTAGA
ATGGAAGACATCAACTTTGCGTCTCTGGCCCCGCGACACGGCTCGCGCCCGTTCATGGGAAACTGGCAAGATATCG
GCACCAGCAATATGAGCGGTGGCGCCTTCAGCTGGGGCTCGCTGTGGAGCGGCATTAAAAATTTCGGTTCCACCGT
TAAGAACTATGGCAGCAAGGCCTGGAACAGCAGCACAGGCCAGATGCTGAGGGATAAGTTGAAAGAGCAAAATTTC
CAACAAAAGGTGGTAGATGGCCTGGCCTCTGGCATTAGCGGGGTGGTGGACCTGGCCAACCAGGCAGTGCAAAATA
AGATTAACAGTAAGCTTGATCCCCGCCCTCCCGTAGAGGAGCCTCCACCGGCCGTGGAGACAGTGTCTCCAGAGGG
GCGTGGCGAAAAGCGTCCGCGCCCCGACAGGGAAGAAACTCTGGTGACGCAAATAGACGAGCCTCCCTCGTACGAG
GAGGCACTAAAGCAAGGCCTGCCCACCACCCGTCCCATCGCGCCCATGGCTACCGGAGTGCTGGGCCAGCACACAC
CCGTAACGCTGGACCTGCCTCCCCCCGCCGACACCCAGCAGAAACCTGTGCTGCCAGGCCCGACCGCCGTTGTTGT
AACCCGTCCTAGCCGCGCGTCCCTGCGCCGCGCCGCCAGCGGTCCGCGATCGTTGCGGCCCGTAGCCAGTGGCAAC
TGGCAAAGCACACTGAACAGCATCGTGGGTCTGGGGGTGCAATCCCTGAAGCGCCGACGATGCTTCTGAATAGCTA
ACGTGTCGTATGTGTGTCATGTATGCGTCCATGTCGCCGCCAGAGGAGCTGCTGAGCCGCCGCGCGCCCGCTTTCC
AAGATGGCTACCCCTTCGATGATGCCGCAGTGGTCTTACATGCACATCTCGGGCCAGGACGCCTCGGAGTACCTGA
GCCCCGGGCTGGTGCAGTTTGCCCGCGCCACCGAGACGTACTTCAGCCTGAATAACAAGTTTAGAAACCCCACGGT
GGCGCCTACGCACGACGTGACCACAGACCGGTCCCAGCGTTTGACGCTGCGGTTCATCCCTGTGGACCGTGAGGAT
ACTGCGTACTCGTACAAGGCGCGGTTCACCCTAGCTGTGGGTGATAACCGTGTGCTGGACATGGCTTCCACGTACT
TTGACATCCGCGGCGTGCTGGACAGGGGCCCTACTTTTAAGCCCTACTCTGGCACTGCCTACAACGCCCTGGCTCC
CAAGGGTGCCCCAAATCCTTGCGAATGGGATGAAGCTGCTACTGCTCTTGAAATAAACCTAGAAGAAGAGGACGAT
GACAACGAAGACGAAGTAGACGAGCAAGCTGAGCAGCAAAAAACTCACGTATTTGGGCAGGCGCCTTATTCTGGTA
TAAATATTACAAAGGAGGGTATTCAAATAGGTGTCGAAGGTCAAACACCTAAATATGCCGATAAAACATTTCAACC
TGAACCTCAAATAGGAGAATCTCAGTGGTACGAAACTGAAATTAATCATGCAGCTGGGAGAGTCCTTAAAAAGACT
ACCCCAATGAAACCATGTTACGGTTCATATGCAAAACCCACAAATGAAAATGGAGGGCAAGGCATTCTTGTAAAGC
AACAAAATGGAAAGCTAGAAAGTCAAGTGGAAATGCAATTTTTCTCAACTACTGAGGCGACCGCAGGCAATGGTGA
TAACTTGACTCCTAAAGTGGTATTGTACAGTGAAGATGTAGATATAGAAACCCCAGACACTCATATTTCTTACATG
CCCACTATTAAGGAAGGTAACTCACGAGAACTAATGGGCCAACAATCTATGCCCAACAGGCCTAATTACATTGCTT
TTAGGGACAATTTTATTGGTCTAATGTATTACAACAGCACGGGTAATATGGGTGTTCTGGCGGGCCAAGCATCGCA
GTTGAATGCTGTTGTAGATTTGCAAGACAGAAACACAGAGCTTTCATACCAGCTTTTGCTTGATTCCATTGGTGAT
AGAACCAGGTACTTTTCTATGTGGAATCAGGCTGTTGACAGCTATGATCCAGATGTTAGAATTATTGAAAATCATG
GAACTGAAGATGAACTTCCAAATTACTGCTTTCCACTGGGAGGTGTGATTAATACAGAGACTCTTACCAAGGTAAA
ACCTAAAACAGGTCAGGAAAATGGATGGGAAAAAGATGCTACAGAATTTTCAGATAAAAATGAAATAAGAGTTGGA
AATAATTTTGCCATGGAAATCAATCTAAATGCCAACCTGTGGAGAAATTTCCTGTACTCCAACATAGCGCTGTATT
TGCCCGACAAGCTAAAGTACAGTCCTTCCAACGTAAAAATTTCTGATAACCCAAACACCTACGACTACATGAACAA
GCGAGTGGTGGCTCCCGGGTTAGTGGACTGCTACATTAACCTTGGAGCACGCTGGTCCCTTGACTATATGGACAAC
GTCAACCCATTTAACCACCACCGCAATGCTGGCCTGCGCTACCGCTCAATGTTGCTGGGCAATGGTCGCTATGTGC
CCTTCCACATCCAGGTGCCTCAGAAGTTCTTTGCCATTAAAAACCTCCTTCTCCTGCCGGGCTCATACACCTACGA
GTGGAACTTCAGGAAGGATGTTAACATGGTTCTGCAGAGCTCCCTAGGAAATGACCTAAGGGTTGACGGAGCCAGC
ATTAAGTTTGATAGCATTTGCCTTTACGCCACCTTCTTCCCCATGGCCCACAACACCGCCTCCACGCTTGAGGCCA
TGCTTAGAAACGACACCAACGACCAGTCCTTTAACGACTATCTCTCCGCCGCCAACATGCTCTACCCTATACCCGC
CAACGCTACCAACGTGCCCATATCCATCCCCTCCCGCAACTGGGCGGCTTTCCGCGGCTGGGCCTTCACGCGCCTT
AAGACTAAGGAAACCCCATCACTGGGCTCGGGCTACGACCCTTATTACACCTACTCTGGCTCTATACCCTACCTAG
ATGGAACCTTTTACCTCAACCACACCTTTAAGAAGGTGGCCATTACCTTTGACTCTTCTGTCAGCTGGCCTGGCAA
TGACCGCCTGCTTACCCCCAACGAGTTTGAAATTAAGCGCTCAGTTGACGGGGAGGGTTACAACGTTGCCCAGTGT
AACATGACCAAAGACTGGTTCCTGGTACAAATGCTAGCTAACTACAACATTGGCTACCAGGGCTTCTATATCCCAG
AGAGCTACAAGGACCGCATGTACTCCTTCTTTAGAAACTTCCAGCCCATGAGCCGTCAGGTGGTGGATGATACTAA
ATACAAGGACTACCAACAGGTGGGCATCCTACACCAACACAACAACTCTGGATTTGTTGGCTACCTTGCCCCCACC
ATGCGCGAAGGACAGGCCTACCCTGCTAACTTCCCCTATCCGCTTATAGGCAAGACCGCAGTTGACAGCATTACCC

FIGURE 11 (cont.)

AGAAAAAGTTTCTTTGCGATCGCACCCTTTGGCGCATCCCATTCTCCAGTAACTTTATGTCCATGGGCGCACTCAC
AGACCTGGGCCAAAACCTTCTCTACGCCAACTCCGCCCACGCGCTAGACATGACTTTTGAGGTGGATCCCATGGAC
GAGCCCACCCTTCTTTATGTTTTGTTTGAAGTCTTTGACGTGGTCCGTGTGCACCGGCCGCACCGCGGCGTCATCG
AAACCGTGTACCTGCGCACGCCCTTCTCGGCCGGCAACGCCACAACATAAAGAAGCAAGCAACATCAACAACAGCT
GCCGCCATGGGCTCCAGTGAGCAGGAACTGAAAGCCATTGTCAAAGATCTTGGTTGTGGGCCATATTTTTTGGGCA
CCTATGACAAGCGCTTTCCAGGCTTTGTTTCTCCACACAAGCTCGCCTGCGCCATAGTCAATACGGCCGGTCGCGA
GACTGGGGGCGTACACTGGATGGCCTTTGCCTGGAACCCGCACTCAAAAACATGCTACCTCTTTGAGCCCTTTGGC
TTTTCTGACCAGCGACTCAAGCAGGTTTACCAGTTTGAGTACGAGTCACTCCTGCGCCGTAGCGCCATTGCTTCTT
CCCCCGACCGCTGTATAACGCTGGAAAAGTCCACCCAAAGCGTACAGGGGCCCAACTCGGCCGCCTGTGGACTATT
CTGCTGCATGTTTCTCCACGCCTTTGCCAACTGGCCCCAAACTCCCATGGATCACAACCCCACCATGAACCTTATT
ACCGGGGTACCCAACTCCATGCTCAACAGTCCCCAGGTACAGCCCACCCTGCGTCGCAACCAGGAACAGCTCTACA
GCTTCCTGGAGCGCCACTCGCCCTACTTCCGCAGCCACAGTGCGCAGATTAGGAGCGCCACTTCTTTTTGTCACTT
GAAAAACATGTAAAAATAATGTACTAGAGACACTTTCAATAAAGGCAAATGCTTTTATTTGTACACTCTCGGGTGA
TTATTTACCCCCACCCTTGCCGTCTGCGCCGTTTAAAAATCAAAGGGGTTCTGCCGCGCATCGCTATGCGCCACTG
GCAGGGACACGTTGCGATACTGGTGTTTAGTGCTCCACTTAAACTCAGGCACAACCATCCGCGGCAGCTCGGTGAA
GTTTTCACTCCACAGGCTGCGCACCATCACCAACGCGTTTAGCAGGTCGGGCGCCGATATCTTGAAGTCGCAGTTG
GGGCCTCCGCCCTGCGCGCGCGAGTTGCGATACACAGGGTTGCAGCACTGGAACACTATCAGCGCCGGGTGGTGCA
CGCTGGCCAGCACGCTCTTGTCGGAGATCAGATCCGCGTCCAGGTCCTCCGCGTTGCTCAGGGCGAACGGAGTCAA
CTTTGGTAGCTGCCTTCCCAAAAAGGGCGCGTGCCCAGGCTTTGAGTTGCACTCGCACCGTAGTGGCATCAAAAGG
TGACCGTGCCCGGTCTGGGCGTTAGGATACAGCGCCTGCATAAAAGCCTTGATCTGCTTAAAAGCCACCTGAGCCT
TTGCGCCTTCAGAGAAGAACATGCCGCAAGACTTGCCGGAAAACTGATTGGCCGGACAGGCCGCGTCGTGCACGCA
GCACCTTGCGTCGGTGTTGGAGATCTGCACCACATTTCGGCCCCACCGGTTCTTCACGATCTTGGCCTTGCTAGAC
TGCTCCTTCAGCGCGCGCTGCCCGTTTTCGCTCGTCACATCCATTTCAATCACGTGCTCCTTATTTATCATAATGC
TTCCGTGTAGACACTTAAGCTCGCCTTCGATCTCAGCGCAGCGGTGCAGCCACAACGCGCAGCCCGTGGGCTCGTG
ATGCTTGTAGGTCACCTCTGCAAACGACTGCAGGTACGCCTGCAGGAATCGCCCCATCATCGTCACAAAGGTCTTG
TTGCTGGTGAAGGTCAGCTGCAACCCGCGGTGCTCCTCGTTCAGCCAGGTCTTGCATACGGCCGCCAGAGCTTCCA
CTTGGTCAGGCAGTAGTTTGAAGTTCGCCTTTAGATCGTTATCCACGTGGTACTTGTCCATCAGCGCGCGCGCAGC
CTCCATGCCCTTCTCCCACGCAGACACGATCGGCACACTCAGCGGGTTCATCACCGTAATTTCACTTTCCGCTTCG
CTGGGCTCTTCCTCTTCCTCTTGCGTCCGCATACCACGCGCCACTGGGTCGTCTTCATTCAGCCGCCGCACTGTGC
GCTTACCTCCTTTGCCATGCTTGATTAGCACCGGTGGGTTGCTGAAACCCACCATTTGTAGCGCCACATCTTCTCT
TTCTTCCTCGCTGTCCACGATTACCTCTGGTGATGGCGGGCGCTCGGGCTTGGGAGAAGGGCGCTTCTTTTTCTTC
TTGGGCGCAATGGCCAAATCCGCCGCCGAGGTCGATGGCCGCGGGCTGGGTGTGCGCGGCACCAGCGCGTCTTGTG
ATGAGTCTTCCTCGTCCTCGGACTCGATACGCCGCCTCATCCGCTTTTTTGGGGGCGCCCGGGGAGGCGGCGGCGA
CGGGGACGGGGACGACACGTCCTCCATGGTTGGGGGACGTCGCGCCGCACCGCGTCCGCGCTCGGGGGTGGTTTCG
CGCTGCTCCTCTTCCCGACTGGCCATTTCCTTCTCCTATAGGCAGAAAAAGATCATGGAGTCAGTCGAGAAGAAGG
ACAGCCTAACCGCCCCCTCTGAGTTCGCCACCACCGCCTCCACCGATGCCGCCAACGCGCCTACCACCTTCCCCGT
CGAGGCACCCCCGCTTGAGGAGGAGGAAGTGATTATCGAGCAGGACCCAGGTTTTGTAAGCGAAGACGACGAGGAC
CGCTCAGTACCAACAGAGGATAAAAAGCAAGACCAGGACAACGCAGAGGCAAACGAGGAACAAGTCGGGCGGGGGG
ACGAAAGGCATGGCGACTACCTAGATGTGGGAGACGACGTGCTGTTGAAGCATCTGCAGCGCCAGTGCGCCATTAT
CTGCGACGCGTTGCAAGAGCGCAGCGATGTGCCCCTCGCCATAGCGGATGTCAGCCTTGCCTACGAACGCCACCTA
TTCTCACCGCGCGTACCCCCCAAACGCCAAGAAAACGGCACATGCGAGCCCAACCCGCGCCTCAACTTCTACCCCG
TATTTGCCGTGCCAGAGGTGCTTGCCACCTATCACATCTTTTTCCAAAACTGCAAGATACCCCTATCCTGCCGTGC
CAACCGCAGCCGAGCGGACAAGCAGCTGGCCTTGCGGCAGGGCGCTGTCATACCTGATATCGCCTCGCTCAACGAA
GTGCCAAAAATCTTTGAGGGTCTTGGACGCGACGAGAAGCGCGCGGCAAACGCTCTGCAACAGGAAAACAGCGAAA
ATGAAAGTCACTCTGGAGTGTTGGTGGAACTCGAGGGTGACAACGCGCGCCTAGCCGTACTAAAACGCAGCATCGA
GGTCACCCACTTTGCCTACCCGGCACTTAACCTACCCCCCAAGGTCATGAGCACAGTCATGAGTGAGCTGATCGTG
CGCCGTGCGCAGCCCCTGGAGAGGGATGCAAATTTGCAAGAACAAACAGAGGAGGGCCTACCCGCAGTTGGCGACG
AGCAGCTAGCGCGCTGGCTTCAAACGCGCGAGCCTGCCGACTTGGAGGAGCGACGCAAACTAATGATGGCCGCAGT
GCTCGTTACCGTGGAGCTTGAGTGCATGCAGCGGTTCTTTGCTGACCCGGAGATGCAGCGCAAGCTAGAGGAAACA
TTGCACTACACCTTTCGACAGGGCTACGTACGCCAGGCCTGCAAGATCTCCAACGTGGAGCTCTGCAACCTGGTCT
CCTACCTTGGAATTTTGCACGAAAACCGCCTTGGGCAAAACGTGCTTCATTCCACGCTCAAGGGCGAGGCGCGCCG
CGACTACGTCCGCGACTGCGTTTACTTATTTCTATGCTACACCTGGCAGACGGCCATGGGCGTTTGGCAGCAGTGC
TTGGAGGAGTGCAACCTCAAGGAGCTGCAGAAACTGCTAAAGCAAAACTTGAAGGACCTATGGACGGCCTTCAACG
AGCGCTCCGTGGCCGCGCACCTGGCGGACATCATTTTCCCCGAACGCCTGCTTAAAACCCTGCAACAGGGTCTGCC
AGACTTCACCAGTCAAAGCATGTTGCAGAACTTTAGGAACTTTATCCTAGAGCGCTCAGGAATCTTGCCCGCCACC
TGCTGTGCACTTCCTAGCGACTTTGTGCCCATTAAGTACCGCGAATGCCCTCCGCCGCTTTGGGGCCACTGCTACC
TTCTGCAGCTAGCCAACTACCTTGCCTACCACTCTGACATAATGGAAGACGTGAGCGGTGACGGTCTACTGGAGTG
TCACTGTCGCTGCAACCTATGCACCCCGCACCGCTCCCTGGTTTGCAATTCGCAGCTGCTTAACGAAAGTCAAATT
ATCGGTACCTTTGAGCTGCAGGGTCCCTCGCCTGACGAAAAGTCCGCGGCTCCGGGGTTGAAACTCACTCCGGGGC
TGTGGACGTCGGCTTACCTTCGCAAATTTGTACCTGAGGACTACCACGCCCACGAGATTAGGTTCTACGAAGACCA
ATCCCGCCCGCCAAATGCGGAGCTTACCGCCTGCGTCATTACCCAGGGCCACATTCTTGGCCAATTGCAAGCCATC

FIGURE 11 (cont.)

AACAAAGCCCGCCAAGAGTTTCTGCTACGAAAGGGACGGGGGGTTTACTTGGACCCCCAGTCCGGCGAGGAGCTCA
ACCCAATCCCCCCGCCGCCGCAGCCCTATCAGCAGCAGCCGCGGGCCCTTGCTTCCCAGGATGGCACCCAAAAAGA
AGCTGCAGCTGCCGCCGCCACCCACGGACGAGGAGGAATACTGGGACAGTCAGGCAGAGGAGGTTTTGGACGAGGA
GGAGGAGGACATGATGGAAGACTGGGAGAGCCTAGACGAGGAAGCTTCCGAGGTCGAAGAGGTGTCAGACGAAACA
CCGTCACCCTCGGTCGCATTCCCCTCGCCGGCGCCCCAGAAATCGGCAACCGGTTCCAGCATGGCTACAACCTCCG
CTCCTCAGGCGCCGCCGGCACTGCCCGTTCGCCGACCCAACCGTAGATGGGACACCACTGGAACCAGGGCCGGTAA
GTCCAAGCAGCCGCCGCCGTTAGCCCAAGAGCAACAACAGCGCCAAGGCTACCGCTCATGGCGCGGGCACAAGAAC
GCCATAGTTGCTTGCTTGCAAGACTGTGGGGGCAACATCTCCTTCGCCCGCCGCTTTCTTCTCTACCATCACGGCG
TGGCCTTCCCCCGTAACATCCTGCATTACTACCGTCATCTCTACAGCCCATACTGCACCGGCGGCAGCGGCAGCGG
CAGCAACAGCAGCGGCCACACAGAAGCAAAGGCGACCGGATAGCAAGACTCTGACAAAGCCCAAGAAATCCACAGC
GGCGGCAGCAGCAGGAGGAGGAGCGCTGCGTCTGGCGCCCAACGAACCCGTATCGACCCGCGAGCTTAGAAACAGG
ATTTTTCCCACTCTGTATGCTATATTTCAACAGAGCAGGGGCCAAGAACAAGAGCTGAAAATAAAAAACAGGTCTC
TGCGATCCCTCACCCGCAGCTGCCTGTATCACAAAAGCGAAGATCAGCTTCGGCGCACGCTGGAAGACGCGGAGGC
TCTCTTCAGTAAATACTGCGCGCTGACTCTTAAGGACTAGTTTCGCGCCCTTTCTCAAATTTAAGCGCGAAAACTA
CGTCATCTCCAGCGGCCACACCCGGCGCCAGCACCTGTCGTCAGCGCCATTATGAGCAAGGAAATTCCCACGCCCT
ACATGTGGAGTTACCAGCCACAAATGGGACTTGCGGCTGGAGCTGCCCAAGACTACTCAACCCGAATAAACTACAT
GAGCGCGGGACCCCACATGATATCCCGGGTCAACGGAATCCGCGCCCACCGAAACCGAATTCTCTTGGAACAGGCG
GCTATTACCACCACACCTCGTAATAACCTTAATCCCCGTAGTTGGCCCGCTGCCCTGGTGTACCAGGAAAGTCCCG
CTCCCACCACTGTGGTACTTCCCAGAGACGCCCAGGCCGAAGTTCAGATGACTAACTCAGGGGCGCAGCTTGCGGG
CGGCTTTCGTCACAGGGTGCGGTCGCCCGGGCAGGGTATAACTCACCTGACAATCAGAGGGCGAGGTATTCAGCTC
AACGACGAGTCGGTGAGCTCCTCGCTTGGTCTCCGTCCGGACGGGACATTTCAGATCGGCGGCGCCGGCCGTCCTT
CATTCACGCCTCGTCAGGCAATCCTAACTCTGCAGACCTCGTCCTCTGAGCCGCGCTCTGGAGGCATTGGAACTCT
GCAATTTATTGAGGAGTTTGTGCCATCGGTCTACTTTAACCCCTTCTCGGGACCTCCCGGCCACTATCCGGATCAA
TTTATTCCTAACTTTGACGCGGTAAAGGACTCGGCGGACGGCTACGACTGAATGTTAAGTGGAGAGGCAGAGCAAC
TGCGCCTGAAACACCTGGTCCACTGTCGCCGCCACAAGTGCTTTGCCCGCGACTCCGGTGAGTTTTGCTACTTTGA
ATTGCCCGAGGATCATATCGAGGGCCCGGCGCACGGCGTCCGGCTTACCGCCCAGGGAGAGCTTGCCCGTAGCCTG
ATTCGGGAGTTTACCCAGCGCCCCCTGCTAGTTGAGCGGACAGGGGACCCTGTGTTCTCACTGTGATTTGCAACT
GTCCTAACCTTGGATTACATCAAGATCCTCTAGTTAATTAACAGCTTGCATGCCTGCAGGTCGACGGATCGGGAGA
TCTCGGCCGCATATTAAGTGCATTGTTCTCGATACCGCTAAGTGCATTGTTCTCGTTAGCTCGATGGACAAGTGCA
TTGTTCTCTTGCTGAAAGCTCGATGGACAAGTGCATTGTTCTCTTGCTGAAAGCTCGATGGACAAGTGCATTGTTC
TCTTGCTGAAAGCTCAGTACCCGGGAGTACCCTCGACCGCCGGAGTATAAATAGAGGCGCTTCGTCTACGGAGCGA
CAATTCAATTCAAACAAGCAAAGTGAACACGTCGCTAAGCGAAAGCTAAGCAAATAAACAAGCGCAGCTGAACAAG
CTAAACAATCTGCAGTAAAGTGCAAGTTAAAGTGAATCAATTAAAAGTAACCAGCAACCAAGTAAATCAACTGCAA
CTACTGAAATCTGCCAAGAAGTAATTATTGAATACAAGAAGAGAACTCTGAATACTTTCAACAAGTTACCGAGAAA
GAAGAACTCACACACAGCTAGCGTTTAAACTTAAGCTTCACCATGGTGGGGCCCTGCATGCTGCTGCTGCTGCTGC
TGCTGGGCCTGAGGCTACAGCTCTCCCTGGGCATCATCCTAGTTGAGGAGGAGAACCCGGACTTCTGGAACCGCGA
GGCAGCCGAGGCCCTGGGTGCCGCCAAGAAGCTGCAGCCTGCACAGACAGCCGCCAAGAACCTCATCATCTTCCTG
GGCGATGGGGTGGGGGTGTCTACGGTGACAGCTGCCAGGATCCTAAAAGGGCAGAAGAAGGACAAACTGGGGCCTG
AGATACCCCTGGCCATGGACCGCTTCCCATATGTGGCTCTGTCCAAGACATACAATGTAGACAAACATGTGCCAGA
CAGTGGAGCCACAGCCACGGCCTACCTGTGCGGGGTCAAGGGCAACTTCCAGACCATTGGCTTGAGTGCAGCCGCC
CGCTTTAACCAGTGCAACACGACACGCGGCAACGAGGTCATCTCCGTGATGAATCGGGCCAAGAAAGCAGGGAAGT
CAGTGGGAGTGGTAACCACCACACGAGTGCAGCACGCCTCGCCAGCCGGCACCTACGCCCACACGGTGAACCGCAA
CTGGTACTCGGACGCCGACGTGCCTGCCTCGGCCCGCCAGGAGGGGTGCCAGGACATCGCTACGCAGCTCATCTCC
AACATGGACATTGACGTGATCCTAGGTGGGGGCCGAAAGTACATGTTTCGCATGGGAACCCCAGACCCTGAGTACC
CAGATGACTACAGCCAAGGTGGACCAGGCTGGACGGGAAGAATCTGGTGCAGGAATGGCTGGCGAAGCACCAGGG
TGCCCGGTACGTGTGGAACCGCACTGAGCTCATGCGGGCTTCCCTGGACCCGTCTGTGGCCCATCTCATGGGTCTC
TTTGAGCCTGGAGACATGAAATACGAGATCCACCGAGACTCCACACTGGACCCCTCCCTGATGGAGATGACAGAGG
CTGCCCTGCGCCTGCTGAGCAGGAACCCCCGCGGCTTCTTCCTCTTCGTGGAGGGTGGTCGCATCGACCATGGTCA
TCATGAAAGCAGGGCTTACCGGGCACTGACTGAGACGATCATGTTCGACGACGCCATTGAGAGGGCGGGCCAGCTC
ACCAGCGAGGAGGACACGCTGAGCCTCGTCACTGCCGACCACTCCCACGTCTTCTCCTTCGGAGGCTGCCCCCTGC
GAGGGGGCTCCATCTTCGGGCTGGCCCCTGGCAAGGCCCGGGACAGGAAGGCCTACACGGTCCTCCTATACGGAAA
CGGTCCAGGCTATGTGCTCAAGGACGGCGCCCGGCCGGATGTTACCGAGAGCGAGAGCGGGAGCCCCGAGTATCGG
CAGCAGTCAGCAGTGCCCCTGGACGAAGAGACCCACGCAGGCGAGGACGTGGCGGTGTTCGCGCGCGGCCCGCAGG
CGCACCTGGTTCACGGCGTGCAGGAGCAGACCTTCATAGCGCACGTCATGGCCTTCGCCGCCTGCCTGGAGCCCTA
CACCGCCTGCGACCTGGCGCCCCCCGCCGGCACCACCGACGCCGCGCACCCGGGGCGGTCCGTGGTCCCCGCGTTG
CTTCCTCTGCTGGCCGGGACCCTGCTGCTGCTGGAGACGGCCACTGCTCCCTGAGTGTCCCGTCCCTGGGGCTCCT
GCTTCCCCATCCCGGAGTTCTCCTGCTCCCCGCCTCCTGTCGTCCTGCCTGGCCTCCAGCCCGAGTCGTCATCCCC
GGAGTCCCTATACAGAGGTCCTGCCATGGAACCTTCCCCTCCCCGTGCGCTCTGGGGACTGAGCCCATGACACCAA
ACCTGCCCCTTGGCTGCTCTCGGACTCCCTACCCCAACCCCAGGGACAGATCTGGCCAGATTTGTAAAACAAATAG
ATTTTAGGCCCAAAGATTATTTAAAGCATTGCCTGGAACGCAGTGAGTTTTTGTTAGAAAAGAGAATAATTCAAAG
TGGCATTGCTTTGCTTCTTATGTTAATTTGGTACAGACCTGTGGCTGAGTTTGCTCAAAGTATTCAGAGCAGAATT

FIGURE 11 (cont.)

GTGGAGTGGAAAGAGAGATTGGACAAAGAGTTTAGTTTGTCAGTGTATCAAAAAATGAAGTTTAATGTGGCTATGG
GAATTGGAGTTTTAGATTGGCTAAGAAACAGTGATGATGATGATGAAGACAGCCAGGAAAATGCTGATAAAAATGA
AGATGGTGGGGAGAAGAACATGGAAGACTCAGGGCATGAAACAGGCATTGATTCACAGTCCCAAGGCTCATTTCAG
GCCCCTCAGTCCTCACAGTCTGTTCATGATCATAATCAGCCATACCACATTTGTAGAGGTTTTACTTGCTTTAAAA
AACCTCCCACACCTCCCCCTGAACCTGAAACATAAAATGAATGCAATTGTTGTTGTTAACTTGTTTATTGCAGCTT
ATAATGGTTACAAATAAAGCAATAGCATCACAAATTTCACAAATAAAGCATTTTTTTCACTGCATTCTAGTTGTGG
TTTGTCCAAACTCATCAATGTATCTTATCATGTCTGGATCCCCAGGAAGCTCCTCTGTGTCCTCATAAACCCTAAC
CTCCTCTACTTGAGAGGACATTCCAATCATAGGCTGCCCATCCACCCTCTGTGTCCTCCTGTTAATTAGGTCACTT
AACAAAAAGGAAATTGGGTAGGGGTTTTTCACAGACCGCTTTCTAAGGGTAATTTTAAAATATCTGGGAAGTCCCT
TCCACTGCTGTGTTCCAGAAGTGTTGGTAAACAGCCCACAAATGTCAACAGCAGAAACATACAAGCTGTCAGCTTT
GCACAAGGGCCCAACACCCTGCTCATCAAGAAGCACTGTGGTTGCTGTGTTAGTAATGTGCAAAACAGGAGGCACA
TTTTCCCCACCTGTGTAGGTTCCAAAATATCTAGTGTTTTCATTTTTACTTGGATCAGGAACCCAGCACTCCACTG
GATAAGCATTATCCTTATCCAAAACAGCCTTGTGGTCAGTGTTCATCTGCTGACTGTCAACTGTAGCATTTTTTGG
GGTTACAGTTTGAGCAGGATATTTGGTCCTGTAGTTTGCTAACACACCCTGCAGCTCCAAAGGTTCCCCACCAACA
GCAAAAAAAATGAAAATTTGACCCTTGAATGGGTTTTCCAGCACCATTTTCATGAGTTTTTTGTGTCCCTGAATGCA
AGTTTAACATAGCAGTTACCCCAATAACCTCAGTTTTAACAGTAACAGCTTCCCACATCAAAATATTTCCACAGGT
TAAGTCCTCATTTAAATTAGGCAAAGGAATTCCACTTCCCACTGCCTTGCTTCCGTCTCCCATTCAAACTTTTATC
AACTGACATTATTCTAAGTAAAATCCTCTTCATTATGTTGTCAGCAATCCATTGCTTGAAGGCCTGGCTCCCCAGA
ACCCCTCGACTGGTATGTCTTCTCCTAGAATACTCCAGAAGAAAAGGAGTGTATGAAGATAGTGACTGCACATTAA
AATGACTGAAACCATAGTAAATTAGGATGAGATTCTGGGCAGATAAACAGACAGCTGGCTAGGATCATTTTTTTAT
GCCTTGGACTTCTTTGGCAATCTGTTGAAGCCTGACATTCCTCAGAATAATGTTTTAAAGCCCAACAATAAGACCC
TGTAGCACATATAATAAGTACTGCAGTTTTGAAGTAGTGATAAGCATAAATGATATTTTGATATATTTATTATAAC
TGTAATGAGATGTGTACATATCTGTGACTTCATAGGTACTGATTGTACTACTGTGATTTTTTTGCCTACTTTCAAA
ATGAAAAGGAATGCTTAATTTCAGTTAGAGGTTAGTAAAGACAAATAGGTAATTTTCTTCTCCAGTGAAGAGCATG
GCGCCCCTTGCTATTCATGGACGCTTGCTTAAAGACTTGTACACAGGCTTGCTTTGTATCAACCTATGACTTCCCC
TTACAGCCGATGATAGGTTTTTATTTGCACCTCCTTCGTGTACAAAGACAGTTTTGGTGGCTACGCCATCATTAAA
CTCATTATTATCATGCTTAAGCCTATAGATGTATCCAGTTCTTCTGTTACATAATTGAAGCTGTAGTGAATTGTCT
ATCTTAAACTGCATCGCTAACTGACTACATTTCACACTTCATTTGCTTCCAACATAGACTAACCTTCTTGGATGTC
CACTATTATTTGAACTTTTGAGATTTTTTTTCCTATTTCTAATATCTTAAAATTTCAGAAGACTTAAAGTTTTGCA
ACTACAGGGCTCCATATAGACATCTAGCTTGAATTTATACACTTTCTTTCATTGATGTCCCTGGACTAAAAAATGT
TAAATATTTCTAACCGCTGTACTTAAAGTCCATTACAAACGAAGACTACTGTTGTTAAGTTGAATAGGCATCTTAT
ATATTTTTCACCGGTGCAATAAATAACTTCTATTCCCTTCTAACATCTGCTTGCGTTGCACTGAGAGTACACTATT
GATTAGCAATAGGTTCGTGATTACAGCCCTTCTATAATTAATTGTTAGGTTAACATATTATTCATAAAATATTATT
TTATTAATTTTTACTTGATTTGCTACTGGATGCTTAGAAATAGCTATGAGTATATTGGTAGAACCAGTACTTATAT
TTTATTACATTTTTACATTTCATAAAATTTAAGTGATATAAAAATCCTGAGGAAGTATGCCACAAAAGTGGTCTCA
GTGGAAATTTAAATATGTTAACATTTATTTTTAAAATGTAGCGTGAAATAGACAACTTTAAAAGCTCAGCTTAAAA
AAAAAACTCAAGGAAGCTGAACTTGACTTTTTAAAGCACTGAAGTGCAATATTTAATGTAGGTCAACATGTTTAAA
TGGGAAAATTTTTTTCCTAATTACAGCCAAATCCCTAGCTGTAATTAACTTAAAATTTGTATACTATTTCACAACA
GAGTCAGCATATACCACTTTCTTATAAAATTAGAAAGATCTAAAATTTTAGAGCTTATTTGGTGAAACAGGCATAT
TGCTACATCTTTGTTTATAAATTATAATGTGCCTTTAGAGCCCAATAACAGATAACAAGATTTTGAAAATTCAGGT
GAATTAGAGTTATCAGAGGGAATGTTAATACACTCTATTCAAATACTATATGAGTAAGACATTTAAAATAGGAAAC
AATACTTTATATATTAAAAAAAATTAATCTTCCAGTCGATTTAATCCACTTTATGAATTCATTTAAATCGATTTAA
ATTCGAATTAATTAACTAGAGTACCCGGGGATCTTATTCCCTTTAACTAATAAAAAAAAATAATAAAGCATCACTT
ACTTAAAATCAGTTAGCAAATTTCTGTCCAGTTTATTCAGCAGCACCTCCTTGCCCTCCTCCCAGCTCTGGTATTG
CAGCTTCCTCCTGGCTGCAAACTTTCTCCACAATCTAAATGGAATGTCAGTTTCCTCCTGTTCCTGTCCATCCGCA
CCCACTATCTTCATGTTGTTGCAGATGAAGCGCGCAAGACCGTCTGAAGATACCTTCAACCCCGTGTATCCATATG
ACACGGAAACCGGTCCTCCAACTGTGCCTTTTCTTACTCCTCCCTTTGTATCCCCCAATGGGTTTCAAGAGAGTCC
CCCTGGGGTACTCTCTTTGCGCCTATCCGAACCTCTAGTTACCTCCAATGGCATGCTTGCGCTCAAAATGGGCAAC
GGCCTCTCTCTGGACGAGGCCGGCAACCTTACCTCCCAAAATGTAACCACTGTGAGCCCACCTCTCAAAAAAACCA
AGTCAAACATAAACCTGGAAATATCTGCACCCCTCACAGTTACCTCAGAAGCCCTAACTGTGGCTGCCGCCGCACC
TCTAATGGTCGCGGGCAACACACTCACCATGCAATCACAGGCCCCGCTAACCGTGCACGACTCCAAACTTAGCATT
GCCACCCAAGGACCCCTCACAGTGTCAGAAGGAAAGCTAGCCCTGCAAACATCAGGCCCCCTCACCACCACCGATA
GCAGTACCCTTACTATCACTGCCTCACCCCCTCTAACTACTGCCACTGGTAGCTTGGGCATTGACTTGAAAGAGCC
CATTTATACACAAAATGGAAAACTAGGACTAAAGTACGGGGCTCCTTTGCATGTAACAGACGACCTAAACACTTTG
ACCGTAGCAACTGGTCCAGGTGTGACTATTAATAATACTTCCTTGCAAACTAAAGTTACTGGAGCCTTGGGTTTTG
ATTCACAAGGCAATATGCAACTTAATGTAGCAGGAGGACTAAGGATTGATTCTCAAAACAGACGCCTTATACTTGA
TGTTAGTTATCCGTTTGATGCTCAAAACCAACTAAATCTAAGACTAGGACAGGGCCCTCTTTTTATAAACTCAGCC
CACAACTTGGATATTAACTACAACAAAGGCCTTTACTTGTTTACAGCTTCAAACAATTCCAAAAAGCTTGAGGTTA
ACCTAAGCACTGCCAAGGGGTTGATGTTTGACGCTACAGCCATAGCCATTAATGCAGGAGATGGGCTTGAATTTGG
TTCACCTAATGCACCAAACACAAATCCCCTCAAAACAAAAATTGGCCATGGCCTAGAATTTGATTCAAACAAGGCT
ATGGTTCCTAAACTAGGAACTGGCCTTAGTTTTGACAGCACAGGTGCCATTACAGTAGGAAACAAAAATAATGATA

FIGURE 11 (cont.)

AGCTAACTTTGTGGACCACACCAGCTCCATCTCCTAACTGTAGACTAAATGCAGAGAAAGATGCTAAACTCACTTT
GGTCTTAACAAAATGTGGCAGTCAAATACTTGCTACAGTTTCAGTTTTGGCTGTTAAAGGCAGTTTGGCTCCAATA
TCTGGAACAGTTCAAAGTGCTCATCTTATTATAAGATTTGACGAAAATGGAGTGCTACTAAACAATTCCTTCCTGG
ACCCAGAATATTGGAACTTTAGAAATGGAGATCTTACTGAAGGCACAGCCTATACAAACGCTGTTGGATTTATGCC
TAACCTATCAGCTTATCCAAAATCTCACGGTAAAACTGCCAAAAGTAACATTGTCAGTCAAGTTTACTTAAACGGA
GACAAAACTAAACCTGTAACACTAACCATTACACTAAACGGTACACAGGAAACAGGAGACACAACTCCAAGTGCAT
ACTCTATGTCATTTTCATGGGACTGGTCTGGCCACAACTACATTAATGAAATATTTGCCACATCCTCTTACACTTT
TTCATACATTGCCCAAGAATAAAGAATCGTTTGTGTTATGTTTCAACGTGTTTATTTTTCAATTGCAGAAAATTTC
AAGTCATTTTTCATTCAGTAGTATAGCCCCACCACCACATAGCTTATACAGATCACCGTACCTTAATCAAACTCAC
AGAACCCTAGTATTCAACCTGCCACCTCCCTCCCAACACACAGAGTACACAGTCCTTTCTCCCCGGCTGGCCTTAA
AAAGCATCATATCATGGGTAACAGACATATTCTTAGGTGTTATATTCCACACGGTTTCCTGTCGAGCCAAACGCTC
ATCAGTGATATTAATAAACTCCCCGGGCAGCTCACTTAAGTTCATGTCGCTGTCCAGCTGCTGAGCCACAGGCTGC
TGTCCAACTTGCGGTTGCTTAACGGGCGGCGAAGGAGAAGTCCACGCCTACATGGGGGTAGAGTCATAATCGTGCA
TCAGGATAGGGCGGTGGTGCTGCAGCAGCGCGCGAATAAACTGCTGCCGCCGCCGCTCCGTCCTGCAGGAATACAA
CATGGCAGTGGTCTCCTCAGCGATGATTCGCACCGCCCGCAGCATAAGGCGCCTTGTCCTCCGGGCACAGCAGCGC
ACCCTGATCTCACTTAAATCAGCACAGTAACTGCAGCACAGCACCACAATATTGTTCAAAATCCCACAGTGCAAGG
CGCTGTATCCAAAGCTCATGGCGGGGACCACAGAACCCACGTGGCCATCATACCACAAGCGCAGGTAGATTAAGTG
GCGACCCCTCATAAACACGCTGGACATAAACATTACCTCTTTTGGCATGTTGTAATTCACCACCTCCCGGTACCAT
ATAAACCTCTGATTAAACATGGCGCCATCCACCACCATCCTAAACCAGCTGGCCAAAACCTGCCCGCCGGCTATAC
ACTGCAGGGAACCGGGACTGGAACAATGACAGTGGAGAGCCCAGGACTCGTAACCATGGATCATCATGCTCGTCAT
GATATCAATGTTGGCACAACACAGGCACACGTGCATACACTTCCTCAGGATTACAAGCTCCTCCCGCGTTAGAACC
ATATCCCAGGGAACAACCCATTCCTGAATCAGCGTAAATCCCACACTGCAGGGAAGACCTCGCACGTAACTCACGT
TGTGCATTGTCAAAGTGTTACATTCGGGCAGCAGCGGATGATCCTCCAGTATGGTAGCGCGGGTTTCTGTCTCAAA
AGGAGGTAGACGATCCCTACTGTACGGAGTGCGCCGAGACAACCGAGATCGTGTTGGTCGTAGTGTCATGCCAAAT
GGAACGCCGGACGTAGTCATATTTCCTGAAGCAAAACCAGGTGCGGGCGTGACAAACAGATCTGCGTCTCCGGTCT
CGCCGCTTAGATCGCTCTGTGTAGTAGTTGTAGTATATCCACTCTCTCAAAGCATCCAGGCGCCCCCTGGCTTCGG
GTTCTATGTAAACTCCTTCATGCGCCGCTGCCCTGATAACATCCACCACCGCAGAATAAGCCACACCCAGCCAACC
TACACATTCGTTCTGCGAGTCACACACGGGAGGAGCGGGAAGAGCTGGAAGAACCATGTTTTTTTTTTTATTCCAA
AAGATTATCCAAAACCTCAAAATGAAGATCTATTAAGTGAACGCGCTCCCCTCCGGTGGCGTGGTCAAACTCTACA
GCCAAAGAACAGATAATGGCATTTGTAAGATGTTGCACAATGGCTTCCAAAAGGCAAACGGCCCTCACGTCCAAGT
GGACGTAAAGGCTAAACCCTTCAGGGTGAATCTCCTCTATAAACATTCCAGCACCTTCAACCATGCCCAAATAATT
CTCATCTCGCCACCTTCTCAATATATCTCTAAGCAAATCCCGAATATTAAGTCCGGCCATTGTAAAAATCTGCTCC
AGAGCGCCCTCCACCTTCAGCCTCAAGCAGCGAATCATGATTGCAAAAATTCAGGTTCCTCACAGACCTGTATAAG
ATTCAAAAGCGGAACATTAACAAAAATACCGCGATCCCGTAGGTCCCTTCGCAGGGCCAGCTGAACATAATCGTGC
AGGTCTGCACGGACCAGCGCGGCCACTTCCCCGCCAGGAACCTTGACAAAAGAACCCACACTGATTATGACACGCA
TACTCGGAGCTATGCTAACCAGCGTAGCCCCGATGTAAGCTTTGTTGCATGGGCGGCGATATAAAATGCAAGGTGC
TGCTCAAAAAATCAGGCAAAGCCTCGCGCAAAAAAGAAAGCACATCGTAGTCATGCTCATGCAGATAAAGGCAGGT
AAGCTCCGGAACCACCACAGAAAAAGACACCATTTTTCTCTCAAACATGTCTGCGGGTTTCTGCATAAACACAAAA
TAAAATAACAAAAAAACATTTAAACATTAGAAGCCTGTCTTACAACAGGAAAAACAACCCTTATAAGCATAAGACG
GACTACGGCCATGCCGGCGTGACCGTAAAAAAACTGGTCACCGTGATTAAAAAGCACCACCGACAGCTCCTCGGTC
ATGTCCGGAGTCATAATGTAAGACTCGGTAAACACATCAGGTTGATTCATCGGTCAGTGCTAAAAAGCGACCGAAA
TAGCCCGGGGGAATACATACCCGCAGGCGTAGAGACAACATTACAGCCCCCATAGGAGGTATAACAAAATTAATAG
GAGAGAAAAACACATAAACACCTGAAAAACCCTCCTGCCTAGGCAAAATAGCACCCTCCCGCTCCAGAACAACATA
CAGCGCTTCACAGCGGCAGCCTAACAGTCAGCCTTACCAGTAAAAAAGAAAACCTATTAAAAAAACACCACTCGAC
ACGGCACCAGCTCAATCAGTCACAGTGTAAAAAAGGGCCAAGTGCAGAGCGAGTATATATAGGACTAAAAAATGAC
GTAACGGTTAAAGTCCACAAAAAACACCCAGAAAACCGCACGCGAACCTACGCCCAGAAACGAAAGCCAAAAAACC
CACAACTTCCTCAAATCGTCACTTCCGTTTTCCCACGTTACGTAACTTCCCATTTTAAGAAAACTACAATTCCCAA
CACATACAAGTTACTCCGCCCTAAAACCTACGTCACCCGCCCCGTTCCCACGCCCCGCGCCACGTCACAAACTCCA
CCCCCTCATTATCATATTGGCTTCAATCCAAAATAAGGTATATTATTGATGATG pD2076#2: A Linear Gutted Virus Carrying Human Dystrophin TP-DNA Complex from (+)lox(+)pol Helper Deproteinized Hirt Prep DNA from ΔFseI.4 pD1940#3 or pD1940#6

1.8 kb plasmid
backbone released by FseI digestion

FIGURE 14 pD1940 sequence (SEQ ID NO:13)

CTAAATTGTAAGCGTTAATATTTTGTTAAAATTCGGCCGGCCATCATCAATAATATACCTTATTTTGGATTGAAGC
CAATATGATAATGAGGGGGTGGAGTTTGTGACGTGGCGCGGGGCGTGGGAACGGGGCGGGTGACGTAGTAGTGTGG
CGGAAGTGTGATGTTGCAAGTGTGGCGGAACACATGTATAACTTCGTATAATGTATGCTATACGAAGTTATACATG
TAAGCGACGGATGTGGCAAAAGTGACGTTTTTGGTGTGCGCCGGTGTACACAGGAAGTGACAATTTTCGCGCGGTT
TTAGGCGGATGTTGTAGTAAATTTGGGCGTAACCGAGTAAGATTTGGCCATTTTCGCGGGAAAACTGAATAAGAGG
AAGTGAAATCTGAATAATTTTGTGTTACTCATAGCGCGTAATATTTGTCTAGGGAGATCTATAACTTCGTATAATG
TATGCTATACGAAGTTATTACCGAAGAAATGGCTCGAGATCTGGAAGGTGCTGAGGTACGATGAGACCCGCACCAG
GTGCAGACCCTGCGAGTGTGGCGGTAAACATATTAGGAACCAGCCTGTGATGCTGGATGTGACCGAGGAGCTGAGG
CCCGATCACTTGGTGCTGGCCTGCACCCGCGCTGAGTTTGGCTCTAGCGATGAAGATACAGATTGAGGTACTGAAA
TGTGTGGGCGTGGCTTAAGGGTGGGAAAGAATATATAAGGTGGGGGTCTTATGTAGTTTTGTATCTGTTTTGCAGC
AGCCGCCGCCGCCATGAGCACCAACTCGTTTGATGGAAGCATTGTGAGCTCATATTTGACAACGCGCATGCCCCCA
TGGGCCGGGGTGCGTCAGAATGTGATGGGCTCCAGCATTGATGGTCGCCCCGTCCTGCCCGCAAACTCTACTACCT
TGACCTACGAGACCGTGTCTGGAACGCCGTTGGAGACTGCAGCCTCCGCCGCCGCTTCAGCCGCTGCAGCCACCGC
CCGCGGGATTGTGACTGACTTTGCTTTCCTGAGCCCGCTTGCAAGCAGTGCAGCTTCCCGTTCATCCGCCCGCGAT
GACAAGTTGACGGCTCTTTTGGCACAATTGGATTCTTTGACCCGGGAACTTAATGTCGTTTCTCAGCAGCTGTTGG
ATCTGCGCCAGCAGGTTTCTGCCCTGAAGGCTTCCTCCCCTCCCAATGCGGTTTAAAACATAAATAAAAAACCAGA
CTCTGTTTGGATTTGGATCAAGCAAGTGTCTTGCTGTCTTTATTTAGGGGTTTTGCGCGCGCGGTAGGCCCGGGAC
CAGCGGTCTCGGTCGTTGAGGGTCCTGTGTATTTTTTCCAGGACGTGGTAAAGGTGACTCTGGATGTTCAGATACA
TGGGCATAAGCCCGTCTCTGGGGTGGAGGTAGCACCACTGCAGAGCTTCATGCTGCGGGGTGGTGTTGTAGATGAT
CCAGTCGTAGCAGGAGCGCTGGGCGTGGTGCCTAAAAATGTCTTTCAGTAGCAAGCTGATTGCCAGGGGCAGGCCC
TTGGTGTAAGTGTTTACAAAGCGGTTAAGCTGGGATGGGTGCATACGTGGGGATATGAGATGCATCTTGGACTGTA
TTTTTAGGTTGGCTATGTTCCCAGCCATATCCCTCCGGGGATTCATGTTGTGCAGAACCACCAGCACAGTGTATCC
GGTGCACTTGGGAAATTTGTCATGTAGCTTAGAAGGAAATGCGTGGAAGAACTTGGAGACGCCCTTGTGACCTCCA
AGATTTTCCATGCATTCGTCCATAATGATGGCAATGGGCCCACGGGCGGCGGCCTGGGCGAAGATATTTCTGGGAT
CACTAACGTCATAGTTGTGTTCCAGGATGAGATCGTCATAGGCCATTTTTACAAAGCGCGGGCGGAGGGTGCCAGA
CTGCGGTATAATGGTTCCATCCGGCCCAGGGGCGTAGTTACCCTCACAGATTTGCATTTCCCACGCTTTGAGTTCA
GATGGGGGGATCATGTCTACCTGCGGGGCGATGAAGAAAACGGTTTCCGGGGTAGGGGAGATCAGCTGGGAAGAAA
GCAGGTTCCTGAGCAGCTGCGACTTACCGCAGCCGGTGGGCCCGTAAATCACACCTATTACCGGGTGCAACTGGTA
GTTAAGAGAGCTGCAGCTGCCGTCATCCCTGAGCAGGGGGGCCACTTCGTTAAGCATGTCCCTGACTCGCATGTTT
TCCCTGACCAAATCCGCCAGAAGGCGCTCGCCGCCCAGCGATAGCAGTTCTTGCAAGGAAGCAAAGTTTTTCAACG
GTTTGAGACCGTCCGCCGTAGGCATGCTTTTGAGCGTTTGACCAAGCAGTTCCAGGCGGTCCCACAGCTCGGTCAC
CTGCTCTACGGCATCTCGATCCAGCATATCTCCTCGTTTCGCGGGTTGGGGCGGCTTTCGCTGTACGGCAGTAGTC
GGTGCTCGTCCAGACGGGCCAGGGTCATGTCTTTCCACGGGCGCAGGGTCCTCGTCAGCGTAGTCTGGGTCACGGT
GAAGGGGTGCGCTCCGGGCTGCGCGCTGGCCAGGGTGCGCTTGAGGCTGGTCCTGCTGGTGCTGAAGCGCTGCCGG
TCTTCGCCCTGCGCGTCGGCCAGGTAGCATTTGACCATGGTGTCATAGTCCAGCCCCTCCGCGGCGTGGCCCTTGG
CGCGCAGCTTGCCCTTGGAGGAGGCGCCGCACGAGGGGCAGTGCAGACTTTTGAGGGCGTAGAGCTTGGGCGCGAG
AAATACCGATTCCGGGGAGTAGGCATCCGCGCCGCAGGCCCCGCAGACGGTCTCGCATTCCACGAGCCAGGTGAGC
TCTGGCCGTTCGGGGTCAAAAACCAGGTTTCCCCCATGCTTTTTGATGCGTTTCTTACCTCTGGTTTCCATGAGCC
GGTGTCCACGCTCGGTGACGAAAAGGCTGTCCGTGTCCCCGTATACAGACTTGAGAGGCCTGTCCTCGAGCGGTGT
TCCGCGGTCCTCCTCGTATAGAAACTCGGACCACTCTGAGACAAAGGCTCGCGTCCAGGCCAGCACGAAGGAGGCT
AAGTGGGAGGGGTAGCGGTCGTTGTCCACTAGGGGGTCCACTCGCTCCAGGGTGTGAAGACACATGTCGCCCTCTT
CGGCATCAAGGAAGGTGATTGGTTTGTAGGTGTAGGCCACGTGACCGGGTGTTCCTGAAGGGGGGCTATAAAAGGG
GGTGGGGGCGCGTTCGTCCTCACTCTCTTCCGCATCGCTGTCTGCGAGGGCCAGCTGTTGGGGTGAGTACTCCCTC
TGAAAAGCGGGCATGACTTCTGCGCTAAGATTGTCAGTTTCCAAAAACGAGGAGGATTTGATATTCACCTGGCCCG
CGGTGATGCCTTTGAGGGTGGCCGCATCCATCTGGTCAGAAAAGACAATCTTTTTGTTGTCAAGCTTGGTGGCAAA
CGACCCGTAGAGGGCGTTGGACAGCAACTTGGCGATGGAGCGCAGGGTTTGGTTTTTGTCGCGATCGGCGCGCTCC
TTGGCCGCGATGTTTAGCTGCACGTATTCGCGCGCAACGCACCGCCATTCGGGAAAGACGGTGGTGCGCTCGTCGG
GCACCAGGTGCACGCGCCAACCGCGGTTGTGCAGGGTGACAAGGTCAACGCTGGTGGCTACCTCTCCGCGTAGGCG
CTCGTTGGTCCAGCAGAGGCGGCCGCCCTTGCGCGAGCAGAATGGCGGTAGGGGGTCTAGCTGCGTCTCGTCCGGG
GGGTCTGCGTCCACGGTAAAGACCCCGGGCAGCAGGCGCGCGTCGAAGTAGTCTATCTTGCATCCTTGCAAGTCTA
GCGCCTGCTGCCATGCGCGGGCGGCAAGCGCGCGCTCGTATGGGTTGAGTGGGGGACCCCATGGCATGGGGTGGGT
GAGCGCGGAGGCGTACATGCCGCAAATGTCGTAAACGTAGAGGGGCTCTCTGAGTATTCCAAGATATGTAGGGTAG
CATCTTCCACCGCGGATGCTGGCGCGCACGTAATCGTATAGTTCGTGCGAGGGAGCGAGGAGGTCGGGACCGAGGT
TGCTACGGGCGGGCTGCTCTGCTCGGAAGACTATCTGCCTGAAGATGGCATGTGAGTTGGATGATATGGTTGGACG
CTGGAAGACGTTGAAGCTGGCGTCTGTGAGACCTACCGCGTCACGCACGAAGGAGGCGTAGGAGTCGCGCAGCTTG
TTGACCAGCTCGGCGGTGACCTGCACGTCTAGGGCGCAGTAGTCCAGGGTTTCCTTGATGATGTCATACTTATCCT
GTCCCTTTTTTTTCCACAGCTCGCGGTTGAGGACAAACTCTTCGCGGTCTTTCCAGTACTCTTGGATCGGAAACCC
GTCGGCCTCCGAACGGTAAGAGCCTAGCATGTAGAACTGGTTGACGGCCTGGTAGGCGCAGCATCCCTTTTCTACG
GGTAGCGCGTATGCCTGCGCGGCCTTCCGGAGCGAGGTGTGGGTGAGCGCAAAGGTGTCCCTGACCATGACTTTGA
GGTACTGGTATTTGAAGTCAGTGTCGTCGCATCCGCCCTGCTCCCAGAGCAAAAAGTCCGTGCGCTTTTTGGAACG
CGGATTTGGCAGGGCGAAGGTGACATCGTTGAAGAGTATCTTTCCCGCGCGAGGCATAAAGTTGCGTGTGATGCGG

FIGURE 14 (cont.)

AAGGGTCCCGGCACCTCGGAACGGTTGTTAATTACCTGGGCGGCGAGCACGATCTCGTCAAAGCCGTTGATGTTGT
GGCCCACAATGTAAAGTTCCAAGAAGCGCGGGATGCCCTTGATGGAAGGCAATTTTTTAAGTTCCTCGTAGGTGAG
CTCTTCAGGGGAGCTGAGCCCGTGCTCTGAAAGGGCCCAGTCTGCAAGATGAGGGTTGGAAGCGACGAATGAGCTC
CACAGGTCACGGGCCATTAGCATTTGCAGGTGGTCGCGAAAGGTCCTAAACTGGCGACCTATGGCCATTTTTTCTG
GGGTGATGCAGTAGAAGGTAAGCGGGTCTTGTTCCCAGCGGTCCCATCCAAGGTTCGCGGCTAGGTCTCGCGCGGC
AGTCACTAGAGGCTCATCTCCGCCGAACTTCATGACCAGCATGAAGGGCACGAGCTGCTTCCCAAAGGCCCCCATC
CAAGTATAGGTCTCTACATCGTAGGTGACAAAGAGACGCTCGGTGCGAGGATGCGAGCCGATCGGGAAGAACTGGA
TCTCCCGCCACCAATTGGAGGAGTGGCTATTGATGTGGTGAAAGTAGAAGTCCCTGCGACGGGCCGAACACTCGTG
CTGGCTTTTGTAAAAACGTGCGCAGTACTGGCAGCGGTGCACGGGCTGTACATCCTGCACGAGGTTGACCTGACGA
CCGCGCACAAGGAAGCAGAGTGGGAATTTGAGCCCCTCGCCTGGCGGGTTTGGCTGGTGGTCTTCTACTTCGGCTG
CTTGTCCTTGACCGTCTGGCTGCTCGAGGGGAGTTACGGTGGATCGGACCACCACGCCGCGCGAGCCCAAAGTCCA
GATGTCCGCGCGCGGCGGTCGGAGCTTGATGACAACATCGCGCAGATGGGAGCTGTCCATGGTCTGGAGCTCCCGC
GGCGTCAGGTCAGGCGGGAGCTCCTGCAGGTTTACCTCGCATAGACGGGTCAGGGCGCGGGCTAGATCCAGGTGAT
ACCTAATTTCCAGGGGCTGGTTGGTGGCGGCGTCGATGGCTTGCAAGAGGCCGCATCCCCGCGGCGCGACTACGGT
ACCGCGCGGCGGGCGGTGGGCCGCGGGGGTGTCCTTGGATGATGCATCTAAAAGCGGTGACGCGGGCGAGCCCCCG
GAGGTAGGGGGGGCTCCGGACCCGCCGGGAGAGGGGGCAGGGGCACGTCGGCGCCGCGCGCGGGCAGGAGCTGGTG
CTGCGCGCGTAGGTTGCTGGCGAACGCGACGACGCGGCGGTTGATCTCCTGAATCTGGCGCCTCTGCGTGAAGACG
ACGGGCCCGGTGAGCTTGAGCCTGAAAGAGAGTTCGACAGAATCAATTTCGGTGTCGTTGACGGCGGCCTGGCGCA
AAATCTCCTGCACGTCTCCTGAGTTGTCTTGATAGGCGATCTCGGCCATGAACTGCTCGATCTCTTCCTCCTGGAG
ATCTCCGCGTCCGGCTCGCTCCACGGTGGCGGCGAGGTCGTTGGAAATGCGGGCCATGAGCTGCGAGAAGGCGTTG
AGGCCTCCCTCGTTCCAGACGCGGCTGTAGACCACGCCCCCTTCGGCATCGCGGGCGCGCATGACCACCTGCGCGA
GATTGAGCTCCACGTGCCGGGCGAAGACGGCGTAGTTTCGCAGGCGCTGAAAGAGGTAGTTGAGGGTGGTGGCGGT
GTGTTCTGCCACGAAGAAGTACATAACCCAGCGTCGCAACGTGGATTCGTTGATATCCCCCAAGGCCTCAAGGCGC
TCCATGGCCTCGTAGAAGTCCACGGCGAAGTTGAAAAACTGGGAGTTGCGCGCCGACACGGTTAACTCCTCCTCCA
GAAGACGGATGAGCTCGGCGACAGTGTCGCGCACCTCGCGCTCAAAGGCTACAGGGGCCTCTTCTTCTTCTTCAAT
CTCCTCTTCCATAAGGGCCTCCCCTTCTTCTTCTTCTGGCGGCGGTGGGGGAGGGGGGACACGGCGGCGACGACGG
CGCACCGGGAGGCGGTCGACAAAGCGCTCGATCATCTCCCCGCGGCGACGGCGCATGGTCTCGGTGACGGCGCGGC
CGTTCTCGCGGGGGCGCAGTTGGAAGACGCCGCCCGTCATGTCCCGGTTATGGGTTGGCGGGGGGCTGCCATGCGG
CAGGGATACGGCGCTAACGATGCATCTCAACAATTGTTGTGTAGGTACTCCGCCGCCGAGGGACCTGAGCGAGTCC
GCATCGACCGGATCGGAAAACCTCTCGAGAAAGGCGTCTAACCAGTCACAGTCGCAAGGTAGGCTGAGCACCGTGG
CGGGCGGCAGCGGGCGGCGGTCGGGGTTGTTTCTGGCGGAGGTGCTGCTGATGATGTAATTAAAGTAGGCGGTCTT
GAGACGGCGGATGGTCGACAGAAGCACCATGTCCTTGGGTCCGGCCTGCTGAATGCGCAGGCGGTCGGCCATGCCC
CAGGCTTCGTTTTGACATCGGCGCAGGTCTTTGTAGTAGTCTTGCATGAGCCTTTCTACCGGCACTTCTTCTTCTC
CTTCCTCTTGTCCTGCATCTCTTGCATCTATCGCTGCGGCGGCGGCGGAGTTTGGCCGTAGGTGGCGCCCTCTTCC
TCCCATGCGTGTGACCCCGAAGCCCCTCATCGGCTGAAGCAGGGCTAGGTCGGCGACAACGCGCTCGGCTAATATG
GCCTGCTGCACCTGCGTGAGGGTAGACTGGAAGTCATCCATGTCCACAAAGCGGTGGTATGCGCCCGTGTTGATGG
TGTAAGTGCAGTTGGCCATAACGGACCAGTTAACGGTCTGGTGACCCGGCTGCGAGAGCTCGGTGTACCTGAGACG
CGAGTAAGCCCTCGAGTCAAATACGTAGTCGTTGCAAGTCCGCACCAGGTACTGGTATCCCACCAAAAAGTGCGGC
GGCGGCTGGCGGTAGAGGGGCCAGCGTAGGGTGGCCGGGGCTCCGGGGGCGAGATCTTCCAACATAAGGCGATGAT
ATCCGTAGATGTACCTGGACATCCAGGTGATGCCGGCGGCGGTGGTGGAGGCGCGCGGAAAGTCGCGGACGCGGTT
CCAGATGTTGCGCAGCGGCAAAAAGTGCTCCATGGTCGGGACGCTCTGGCCGGTCAGGCGCGCGCAATCGTTGACG
CTCTACCGTGCAAAAGGAGAGCCTGTAAGCGGGCACTCTTCCGTGGTCTGGTGGATAAATTCGCAAGGGTATCATG
GCGGACGACCGGGGTTCGAGCCCCGTATCCGGCCGTCCGCCGTGATCCATGCGGTTACCGCCCGCGTGTCGAACCC
AGGTGTGCGACGTCAGACAACGGGGGAGTGCTCCTTTTGGCTTCCTTCCAGGCGCGGCGGCTGCTGCGCTAGCTTT
TTTGGCCACTGGCCGCGCGCAGCGTAAGCGGTTAGGCTGGAAAGCGAAAGCATTAAGTGGCTCGCTCCCTGTAGCC
GGAGGGTTATTTTCCAAGGGTTGAGTCGCGGGACCCCCGGTTCGAGTCTCGGACCGGCCGGACTGCGGCGAACGGG
GGTTTGCCTCCCCGTCATGCAAGACCCCGCTTGCAAATTCCTCCGGAAACAGGGACGAGCCCCTTTTTTGCTTTTC
CCAGATGCATCCGGTGCTGCGGCAGATGCGCCCCCCTCCTCAGCAGCGGCAAGAGCAAGAGCAGCGGCAGACATGC
AGGGCACCCTCCCCTCCTCCTACCGCGTCAGGAGGGGCGACATCCGCGGTTGACGCGGCAGCAGATGGTGATTACG
AACCCCCGCGGCGCCGGGCCCGGCACTACCTGGACTTGGAGGAGGGCGAGGGCCTGGCGCGGCTAGGAGCGCCCTC
TCCTGAGCGGTACCCAAGGGTGCAGCTGAAGCGTGATACGCGTGAGGCGTACGTGCCGCGGCAGAACCTGTTTCGC
GACCGCGAGGGAGAGGAGCCCGAGGAGATGCGGGATCGAAAGTTCCACGCAGGGCGCGAGCTGCGGCATGGCCTGA
ATCGCGAGCGGTTGCTGCGCGAGGAGGACTTTGAGCCCGACGCGCGAACCGGGATTAGTCCCGCGCGCGCACACGT
GGCGGCCGCCGACCTGGTAACCGCATACGAGCAGACGGTGAACCAGGAGATTAACTTTCAAAAAAGCTTTAACAAC
CACGTGCGTACGCTTGTGGCGCGCGAGGAGGTGGCTATAGGACTGATGCATCTGTGGGACTTTGTAAGCGCGCTGG
AGCAAAACCCAAATAGCAAGCCGCTCATGGCGCAGCTGTTCCTTATAGTGCAGCACAGCAGGGACAACGAGGCATT
CAGGGATGCGCTGCTAAACATAGTAGAGCCCGAGGGCCGCTGGCTGCTCGATTTGATAAACATCCTGCAGAGCATA
GTGGTGCAGGAGCGCAGCTTGAGCCTGGCTGACAAGGTGGCCGCCATCAACTATTCCATGCTTAGCCTGGGCAAGT
TTTACGCCCGCAAGATATACCATACCCCTTACGTTCCCATAGACAAGGAGGTAAAGATCGAGGGGTTCTACATGCG
CATGGCGCTGAAGGTGCTTACCTTGAGCGACGACCTGGGCGTTTATCGCAACGAGCGCATCCACAAGGCCGTGAGC
GTGAGCCGGCGGCGCGAGCTCAGCGACCGCGAGCTGATGCACAGCCTGCAAAGGGCCCTGGCTGGCACGGGCAGCG

FIGURE 14 (cont.)

GCGATAGAGAGGCCGAGTCCTACTTTGACGCGGGCGCTGACCTGCGCTGGGCCCCAAGCCGACGCGCCCTGGAGGC
AGCTGGGGCCGGACCTGGGCTGGCGGTGGCACCCGCGCGCGCTGGCAACGTCGGCGGCGTGGAGGAATATGACGAG
GACGATGAGTACGAGCCAGAGGACGGCGAGTACTAAGCGGTGATGTTTCTGATCAGATGATGCAAGACGCAACGGA
CCCGGCGGTGCGGGCGGCGCTGCAGAGCCAGCCGTCCGGCCTTAACTCCACGGACGACTGGCGCCAGGTCATGGAC
CGCATCATGTCGCTGACTGCGCGCAATCCTGACGCGTTCCGGCAGCAGCCGCAGGCCAACCGGCTCTCCGCAATTC
TGGAAGCGGTGGTCCCGGCGCGCGCAAACCCCACGCACGAGAAGGTGCTGGCGATCGTAAACGCGCTGGCCGAAAA
CAGGGCCATCCGGCCCGACGAAGCCGGCCTGGTCTACGACGCGCTGCTTCAGCGCGTGGCTCGTTACAACAGCGGC
AACGTGCAGACCAACCTGGACCGGCTGGTGGGGATGTGCGCGAGGCCGTGGCGCAGCGTGAGCGCGCGCAGCAGC
AGGGCAACCTGGGCTCCATGGTTGCACTAAACGCCTTCCTGAGTACACAGCCCGCCAACGTGCCGCGGGGACAGGA
GGACTACACCAACTTTGTGAGCGCACTGCGGCTAATGGTGACTGAGACACCGCAAAGTGAGGTGTACCAGTCTGGG
CCAGACTATTTTTTCCAGACCAGTAGACAAGGCCTGCAGACCGTAAACCTGAGCCAGGCTTTCAAAAACTTGCAGG
GGCTGTGGGGGGTGCGGGCTCCCACAGGCGACCGCGCGACCGTGTCTAGCTTGCTGACGCCCAACTCGCGCCTGTT
GCTGCTGCTAATAGCGCCCTTCACGGACAGTGGCAGCGTGTCCCGGGACACATACCTAGGTCACTTGCTGACACTG
TACCGCGAGGCCATAGGTCAGGCGCATGTGGACGAGCATACTTTCCAGGAGATTACAAGTGTCAGCCGCGCGCTGG
GGCAGGAGGACACGGGCAGCCTGGAGGCAACCCTAAACTACCTGCTGACCAACCGGCGGCAGAAGATCCCCTCGTT
GCACAGTTTAAACAGCGAGGAGGAGCGCATTTTGCGCTACGTGCAGCAGAGCGTGAGCCTTAACCTGATGCGCGAC
GGGGTAACGCCCAGCGTGGCGCTGGACATGACCGCGCGCAACATGGAACCGGGCATGTATGCCTCAAACCGGCCGT
TTATCAACCGCCTAATGGACTACTTGCATCGCGCGGCCGCCGTGAACCCCGAGTATTTCACCAATGCCATCTTGAA
CCCGCACTGGCTACCGCCCCCTGGTTTCTACACCGGGGGATTCGAGGTGCCCGAGGGTAACGATGGATTCCTCTGG
GACGACATAGACGACAGCGTGTTTTCCCCGCAACCGCAGACCCTGCTAGAGTTGCAACAGCGCGAGCAGGCAGAGG
CGGCGCTGCGAAAGGAAAGCTTCCGCAGGCCAAGCAGCTTGTCCGATCTAGGCGCTGCGGCCCCGCGGTCAGATGC
TAGTAGCCCATTTCCAAGCTTGATAGGGTCTCTTACCAGCACTCGCACCACCCGCCCGCGCCTGCTGGGCGAGGAG
GAGTACCTAAACAACTCGCTGCTGCAGCCGCAGCGCGAAAAAAACCTGCCTCCGGCATTTCCCAACAACGGGATAG
AGAGCCTAGTGGACAAGATGAGTAGATGGAAGACGTACGCGCAGGAGCACAGGGACGTGCCAGGCCCGCGCCCGCC
CACCCGTCGTCAAAGGCACGACCGTCAGCGGGGTCTGGTGTGGGAGGACGATGACTCGGCAGACGACAGCAGCGTC
CTGGATTTGGGAGGGAGTGGCAACCCGTTTGCGCACCTTCGCCCCAGGCTGGGGAGAATGTTTTAAAAAAAAAAAA
GCATGATGCAAAATAAAAAACTCACCAAGGCCATGGCACCGAGCGTTGGTTTTCTTGTATTCCCCTTAGTATGCGG
CGCGCGGCGATGTATGAGGAAGGTCCTCCTCCCTCCTACGAGAGTGTGGTGAGCGCGGCGCCAGTGGCGGCGGCGC
TGGGTTCTCCCTTCGATGCTCCCCTGGACCCGCCGTTTGTGCCTCCGCGGTACCTGCGGCCTACCGGGGGGAGAAA
CAGCATCCGTTACTCTGAGTTGGCACCCCTATTCGACACCACCCGTGTGTACCTGGTGGACAACAAGTCAACGGAT
GTGGCATCCCTGAACTACCAGAACGACCACAGCAACTTTCTGACCACGGTCATTCAAAACAATGACTACAGCCCGG
GGGAGGCAAGCACACAGACCATCAATCTTGACGACCGGTCGCACTGGGGCGGCGACCTGAAAACCATCCTGCATAC
CAACATGCCAAATGTGAACGAGTTCATGTTTACCAATAAGTTTAAGGCGCGGGTGATGGTGTCGCGCTTGCCTACT
AAGGACAATCAGGTGGAGCTGAAATACGAGTGGGTGGAGTTCACGCTGCCCGAGGGCAACTACTCCGAGACCATGA
CCATAGACCTTATGAACAACGCGATCGTGGAGCACTACTTGAAAGTGGGCAGACAGAACGGGGTTCTGGAAAGCGA
CATCGGGGTAAAGTTTGACACCCGCAACTTCAGACTGGGGTTTGACCCCGTCACTGGTCTTGTCATGCCTGGGGTA
TATACAAACGAAGCCTTCCATCCAGACATCATTTTGCTGCCAGGATGCGGGGTGGACTTCACCCACAGCCGCCTGA
GCAACTTGTTGGGCATCCGCAAGCGGCAACCCTTCCAGGAGGGCTTTAGGATCACCTACGATGATCTGGAGGGTGG
TAACATTCCCGCACTGTTGGATGTGGACGCCTACCAGGCGAGCTTGAAAGATGACACCGAACAGGGCGGGGGTGGC
GCAGGCGGCAGCAACAGCAGTGGCAGCGGCGCGGAAGAGAACTCCAACGCGGCAGCCGCGGCAATGCAGCCGGTGG
AGGACATGAACGATCATGCCATTCGCGGCGACACCTTTGCCACACGGGCTGAGGAGAAGCGCGCTGAGGCCGAAGC
AGCGGCCGAAGCTGCCGCCCCCGCTGCGCAACCCGAGGTCGAGAAGCCTCAGAAGAAACCGGTGATCAAACCCCTG
ACAGAGGACAGCAAGAAACGCAGTTACAACCTAATAAGCAATGACAGCACCTTCACCCAGTACCGCAGCTGGTACC
TTGCATACAACTACGGCGACCCTCAGACCGGAATCCGCTCATGGACCCTGCTTTGCACTCCTGACGTAACCTGCGG
CTCGGAGCAGGTCTACTGGTCGTTGCCAGACATGATGCAAGACCCCGTGACCTTCCGCTCCACGCGCCAGATCAGC
AACTTTCCGGTGGTGGGCGCCGAGCTGTTGCCCGTGCACTCCAAGAGCTTCTACAACGACCAGGCCGTCTACTCCC
AACTCATCCGCCAGTTTACCTCTCTGACCCACGTGTTCAATCGCTTTCCCGAGAACCAGATTTTGGCGCGCCCGCC
AGCCCCCACCATCACCACCGTCAGTGAAAACGTTCCTGCTCTCACAGATCACGGGACGCTACCGCTGCGCAACAGC
ATCGGAGGAGTCCAGCGAGTGACCATTACTGACGCCAGACGCCGCACCTGCCCCTACGTTTACAAGGCCCTGGGCA
TAGTCTCGCCGCGCGTCCTATCGAGCCGCACTTTTTGAGCAAGCATGTCCATCCTTATATCGCCCAGCAATAACAC
AGGCTGGGGCCTGCGCTTCCCAAGCAAGATGTTTGGCGGGGCCAAGAAGCGCTCCGACCAACACCCAGTGCGCGTG
CGCGGGCACTACCGCGCGCCCTGGGGCGCGCACAAACGCGGCCGCACTGGGCGCACCACCGTCGATGACGCCATCG
ACGCGGTGGTGGAGGAGGCGCGCAACTACACGCCCACGCCGCCACCAGTGTCCACAGTGGACGCGGCCATTCAGAC
CGTGGTGCGCGGAGCCCGGCGCTATGCTAAAATGAAGAGACGGCGGAGGCGCGTAGCACGTCGCCACCGCCGCCGA
CCCGGCACTGCCGCCCAACGCGCGGCGGCGGCCCTGCTTAACCGCGCACGTCGCACCGGCCGACGGGCGGCCATGC
GGGCCGCTCGAAGGCTGGCCGCGGGTATTGTCACTGTGCCCCCCAGGTCCAGGCGACGAGCGGCCGCCGCAGCAGC
CGCGGCCATTAGTGCTATGACTCAGGGTCGCAGGGGCAACGTGTATTGGGTGCGCGACTCGGTTAGCGGCCTGCGC
GTGCCCGTGCGCACCCGCCCCCCGCGCAACTAGATTGCAAGAAAAAACTACTTAGACTCGTACTGTTGTATGTATC
CAGCGGCGGCGGCGCGCAACGAAGCTATGTCCAAGCGCAAAATCAAAGAAGAGATGCTCCAGGTCATCGCGCCGGA
GATCTATGGCCCCCCGAAGAAGGAAGAGCAGGATTACAAGCCCCGAAAGCTAAAGCGGGTCAAAAAGAAAAAGAAA
GATGATGATGATGAACTTGACGACGAGGTGGAACTGCTGCACGCTACCGCGCCCAGGCGACGGGTACAGTGGAAAG

FIGURE 14 (cont.)

GTCGACGCGTAAAACGTGTTTTGCGACCCGGCACCACCGTAGTCTTTACGCCCGGTGAGCGCTCCACCCGCACCTA
CAAGCGCGTGTATGATGAGGTGTACGGCGACGAGGACCTGCTTGAGCAGGCCAACGAGCGCCTCGGGGAGTTTGCC
TACGGAAAGCGGCATAAGGACATGCTGGCGTTGCCGCTGGACGAGGGCAACCCAACACCTAGCCTAAAGCCCGTAA
CACTGCAGCAGGTGCTGCCCGCGCTTGCACCGTCCGAAGAAAAGCGCGGCCTAAAGCGCGAGTCTGGTGACTTGGC
ACCCACCGTGCAGCTGATGGTACCCAAGCGCCAGCGACTGGAAGATGTCTTGGAAAAAATGACCGTGGAACCTGGG
CTGGAGCCCGAGGTCCGCGTGCGGCCAATCAAGCAGGTGGCGCCGGGACTGGGCGTGCAGACCGTGGACGTTCAGA
TACCCACTACCAGTAGCACCAGTATTGCCACCGCCACAGAGGGCATGGAGACACAAACGTCCCCGGTTGCCTCAGC
GGTGGCGGATGCCGCGGTGCAGGCGGTCGCTGCGGCCGCGTCCAAGACCTCTACGGAGGTGCAAACGGACCCGTGG
ATGTTTCGCGTTTCAGCCCCCCGGCGCCCGCGCGGTTCGAGGAAGTACGGCGCCGCCAGCGCGCTACTGCCCGAAT
ATGCCCTACATCCTTCCATTGCGCCTACCCCCGGCTATCGTGGCTACACCTACCGCCCCAGAAGACGAGCAACTAC
CCGACGCCGAACCACCACTGGAACCCGCCGCCGCCGTCGCCGTCGCCAGCCCGTGCTGGCCCCGATTTCCGTGCGC
AGGGTGGCTCGCGAAGGAGGCAGGACCCTGGTGCTGCCAACAGCGCGCTACCACCCCAGCATCGTTTAAAAGCCGG
TCTTTGTGGTTCTTGCAGATATGGCCCTCACCTGCCGCCTCCGTTTCCCGGTGCCGGGATTCCGAGGAAGAATGCA
CCGTAGGAGGGGCATGGCCGGCTACGGCCTGACGGGCGGCATGCGTCGTGCGCACCACCGGCGGCGGCGCGCGTCG
CACCGTCGCATGCGCGGCGGTATCCTGCCCCTCCTTATTCCACTGATCGCCGCGGCGATTGGCGCCGTGCCCGGAA
TTGCATCCGTGGCCTTGCAGGCGCAGAGACACTGATTAAAAACAAGTTGCATGTGGAAAAATCAAAATAAAAAGTC
TGGACTCTCACGCTCGCTTGGTCCTGTAACTATTTTGTAGAATGGAAGACATCAACTTTGCGTCTCTGGCCCCGCG
ACACGGCTCGCGCCCGTTCATGGGAAACTGGCAAGATATCGGCACCAGCAATATGAGCGGTGGCGCCTTCAGCTGG
GGCTCGCTGTGGAGCGGCATTAAAAATTTCGGTTCCACCGTTAAGAACTATGGCAGCAAGGCCTGGAACAGCAGCA
CAGGCCAGATGCTGAGGGATAAGTTGAAAGAGCAAAATTTCCAACAAAAGGTGGTAGATGGCCTGGCCTCTGGCAT
TAGCGGGGTGGTGGACCTGGCCAACCAGGCAGTGCAAAATAAGATTAACAGTAAGCTTGATCCCCGCCCTCCCGTA
GAGGAGCCTCCACCGGCCGTGGAGACAGTGTCTCCAGAGGGGCGTGGCGAAAAGCGTCCGCGCCCCGACAGGGAAG
AAACTCTGGTGACGCAAATAGACGAGCCTCCCTCGTACGAGGAGGCACTAAAGCAAGGCCTGCCCACCACCCGTCC
CATCGCGCCCATGGCTACCGGAGTGCTGGGCCAGCACACACCCGTAACGCTGGACCTGCCTCCCCCCGCCGACACC
CAGCAGAAACCTGTGCTGCCAGGCCCGACCGCCGTTGTTGTAACCCGTCCTAGCCGCGCGTCCCTGCGCCGCGCCG
CCAGCGGTCCGCGATCGTTGCGGCCCGTAGCCAGTGGCAACTGGCAAAGCACACTGAACAGCATCGTGGGTCTGGG
GGTGCAATCCCTGAAGCGCCGACGATGCTTCTGAATAGCTAACGTGTCGTATGTGTGTCATGTATGCGTCCATGTC
GCCGCCAGAGGAGCTGCTGAGCCGCCGCGCGCCCGCTTTCCAAGATGGCTACCCCTTCGATGATGCCGCAGTGGTC
TTACATGCACATCTCGGGCCAGGACGCCTCGGAGTACCTGAGCCCCGGGCTGGTGCAGTTTGCCCGCGCCACCGAG
ACGTACTTCAGCCTGAATAACAAGTTTAGAAACCCCACGGTGGCGCCTACGCACGACGTGACCACAGACCGGTCCC
AGCGTTTGACGCTGCGGTTCATCCCTGTGGACCGTGAGGATACTGCGTACTCGTACAAGGCGCGGTTCACCCTAGC
TGTGGGTGATAACCGTGTGCTGGACATGGCTTCCACGTACTTTGACATCCGCGGCGTGCTGGACAGGGGCCCTACT
TTTAAGCCCTACTCTGGCACTGCCTACAACGCCCTGGCTCCCAAGGGTGCCCCAAATCCTTGCGAATGGGATGAAG
CTGCTACTGCTCTTGAAATAAACCTAGAAGAAGAGGACGATGACAACGAAGACGAAGTAGACGAGCAAGCTGAGCA
GCAAAAAACTCACGTATTTGGGCAGGCGCCTTATTCTGGTATAAATATTACAAAGGAGGGTATTCAAATAGGTGTC
GAAGGTCAAACACCTAAATATGCCGATAAAACATTTCAACCTGAACCTCAAATAGGAGAATCTCAGTGGTACGAAA
CTGAAATTAATCATGCAGCTGGGAGAGTCCTTAAAAAGACTACCCCAATGAAACCATGTTACGGTTCATATGCAAA
ACCCACAAATGAAAATGGAGGGCAAGGCATTCTTGTAAAGCAACAAAATGGAAAGCTAGAAAGTCAAGTGGAAATG
CAATTTTTCTCAACTACTGAGGCGACCGCAGGCAATGGTGATAACTTGACTCCTAAAGTGGTATTGTACAGTGAAG
ATGTAGATATAGAAACCCCAGACACTCATATTTCTTACATGCCCACTATTAAGGAAGGTAACTCACGAGAACTAAT
GGGCCAACAATCTATGCCCAACAGGCCTAATTACATTGCTTTTAGGGACAATTTTATTGGTCTAATGTATTACAAC
AGCACGGGTAATATGGGTGTTCTGGCGGGCCAAGCATCGCAGTTGAATGCTGTTGTAGATTTGCAAGACAGAAACA
CAGAGCTTTCATACCAGCTTTTGCTTGATTCCATTGGTGATAGAACCAGGTACTTTTCTATGTGGAATCAGGCTGT
TGACAGCTATGATCCAGATGTTAGAATTATTGAAAATCATGGAACTGAAGATGAACTTCCAAATTACTGCTTTCCA
CTGGGAGGTGTGATTAATACAGAGACTCTTACCAAGGTAAAACCTAAAACAGGTCAGGAAAATGGATGGGAAAAAG
ATGCTACAGAATTTTCAGATAAAAATGAAATAAGAGTTGGAAATAATTTTGCCATGGAAATCAATCTAAATGCCAA
CCTGTGGAGAAATTTCCTGTACTCCAACATAGCGCTGTATTTGCCCGACAAGCTAAAGTACAGTCCTTCCAACGTA
AAAATTTCTGATAACCCAAACACCTACGACTACATGAACAAGCGAGTGGTGGCTCCCGGGTTAGTGGACTGCTACA
TTAACCTTGGAGCACGCTGGTCCCTTGACTATATGGACAACGTCAACCCATTTAACCACCACCGCAATGCTGGCCT
GCGCTACCGCTCAATGTTGCTGGGCAATGGTCGCTATGTGCCCTTCCACATCCAGGTGCCTCAGAAGTTCTTTGCC
ATTAAAAACCTCCTTCTCCTGCCGGGCTCATACACCTACGAGTGGAACTTCAGGAAGGATGTTAACATGGTTCTGC
AGAGCTCCCTAGGAAATGACCTAAGGGTTGACGGAGCCAGCATTAAGTTTGATAGCATTTGCCTTTACGCCACCTT
CTTCCCCATGGCCCACAACACCGCCTCCACGCTTGAGGCCATGCTTAGAAACGACACCAACGACCAGTCCTTTAAC
GACTATCTCTCCGCCGCCAACATGCTCTACCCTATACCCGCCAACGCTACCAACGTGCCCATATCCATCCCCTCCC
GCAACTGGGCGGCTTTCCGCGGCTGGGCCTTCACGCGCCTTAAGACTAAGGAAACCCCATCACTGGGCTCGGGCTA
CGACCCTTATTACACCTACTCTGGCTCTATACCCTACCTAGATGGAACCTTTTACCTCAACCACACCTTTAAGAAG
GTGGCCATTACCTTTGACTCTTCTGTCAGCTGGCCTGGCAATGACCGCCTGCTTACCCCCAACGAGTTTGAAATTA
AGCGCTCAGTTGACGGGGAGGGTTACAACGTTGCCCAGTGTAACATGACCAAAGACTGGTTCCTGGTACAAATGCT
AGCTAACTACAACATTGGCTACCAGGGCTTCTATATCCCAGAGAGCTACAAGGACCGCATGTACTCCTTCTTTAGA
AACTTCCAGCCCATGAGCCGTCAGGTGGTGGATGATACTAAATACAAGGACTACCAACAGGTGGGCATCCTACACC
AACACAACAACTCTGGATTTGTTGGCTACCTTGCCCCCACCATGCGCGAAGGACAGGCCTACCCTGCTAACTTCCC

FIGURE 14 (cont.)

CTATCCGCTTATAGGCAAGACCGCAGTTGACAGCATTACCCAGAAAAAGTTTCTTTGCGATCGCACCCTTTGGCGC
ATCCCATTCTCCAGTAACTTTATGTCCATGGGCGCACTCACAGACCTGGGCCAAAACCTTCTCTACGCCAACTCCG
CCCACGCGCTAGACATGACTTTTGAGGTGGATCCCATGGACGAGCCCACCCTTCTTTATGTTTTGTTTGAAGTCTT
TGACGTGGTCCGTGTGCACCGGCCGCACCGCGGCGTCATCGAAACCGTGTACCTGCGCACGCCCTTCTCGGCCGGC
AACGCCACAACATAAAGAAGCAAGCAACATCAACAACAGCTGCCGCCATGGGCTCCAGTGAGCAGGAACTGAAAGC
CATTGTCAAAGATCTTGGTTGTGGGCCATATTTTTTGGGCACCTATGACAAGCGCTTTCCAGGCTTTGTTTCTCCA
CACAAGCTCGCCTGCGCCATAGTCAATACGGCCGGTCGCGAGACTGGGGGCGTACACTGGATGGCCTTTGCCTGGA
ACCCGCACTCAAAAACATGCTACCTCTTTGAGCCCTTTGGCTTTTCTGACCAGCGACTCAAGCAGGTTTACCAGTT
TGAGTACGAGTCACTCCTGCGCCGTAGCGCCATTGCTTCTTCCCCCGACCGCTGTATAACGCTGGAAAAGTCCACC
CAAAGCGTACAGGGGCCCAACTCGGCCGCCTGTGGACTATTCTGCTGCATGTTTCTCCACGCCTTTGCCAACTGGC
CCCAAACTCCCATGGATCACAACCCCACCATGAACCTTATTACCGGGGTACCCAACTCCATGCTCAACAGTCCCCA
GGTACAGCCCACCCTGCGTCGCAACCAGGAACAGCTCTACAGCTTCCTGGAGCGCCACTCGCCCTACTTCCGCAGC
CACAGTGCGCAGATTAGGAGCGCCACTTCTTTTTGTCACTTGAAAAACATGTAAAAATAATGTACTAGAGACACTT
TCAATAAAGGCAAATGCTTTTATTTGTACACTCTCGGGTGATTATTTACCCCCACCCTTGCCGTCTGCGCCGTTTA
AAAATCAAAGGGGTTCTGCCGCGCATCGCTATGCGCCACTGGCAGGGACACGTTGCGATACTGGTGTTTAGTGCTC
CACTTAAACTCAGGCACAACCATCCGCGGCAGCTCGGTGAAGTTTTCACTCCACAGGCTGCGCACCATCACCAACG
CGTTTAGCAGGTCGGGCGCCGATATCTTGAAGTCGCAGTTGGGGCCTCCGCCCTGCGCGCGCGAGTTGCGATACAC
AGGGTTGCAGCACTGGAACACTATCAGCGCCGGGTGGTGCACGCTGGCCAGCACGCTCTTGTCGGAGATCAGATCC
GCGTCCAGGTCCTCCGCGTTGCTCAGGGCGAACGGAGTCAACTTTGGTAGCTGCCTTCCCAAAAAGGGCGCGTGCC
CAGGCTTTGAGTTGCACTCGCACCGTAGTGGCATCAAAAGGTGACCGTGCCCGGTCTGGGCGTTAGGATACAGCGC
CTGCATAAAAGCCTTGATCTGCTTAAAAGCCACCTGAGCCTTTGCGCCTTCAGAGAAGAACATGCCGCAAGACTTG
CCGGAAAACTGATTGGCCGGACAGGCCGCGTCGTGCACGCAGCACCTTGCGTCGGTGTTGGAGATCTGCACCACAT
TTCGGCCCCACCGGTTCTTCACGATCTTGGCCTTGCTAGACTGCTCCTTCAGCGCGCGCTGCCCGTTTTCGCTCGT
CACATCCATTTCAATCACGTGCTCCTTATTTATCATAATGCTTCCGTGTAGACACTTAAGCTCGCCTTCGATCTCA
GCGCAGCGGTGCAGCCACAACGCGCAGCCCGTGGGCTCGTGATGCTTGTAGGTCACCTCTGCAAACGACTGCAGGT
ACGCCTGCAGGAATCGCCCCATCATCGTCACAAAGGTCTTGTTGCTGGTGAAGGTCAGCTGCAACCCGCGGTGCTC
CTCGTTCAGCCAGGTCTTGCATACGGCCGCCAGAGCTTCCACTTGGTCAGGCAGTAGTTTGAAGTTCGCCTTTAGA
TCGTTATCCACGTGGTACTTGTCCATCAGCGCGCGCGCAGCCTCCATGCCCTTCTCCCACGCAGACACGATCGGCA
CACTCAGCGGGTTCATCACCGTAATTTCACTTTCCGCTTCGCTGGGCTCTTCCTCTTCCTCTTGCGTCCGCATACC
ACGCGCCACTGGGTCGTCTTCATTCAGCCGCCGCACTGTGCGCTTACCTCCTTTGCCATGCTTGATTAGCACCGGT
GGGTTGCTGAAACCCACCATTTGTAGCGCCACATCTTCTCTTTCTTCCTCGCTGTCCACGATTACCTCTGGTGATG
GCGGGCGCTCGGGCTTGGGAGAAGGGCGCTTCTTTTTCTTCTTGGGCGCAATGGCCAAATCCGCCGCCGAGGTCGA
TGGCCGCGGGCTGGGTGTGCGCGGCACCAGCGCGTCTTGTGATGAGTCTTCCTCGTCCTCGGACTCGATACGCCGC
CTCATCCGCTTTTTTGGGGGCGCCCGGGGAGGCGGCGGCGACGGGGACGGGGACGACACGTCCTCCATGGTTGGGG
GACGTCGCGCCGCACCGCGTCCGCGCTCGGGGGTGGTTTCGCGCTGCTCCTCTTCCCGACTGGCCATTTCCTTCTC
CTATAGGCAGAAAAAGATCATGGAGTCAGTCGAGAAGAAGGACAGCCTAACCGCCCCCTCTGAGTTCGCCACCACC
GCCTCCACCGATGCCGCCAACGCGCCTACCACCTTCCCCGTCGAGGCACCCCCGCTTGAGGAGGAGGAAGTGATTA
TCGAGCAGGACCCAGGTTTTGTAAGCGAAGACGACGAGGACCGCTCAGTACCAACAGAGGATAAAAAGCAAGACCA
GGACAACGCAGAGGCAAACGAGGAACAAGTCGGGCGGGGGGACGAAAGGCATGGCGACTACCTAGATGTGGGAGAC
GACGTGCTGTTGAAGCATCTGCAGCGCCAGTGCGCCATTATCTGCGACGCGTTGCAAGAGCGCAGCGATGTGCCCC
TCGCCATAGCGGATGTCAGCCTTGCCTACGAACGCCACCTATTCTCACCGCGCGTACCCCCCAAACGCCAAGAAAA
CGGCACATGCGAGCCCAACCCGCGCCTCAACTTCTACCCCGTATTTGCCGTGCCAGAGGTGCTTGCCACCTATCAC
ATCTTTTTCCAAAACTGCAAGATACCCCTATCCTGCCGTGCCAACCGCAGCCGAGCGGACAAGCAGCTGGCCTTGC
GGCAGGGCGCTGTCATACCTGATATCGCCTCGCTCAACGAAGTGCCAAAAATCTTTGAGGGTCTTGGACGCGACGA
GAAGCGCGCGGCAAACGCTCTGCAACAGGAAAACAGCGAAAATGAAAGTCACTCTGGAGTGTTGGTGGAACTCGAG
GGTGACAACGCGCGCCTAGCCGTACTAAAACGCAGCATCGAGGTCACCCACTTTGCCTACCCGGCACTTAACCTAC
CCCCCAAGGTCATGAGCACAGTCATGAGTGAGCTGATCGTGCGCCGTGCGCAGCCCCTGGAGAGGGATGCAAATTT
GCAAGAACAAACAGAGGAGGGCCTACCCGCAGTTGGCGACGAGCAGCTAGCGCGCTGGCTTCAAACGCGCGAGCCT
GCCGACTTGGAGGAGCGACGCAAACTAATGATGGCCGCAGTGCTCGTTACCGTGGAGCTTGAGTGCATGCAGCGGT
TCTTTGCTGACCCGGAGATGCAGCGCAAGCTAGAGGAAACATTGCACTACACCTTTCGACAGGGCTACGTACGCCA
GGCCTGCAAGATCTCCAACGTGGAGCTCTGCAACCTGGTCTCCTACCTTGGAATTTTGCACGAAAACCGCCTTGGG
CAAAACGTGCTTCATTCCACGCTCAAGGGCGAGGCGCGCCGCGACTACGTCCGCGACTGCGTTTACTTATTTCTAT
GCTACACCTGGCAGACGGCCATGGGCGTTTGGCAGCAGTGCTTGGAGGAGTGCAACCTCAAGGAGCTGCAGAAACT
GCTAAAGCAAAACTTGAAGGACCTATGGACGGCCTTCAACGAGCGCTCCGTGGCCGCGCACCTGGCGGACATCATT
TTCCCCGAACGCCTGCTTAAAACCCTGCAACAGGGTCTGCCAGACTTCACCAGTCAAAGCATGTTGCAGAACTTTA
GGAACTTTATCCTAGAGCGCTCAGGAATCTTGCCCGCCACCTGCTGTGCACTTCCTAGCGACTTTGTGCCCATTAA
GTACCGCGAATGCCCTCCGCCGCTTTGGGGCCACTGCTACCTTCTGCAGCTAGCCAACTACCTTGCCTACCACTCT
GACATAATGGAAGACGTGAGCGGTGACGGTCTACTGGAGTGTCACTGTCGCTGCAACCTATGCACCCCGCACCGCT
CCCTGGTTTGCAATTCGCAGCTGCTTAACGAAAGTCAAATTATCGGTACCTTTGAGCTGCAGGGTCCCTCGCCTGA
CGAAAAGTCCGCGGCTCCGGGGTTGAAACTCACTCCGGGGCTGTGGACGTCGGCTTACCTTCGCAAATTTGTACCT
GAGGACTACCACGCCCACGAGATTAGGTTCTACGAAGACCAATCCCGCCCGCCAAATGCGGAGCTTACCGCCTGCG

FIGURE 14 (cont.)

TCATTACCCAGGGCCACATTCTTGGCCAATTGCAAGCCATCAACAAAGCCCGCCAAGAGTTTCTGCTACGAAAGGG
ACGGGGGGTTTACTTGGACCCCCAGTCCGGCGAGGAGCTCAACCCAATCCCCCCGCCGCCGCAGCCCTATCAGCAG
CAGCCGCGGGCCCTTGCTTCCCAGGATGGCACCCAAAAAGAAGCTGCAGCTGCCGCCGCCACCCACGGACGAGGAG
GAATACTGGGACAGTCAGGCAGAGGAGGTTTTGGACGAGGAGGAGGAGGACATGATGGAAGACTGGGAGAGCCTAG
ACGAGGAAGCTTCCGAGGTCGAAGAGGTGTCAGACGAAACACCGTCACCCTCGGTCGCATTCCCCTCGCCGGCGCC
CCAGAAATCGGCAACCGGTTCCAGCATGGCTACAACCTCCGCTCCTCAGGCGCCGCCGGCACTGCCCGTTCGCCGA
CCCAACCGTAGATGGGACACCACTGGAACCAGGGCCGGTAAGTCCAAGCAGCCGCCGCCGTTAGCCCAAGAGCAAC
AACAGCGCCAAGGCTACCGCTCATGGCGCGGGCACAAGAACGCCATAGTTGCTTGCTTGCAAGACTGTGGGGGCAA
CATCTCCTTCGCCCGCCGCTTTCTTCTCTACCATCACGGCGTGGCCTTCCCCCGTAACATCCTGCATTACTACCGT
CATCTCTACAGCCCATACTGCACCGGCGGCAGCGGCAGCGGCAGCAACAGCAGCGGCCACACAGAAGCAAAGGCGA
CCGGATAGCAAGACTCTGACAAAGCCCAAGAAATCCACAGCGGCGGCAGCAGCAGGAGGAGGAGCGCTGCGTCTGG
CGCCCAACGAACCCGTATCGACCCGCGAGCTTAGAAACAGGATTTTTCCCACTCTGTATGCTATATTTCAACAGAG
CAGGGGCCAAGAACAAGAGCTGAAAATAAAAAACAGGTCTCTGCGATCCCTCACCCGCAGCTGCCTGTATCACAAA
AGCGAAGATCAGCTTCGGCGCACGCTGGAAGACGCGGAGGCTCTCTTCAGTAAATACTGCGCGCTGACTCTTAAGG
ACTAGTTTCGCGCCCTTTCTCAAATTTAAGCGCGAAAACTACGTCATCTCCAGCGGCCACACCCGGCGCCAGCACC
TGTCGTCAGCGCCATTATGAGCAAGGAAATTCCCACGCCCTACATGTGGAGTTACCAGCCACAAATGGGACTTGCG
GCTGGAGCTGCCCAAGACTACTCAACCCGAATAAACTACATGAGCGCGGGACCCCACATGATATCCCGGGTCAACG
GAATCCGCGCCCACCGAAACCGAATTCTCTTGGAACAGGCGGCTATTACCACCACACCTCGTAATAACCTTAATCC
CCGTAGTTGGCCCGCTGCCCTGGTGTACCAGGAAAGTCCCGCTCCCACCACTGTGGTACTTCCCAGAGACGCCCAG
GCCGAAGTTCAGATGACTAACTCAGGGGCGCAGCTTGCGGGCGGCTTTCGTCACAGGGTGCGGTCGCCCGGGCAGG
GTATAACTCACCTGACAATCAGAGGGCGAGGTATTCAGCTCAACGACGAGTCGGTGAGCTCCTCGCTTGGTCTCCG
TCCGGACGGGACATTTCAGATCGGCGGCGCCGGCCGTCCTTCATTCACGCCTCGTCAGGCAATCCTAACTCTGCAG
ACCTCGTCCTCTGAGCCGCGCTCTGGAGGCATTGGAACTCTGCAATTTATTGAGGAGTTTGTGCCATCGGTCTACT
TTAACCCCTTCTCGGGACCTCCCGGCCACTATCCGGATCAATTTATTCCTAACTTTGACGCGGTAAAGGACTCGGC
GGACGGCTACGACTGAATGTTAAGTGGAGAGGCAGAGCAACTGCGCCTGAAACACCTGGTCCACTGTCGCCGCCAC
AAGTGCTTTGCCCGCGACTCCGGTGAGTTTTGCTACTTTGAATTGCCCGAGGATCATATCGAGGGCCCGGCGCACG
GCGTCCGGCTTACCGCCCAGGGAGAGCTTGCCCGTAGCCTGATTCGGGAGTTTACCCAGCGCCCCCTGCTAGTTGA
GCGGGACAGGGGACCCTGTGTTCTCACTGTGATTTGCAACTGTCCTAACCTTGGATTACATCAAGATCCTCTAGTT
AATTAACAGCTTGCATGCCTGCAGGTCGACGGATCGGGAGATCTCGGCCGCATATTAAGTGCATTGTTCTCGATAC
CGCTAAGTGCATTGTTCTCGTTAGCTCGATGGACAAGTGCATTGTTCTCTTGCTGAAAGCTCGATGGACAAGTGCA
TTGTTCTCTTGCTGAAAGCTCGATGGACAAGTGCATTGTTCTCTTGCTGAAAGCTCAGTACCCGGGAGTACCCTCG
ACCGCCGGAGTATAAATAGAGGCGCTTCGTCTACGGAGCGACAATTCAATTCAAACAAGCAAAGTGAACACGTCGC
TAAGCGAAAGCTAAGCAAATAAACAAGCGCAGCTGAACAAGCTAAACAATCTGCAGTAAAGTGCAAGTTAAAGTGA
ATCAATTAAAAGTAACCAGCAACCAAGTAAATCAACTGCAACTACTGAAATCTGCCAAGAAGTAATTATTGAATAC
AAGAAGAGAACTCTGAATACTTTCAACAAGTTACCGAGAAAGAAGAACTCACACACAGCTAGCGTTTAAACTTAAG
CTTCACCATGGTGGGGCCCTGCATGCTGCTGCTGCTGCTGCTGCTGGGCCTGAGGCTACAGCTCTCCCTGGGCATC
ATCCTAGTTGAGGAGGAGAACCCGGACTTCTGGAACCGCGAGGCAGCCGAGGCCCTGGGTGCCGCCAAGAAGCTGC
AGCCTGCACAGACAGCCGCCAAGAACCTCATCATCTTCCTGGGCGATGGGGTGGGGGTGTCTACGGTGACAGCTGC
CAGGATCCTAAAAGGGCAGAAGAAGGACAAACTGGGGCCTGAGATACCCCTGGCCATGGACCGCTTCCCATATGTG
GCTCTGTCCAAGACATACAATGTAGACAAACATGTGCCAGACAGTGGAGCCACAGCCACGGCCTACCTGTGCGGGG
TCAAGGGCAACTTCCAGACCATTGGCTTGAGTGCAGCCGCCCGCTTTAACCAGTGCAACACGACACGCGGCAACGA
GGTCATCTCCGTGATGAATCGGGCCAAGAAAGCAGGGAAGTCAGTGGGAGTGGTAACCACCACACGAGTGCAGCAC
GCCTCGCCAGCCGGCACCTACGCCCACACGGTGAACCGCAACTGGTACTCGGACGCCGACGTGCCTGCCTCGGCCC
GCCAGGAGGGGTGCCAGGACATCGCTACGCAGCTCATCTCCAACATGGACATTGACGTGATCCTAGGTGGGGGCCG
AAAGTACATGTTTCGCATGGGAACCCCAGACCCTGAGTACCCAGATGACTACAGCCAAGGTGGGACCAGGCTGGAC
GGGAAGAATCTGGTGCAGGAATGGCTGGCGAAGCACCAGGGTGCCCGGTACGTGTGGAACCGCACTGAGCTCATGC
GGGCTTCCCTGGACCCGTCTGTGGCCCATCTCATGGGTCTCTTTGAGCCTGGAGACATGAAATACGAGATCCACCG
AGACTCCACACTGGACCCCTCCCTGATGGAGATGACAGAGGCTGCCCTGCGCCTGCTGAGCAGGAACCCCCGCGGC
TTCTTCCTCTTCGTGGAGGGTGGTCGCATCGACCATGGTCATCATGAAAGCAGGGCTTACCGGGCACTGACTGAGA
CGATCATGTTCGACGACGCCATTGAGAGGGCGGGCCAGCTCACCAGCGAGGAGGACACGCTGAGCCTCGTCACTGC
CGACCACTCCCACGTCTTCTCCTTCGGAGGCTGCCCCCTGCGAGGGGGCTCCATCTTCGGGCTGGCCCCTGGCAAG
GCCCGGGACAGGAAGGCCTACACGGTCCTCCTATACGGAAACGGTCCAGGCTATGTGCTCAAGGACGGCGCCCGGC
CGGATGTTACCGAGAGCGAGAGCGGGAGCCCCGAGTATCGGCAGCAGTCAGCAGTGCCCCTGGACGAAGAGACCCA
CGCAGGCGAGGACGTGGCGGTGTTCGCGCGCGGCCCGCAGGCGCACCTGGTTCACGGCGTGCAGGAGCAGACCTTC
ATAGCGCACGTCATGGCCTTCGCCGCCTGCCTGGAGCCCTACACCGCCTGCGACCTGGCGCCCCCCGCCGGCACCA
CCGACGCCGCGCACCCGGGGCGGTCCGTGGTCCCCGCGTTGCTTCCTCTGCTGGCCGGGACCCTGCTGCTGCTGGA
GACGGCCACTGCTCCCTGAGTGTCCCGTCCCTGGGGCTCCTGCTTCCCCATCCCGGAGTTCTCCTGCTCCCCGCCT
CCTGTCGTCCTGCCTGGCCTCCAGCCCGAGTCGTCATCCCCGGAGTCCCTATACAGAGGTCCTGCCATGGAACCTT
CCCCTCCCCGTGCGCTCTGGGGACTGAGCCCATGACACCAAACCTGCCCCTTGGCTGCTCTCGGACTCCCTACCCC
AACCCCAGGGACAGATCTGGCCAGATTTGTAAAACAAATAGATTTTAGGCCCAAAGATTATTTAAAGCATTGCCTG
GAACGCAGTGAGTTTTTGTTAGAAAAGAGAATAATTCAAAGTGGCATTGCTTTGCTTCTTATGTTAATTTGGTACA

FIGURE 14 (cont.)

GACCTGTGGCTGAGTTTGCTCAAAGTATTCAGAGCAGAATTGTGGAGTGGAAAGAGAGATTGGACAAAGAGTTTAG
TTTGTCAGTGTATCAAAAAATGAAGTTTAATGTGGCTATGGAATTGGAGTTTTAGATTGGCTAAGAAACAGTGAT
GATGATGATGAAGACAGCCAGGAAAATGCTGATAAAAATGAAGATGGTGGGGAGAAGAACATGGAAGACTCAGGGC
ATGAAACAGGCATTGATTCACAGTCCCAAGGCTCATTTCAGGCCCCTCAGTCCTCACAGTCTGTTCATGATCATAA
TCAGCCATACCACATTTGTAGAGGTTTTACTTGCTTTAAAAAACCTCCCACACCTCCCCCTGAACCTGAAACATAA
AATGAATGCAATTGTTGTTGTTAACTTGTTTATTGCAGCTTATAATGGTTACAAATAAAGCAATAGCATCACAAAT
TTCACAAATAAAGCATTTTTTTCACTGCATTCTAGTTGTGGTTTGTCCAAACTCATCAATGTATCTTATCATGTCT
GGATCCCCAGGAAGCTCCTCTGTGTCCTCATAAACCCTAACCTCCTCTACTTGAGAGGACATTCCAATCATAGGCT
GCCCATCCACCCTCTGTGTCCTCCTGTTAATTAGGTCACTTAACAAAAAGGAAATTGGGTAGGGGTTTTTCACAGA
CCGCTTTCTAAGGGTAATTTTAAAATATCTGGGAAGTCCCTTCCACTGCTGTGTTCCAGAAGTGTTGGTAAACAGC
CCACAAATGTCAACAGCAGAAACATACAAGCTGTCAGCTTTGCACAAGGGCCCAACACCCTGCTCATCAAGAAGCA
CTGTGGTTGCTGTGTTAGTAATGTGCAAAACAGGAGGCACATTTTCCCCACCTGTGTAGGTTCCAAAATATCTAGT
GTTTTCATTTTTACTTGGATCAGGAACCCAGCACTCCACTGGATAAGCATTATCCTTATCCAAAACAGCCTTGTGG
TCAGTGTTCATCTGCTGACTGTCAACTGTAGCATTTTTTGGGGTTACAGTTTGAGCAGGATATTTGGTCCTGTAGT
TTGCTAACACACCCTGCAGCTCCAAAGGTTCCCCACCAACAGCAAAAAAATGAAAATTTGACCCTTGAATGGGTTT
TCCAGCACCATTTTCATGAGTTTTTTGTGTCCCTGAATGCAAGTTTAACATAGCAGTTACCCCAATAACCTCAGTT
TTAACAGTAACAGCTTCCCACATCAAAATATTTCCACAGGTTAAGTCCTCATTTAAATTAGGCAAAGGAATTCCAC
TTCCCACTGCCTTGCTTCCGTCTCCCATTCAAACTTTTATCAACTGACATTATTCTAAGTAAAATCCTCTTCATTA
TGTTGTCAGCAATCCATTGCTTGAAGGCCTGGCTCCCCAGAACCCCTCGACTGGTATGTCTTCTCCTAGAATACTC
CAGAAGAAAAGGAGTGTATGAAGATAGTGACTGCACATTAAAATGACTGAAACCATAGTAAATTAGGATGAGATTC
TGGGCAGATAAACAGACAGCTGGCTAGGATCATTTTTTTATGCCTTGGACTTCTTTGGCAATCTGTTGAAGCCTGA
CATTCCTCAGAATAATGTTTTAAAGCCCAACAATAAGACCCTGTAGCACATATAATAAGTACTGCAGTTTTGAAGT
AGTGATAAGCATAAATGATATTTTGATATATTTATTATAACTGTAATGAGATGTGTACATATCTGTGACTTCATAG
GTACTGATTGTACTACTGTGATTTTTTTGCCTACTTTCAAAATGAAAAGGAATGCTTAATTTCAGTTAGAGGTTAG
TAAAGACAAATAGGTAATTTTCTTCTCCAGTGAAGAGCATGGCGCCCCTTGCTATTCATGGACGCTTGCTTAAAGA
CTTGTACACAGGCTTGCTTTGTATCAACCTATGACTTCCCCTTACAGCCGATGATAGGTTTTTATTTGCACCTCCT
TCGTGTACAAAGACAGTTTTGGTGGCTACGCCATCATTAAACTCATTATTATCATGCTTAAGCCTATAGATGTATC
CAGTTCTTCTGTTACATAATTGAAGCTGTAGTGAATTGTCTATCTTAAACTGCATCGCTAACTGACTACATTTCAC
ACTTCATTTGCTTCCAACATAGACTAACCTTCTTGGATGTCCACTATTATTTGAACTTTTGAGATTTTTTTTCCTA
TTTCTAATATCTTAAAATTTCAGAAGACTTAAAGTTTTGCAACTACAGGGCTCCATATAGACATCTAGCTTGAATT
TATACACTTTCTTTCATTGATGTCCCTGGACTAAAAAATGTTAAATATTTCTAACCGCTGTACTTAAAGTCCATTA
CAAACGAAGACTACTGTTGTTAAGTTGAATAGGCATCTTATATATTTTTCACCGGTGCAATAAATAACTTCTATTC
CCTTCTAACATCTGCTTGCGTTGCACTGAGAGTACACTATTGATTAGCAATAGGTTCGTGATTACAGCCCTTCTAT
AATTAATTGTTAGGTTAACATATTATTCATAAAATATTATTTTATTAATTTTTACTTGATTTGCTACTGGATGCTT
AGAAATAGCTATGAGTATATTGGTAGAACCAGTACTTATATTTTATTACATTTTTACATTTCATAAAATTTAAGTG
ATATAAAAATCCTGAGGAAGTATGCCACAAAAGTGGTCTCAGTGGAAATTTAAATATGTTAACATTTATTTTTAAA
ATGTAGCGTGAAATAGACAACTTTAAAAGCTCAGCTTAAAAAAAAAACTCAAGGAAGCTGAACTTGACTTTTTAAA
GCACTGAAGTGCAATATTTAATGTAGGTCAACATGTTTAAATGGGAAAATTTTTTTCCTAATTACAGCCAAATCCC
TAGCTGTAATTAACTTAAAATTTGTATACTATTTCACAACAGAGTCAGCATATACCACTTTCTTATAAAATTAGAA
AGATCTAAAATTTTAGAGCTTATTTGGTGAAACAGGCATATTGCTACATCTTTGTTTATAAATTATAATGTGCCTT
TAGAGCCCAATAACAGATAACAAGATTTTGAAAATTCAGGTGAATTAGAGTTATCAGAGGGAATGTTAATACACTC
TATTCAAATACTATATGAGTAAGACATTTAAAATAGGAAACAATACTTTATATATTAAAAAAAATTAATCTTCCAG
TCGATTTAATCCACTTTATGAATTCATTTAAATCGATTTAAATTCGAATTAATTAACTAGAGTACCCGGGGATCTT
ATTCCCTTTAACTAATAAAAAAAAAATAATAAAGCATCACTTACTTAAAATCAGTTAGCAAATTTCTGTCCAGTTTA
TTCAGCAGCACCTCCTTGCCCTCCTCCCAGCTCTGGTATTGCAGCTTCCTCCTGGCTGCAAACTTTCTCCACAATC
TAAATGGAATGTCAGTTTCCTCCTGTTCCTGTCCATCCGCACCCACTATCTTCATGTTGTTGCAGATGAAGCGCGC
AAGACCGTCTGAAGATACCTTCAACCCCGTGTATCCATATGACACGGAAACCGGTCCTCCAACTGTGCCTTTTCTT
ACTCCTCCCTTTGTATCCCCCAATGGGTTTCAAGAGAGTCCCCCTGGGGTACTCTCTTTGCGCCTATCCGAACCTC
TAGTTACCTCCAATGGCATGCTTGCGCTCAAAATGGGCAACGGCCTCTCTCTGGACGAGGCCGGCAACCTTACCTC
CCAAAATGTAACCACTGTGAGCCCACCTCTCAAAAAAACCAAGTCAAACATAAACCTGGAAATATCTGCACCCCTC
ACAGTTACCTCAGAAGCCCTAACTGTGGCTGCCGCCGCACCTCTAATGGTCGCGGGCAACACACTCACCATGCAAT
CACAGGCCCCGCTAACCGTGCACGACTCCAAACTTAGCATTGCCACCCAAGGACCCCTCACAGTGTCAGAAGGAAA
GCTAGCCCTGCAAACATCAGGCCCCCTCACCACCACCGATAGCAGTACCCTTACTATCACTGCCTCACCCCCTCTA
ACTACTGCCACTGGTAGCTTGGGCATTGACTTGAAAGAGCCCATTTATACACAAAATGGAAAACTAGGACTAAAGT
ACGGGGCTCCTTTGCATGTAACAGACGACCTAAACACTTTGACCGTAGCAACTGGTCCAGGTGTGACTATTAATAA
TACTTCCTTGCAAACTAAAGTTACTGGAGCCTTGGGTTTTGATTCACAAGGCAATATGCAACTTAATGTAGCAGGA
GGACTAAGGATTGATTCTCAAAACAGACGCCTTATACTTGATGTTAGTTATCCGTTTGATGCTCAAAACCAACTAA
ATCTAAGACTAGGACAGGGCCCTCTTTTTATAAACTCAGCCCACAACTTGGATATTAACTACAACAAAGGCCTTTA
CTTGTTTACAGCTTCAAACAATTCCAAAAAGCTTGAGGTTAACCTAAGCACTGCCAAGGGGTTGATGTTTGACGCT
ACAGCCATAGCCATTAATGCAGGAGATGGGCTTGAATTTGGTTCACCTAATGCACCAAACACAAATCCCCTCAAAA
CAAAAATTGGCCATGGCCTAGAATTTGATTCAAACAAGGCTATGGTTCCTAAACTAGGAACTGGCCTTAGTTTGA

FIGURE 14 (cont.)

CAGCACAGGTGCCATTACAGTAGGAAACAAAAATAATGATAAGCTAACTTTGTGGACCACACCAGCTCCATCTCCT
AACTGTAGACTAAATGCAGAGAAAGATGCTAAACTCACTTTGGTCTTAACAAAATGTGGCAGTCAAATACTTGCTA
CAGTTTCAGTTTTGGCTGTTAAAGGCAGTTTGGCTCCAATATCTGGAACAGTTCAAAGTGCTCATCTTATTATAAG
ATTTGACGAAAATGGAGTGCTACTAAACAATTCCTTCCTGGACCCAGAATATTGGAACTTTAGAAATGGAGATCTT
ACTGAAGGCACAGCCTATACAAACGCTGTTGGATTTATGCCTAACCTATCAGCTTATCCAAAATCTCACGGTAAAA
CTGCCAAAAGTAACATTGTCAGTCAAGTTTACTTAAACGGAGACAAAACTAAACCTGTAACACTAACCATTACACT
AAACGGTACACAGGAAACAGGAGACACAACTCCAAGTGCATACTCTATGTCATTTTCATGGGACTGGTCTGGCCAC
AACTACATTAATGAAATATTTGCCACATCCTCTTACACTTTTTCATACATTGCCCAAGAATAAAGAATCGTTTGTG
TTATGTTTCAACGTGTTTATTTTTCAATTGCAGAAAATTTCAAGTCATTTTTCATTCAGTAGTATAGCCCCACCAC
CACATAGCTTATACAGATCACCGTACCTTAATCAAACTCACAGAACCCTAGTATTCAACCTGCCACCTCCCTCCCA
ACACACAGAGTACACAGTCCTTTCTCCCCGGCTGGCCTTAAAAAGCATCATATCATGGGTAACAGACATATTCTTA
GGTGTTATATTCCACACGGTTTCCTGTCGAGCCAAACGCTCATCAGTGATATTAATAAACTCCCCGGGCAGCTCAC
TTAAGTTCATGTCGCTGTCCAGCTGCTGAGCCACAGGCTGCTGTCCAACTTGCGGTTGCTTAACGGGCGGCGAAGG
AGAAGTCCACGCCTACATGGGGGTAGAGTCATAATCGTGCATCAGGATAGGGCGGTGGTGCTGCAGCAGCGCGCGA
ATAAACTGCTGCCGCCGCCGCTCCGTCCTGCAGGAATACAACATGGCAGTGGTCTCCTCAGCGATGATTCGCACCG
CCCGCAGCATAAGGCGCCTTGTCCTCCGGGCACAGCAGCGCACCCTGATCTCACTTAAATCAGCACAGTAACTGCA
GCACAGCACCACAATATTGTTCAAAATCCCACAGTGCAAGGCGCTGTATCCAAAGCTCATGGCGGGGACCACAGAA
CCCACGTGGCCATCATACCACAAGCGCAGGTAGATTAAGTGGCGACCCCTCATAAACACGCTGGACATAAACATTA
CCTCTTTTGGCATGTTGTAATTCACCACCTCCCGGTACCATATAAACCTCTGATTAAACATGGCGCCATCCACCAC
CATCCTAAACCAGCTGGCCAAAACCTGCCCGCCGGCTATACACTGCAGGGAACCGGGACTGGAACAATGACAGTGG
AGAGCCCAGGACTCGTAACCATGGATCATCATGCTCGTCATGATATCAATGTTGGCACAACACAGGCACACGTGCA
TACACTTCCTCAGGATTACAAGCTCCTCCCGCGTTAGAACCATATCCCAGGGAACAACCCATTCCTGAATCAGCGT
AAATCCCACACTGCAGGGAAGACCTCGCACGTAACTCACGTTGTGCATTGTCAAAGTGTTACATTCGGGCAGCAGC
GGATGATCCTCCAGTATGGTAGCGCGGGTTTCTGTCTCAAAAGGAGGTAGACGATCCCTACTGTACGGAGTGCGCC
GAGACAACCGAGATCGTGTTGGTCGTAGTGTCATGCCAAATGGAACGCCGGACGTAGTCATATTTCCTGAAGCAAA
ACCAGGTGCGGGCGTGACAAACAGATCTGCGTCTCCGGTCTCGCCGCTTAGATCGCTCTGTGTAGTAGTTGTAGTA
TATCCACTCTCTCAAAGCATCCAGGCGCCCCCTGGCTTCGGGTTCTATGTAAACTCCTTCATGCGCCGCTGCCCTG
ATAACATCCACCACCGCAGAATAAGCCACACCCAGCCAACCTACACATTCGTTCTGCGAGTCACACACGGGAGGAG
CGGGAAGAGCTGGAAGAACCATGTTTTTTTTTTTATTCCAAAAGATTATCCAAAACCTCAAAATGAAGATCTATTA
AGTGAACGCGCTCCCCTCCGGTGGCGTGGTCAAACTCTACAGCCAAAGAACAGATAATGGCATTTGTAAGATGTTG
CACAATGGCTTCCAAAAGGCAAACGGCCCTCACGTCCAAGTGGACGTAAAGGCTAAACCCTTCAGGGTGAATCTCC
TCTATAAACATTCCAGCACCTTCAACCATGCCCAAATAATTCTCATCTCGCCACCTTCTCAATATATCTCTAAGCA
AATCCCGAATATTAAGTCCGGCCATTGTAAAAATCTGCTCCAGAGCGCCCTCCACCTTCAGCCTCAAGCAGCGAAT
CATGATTGCAAAAATTCAGGTTCCTCACAGACCTGTATAAGATTCAAAAGCGGAACATTAACAAAAATACCGCGAT
CCCGTAGGTCCCTTCGCAGGGCCAGCTGAACATAATCGTGCAGGTCTGCACGGACCAGCGCGGCCACTTCCCCGCC
AGGAACCTTGACAAAAGAACCCACACTGATTATGACACGCATACTCGGAGCTATGCTAACCAGCGTAGCCCCGATG
TAAGCTTTGTTGCATGGGCGGCGATATAAAATGCAAGGTGCTGCTCAAAAAATCAGGCAAAGCCTCGCGCAAAAAA
GAAAGCACATCGTAGTCATGCTCATGCAGATAAAGGCAGGTAAGCTCCGGAACCACCACAGAAAAAGACACCATTT
TTCTCTCAAACATGTCTGCGGGTTTCTGCATAAACACAAAATAAAATAACAAAAAAACATTTAAACATTAGAAGCC
TGTCTTACAACAGGAAAAACAACCCTTATAAGCATAAGACGGACTACGGCCATGCCGGCGTGACCGTAAAAAAACT
GGTCACCGTGATTAAAAAGCACCACCGACAGCTCCTCGGTCATGTCCGGAGTCATAATGTAAGACTCGGTAAACAC
ATCAGGTTGATTCATCGGTCAGTGCTAAAAAGCGACCGAAATAGCCCGGGGGAATACATACCCGCAGGCGTAGAGA
CAACATTACAGCCCCCATAGGAGGTATAACAAAATTAATAGGAGAGAAAAACACATAAACACCTGAAAAACCCTCC
TGCCTAGGCAAAATAGCACCCTCCCGCTCCAGAACAACATACAGCGCTTCACAGCGGCAGCCTAACAGTCAGCCTT
ACCAGTAAAAAAGAAAACCTATTAAAAAAACACCACTCGACACGGCACCAGCTCAATCAGTCACAGTGTAAAAAAG
GGCCAAGTGCAGAGCGAGTATATATAGGACTAAAAAATGACGTAACGGTTAAAGTCCACAAAAAACACCCAGAAAA
CCGCACGCGAACCTACGCCCAGAAACGAAAGCCAAAAAACCCACAACTTCCTCAAATCGTCACTTCCGTTTTCCCA
CGTTACGTAACTTCCCATTTTAAGAAAACTACAATTCCCAACACATACAAGTTACTCCGCCCTAAAACCTACGTCA
CCCGCCCCGTTCCCACGCCCCGCGCCACGTCACAAACTCCACCCCCTCATTATCATATTGGCTTCAATCCAAAATA
AGGTATATTATTGATGATGGCCGGCCGAATTGAATCAGGGGATAACGCAGGAAAGAACATGTGAGCAAAAGGCCAG
CAAAAGGCCAGGAACCGTAAAAAGGCCGCGTTGCTGGCGTTTTTCCATAGGCTCCGCCCCCCTGACGAGCATCACA
AAAATCGACGCTCAAGTCAGAGGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCTCCAAGCTGGGCTGTGTGCACGAAC
CCCCCGTTCAGCCCGACCGCTGCGCCTTATCCGGTAACTATCGTCTTGAGTCCAACCCGGTAAGACACGACTTATC
GCCACTGGCAGCAGCCACTGGTAACAGGATTAGCAGAGCGAGGTATGTAGGCGGTGCTACAGAGTTCTTGAAGTGG
TGGCCTAACTACGGCTACACTAGAAGGACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTTTTTTTGTTTGCAAGCAGCAGATTAC
GCGCAGAAAAAAAGGATCTCAAGAAGATCCTTTGATCTTTTCTACGGGGTCTGACGCTCAGTGGAACGAAAACTCA
CGTTAAGGGATTTTGGTCATGAGATTATCAAAAAGGATCTTCACCTAGATCCTTTTAAATTAAAAATGAAGTTTTA
AATCAATCTAAAGTATATATGAGTAAACTTGGTCTGACAGTTACCAATGCTTAATCAGTGAGGCACCTATCTCAGC

FIGURE 14 (cont.)

GATCTGTCTATTTCGTTCATCCATAGTTGCCTGACTCCCCGTCGTGTAGATAACTACGATACGGGAGGGCTTACCA
TCTGGCCCCAGTGCTGCAATGATACCGCGAGACCCACGCTCACCGGCTCCAGATTTATCAGCAATAAACCAGCCAG
CCGGAAGGGCCGAGCGCAGAAGTGGTCCTGCAACTTTATCCGCCTCCATCCAGTCTATTAATTGTTGCCGGGAAGC
TAGAGTAAGTAGTTCGCCAGTTAATAGTTTGCGCAACGTTGTTGCCATTGCTACAGGCATCGTGGTGTCACGCTCG
TCGTTTGGTATGGCTTCATTCAGCTCCGGTTCCCAACGATCAAGGCGAGTTACATGATCCCCCATGTTGTGCAAAA
AAGCGGTTAGCTCCTTCGGTCCTCCGATCGTTGTCAGAAGTAAGTTGGCCGCAGTGTTATCACTCATGGTTATGGC
AGCACTGCATAATTCTCTTACTGTCATGCCATCCGTAAGATGCTTTTCTGTGACTGGTGAGTACTCAACCAAGTCA
TTCTGAGAATAGTGTATGCGGCGACCGAGTTGCTCTTGCCCGGCGTCAATACGGGATAATACCGCGCCACATAGCA
GAACTTTAAAAGTGCTCATCATTGGAAAACGTTCTTCGGGGCGAAAACTCTCAAGGATCTTACCGCTGTTGAGATC
CAGTTCGATGTAACCCACTCGTGCACCCAACTGATCTTCAGCATCTTTTACTTTCACCAGCGTTTCTGGGTGAGCA
AAAACAGGAAGGCAAAATGCCGCAAAAAAGGGAATAAGGGCGACACGGAAATGTTGAATACTCATACTCTTCCTTT
TTCAATATTATTGAAGCATTTATCAGGGTTATTGTCTCATGAGCGGATACATATTTGAATGTATTTAGAAAAATAA
ACAAATAGGGGTTCCGCGCACATTTCCCCGAAAAGTGCCAC

FIGURE 15 pD1962delBbsI-pIX (SEQ ID NO:14)

TCTAGAGTCGACCGGTCATGGCTGCGCCCCGACACCCGCCAACACCCGCTGACGCGCCCTGACGGGCTTGTCTGCT
CCCGGCATCCGCTTACAGACAAGCTGTGACCGTCTCCGGGAGCTGCATGTGTCAGAGGTTTTCACCGTCATCACCG
AAACGCGCGAGGCAGCCGGATCATAATCAGCCATACCACATTTGTAGAGGTTTTACTTGCTTTAAAAAACCTCCCC
ACCTCCCCCTGAACCTGAAACATAAAATGAATGCAATTGTTGTTGTTAACTTGTTTATTGCAGCTTATAATGGTTA
CAAATAAAGCAATAGCATCACAAATTTCACAAATAAAGCATTTTTTTCACTGCATTCTAGTTGTGGTTTGTCCAAA
CTCATCAATGTATCTTATCATGTCTGGATCCAGTTCGATGTAACCCACTCGTGCACCCAACTGATCTTCAGCATCT
TTTACTTTCACCAGCGTTTCTGGGTGAGCAAAAACAGGAAGGCAAAATGCCGCAAAAAAGGGAATAAGGGCGACAC
GGAAATGTTGAATACTCATACTCTTCCTTTTTCAATATTATTGAAGCATTTATCAGGGTTATTGTCTCATGAGCGG
ATACATATTTGAATGTATTTAGAAAAATAAACAAATAGGGGTTCCGCGCACATTTCCCCGAAAAGTGCCACCTGAC
GTCCATTGTTCATTCCACGGACAAAAACAGAGAAAGGAAACGACAGAGGCCAAAAAGCCTCGCTTTCAGCACCTGT
CGTTTCCTTTCTTTTCAGAGGGTATTTTAAATAAAAACATTAAGTTATGACGAAGAAGAACGGAAACGCCTTAAAC
CGGAAAATTTTCATAAATAGCGAAAACCCGCGAGGTCGCCGCCCCGTAACCTGTCGGATCACCGGAAAGGACCCGT
AAAGTGATAATGATTATCATCTAGACTACATCGATGGGTCGTGCGCTCCTTTCGGTCGGGCGCTGCGGGTCGTGGG
GCGGGCGTCAGGCACCGGGCTTGCGGGTCATGCACCAGGTCGCGCGGTCCTTCGGGCACTCGACGTCGGCGGTGAC
GGTGAAGCCGAGCCGCTCGTAGAAGGGGAGGTTGCGGGGCGCGGAGGTCTCCAGGAAGGCGGGCACCCCGGCGCGC
TCGGCCGCCTCCACTCCGGGGAGCACGACGGCGCTGCCCAGACCCTTGCCCTGGTGGTCGGGCGAGACGCCGACGG
TGGCCAGGAACCACGCGGGCTCCTTGGGCCGGTGCGGCGCCAGGAGGCCTTCCATCTGTTGCTGCGCGGCCAGCCG
GGAACCGCTCAACTCGGCCATGCGCGGGCCGATCTCGGCGAACACCGCCCCCGCTTCGACGCTCTCCGGCGTGGTC
CAGACCGCCACCGCGGCGCCGTCGTCCGCGACCCACACCTTGCCGATGTCGAGCCCGACGCGCGTGAGGAAGAGTT
CTTGCAGCTCGGTGACCCGCTCGATGTGGCGGTCCGGATCGACGGTGTGGCGCGTGGCGGGGTAGTCGGCGAACGC
GGCGGCGAGGGTGCGTACGGCCCTGGGGACGTCGTCGCGGGTGGCGAGGCGCACCGTGGGCTTGTACTCGGTCATG
GTAAGCTTGCTAGCAGCTGGTACCCAGCTTCTAGAGATCTGACGGTTCACTAAACGAGCTCTGCTTATATAGACCT
CCCACCGTACACGCCTACCGCCCATTTGCGTCAACGGGGCGGGGTTATTACGACATTTTGGAAAGTCCCGTTGATT
TTGGTGCCAAAACAAACTCCCATTGACGTCAATGGGGTGGAGACTTGGAAATCCCCGTGAGTCAAACCGCTATCCA
CGCCCATTGGTGTACTGCCAAAACCGCATCACCATGGTAATAGCGATGACTAATACGTAGATGTACTGCCAAGTAG
GAAAGTCCCGTAAGGTCATGTACTGGGCATAATGCCAGGCGGGCCATTTACCGTCATTGACGTCAATAGGGGGCGG
ACTTGGCATATGATACACTTGATGTACTGCCAAGTGGGCAGTTTACCGTAAATACTCCACCCATTGACGTCAATGG
AAAGTCCCTATTGGCGTTACTATGGGAACATACGTCATTATTGACGTCAATGGGCGGGGGTCGTTGGGCGGTCAGC
CAGGCGGGCCATTTACCGTAAGTTATGTAACGCGGAACTCCATATATGGGCTATGAACTAATGACCCCGTAATTGA
TTACTATTAATAACTAGTCAATAATCAATGTCAACATGGCGGTCATATTGGACATGAGCCAATATAAATGTACATA
TTATGATATAGATACAACGTATGCAATGGCCAATAGCCAATATTGATTTATGCTATATAACCAATGACTAATATGG
CTAATTGCCAATATTGATTCAATGTATAGATCTTCCATACCTACCAGTTCTGCGCCTGCAGCAATGCAACAACGTT
GCCCGGATCTGCGATGATAAGCTGTCAAACATGAGAATTGGTCGACTAGCTTGGCACGCCAGAAATCCGCGCGGTG
GTTTTTGGGGGTCGGGGGTGTTTGGCAGCCACAGACGCCCGGTGTTCGTGTCGCGCCAGTACATGCGGTCCATGCC
CAGGCCATCCAAAAACCATGGGTCTGTCTGCTCAGTCCAGTCGTGGACCAGACCCCACGCAACGCCCAAAATAATA
ACCCCCACGAACCATAAACCATTCCCCATGGGGGACCCCGTCCCTAACCCACGGGGCCAGTGGCTATGGCAGGGCC
TGCCGCCCCGACGTTGGCTGCGAGCCCTGGGCCTTCACCCGAACTTGGGGGTGGGGTGGGGAAAAGGAAGAAACG
CGGGCGTATTGGCCCCAATGGGGTCTCGGTGGGGTATCGACAGAGTGCCAGCCCTGGGACCGAACCCCGCGTTTAT
GAACAAACGACCCAACACCCGTGCGTTTTATTCTGTCTTTTTATTGCCGTCATAGCGCGGGTTCCTTCCGGTATTG
TCTCCTTCCGTGTTTCAGTTAGCCTCCCCCATCTCCCCTATTCCTTTGCCCTCGGACGAGTGCTGGGGCGTCGGTT
TCCACTATCGGCGAGTACTTCTACACAGCCATCGGTCCAGACGGCCGCGCTTCTGCGGGCGATTTGTGTACGCCCG
ACAGTCCCGGCTCCGGATCGGACGATTGCGTCGCATCGACCCTGCGCCCAAGCTGCATCATCGAAATTGCCGTCAA
CCAAGCTCTGATAGAGTTGGTCAAGACCAATGCGGAGCATATACGCCCGGAGCCGCGGCGATCCTGCAAGCTCCGG
ATGCCTCCGCTCGAAGTAGCGCGTCTGCTGCTCCATACAAGCCAACCACGGCCTCCAGAAGAAGATGTTGGCGACC
TCGTATTGGGAATCCCCGAACATCGCCTCGCTCCAGTCAATGACCGCTGTTATGCGGCCATTGTCCGTCAGGACAT
TGTTGGAGCCGAAATCCGCGTGCACGAGGTGCCGGACTTCGGGGCAGTCCTCGGCCCAAAGCATCAGCTCATCGAG
AGCCTGCGCGACGGACGCACTGACGGTGTCGTCCATCACAGTTTGCCAGTGATACACATGGGGATCAGCAATCGCG
CATATGAAATCACGCCATGTAGTGTATTGACCGATTCCTTGCGGTCCGAATGGGCCGAACCCGCTCGTCTGGCTAA
GATCGGCCGCAGCGCGCGCAAAACCCCTAAATAAAGACAGCAAGACACTTGCTTGATCCAAATCCAAACAGAGTCT
GGTTTTTTATTTATGTTTTAAACCGCATTGGAGGGGAGGAAGCCTTCAGGGCAGAAACCTGCTGGCGCAGATCCA
ACAGCTGCTGAGAAACGACATTAAGTTCCCGGGTCAAAGAATCCAATTGTGCCAAAAGAGCCGTCAACTTGTCATC
GCGGGCGGATGAACGGGAAGCTGCACTGCTTGCAAGCGGGCTCAGGAAAGCAAAGTCAGTCACAATCCCGCGGGCG
GTGGCTGCAGCGGCTGAAGCGGCGGCGGAGGCTGCAGTCTCCAACGGCGTTCCAGACACGGTCTCGTAGGTCAAGG
TAGTAGAGTTTGCGGGCAGGACGGGGCGACCATCAATGCTGGAGCCCATCACATTCTGACGCACCCCGGCCCATGG
GGGCATGCGCGTTGTCAAATATGAGCTCACAATGCTTCCATCAAACGAGTTGGTGCTCATGGCGGCGGCGGCTGCT
GCAAAACAGATACAAAACTACATAAGACCCCCACCTTATATATTCTTTCCCACCCGGGATCTGCGGCACGCTGTTG
ACGCTGTTAAGCGGGTCGCTGCAGGGTCGCTCGGTGTTCGAGGCCACACGCGTCACCTTAATATGCGAAGTGGACC
TGGGACCGCGCCGCCCCGACTGCATCTGCGTGTTCGAATTCGCCAATGACAAGACGCTGGCGGGGTTTGTGTCAT
CATAGAACTAAAGACATGCAAATATATTTCTTCCGGGGACACCGCCAGCAAACGCGAGCAACGGGCCACGGGGATG
AAGCAGGGCATGGCGGCCGACGCGCTGGGCTACGTCTTGCTGGCGTTCGCGACGCGAGGCTGGATGGCCTTCCCCA
TTATGATTCTTCTCGCTTCCGGCGGCATCGGGATGCCCGCGTTGCAGGCCATGCTGTCCAGGCAGGTAGATGACGA

FIGURE 15 (cont.)

CCATCAGGGACAGCTTCAAGGATCGCTCGCGGCTCTTACCAGCCTAACTTCGATCACTGGACCGCTGATCGTCACG
GCGATTTATGCCGCCTCGGCGAGCACATGGAACGGGTTGGCATGGATTGTAGGCGCCGCCCTATACCTTGTCTGCC
TCCCCGCGTTGCGTCGCGGTGCATGGAGCCGGGCCACCTCGACCTGAATGGAAGCCGGCGGCACCTCGCTAACGGA
TTCACCACTCCAAGAATTGGAGCCAATCAATTCTTGCGGAGAACTGTGAATGCGCAAACCAACCCTTGGCAGAACA
TATCCATCGCGTCCGCCATCTCCAGCAGCCGCACGCGGCGCAGCAAAAGGCCAGGAACCGTAAAAAGGCCGCGTTG
CTGGCGTTTTTCCATAGGCTCCGCCCCCCTGACGAGCATCACAAAAATCGACGCTCAAGTCAGAGGTGGCGAAACC
CGACAGGACTATAAAGATACCAGGCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCATAGCTCACGCTGTAGGTATCTCAGT
TCGGTGTAGGTCGTTCGCTCCAAGCTGGGCTGTGTGCACGAACCCCCCGTTCAGCCCGACCGCTGCGCCTTATCCG
GTAACTATCGTCTTGAGTCCAACCCGGTAAGACACGACTTATCGCCACTGGCAGCAGCCACTGGTAACAGGATTAG
CAGAGCGAGGTATGTAGGCGGTGCTACAGAGTTCTTGAAGTGGTGGCCTAACTACGGCTACACTAGAAGGACAGTA
TTTGGTATCTGCGCTCTGCTGAAGCCAGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGAAAAAAAGGATCTCAAGAAGATCCTTT
GATCTTTTCTACGGGGTCTGACGCTCAGTGGAACGAAAACTCACGTTAAGGGATTTTGGTCATGAGATTATCAAAA
AGGATCTTCACCTAGATCCTTTTAAATTAAAAATGAAGTTTTAAATCAATCTAAAGTATATATGAGTAAACTTGGT
CTGACAGTTACCAATGCTTAATCAGTGAGGCACCTATCTCAGCGATCTGTCTATTTCGTTCATCCATAGTTGCCTG
ACTCCCCGTCGTGTAGATAACTACGATACGGGAGGGCTTACCATCTGGCCCCAGTGCTGCAATGATACCGCGAGAC
CCACGCTCACCGGCTCCAGATTTATCAGCAATAAACCAGCCAGCCGGAAGGGCCGAGCGCAGAAGTGGTCCTGCAA
CTTTATCCGCCTCCATCCAGTCTATTAATTGTTGCCGGGAAGCTAGAGTAAGTAGTTCGCCAGTTAATAGTTTGCG
CAACGTTGTTGCCATTGCTGCAGGCATCGTGGTGTCACGCTCGTCGTTTGGTATGGCTTCATTCAGCTCCGGTTCC
CAACGATCAAGGCGAGTTACATGATCCCCCATGTTGTGCAAAAAAGCGGTTAGCTCCTTCGGTCCTCCGATCGTTG
TCAGAAGTAAGTTGGCCGCAGTGTTATCACTCATGGTTATGGCAGCACTGCATAATTCTCTTACTGTCATGCCATC
CGTAAGATGCTTTTCTGTGACTGGTGAGTACTCAACCAAGTCATTCTGAGAATAGTGTATGCGGCGACCGAGTTGC
TCTTGCCCGGCGTCAACACGGGATAATACCGCGCCACATAGCAGAACTTTAAAAGTGCTCATCATTGGAAAACGTT
CTTCGGGGCGAAAACTCTCAAGGATCTTACCGCTGTTGAGATCCAGTTCGATGTAACCCACTCGTGCACCCAACTG
ATCTTCAGCATCTTTTACTTTCACCAGCGTTTCTGGGTGAGCAAAAACAGGAAGGCAAAATGCCGCAAAAAAGGGA
ATAAGGGCGACACGGAAATGTTGAATACTCATACTCTTCCTTTTTCAATATTATTGAAGCATTTATCAGGGTTATT
GTCTCATGAGCGGATACATATTTGAATGTATTTAGAAAAATAAACAAATAGGGGTTCCGCGCACATTTCCCCGAAA
AGTGCCACCTGACGTCTAAGAAACCATTATTATCATGACATTAACCTATAAAAATAGGCGTATCACGAGGCCCTTC
CCGTAGTCTTCCTGGGCCCCTGGGAGGTACATGTCCCCCAGCATTGGTGTAAGAGCTTCAGCCAAGAGTTACACAT
AAAGGCAATGTTGTGTTGCAGTCCACAGACTGCAAAGTCTGCTCCAGGATGAAAGCCACTCAGTGTTGGCAAATGT
GCACATCCATTTATAAGGATGTCAACTACAGTCAGAGAACCCCTTTGTGTTTGGTCCCCCCCCGTGTCACATGTGG
AACAGGGCCCAGTTGGCAAGTTGTACCAACCAACTGAAGGGATTACATGCACTGCCCCGCGAAGAAGGGGCAGAGA
TGCCGTAGTCAGGTTTAGTTCGTCCGGCGGCGGGGC

FIGURE 17 HΔIX#3 (SEQ ID NO:15)

CTAAATTGTAAGCGTTAATATTTTGTTAAAATTCGGCCGGCCATCATCAATAATATACCTTATTTTGGATTGAAGC
CAATATGATAATGAGGGGGTGGAGTTTGTGACGTGGCGCGGGGCGTGGGAACGGGGCGGGTGACGTAGTAGTGTGG
CGGAAGTGTGATGTTGCAAGTGTGGCGGAACACATGTATAACTTCGTATAATGTATGCTATACGAAGTTATACATG
TAAGCGACGGATGTGGCAAAAGTGACGTTTTTGGTGTGCGCCGGTGTACACAGGAAGTGACAATTTTCGCGCGGTT
TTAGGCGGATGTTGTAGTAAATTTGGGCGTAACCGAGTAAGATTTGGCCATTTTCGCGGGAAAACTGAATAAGAGG
AAGTGAAATCTGAATAATTTTGTGTTACTCATAGCGCGTAATATTTGTCTAGGGAGATCAATTGGATTCTTTGACC
CGGGAACTTAATGTCGTTTCTCAGCAGCTGTTGGATCTGCGCCAGCAGGTTTCTGCCCTGAAGGCTTCCTCCCCTC
CCAATGCGGTTTAAAACATAAATAAAAAACCAGACTCTGTTTGGATTTGGATCAAGCAAGTGTCTTGCTGTCTTTA
TTTAGGGGTTTTGCGCGCGCGGTAGGCCCGGGACCAGCGGTCTCGGTCGTTGAGGGTCCTGTGTATTTTTTCCAGG
ACGTGGTAAAGGTGACTCTGGATGTTCAGATACATGGGCATAAGCCCGTCTCTGGGGTGGAGGTAGCACCACTGCA
GAGCTTCATGCTGCGGGGTGGTGTTGTAGATGATCCAGTCGTAGCAGGAGCGCTGGGCGTGGTGCCTAAAAATGTC
TTTCAGTAGCAAGCTGATTGCCAGGGGCAGGCCCTTGGTGTAAGTGTTTACAAAGCGGTTAAGCTGGGATGGGTGC
ATACGTGGGGATATGAGATGCATCTTGGACTGTATTTTTAGGTTGGCTATGTTCCCAGCCATATCCCTCCGGGGAT
TCATGTTGTGCAGAACCACCAGCACAGTGTATCCGGTGCACTTGGGAAATTTGTCATGTAGCTTAGAAGGAAATGC
GTGGAAGAACTTGGAGACGCCCTTGTGACCTCCAAGATTTTCCATGCATTCGTCCATAATGATGGCAATGGGCCCA
CGGGCGGCGGCCTGGGCGAAGATATTTCTGGGATCACTAACGTCATAGTTGTGTTCCAGGATGAGATCGTCATAGG
CCATTTTTACAAAGCGCGGGCGGAGGGTGCCAGACTGCGGTATAATGGTTCCATCCGGCCCAGGGGCGTAGTTACC
CTCACAGATTTGCATTTCCCACGCTTTGAGTTCAGATGGGGGGATCATGTCTACCTGCGGGGCGATGAAGAAAACG
GTTTCCGGGGTAGGGGAGATCAGCTGGGAAGAAAGCAGGTTCCTGAGCAGCTGCGACTTACCGCAGCCGGTGGGCC
CGTAAATCACACCTATTACCGGGTGCAACTGGTAGTTAAGAGAGCTGCAGCTGCCGTCATCCCTGAGCAGGGGGGC
CACTTCGTTAAGCATGTCCCTGACTCGCATGTTTTCCCTGACCAAATCCGCCAGAAGGCGCTCGCCGCCCAGCGAT
AGCAGTTCTTGCAAGGAAGCAAAGTTTTTCAACGGTTTGAGACCGTCCGCCGTAGGCATGCTTTTGAGCGTTTGAC
CAAGCAGTTCCAGGCGGTCCCACAGCTCGGTCACCTGCTCTACGGCATCTCGATCCAGCATATCTCCTCGTTTCGC
GGGTTGGGGCGGCTTTCGCTGTACGGCAGTAGTCGGTGCTCGTCCAGACGGGCCAGGGTCATGTCTTTCCACGGGC
GCAGGGTCCTCGTCAGCGTAGTCTGGGTCACGGTGAAGGGGTGCGCTCCGGGCTGCGCGCTGGCCAGGGTGCGCTT
GAGGCTGGTCCTGCTGGTGCTGAAGCGCTGCCGGTCTTCGCCCTGCGCGTCGGCCAGGTAGCATTTGACCATGGTG
TCATAGTCCAGCCCCTCGGCGGCGTGGCCCTTGGCGCGCAGCTTGCCCTTGGAGGAGGCGCCGCACGAGGGGCAGT
GCAGACTTTTGAGGGCGTAGAGCTTGGGCGCGAGAAATACCGATTCCGGGGAGTAGGCATCCGCGCCGCAGGCCCC
GCAGACGGTCTCGCATTCCACGAGCCAGGTGAGCTCTGGCCGTTCGGGGTCAAAAACCAGGTTTCCCCCATGCTTT
TTGATGCGTTTCTTACCTCTGGTTTCCATGAGCCGGTGTCCACGCTCGGTGACGAAAAGGCTGTCCGTGTCCCCGT
ATACAGACTTGAGAGGCCTGTCCTCGAGCGGTGTTCCGCGGTCCTCCTCGTATAGAAACTCGGACCACTCTGAGAC
AAAGGCTCGCGTCCAGGCCAGCACGAAGGAGGCTAAGTGGGAGGGGTAGCGGTCGTTGTCCACTAGGGGGTCCACT
CGCTCCAGGGTGTGAAGACACATGTCGCCCTCTTCGGCATCAAGGAAGGTGATTGGTTTGTAGGTGTAGGCCACGT
GACCGGGTGTTCCTGAAGGGGGGCTATAAAAGGGGGTGGGGGCGCGTTCGTCCTCACTCTCTTCCGCATCGCTGTC
TGCGAGGGCCAGCTGTTGGGGTGAGTACTCCCTCTGAAAAGCGGGCATGACTTCTGCGCTAAGATTGTCAGTTTCC
AAAAACGAGGAGGATTTGATATTCACCTGGCCCGCGGTGATGCCTTTGAGGGTGGCCGCATCCATCTGGTCAGAAA
AGACAATCTTTTTGTTGTCAAGCTTGGTGGCAAACGACCCGTAGAGGGCGTTGGACAGCAACTTGGCGATGGAGCG
CAGGGTTTGGTTTTTGTCGCGATCGGCGCGCTCCTTGGCCGCGATGTTTAGCTGCACGTATTCGCGCGCAACGCAC
CGCCATTCGGGAAAGACGGTGGTGCGCTCGTCGGGCACCAGGTGCACGCGCCAACCGCGGTTGTGCAGGGTGACAA
GGTCAACGCTGGTGGCTACCTCTCCGCGTAGGCGCTCGTTGGTCCAGCAGAGGCGGCCGCCCTTGCGCGAGCAGAA
TGGCGGTAGGGGGTCTAGCTGCGTCTCGTCCGGGGGGTCTGCGTCCACGGTAAAGACCCCGGGCAGCAGGCGCGCG
TCGAAGTAGTCTATCTTGCATCCTTGCAAGTCTAGCGCCTGCTGCCATGCGCGGGCGGCAAGCGCGCGCTCGTATG
GGTTGAGTGGGGGACCCCATGGCATGGGGTGGGTGAGCGCGGAGGCGTACATGCCGCAAATGTCGTAAACGTAGAG
GGGCTCTCTGAGTATTCCAAGATATGTAGGGTAGCATCTTCCACCGCGGATGCTGGCGCGCACGTAATCGTATAGT
TCGTGCGAGGGAGCGAGGAGGTCGGGACCGAGGTTGCTACGGGCGGGCTGCTCTGCTCGGAAGACTATCTGCCTGA
AGATGGCATGTGAGTTGGATGATATGGTTGGACGCTGGAAGACGTTGAAGCTGGCGTCTGTGAGACCTACCGCGTC
ACGCACGAAGGAGGCGTAGGAGTCGCGCAGCTTGTTGACCAGCTCGGCGGTGACCTGCACGTCTAGGGCGCAGTAG
TCCAGGGTTTCCTTGATGATGTCATACTTATCCTGTCCCTTTTTTTTCCACAGCTCGCGGTTGAGGACAAACTCTT
CGCGGTCTTTCCAGTACTCTTGGATCGGAAACCCGTCGGCCTCCGAACGGTAAGAGCCTAGCATGTAGAACTGGTT
GACGGCCTGGTAGGCGCAGCATCCCTTTTCTACGGGTAGCGCGTATGCCTGCGCGGCCTTCCGGAGCGAGGTGTGG
GTGAGCGCAAAGGTGTCCCTGACCATGACTTTGAGGTACTGGTATTTGAAGTCAGTGTCGTCGCATCCGCCCTGCT
CCCAGAGCAAAAAGTCCGTGCGCTTTTTGGAACGCGGATTTGGCAGGGCGAAGGTGACATCGTTGAAGAGTATCTT
TCCCGCGCGAGGCATAAAGTTGCGTGTGATGCGGAAGGGTCCCGGCACCTCGGAACGGTTGTTAATTACCTGGGCG
GCGAGCACGATCTCGTCAAAGCCGTTGATGTTGTGGCCCACAATGTAAAGTTCCAAGAAGCGCGGGATGCCCTTGA
TGGAAGGCAATTTTTTAAGTTCCTCGTAGGTGAGCTCTTCAGGGGAGCTGAGCCCGTGCTCTGAAAGGGCCCAGTC
TGCAAGATGAGGGTTGGAAGCGACGAATGAGCTCCACAGGTCACGGCCATTAGCATTTGCAGGTGGTCGCGAAAG
GTCCTAAACTGGCGACCTATGGCCATTTTTTCTGGGGTGATGCAGTAGAAGGTAAGCGGGTCTTGTTCCCAGCGGT
CCCATCCAAGGTTCGCGGCTAGGTCTCGCGCGGCAGTCACTAGAGGCTCATCTCCGCCGAACTTCATGACCAGCAT
GAAGGGCACGAGCTGCTTCCCAAAGGCCCCCATCCAAGTATAGGTCTCTACATCGTAGGTGACAAAGAGACGCTCG
GTGCGAGGATGCGAGCCGATCGGGAAGAACTGGATCTCCCGCCACCAATTGGAGGAGTGGCTATTGATGTGGTGAA
AGTAGAAGTCCCTGCGACGGGCCGAACACTCGTGCTGGCTTTTGTAAAAACGTGCGCAGTACTGGCAGCGGTGCAC

FIGURE 17 (cont.)

GGGCTGTACATCCTGCACGAGGTTGACCTGACGACCGCGCACAAGGAAGCAGAGTGGGAATTTGAGCCCCTCGCCT
GGCGGGTTTGGCTGGTGGTCTTCTACTTCGGCTGCTTGTCCTTGACCGTCTGGCTGCTCGAGGGGAGTTACGGTGG
ATCGGACCACCACGCCGCGCGAGCCCAAAGTCCAGATGTCCGCGCGCGGCGGTCGGAGCTTGATGACAACATCGCG
CAGATGGGAGCTGTCCATGGTCTGGAGCTCCCGCGGCGTCAGGTCAGGCGGGAGCTCCTGCAGGTTTACCTCGCAT
AGACGGGTCAGGGCGCGGGCTAGATCCAGGTGATACCTAATTTCCAGGGGCTGGTTGGTGGCGGCGTCGATGGCTT
GCAAGAGGCCGCATCCCCGCGGCGCGACTACGGTACCGCGCGGCGGGCGGTGGGCCGCGGGGGTGTCCTTGGATGA
TGCATCTAAAAGCGGTGACGCGGGCGAGCCCCCGGAGGTAGGGGGGGCTCCGGACCCGCCGGGAGAGGGGGCAGGG
GCACGTCGGCGCCGCGCGCGGGCAGGAGCTGGTGCTGCGCGCGTAGGTTGCTGGCGAACGCGACGACGCGGCGGTT
GATCTCCTGAATCTGGCGCCTCTGCGTGAAGACGACGGGCCCGGTGAGCTTGAGCCTGAAAGAGAGTTCGACAGAA
TCAATTTCGGTGTCGTTGACGGCGGCCTGGCGCAAAATCTCCTGCACGTCTCCTGAGTTGTCTTGATAGGCGATCT
CGGCCATGAACTGCTCGATCTCTTCCTCCTGGAGATCTCCGCGTCCGGCTCGCTCCACGGTGGCGGCGAGGTCGTT
GGAAATGCGGGCCATGAGCTGCGAGAAGGCGTTGAGGCCTCCCTCGTTCCAGACGCGGCTGTAGACCACGCCCCCT
TCGGCATCGCGGGCGCGCATGACCACCTGCGCGAGATTGAGCTCCACGTGCCGGGCGAAGACGGCGTAGTTTCGCA
GGCGCTGAAAGAGGTAGTTGAGGGTGGTGGCGGTGTGTTCTGCCACGAAGAAGTACATAACCCAGCGTCGCAACGT
GGATTCGTTGATATCCCCCAAGGCCTCAAGGCGCTCCATGGCCTCGTAGAAGTCCACGGCGAAGTTGAAAAACTGG
GAGTTGCGCGCCGACACGGTTAACTCCTCCTCCAGAAGACGGATGAGCTCGGCGACAGTGTCGCGCACCTCGCGCT
CAAAGGCTACAGGGGCCTCTTCTTCTTCTTCAATCTCCTCTTCCATAAGGGCCTCCCCTTCTTCTTCTTCTGGCGG
CGGTGGGGGAGGGGGGACACGGCGGCGACGACGGCGCACCGGGAGGCGGTCGACAAAGCGCTCGATCATCTCCCCG
CGGCGACGGCGCATGGTCTCGGTGACGGCGCGGCCGTTCTCGCGGGGGCGCAGTTGGAAGACGCCGCCCGTCATGT
CCCGGTTATGGGTTGGCGGGGGGCTGCCATGCGGCAGGGATACGGCGCTAACGATGCATCTCAACAATTGTTGTGT
AGGTACTCCGCCGCCGAGGGACCTGAGCGAGTCCGCATCGACCGGATCGGAAAACCTCTCGAGAAAGGCGTCTAAC
CAGTCACAGTCGCAAGGTAGGCTGAGCACCGTGGCGGGCGGCAGCGGGCGGCGGTCGGGGTTGTTTCTGGCGGAGG
TGCTGCTGATGATGTAATTAAAGTAGGCGGTCTTGAGACGGCGGATGGTCGACAGAAGCACCATGTCCTTGGGTCC
GGCCTGCTGAATGCGCAGGCGGTCGGCCATGCCCCAGGCTTCGTTTTGACATCGGCGCAGGTCTTTGTAGTAGTCT
TGCATGAGCCTTTCTACCGGCACTTCTTCTTCTCCTTCCTCTTGTCCTGCATCTCTTGCATCTATCGCTGCGGCGG
CGGCGGAGTTTGGCCGTAGGTGGCGCCCTCTTCCTCCCATGCGTGTGACCCCGAAGCCCCTCATCGGCTGAAGCAG
GGCTAGGTCGGCGACAACGCGCTCGGCTAATATGGCCTGCTGCACCTGCGTGAGGGTAGACTGGAAGTCATCCATG
TCCACAAAGCGGTGGTATGCGCCCGTGTTGATGGTGTAAGTGCAGTTGGCCATAACGGACCAGTTAACGGTCTGGT
GACCCGGCTGCGAGAGCTCGGTGTACCTGAGACGCGAGTAAGCCCTCGAGTCAAATACGTAGTCGTTGCAAGTCCG
CACCAGGTACTGGTATCCCACCAAAAAGTGCGGCGGCGGCTGGCGGTAGAGGGGCCAGCGTAGGGTGGCCGGGGCT
CCGGGGGCGAGATCTTCCAACATAAGGCGATGATATCCGTAGATGTACCTGGACATCCAGGTGATGCCGGCGGCGG
TGGTGGAGGCGCGCGGAAAGTCGCGGACGCGGTTCCAGATGTTGCGCAGCGGCAAAAAGTGCTCCATGGTCGGGAC
GCTCTGGCCGGTCAGGCGCGCGCAATCGTTGACGCTCTACCGTGCAAAAGGAGAGCCTGTAAGCGGGCACTCTTCC
GTGGTCTGGTGGATAAATTCGCAAGGGTATCATGGCGGACGACCGGGGTTCGAGCCCCGTATCCGGCCGTCCGCCG
TGATCCATGCGGTTACCGCCCGCGTGTCGAACCCAGGTGTGCGACGTCAGACAACGGGGGAGTGCTCCTTTTGGCT
TCCTTCCAGGCGCGGCGGCTGCTGCGCTAGCTTTTTTGGCCACTGGCCGCGCGCAGCGTAAGCGGTTAGGCTGGAA
AGCGAAAGCATTAAGTGGCTCGCTCCCTGTAGCCGGAGGGTTATTTTCCAAGGGTTGAGTCGCGGGACCCCCGGTT
CGAGTCTCGGACCGGCCGGACTGCGGCGAACGGGGGTTTGCCTCCCCGTCATGCAAGACCCCGCTTGCAAATTCCT
CCGGAAACAGGGACGAGCCCCTTTTTTGCTTTTCCCAGATGCATCCGGTGCTGCGGCAGATGCGCCCCCCTCCTCA
GCAGCGGCAAGAGCAAGAGCAGCGGCAGACATGCAGGGCACCCTCCCCTCCTCCTACCGCGTCAGGAGGGGCGACA
TCCGCGGTTGACGCGGCAGCAGATGGTGATTACGAACCCCCGCGGCGCCGGGCCCGGCACTACCTGGACTTGGAGG
AGGGCGAGGGCCTGGCGCGGCTAGGAGCGCCCTCTCCTGAGCGGTACCCAAGGGTGCAGCTGAAGCGTGATACGCG
TGAGGCGTACGTGCCGCGGCAGAACCTGTTTCGCGACCGCGAGGGAGAGGAGCCCGAGGAGATGCGGGATCGAAAG
TTCCACGCAGGGCGCGAGCTGCGGCATGGCCTGAATCGCGAGCGGTTGCTGCGCGAGGAGGACTTTGAGCCCGACG
CGCGAACCGGGATTAGTCCCGCGCGCGCACACGTGGCGGCCGCCGACCTGGTAACCGCATACGAGCAGACGGTGAA
CCAGGAGATTAACTTTCAAAAAAGCTTTAACAACCACGTGCGTACGCTTGTGGCGCGCGAGGAGGTGGCTATAGGA
CTGATGCATCTGTGGGACTTTGTAAGCGCGCTGGAGCAAAACCCAAATAGCAAGCCGCTCATGGCGCAGCTGTTCC
TTATAGTGCAGCACAGCAGGGACAACGAGGCATTCAGGGATGCGCTGCTAAACATAGTAGAGCCCGAGGGCCGCTG
GCTGCTCGATTTGATAAACATCCTGCAGAGCATAGTGGTGCAGGAGCGCAGCTTGAGCCTGGCTGACAAGGTGGCC
GCCATCAACTATTCCATGCTTAGCCTGGGCAAGTTTTACGCCCGCAAGATATACCATACCCCTTACGTTCCCATAG
ACAAGGAGGTAAAGATCGAGGGGTTCTACATGCGCATGGCGCTGAAGGTGCTTACCTTGAGCGACGACCTGGGCGT
TTATCGCAACGAGCGCATCCACAAGGCCGTGAGCGTGAGCCGGCGGCGCGAGCTCAGCGACCGCGAGCTGATGCAC
AGCCTGCAAAGGGCCCTGGCTGGCACGGGCAGCGGCGATAGAGAGGCCGAGTCCTACTTTGACGCGGGCGCTGACC
TGCGCTGGGCCCCAAGCCGACGCGCCCTGGAGGCAGCTGGGGCCGGACCTGGGCTGGCGGTGGCACCCGCGCGCGC
TGGCAACGTCGGCGGCGTGGAGGAATATGACGAGGACGATGAGTACGAGCCAGAGGACGGCGAGTACTAAGCGGTG
ATGTTTCTGATCAGATGATGCAAGACGCAACGGACCCGGCGGTGCGGGCGGCGCTGCAGAGCCAGCCGTCCGGCCT
TAACTCCACGGACGACTGGCGCCAGGTCATGGACCGCATCATGTCGCTGACTGCGCGCAATCCTGACGCGTTCCGG
CAGCAGCCGCAGGCCAACCGGCTCTCCGCAATTCTGGAAGCGGTGGTCCCGGCGCGCGCAAACCCCACGCACGAGA
AGGTGCTGGCGATCGTAAACGCGCTGGCCGAAAACAGGGCCATCCGGCCCGACGAAGCCGGCCTGGTCTACGACGC
GCTGCTTCAGCGCGTGGCTCGTTACAACAGCGGCAACGTGCAGACCAACCTGGACCGGCTGGTGGGGGATGTGCGC
GAGGCCGTGGCGCAGCGTGAGCGCGCGCAGCAGCAGGGCAACCTGGGCTCCATGGTTGCACTAAACGCCTTCCTGA

FIGURE 17 (cont.)

GTACACAGCCCGCCAACGTGCCGCGGGGACAGGAGGACTACACCAACTTTGTGAGCGCACTGCGGCTAATGGTGAC
TGAGACACCGCAAAGTGAGGTGTACCAGTCTGGGCCAGACTATTTTTTCCAGACCAGTAGACAAGGCCTGCAGACC
GTAAACCTGAGCCAGGCTTTCAAAAACTTGCAGGGGCTGTGGGGGGTGCGGGCTCCCACAGGCGACCGCGCGACCG
TGTCTAGCTTGCTGACGCCCAACTCGCGCCTGTTGCTGCTGCTAATAGCGCCCTTCACGGACAGTGGCAGCGTGTC
CCGGGACACATACCTAGGTCACTTGCTGACACTGTACCGCGAGGCCATAGGTCAGGCGCATGTGGACGAGCATACT
TTCCAGGAGATTACAAGTGTCAGCCGCGCGCTGGGGCAGGAGGACACGGGCAGCCTGGAGGCAACCCTAAACTACC
TGCTGACCAACCGGCGGCAGAAGATCCCCTCGTTGCACAGTTTAAACAGCGAGGAGGAGCGCATTTTGCGCTACGT
GCAGCAGAGCGTGAGCCTTAACCTGATGCGCGACGGGGTAACGCCCAGCGTGGCGCTGGACATGACCGCGCGCAAC
ATGGAACCGGGCATGTATGCCTCAAACCGGCCGTTTATCAACCGCCTAATGGACTACTTGCATCGCGCGGCCGCCG
TGAACCCCGAGTATTTCACCAATGCCATCTTGAACCCGCACTGGCTACCGCCCCCTGGTTTCTACACCGGGGGATT
CGAGGTGCCCGAGGGTAACGATGGATTCCTCTGGGACGACATAGACGACAGCGTGTTTTCCCCGCAACCGCAGACC
CTGCTAGAGTTGCAACAGCGCGAGCAGGCAGAGGCGGCGCTGCGAAAGGAAAGCTTCCGCAGGCCAAGCAGCTTGT
CCGATCTAGGCGCTGCGGCCCCGCGGTCAGATGCTAGTAGCCCATTTCCAAGCTTGATAGGGTCTCTTACCAGCAC
TCGCACCACCCGCCCGCGCCTGCTGGGCGAGGAGGAGTACCTAAACAACTCGCTGCTGCAGCCGCAGCGCGAAAAA
AACCTGCCTCCGGCATTTCCCAACAACGGGATAGAGAGCCTAGTGGACAAGATGAGTAGATGGAAGACGTACGCGC
AGGAGCACAGGGACGTGCCAGGCCCGCGCCCGCCCACCCGTCGTCAAAGGCACGACCGTCAGCGGGGTCTGGTGTG
GGAGGACGATGACTCGGCAGACGACAGCAGCGTCCTGGATTTGGGAGGGAGTGGCAACCCGTTTGCGCACCTTCGC
CCCAGGCTGGGGAGAATGTTTTAAAAAAAAAAAAGCATGATGCAAAATAAAAAACTCACCAAGGCCATGGCACCGA
GCGTTGGTTTTCTTGTATTCCCCTTAGTATGCGGCGCGCGGCGATGTATGAGGAAGGTCCTCCTCCCTCCTACGAG
AGTGTGGTGAGCGCGGCGCCAGTGGCGGCGGCGCTGGGTTCTCCCTTCGATGCTCCCCTGGACCCGCCGTTTGTGC
CTCCGCGGTACCTGCGGCCTACCGGGGGGAGAAACAGCATCCGTTACTCTGAGTTGGCACCCCTATTCGACACCAC
CCGTGTGTACCTGGTGGACAACAAGTCAACGGATGTGGCATCCCTGAACTACCAGAACGACCACAGCAACTTTCTG
ACCACGGTCATTCAAAACAATGACTACAGCCCGGGGGAGGCAAGCACACAGACCATCAATCTTGACGACCGGTCGC
ACTGGGGCGGCGACCTGAAAACCATCCTGCATACCAACATGCCAAATGTGAACGAGTTCATGTTTACCAATAAGTT
TAAGGCGCGGGTGATGGTGTCGCGCTTGCCTACTAAGGACAATCAGGTGGAGCTGAAATACGAGTGGGTGGAGTTC
ACGCTGCCCGAGGGCAACTACTCCGAGACCATGACCATAGACCTTATGAACAACGCGATCGTGGAGCACTACTTGA
AAGTGGGCAGACAGAACGGGGTTCTGGAAAGCGACATCGGGGTAAAGTTTGACACCCGCAACTTCAGACTGGGGTT
TGACCCCGTCACTGGTCTTGTCATGCCTGGGGTATATACAAACGAAGCCTTCCATCCAGACATCATTTTGCTGCCA
GGATGCGGGGTGGACTTCACCCACAGCCGCCTGAGCAACTTGTTGGGCATCCGCAAGCGGCAACCCTTCCAGGAGG
GCTTTAGGATCACCTACGATGATCTGGAGGGTGGTAACATTCCCGCACTGTTGGATGTGGACGCCTACCAGGCGAG
CTTGAAAGATGACACCGAACAGGGCGGGGGTGGCGCAGGCGGCAGCAACAGCAGTGGCAGCGGCGCGGAAGAGAAC
TCCAACGCGGCAGCCGCGGCAATGCAGCCGGTGGAGGACATGAACGATCATGCCATTCGCGGCGACACCTTTGCCA
CACGGGCTGAGGAGAAGCGCGCTGAGGCCGAAGCAGCGGCCGAAGCTGCCGCCCCCGCTGCGCAACCCGAGGTCGA
GAAGCCTCAGAAGAAACCGGTGATCAAACCCCTGACAGAGGACAGCAAGAAACGCAGTTACAACCTAATAAGCAAT
GACAGCACCTTCACCCAGTACCGCAGCTGGTACCTTGCATACAACTACGGCGACCCTCAGACCGGAATCCGCTCAT
GGACCCTGCTTTGCACTCCTGACGTAACCTGCGGCTCGGAGCAGGTCTACTGGTCGTTGCCAGACATGATGCAAGA
CCCCGTGACCTTCCGCTCCACGCGCCAGATCAGCAACTTTCCGGTGGTGGGCGCCGAGCTGTTGCCCGTGCACTCC
AAGAGCTTCTACAACGACCAGGCCGTCTACTCCCAACTCATCCGCCAGTTTACCTCTCTGACCCACGTGTTCAATC
GCTTTCCCGAGAACCAGATTTTGGCGCGCCCGCCAGCCCCCACCATCACCACCGTCAGTGAAAACGTTCCTGCTCT
CACAGATCACGGGACGCTACCGCTGCGCAACAGCATCGGAGGAGTCCAGCGAGTGACCATTACTGACGCCAGACGC
CGCACCTGCCCCTACGTTTACAAGGCCCTGGGCATAGTCTCGCCGCGCGTCCTATCGAGCCGCACTTTTTGAGCAA
GCATGTCCATCCTTATATCGCCCAGCAATAACACAGGCTGGGGCCTGCGCTTCCCAAGCAAGATGTTTGGCGGGGC
CAAGAAGCGCTCCGACCAACACCCAGTGCGCGTGCGCGGGCACTACCGCGCGCCCTGGGGCGCGCACAAACGCGGC
CGCACTGGGCGCACCACCGTCGATGACGCCATCGACGCGGTGGTGGAGGAGGCGCGCAACTACACGCCCACGCCGC
CACCAGTGTCCACAGTGGACGCGGCCATTCAGACCGTGGTGCGCGGAGCCCGGCGCTATGCTAAAATGAAGAGACG
GCGGAGGCGCGTAGCACGTCGCCACCGCCGCCGACCCGGCACTGCCGCCCAACGCGCGGCGGCGGCCCTGCTTAAC
CGCGCACGTCGCACCGGCCGACGGGCGGCCATGCGGGCCGCTCGAAGGCTGGCCGCGGGTATTGTCACTGTGCCCC
CCAGGTCCAGGCGACGAGCGGCCGCCGCAGCAGCCGCGGCCATTAGTGCTATGACTCAGGGTCGCAGGGGCAACGT
GTATTGGGTGCGCGACTCGGTTAGCGGCCTGCGCGTGCCCGTGCGCACCCGCCCCCCGCGCAACTAGATTGCAAGA
AAAAACTACTTAGACTCGTACTGTTGTATGTATCCAGCGGCGGCGGCGCGCAACGAAGCTATGTCCAAGCGCAAAA
TCAAAGAAGAGATGCTCCAGGTCATCGCGCCGGAGATCTATGGCCCCCCGAAGAAGGAAGAGCAGGATTACAAGCC
CCGAAAGCTAAAGCGGGTCAAAAAGAAAAAGAAAGATGATGATGATGAACTTGACGACGAGGTGGAACTGCTGCAC
GCTACCGCGCCCAGGCGACGGGTACAGTGGAAAGGTCGACGCGTAAAACGTGTTTTGCGACCCGGCACCACCGTAG
TCTTTACGCCCGGTGAGCGCTCCACCCGCACCTACAAGCGCGTGTATGATGAGGTGTACGGCGACGAGGACCTGCT
TGAGCAGGCCAACGAGCGCCTCGGGGAGTTTGCCTACGGAAAGCGGCATAAGGACATGCTGGCGTTGCCGCTGGAC
GAGGGCAACCCAACACCTAGCCTAAAGCCCGTAACACTGCAGCAGGTGCTGCCCGCGCTTGCACCGTCCGAAGAAA
AGCGCGGCCTAAAGCGCGAGTCTGGTGACTTGGCACCCACCGTGCAGCTGATGGTACCCAAGCGCCAGCGACTGGA
AGATGTCTTGGAAAAAATGACCGTGGAACCTGGGCTGGAGCCCGAGGTCCGCGTGCGGCCAATCAAGCAGGTGGCG
CCGGGACTGGGCGTGCAGACCGTGGACGTTCAGATACCCACTACCAGTAGCACCAGTATTGCCACCGCCACAGAGG
GCATGGAGACACAAACGTCCCCGGTTGCCTCAGCGGTGGCGGATGCCGCGGTGCAGGCGGTCGCTGCGGCCGCGTC
CAAGACCTCTACGGAGGTGCAAACGGACCCGTGGATGTTTCGCGTTTCAGCCCCCCGGCGCCCGCGCGGTTCGAGG

FIGURE 17 (cont.)

AAGTACGGCGCCGCCAGCGCGCTACTGCCCGAATATGCCCTACATCCTTCCATTGCGCCTACCCCCGGCTATCGTG
GCTACACCTACCGCCCCAGAAGACGAGCAACTACCCGACGCCGAACCACCACTGGAACCCGCCGCCGCCGTCGCCG
TCGCCAGCCCGTGCTGGCCCCGATTTCCGTGCGCAGGGTGGCTCGCGAAGGAGGCAGGACCCTGGTGCTGCCAACA
GCGCGCTACCACCCCAGCATCGTTTAAAAGCCGGTCTTTGTGGTTCTTGCAGATATGGCCCTCACCTGCCGCCTCC
GTTTCCCGGTGCCGGGATTCCGAGGAAGAATGCACCGTAGGAGGGGCATGGCCGGCTACGGCCTGACGGGCGGCAT
GCGTCGTGCGCACCACCGGCGGCGGCGCGCGTCGCACCGTCGCATGCGCGGCGGTATCCTGCCCCTCCTTATTCCA
CTGATCGCCGCGGCGATTGGCGCCGTGCCCGGAATTGCATCCGTGGCCTTGCAGGCGCAGAGACACTGATTAAAAA
CAAGTTGCATGTGGAAAAATCAAAATAAAAAGTCTGGACTCTCACGCTCGCTTGGTCCTGTAACTATTTTGTAGAA
TGGAAGACATCAACTTTGCGTCTCTGGCCCCGCGACACGGCTCGCGCCCGTTCATGGGAAACTGGCAAGATATCGG
CACCAGCAATATGAGCGGTGGCGCCTTCAGCTGGGGCTCGCTGTGGAGCGGCATTAAAAATTTCGGTTCCACCGTT
AAGAACTATGGCAGCAAGGCCTGGAACAGCAGCACAGGCCAGATGCTGAGGGATAAGTTGAAAGAGCAAAATTTCC
AACAAAAGGTGGTAGATGGCCTGGCCTCTGGCATTAGCGGGGTGGTGGACCTGGCCAACCAGGCAGTGCAAAATAA
GATTAACAGTAAGCTTGATCCCCGCCCTCCCGTAGAGGAGCCTCCACCGGCCGTGGAGACAGTGTCTCCAGAGGGG
CGTGGCGAAAAGCGTCCGCGCCCCGACAGGGAAGAAACTCTGGTGACGCAAATAGACGAGCCTCCCTCGTACGAGG
AGGCACTAAAGCAAGGCCTGCCCACCACCCGTCCCATCGCGCCCATGGCTACCGGAGTGCTGGGCCAGCACACACC
CGTAACGCTGGACCTGCCTCCCCCCGCCGACACCCAGCAGAAACCTGTGCTGCCAGGCCCGACCGCCGTTGTTGTA
ACCCGTCCTAGCCGCGCGTCCCTGCGCCGCGCCGCCAGCGGTCCGCGATCGTTGCGGCCCGTAGCCAGTGGCAACT
GGCAAAGCACACTGAACAGCATCGTGGGTCTGGGGGTGCAATCCCTGAAGCGCCGACGATGCTTCTGAATAGCTAA
CGTGTCGTATGTGTGTCATGTATGCGTCCATGTCGCCGCCAGAGGAGCTGCTGAGCCGCCGCGCGCCCGCTTTCCA
AGATGGCTACCCCTTCGATGATGCCGCAGTGGTCTTACATGCACATCTCGGGCCAGGACGCCTCGGAGTACCTGAG
CCCCGGGCTGGTGCAGTTTGCCCGCGCCACCGAGACGTACTTCAGCCTGAATAACAAGTTTAGAAACCCCACGGTG
GCGCCTACGCACGACGTGACCACAGACCGGTCCCAGCGTTTGACGCTGCGGTTCATCCCTGTGGACCGTGAGGATA
CTGCGTACTCGTACAAGGCGCGGTTCACCCTAGCTGTGGGTGATAACCGTGTGCTGGACATGGCTTCCACGTACTT
TGACATCCGCGGCGTGCTGGACAGGGGCCCTACTTTTAAGCCCTACTCTGGCACTGCCTACAACGCCCTGGCTCCC
AAGGGTGCCCCAAATCCTTGCGAATGGGATGAAGCTGCTACTGCTCTTGAAATAAACCTAGAAGAAGAGGACGATG
ACAACGAAGACGAAGTAGACGAGCAAGCTGAGCAGCAAAAAACTCACGTATTTGGGCAGGCGCCTTATTCTGGTAT
AAATATTACAAAGGAGGGTATTCAAATAGGTGTCGAAGGTCAAACACCTAAATATGCCGATAAAACATTTCAACCT
GAACCTCAAATAGGAGAATCTCAGTGGTACGAAACTGAAATTAATCATGCAGCTGGGAGAGTCCTTAAAAAGACTA
CCCCAATGAAACCATGTTACGGTTCATATGCAAAACCCACAAATGAAAATGGAGGGCAAGGCATTCTTGTAAAGCA
ACAAAATGGAAAGCTAGAAAGTCAAGTGGAAATGCAATTTTTCTCAACTACTGAGGCGACCGCAGGCAATGGTGAT
AACTTGACTCCTAAAGTGGTATTGTACAGTGAAGATGTAGATATAGAAACCCCAGACACTCATATTTCTTACATGC
CCACTATTAAGGAAGGTAACTCACGAGAACTAATGGGCCAACAATCTATGCCCAACAGGCCTAATTACATTGCTTT
TAGGGACAATTTTATTGGTCTAATGTATTACAACAGCACGGGTAATATGGGTGTTCTGGCGGGCCAAGCATCGCAG
TTGAATGCTGTTGTAGATTTGCAAGACAGAAACACAGAGCTTTCATACCAGCTTTTGCTTGATTCCATTGGTGATA
GAACCAGGTACTTTTCTATGTGGAATCAGGCTGTTGACAGCTATGATCCAGATGTTAGAATTATTGAAAATCATGG
AACTGAAGATGAACTTCCAAATTACTGCTTTCCACTGGGAGGTGTGATTAATACAGAGACTCTTACCAAGGTAAAA
CCTAAAACAGGTCAGGAAAATGGATGGGAAAAAGATGCTACAGAATTTTCAGATAAAAATGAAATAAGAGTTGGAA
ATAATTTTGCCATGGAAATCAATCTAAATGCCAACCTGTGGAGAAATTTCCTGTACTCCAACATAGCGCTGTATTT
GCCCGACAAGCTAAAGTACAGTCCTTCCAACGTAAAAATTTCTGATAACCCAAACACCTACGACTACATGAACAAG
CGAGTGGTGGCTCCCGGGTTAGTGGACTGCTACATTAACCTTGGAGCACGCTGGTCCCTTGACTATATGGACAACG
TCAACCCATTTAACCACCACCGCAATGCTGGCCTGCGCTACCGCTCAATGTTGCTGGGCAATGGTCGCTATGTGCC
CTTCCACATCCAGGTGCCTCAGAAGTTCTTTGCCATTAAAAACCTCCTTCTCCTGCCGGGCTCATACACCTACGAG
TGGAACTTCAGGAAGGATGTTAACATGGTTCTGCAGAGCTCCCTAGGAAATGACCTAAGGGTTGACGGAGCCAGCA
TTAAGTTTGATAGCATTTGCCTTTACGCCACCTTCTTCCCCATGGCCCACAACACCGCCTCCACGCTTGAGGCCAT
GCTTAGAAACGACACCAACGACCAGTCCTTTAACGACTATCTCTCCGCCGCCAACATGCTCTACCCTATACCCGCC
AACGCTACCAACGTGCCCATATCCATCCCCTCCCGCAACTGGGCGGCTTTCCGCGGCTGGGCCTTCACGCGCCTTA
AGACTAAGGAAACCCCATCACTGGGCTCGGGCTACGACCCTTATTACACCTACTCTGGCTCTATACCCTACCTAGA
TGGAACCTTTTACCTCAACCACACCTTTAAGAAGGTGGCCATTACCTTTGACTCTTCTGTCAGCTGGCCTGGCAAT
GACCGCCTGCTTACCCCCAACGAGTTTGAAATTAAGCGCTCAGTTGACGGGGAGGGTTACAACGTTGCCCAGTGTA
ACATGACCAAAGACTGGTTCCTGGTACAAATGCTAGCTAACTACAACATTGGCTACCAGGGCTTCTATATCCCAGA
GAGCTACAAGGACCGCATGTACTCCTTCTTTAGAAACTTCCAGCCCATGAGCCGTCAGGTGGTGGATGATACTAAA
TACAAGGACTACCAACAGGTGGGCATCCTACACCAACACAACAACTCTGGATTTGTTGGCTACCTTGCCCCCACCA
TGCGCGAAGGACAGGCCTACCCTGCTAACTTCCCCTATCCGCTTATAGGCAAGACCGCAGTTGACAGCATTACCCA
GAAAAAGTTTCTTTGCGATCGCACCCTTTGGCGCATCCCATTCTCCAGTAACTTTATGTCCATGGGCGCACTCACA
GACCTGGGCCAAAACCTTCTCTACGCCAACTCCGCCCACGCGCTAGACATGACTTTTGAGGTGGATCCCATGGACG
AGCCCACCCTTCTTTATGTTTTGTTTGAAGTCTTTGACGTGGTCCGTGTGCACCGGCCGCACCGCGGCGTCATCGA
AACCGTGTACCTGCGCACGCCCTTCTCGGCCGGCAACGCCACAACATAAAGAAGCAAGCAACATCAACAACAGCTG
CCGCCATGGGCTCCAGTGAGCAGGAACTGAAAGCCATTGTCAAAGATCTTGGTTGTGGGCCATATTTTTTGGGCAC
CTATGACAAGCGCTTTCCAGGCTTTGTTTCTCCACACAAGCTCGCCTGCGCCATAGTCAATACGGCCGGTCGCGAG
ACTGGGGGCGTACACTGGATGGCCTTTGCCTGGAACCCGCACTCAAAAACATGCTACCTCTTTGAGCCCTTTGGCT
TTTCTGACCAGCGACTCAAGCAGGTTTACCAGTTTGAGTACGAGTCACTCCTGCGCCGTAGCGCCATTGCTTCTTC

FIGURE 17 (cont.)

CCCCGACCGCTGTATAACGCTGGAAAAGTCCACCCAAAGCGTACAGGGGCCCAACTCGGCCGCCTGTGGACTATTC
TGCTGCATGTTTCTCCACGCCTTTGCCAACTGGCCCCAAACTCCCATGGATCACAACCCCACCATGAACCTTATTA
CCGGGGTACCCAACTCCATGCTCAACAGTCCCCAGGTACAGCCCACCCTGCGTCGCAACCAGGAACAGCTCTACAG
CTTCCTGGAGCGCCACTCGCCCTACTTCCGCAGCCACAGTGCGCAGATTAGGAGCGCCACTTCTTTTTGTCACTTG
AAAAACATGTAAAAATAATGTACTAGAGACACTTTCAATAAAGGCAAATGCTTTTATTTGTACACTCTCGGGTGAT
TATTTACCCCCACCCTTGCCGTCTGCGCCGTTTAAAAATCAAAGGGGTTCTGCCGCGCATCGCTATGCGCCACTGG
CAGGGACACGTTGCGATACTGGTGTTTAGTGCTCCACTTAAACTCAGGCACAACCATCCGCGGCAGCTCGGTGAAG
TTTTCACTCCACAGGCTGCGCACCATCACCAACGCGTTTAGCAGGTCGGGCGCCGATATCTTGAAGTCGCAGTTGG
GGCCTCCGCCCTGCGCGCGCGAGTTGCGATACACAGGGTTGCAGCACTGGAACACTATCAGCGCCGGGTGGTGCAC
GCTGGCCAGCACGCTCTTGTCGGAGATCAGATCCGCGTCCAGGTCCTCCGCGTTGCTCAGGGCGAACGGAGTCAAC
TTTGGTAGCTGCCTTCCCAAAAAGGGCGCGTGCCCAGGCTTTGAGTTGCACTCGCACCGTAGTGGCATCAAAAGGT
GACCGTGCCCGGTCTGGGCGTTAGGATACAGCGCCTGCATAAAAGCCTTGATCTGCTTAAAAGCCACCTGAGCCTT
TGCGCCTTCAGAGAAGAACATGCCGCAAGACTTGCCGGAAAACTGATTGGCCGGACAGGCCGCGTCGTGCACGCAG
CACCTTGCGTCGGTGTTGGAGATCTGCACCACATTTCGGCCCCACCGGTTCTTCACGATCTTGGCCTTGCTAGACT
GCTCCTTCAGCGCGCGCTGCCCGTTTTCGCTCGTCACATCCATTTCAATCACGTGCTCCTTATTTATCATAATGCT
TCCGTGTAGACACTTAAGCTCGCCTTCGATCTCAGCGCAGCGGTGCAGCCACAACGCGCAGCCCGTGGGCTCGTGA
TGCTTGTAGGTCACCTCTGCAAACGACTGCAGGTACGCCTGCAGGAATCGCCCCATCATCGTCACAAAGGTCTTGT
TGCTGGTGAAGGTCAGCTGCAACCCGCGGTGCTCCTCGTTCAGCCAGGTCTTGCATACGGCCGCCAGAGCTTCCAC
TTGGTCAGGCAGTAGTTTGAAGTTCGCCTTTAGATCGTTATCCACGTGGTACTTGTCCATCAGCGCGCGCGCAGCC
TCCATGCCCTTCTCCCACGCAGACACGATCGGCACACTCAGCGGGTTCATCACCGTAATTTCACTTTCCGCTTCGC
TGGGCTCTTCCTCTTCCTCTTGCGTCCGCATACCACGCGCCACTGGGTCGTCTTCATTCAGCCGCCGCACTGTGCG
CTTACCTCCTTTGCCATGCTTGATTAGCACCGGTGGGTTGCTGAAACCCACCATTTGTAGCGCCACATCTTCTCTT
TCTTCCTCGCTGTCCACGATTACCTCTGGTGATGGCGGGCGCTCGGGCTTGGGAGAAGGGCGCTTCTTTTTCTTCT
TGGGCGCAATGGCCAAATCCGCCGCCGAGGTCGATGGCCGCGGGCTGGGTGTGCGCGGCACCAGCGCGTCTTGTGA
TGAGTCTTCCTCGTCCTCGGACTCGATACGCCGCCTCATCCGCTTTTTTGGGGGCGCCCGGGGAGGCGGCGGCGAC
GGGGACGGGGACGACACGTCCTCCATGGTTGGGGGACGTCGCGCCGCACCGCGTCCGCGCTCGGGGGTGGTTTCGC
GCTGCTCCTCTTCCCGACTGGCCATTTCCTTCTCCTATAGGCAGAAAAAGATCATGGAGTCAGTCGAGAAGAAGGA
CAGCCTAACCGCCCCCTCTGAGTTCGCCACCACCGCCTCCACCGATGCCGCCAACGCGCCTACCACCTTCCCCGTC
GAGGCACCCCCGCTTGAGGAGGAGGAAGTGATTATCGAGCAGGACCCAGGTTTTGTAAGCGAAGACGACGAGGACC
GCTCAGTACCAACAGAGGATAAAAAGCAAGACCAGGACAACGCAGAGGCAAACGAGGAACAAGTCGGGCGGGGGGA
CGAAAGGCATGGCGACTACCTAGATGTGGGAGACGACGTGCTGTTGAAGCATCTGCAGCGCCAGTGCGCCATTATC
TGCGACGCGTTGCAAGAGCGCAGCGATGTGCCCCTCGCCATAGCGGATGTCAGCCTTGCCTACGAACGCCACCTAT
TCTCACCGCGCGTACCCCCCAAACGCCAAGAAAACGGCACATGCGAGCCCAACCCGCGCCTCAACTTCTACCCCGT
ATTTGCCGTGCCAGAGGTGCTTGCCACCTATCACATCTTTTTCCAAAACTGCAAGATACCCCTATCCTGCCGTGCC
AACCGCAGCCGAGCGGACAAGCAGCTGGCCTTGCGGCAGGGCGCTGTCATACCTGATATCGCCTCGCTCAACGAAG
TGCCAAAAATCTTTGAGGGTCTTGGACGCGACGAGAAGCGCGCGGCAAACGCTCTGCAACAGGAAAACAGCGAAAA
TGAAAGTCACTCTGGAGTGTTGGTGGAACTCGAGGGTGACAACGCGCGCCTAGCCGTACTAAAACGCAGCATCGAG
GTCACCCACTTTGCCTACCCGGCACTTAACCTACCCCCCAAGGTCATGAGCACAGTCATGAGTGAGCTGATCGTGC
GCCGTGCGCAGCCCCTGGAGAGGGATGCAAATTTGCAAGAACAAACAGAGGAGGGCCTACCCGCAGTTGGCGACGA
GCAGCTAGCGCGCTGGCTTCAAACGCGCGAGCCTGCCGACTTGGAGGAGCGACGCAAACTAATGATGGCCGCAGTG
CTCGTTACCGTGGAGCTTGAGTGCATGCAGCGGTTCTTTGCTGACCCGGAGATGCAGCGCAAGCTAGAGGAAACAT
TGCACTACACCTTTCGACAGGGCTACGTACGCCAGGCCTGCAAGATCTCCAACGTGGAGCTCTGCAACCTGGTCTC
CTACCTTGGAATTTTGCACGAAAACCGCCTTGGGCAAAACGTGCTTCATTCCACGCTCAAGGGCGAGGCGCGCCGC
GACTACGTCCGCGACTGCGTTTACTTATTTCTATGCTACACCTGGCAGACGGCCATGGGCGTTTGGCAGCAGTGCT
TGGAGGAGTGCAACCTCAAGGAGCTGCAGAAACTGCTAAAGCAAAACTTGAAGGACCTATGGACGGCCTTCAACGA
GCGCTCCGTGGCCGCGCACCTGGCGGACATCATTTTCCCCGAACGCCTGCTTAAAACCCTGCAACAGGGTCTGCCA
GACTTCACCAGTCAAAGCATGTTGCAGAACTTTAGGAACTTTATCCTAGAGCGCTCAGGAATCTTGCCCGCCACCT
GCTGTGCACTTCCTAGCGACTTTGTGCCCATTAAGTACCGCGAATGCCCTCCGCCGCTTTGGGGCCACTGCTACCT
TCTGCAGCTAGCCAACTACCTTGCCTACCACTCTGACATAATGGAAGACGTGAGCGGTGACGGTCTACTGGAGTGT
CACTGTCGCTGCAACCTATGCACCCCGCACCGCTCCCTGGTTTGCAATTCGCAGCTGCTTAACGAAAGTCAAATTA
TCGGTACCTTTGAGCTGCAGGGTCCCTCGCCTGACGAAAAGTCCGCGGCTCCGGGGTTGAAACTCACTCCGGGGCT
GTGGACGTCGGCTTACCTTCGCAAATTTGTACCTGAGGACTACCACGCCCACGAGATTAGGTTCTACGAAGACCAA
TCCCGCCCGCCAAATGCGGAGCTTACCGCCTGCGTCATTACCCAGGGCCACATTCTTGGCCAATTGCAAGCCATCA
ACAAAGCCCGCCAAGAGTTTCTGCTACGAAAGGGACGGGGGGTTTACTTGGACCCCCAGTCCGGCGAGGAGCTCAA
CCCAATCCCCCCGCCGCCGCAGCCCTATCAGCAGCAGCCGCGGGCCCTTGCTTCCCAGGATGGCACCCAAAAAGAA
GCTGCAGCTGCCGCCGCCACCCACGGACGAGGAGGAATACTGGGACAGTCAGGCAGAGGAGGTTTTGGACGAGGAG
GAGGAGGACATGATGGAAGACTGGGAGAGCCTAGACGAGGAAGCTTCCGAGGTCGAAGAGGTGTCAGACGAAACAC
CGTCACCCTCGGTCGCATTCCCCTCGCCGGCGCCCCAGAAATCGGCAACCGGTTCCAGCATGGCTACAACCTCCGC
TCCTCAGGCGCCGCCGGCACTGCCCGTTCGCCGACCCAACCGTAGATGGGACACCACTGGAACCAGGGCCGGTAAG
TCCAAGCAGCCGCCGCCGTTAGCCCAAGAGCAACAACAGCGCCAAGGCTACCGCTCATGGCGCGGGCACAAGAACG
CCATAGTTGCTTGCTTGCAAGACTGTGGGGGCAACATCTCCTTCGCCCGCCGCTTTCTTCTCTACCATCACGGCGT

FIGURE 17 (cont.)

GGCCTTCCCCCGTAACATCCTGCATTACTACCGTCATCTCTACAGCCCATACTGCACCGGCGGCAGCGGCAGCGGC
AGCAACAGCAGCGGCCACACAGAAGCAAAGGCGACCGGATAGCAAGACTCTGACAAAGCCCAAGAAATCCACAGCG
GCGGCAGCAGCAGGAGGAGGAGCGCTGCGTCTGGCGCCCAACGAACCCGTATCGACCCGCGAGCTTAGAAACAGGA
TTTTTCCCACTCTGTATGCTATATTTCAACAGAGCAGGGGCCAAGAACAAGAGCTGAAAATAAAAAACAGGTCTCT
GCGATCCCTCACCCGCAGCTGCCTGTATCACAAAAGCGAAGATCAGCTTCGGCGCACGCTGGAAGACGCGGAGGCT
CTCTTCAGTAAATACTGCGCGCTGACTCTTAAGGACTAGTTTCGCGCCCTTTCTCAAATTTAAGCGCGAAAACTAC
GTCATCTCCAGCGGCCACACCCGGCGCCAGCACCTGTCGTCAGCGCCATTATGAGCAAGGAAATTCCCACGCCCTA
CATGTGGAGTTACCAGCCACAAATGGGACTTGCGGCTGGAGCTGCCCAAGACTACTCAACCCGAATAAACTACATG
AGCGCGGGACCCCACATGATATCCCGGGTCAACGGAATCCGCGCCCACCGAAACCGAATTCTCTTGGAACAGGCGG
CTATTACCACCACACCTCGTAATAACCTTAATCCCCGTAGTTGGCCCGCTGCCCTGGTGTACCAGGAAAGTCCCGC
TCCCACCACTGTGGTACTTCCCAGAGACGCCCAGGCCGAAGTTCAGATGACTAACTCAGGGGCGCAGCTTGCGGGC
GGCTTTCGTCACAGGGTGCGGTCGCCCGGGCAGGGTATAACTCACCTGACAATCAGAGGGCGAGGTATTCAGCTCA
ACGACGAGTCGGTGAGCTCCTCGCTTGGTCTCCGTCCGGACGGGACATTTCAGATCGGCGGCGCCGGCCGTCCTTC
ATTCACGCCTCGTCAGGCAATCCTAACTCTGCAGACCTCGTCCTCTGAGCCGCGCTCTGGAGGCATTGGAACTCTG
CAATTTATTGAGGAGTTTGTGCCATCGGTCTACTTTAACCCCTTCTCGGGACCTCCCGGCCACTATCCGGATCAAT
TTATTCCTAACTTTGACGCGGTAAAGGACTCGGCGGACGGCTACGACTGAATGTTAAGTGGAGAGGCAGAGCAACT
GCGCCTGAAACACCTGGTCCACTGTCGCCGCCACAAGTGCTTTGCCCGCGACTCCGGTGAGTTTTGCTACTTTGAA
TTGCCCGAGGATCATATCGAGGGCCCGGCGCACGGCGTCCGGCTTACCGCCCAGGGAGAGCTTGCCCGTAGCCTGA
TTCGGGAGTTTACCCAGCGCCCCCTGCTAGTTGAGCGGGACAGGGGACCCTGTGTTCTCACTGTGATTTGCAACTG
TCCTAACCTTGGATTACATCAAGATCCTCTAGTTAATTAACAGCTTGCATGCCTGCAGGTCGACGGATCGGGAGAT
CTCGGCCGCATATTAAGTGCATTGTTCTCGATACCGCTAAGTGCATTGTTCTCGTTAGCTCGATGGACAAGTGCAT
TGTTCTCTTGCTGAAAGCTCGATGGACAAGTGCATTGTTCTCTTGCTGAAAGCTCGATGGACAAGTGCATTGTTCT
CTTGCTGAAAGCTCAGTACCCGGGAGTACCCTCGACCGCCGGAGTATAAATAGAGGCGCTTCGTCTACGGAGCGAC
AATTCAATTCAAACAAGCAAAGTGAACACGTCGCTAAGCGAAAGCTAAGCAAATAAACAAGCGCAGCTGAACAAGC
TAAACAATCTGCAGTAAAGTGCAAGTTAAAGTGAATCAATTAAAAGTAACCAGCAACCAAGTAAATCAACTGCAAC
TACTGAAATCTGCCAAGAAGTAATTATTGAATACAAGAAGAGAACTCTGAATACTTTCAACAAGTTACCGAGAAAG
AAGAACTCACACACAGCTAGCGTTTAAACTTAAGCTTCACCATGGTGGGGCCCTGCATGCTGCTGCTGCTGCTGCT
GCTGGGCCTGAGGCTACAGCTCTCCCTGGGCATCATCCTAGTTGAGGAGGAGAACCCGGACTTCTGGAACCGCGAG
GCAGCCGAGGCCCTGGGTGCCGCCAAGAAGCTGCAGCCTGCACAGACAGCCGCCAAGAACCTCATCATCTTCCTGG
GCGATGGGGTGGGGGTGTCTACGGTGACAGCTGCCAGGATCCTAAAAGGGCAGAAGAAGGACAAACTGGGGCCTGA
GATACCCCTGGCCATGGACCGCTTCCCATATGTGGCTCTGTCCAAGACATACAATGTAGACAAACATGTGCCAGAC
AGTGGAGCCACAGCCACGGCCTACCTGTGCGGGGTCAAGGGCAACTTCCAGACCATTGGCTTGAGTGCAGCCGCCC
GCTTTAACCAGTGCAACACGACACGCGGCAACGAGGTCATCTCCGTGATGAATCGGGCCAAGAAAGCAGGGAAGTC
AGTGGGAGTGGTAACCACCACACGAGTGCAGCACGCCTCGCCAGCCGGCACCTACGCCCACACGGTGAACCGCAAC
TGGTACTCGGACGCCGACGTGCCTGCCTCGGCCCGCCAGGAGGGGTGCCAGGACATCGCTACGCAGCTCATCTCCA
ACATGGACATTGACGTGATCCTAGGTGGGGGCCGAAAGTACATGTTTCGCATGGGAACCCCAGACCCTGAGTACCC
AGATGACTACAGCCAAGGTGGGACCAGGCTGGACGGGAAGAATCTGGTGCAGGAATGGCTGGCGAAGCACCAGGGT
GCCCGGTACGTGTGGAACCGCACTGAGCTCATGCGGGCTTCCCTGGACCCGTCTGTGGCCCATCTCATGGGTCTCT
TTGAGCCTGGAGACATGAAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCGCATCGACCATGGTCAT
CATGAAAGCAGGGCTTACCGGGCACTGACTGAGACGATCATGTTCGACGACGCCATTGAGAGGGCGGGCCAGCTCA
CCAGCGAGGAGGACACGCTGAGCCTCGTCACTGCCGACCACTCCCACGTCTTCTCCTTCGGAGGCTGCCCCCTGCG
AGGGGGCTCCATCTTCGGGCTGGCCCCTGGCAAGGCCCGGGACAGGAAGGCCTACACGGTCCTCCTATACGGAAAC
GGTCCAGGCTATGTGCTCAAGGACGGCGCCCGGCCGGATGTTACCGAGAGCGAGAGCGGGAGCCCCGAGTATCGGC
AGCAGTCAGCAGTGCCCCTGGACGAAGAGACCCACGCAGGCGAGGACGTGGCGGTGTTCGCGCGCGGCCCGCAGGC
GCACCTGGTTCACGGCGTGCAGGAGCAGACCTTCATAGCGCACGTCATGGCCTTCGCCGCCTGCCTGGAGCCCTAC
ACCGCCTGCGACCTGGCGCCCCCCGCCGGCACCACCGACGCCGCGCACCCGGGGCGGTCCGTGGTCCCCGCGTTGC
TTCCTCTGCTGGCCGGGACCCTGCTGCTGCTGGAGACGGCCACTGCTCCCTGAGTGTCCCGTCCCTGGGGCTCCTG
CTTCCCCATCCCGGAGTTCTCCTGCTCCCCGCCTCCTGTCGTCCTGCCTGGCCTCCAGCCCGAGTCGTCATCCCCG
GAGTCCCTATACAGAGGTCCTGCCATGGAACCTTCCCCTCCCCGTGCGCTCTGGGGACTGAGCCCATGACACCAAA
CCTGCCCCTTGGCTGCTCTCGGACTCCCTACCCCAACCCCAGGGACAGATCTGGCCAGATTTGTAAAACAAATAGA
TTTTAGGCCCAAAGATTATTTAAAGCATTGCCTGGAACGCAGTGAGTTTTTGTTAGAAAAGAGAATAATTCAAAGT
GGCATTGCTTTGCTTCTTATGTTAATTTGGTACAGACCTGTGGCTGAGTTTGCTCAAAGTATTCAGAGCAGAATTG
TGGAGTGGAAAGAGAGATTGGACAAAGAGTTTAGTTTGTCAGTGTATCAAAAAATGAAGTTTAATGTGGCTATGGG
AATTGGAGTTTTAGATTGGCTAAGAAACAGTGATGATGATGATGAAGACAGCCAGGAAAATGCTGATAAAAATGAA
GATGGTGGGGAGAAGAACATGGAAGACTCAGGGCATGAAACAGGCATTGATTCACAGTCCCAAGGCTCATTTCAGG
CCCCTCAGTCCTCACAGTCTGTTCATGATCATAATCAGCCATACCACATTTGTAGAGGTTTTACTTGCTTTAAAAA
ACCTCCCACACCTCCCCCTGAACCTGAAACATAAAATGAATGCAATTGTTGTTGTTAACTTGTTTATTGCAGCTTA
TAATGGTTACAAATAAAGCAATAGCATCACAAATTTCACAAATAAAGCATTTTTTTCACTGCATTCTAGTTGTGGT
TTGTCCAAACTCATCAATGTATCTTATCATGTCTGGATCCCCAGGAAGCTCCTCTGTGTCCTCATAAACCCTAACC
TCCTCTACTTGAGAGGACATTCCAATCATAGGCTGCCCATCCACCCTCTGTGTCCTCCTGTTAATTAGGTCACTTA

FIGURE 17 (cont.)

ACAAAAAGGAAATTGGGTAGGGGTTTTCACAGACCGCTTTCTAAGGGTAATTTTAAAATATCTGGGAAGTCCCTT
CCACTGCTGTGTTCCAGAAGTGTTGGTAAACAGCCCACAAATGTCAACAGCAGAAACATACAAGCTGTCAGCTTTG
CACAAGGGCCCAACACCCTGCTCATCAAGAAGCACTGTGGTTGCTGTGTTAGTAATGTGCAAAACAGGAGGCACAT
TTTCCCCACCTGTGTAGGTTCCAAAATATCTAGTGTTTTCATTTTTACTTGGATCAGGAACCCAGCACTCCACTGG
ATAAGCATTATCCTTATCCAAAACAGCCTTGTGGTCAGTGTTCATCTGCTGACTGTCAACTGTAGCATTTTTTGGG
GTTACAGTTTGAGCAGGATATTTGGTCCTGTAGTTTGCTAACACACCCTGCAGCTCCAAAGGTTCCCCACCAACAG
CAAAAAAATGAAAATTTGACCCTTGAATGGGTTTTCCAGCACCATTTTCATGAGTTTTTTGTGTCCCTGAATGCAA
GTTTAACATAGCAGTTACCCCAATAACCTCAGTTTTAACAGTAACAGCTTCCCACATCAAAATATTTCCACAGGTT
AAGTCCTCATTTAAATTAGGCAAAGGAATTCCACTTCCCACTGCCTTGCTTCCGTCTCCCATTCAAACTTTTATCA
ACTGACATTATTCTAAGTAAAATCCTCTTCATTATGTTGTCAGCAATCCATTGCTTGAAGGCCTGGCTCCCCAGAA
CCCCTCGACTGGTATGTCTTCTCCTAGAATACTCCAGAAGAAAAGGAGTGTATGAAGATAGTGACTGCACATTAAA
ATGACTGAAACCATAGTAAATTAGGATGAGATTCTGGGCAGATAAACAGACAGCTGGCTAGGATCATTTTTTTATG
CCTTGGACTTCTTTGGCAATCTGTTGAAGCCTGACATTCCTCAGAATAATGTTTTAAAGCCCAACAATAAGACCCT
GTAGCACATATAATAAGTACTGCAGTTTTGAAGTAGTGATAAGCATAAATGATATTTTGATATATTTATTATAACT
GTAATGAGATGTGTACATATCTGTGACTTCATAGGTACTGATTGTACTACTGTGATTTTTTTGCCTACTTTCAAAA
TGAAAAGGAATGCTTAATTTCAGTTAGAGGTTAGTAAAGACAAATAGGTAATTTTCTTCTCCAGTGAAGAGCATGG
CGCCCCTTGCTATTCATGGACGCTTGCTTAAAGACTTGTACACAGGCTTGCTTTGTATCAACCTATGACTTCCCCT
TACAGCCGATGATAGGTTTTTATTTGCACCTCCTTCGTGTACAAAGACAGTTTTGGTGGCTACGCCATCATTAAAC
TCATTATTATCATGCTTAAGCCTATAGATGTATCCAGTTCTTCTGTTACATAATTGAAGCTGTAGTGAATTGTCTA
TCTTAAACTGCATCGCTAACTGACTACATTTCACACTTCATTTGCTTCCAACATAGACTAACCTTCTTGGATGTCC
ACTATTATTTGAACTTTTGAGATTTTTTTTCCTATTTCTAATATCTTAAAAATTTCAGAAGACTTAAAGTTTTGCAA
CTACAGGGCTCCATATAGACATCTAGCTTGAATTTATACACTTTCTTTCATTGATGTCCCTGGACTAAAAAATGTT
AAATATTTCTAACCGCTGTACTTAAAGTCCATTACAAACGAAGACTACTGTTGTTAAGTTGAATAGGCATCTTATA
TATTTTTCACCGGTGCAATAAATAACTTCTATTCCCTTCTAACATCTGCTTGCGTTGCACTGAGAGTACACTATTG
ATTAGCAATAGGTTCGTGATTACAGCCCTTCTATAATTAATTGTTAGGTTAACATATTATTCATAAAATATTATTT
TATTAATTTTTACTTGATTTGCTACTGGATGCTTAGAAATAGCTATGAGTATATTGGTAGAACCAGTACTTATATT
TTATTACATTTTTACATTTCATAAAATTTAAGTGATATAAAAATCCTGAGGAAGTATGCCACAAAAGTGGTCTCAG
TGGAAATTTAAATATGTTAACATTTATTTTTAAAATGTAGCGTGAAATAGACAACTTTAAAAGCTCAGCTTAAAAA
AAAAACTCAAGGAAGCTGAACTTGACTTTTTAAAGCACTGAAGTGCAATATTTAATGTAGGTCAACATGTTTAAAT
GGGAAAATTTTTTTCCTAATTACAGCCAAATCCCTAGCTGTAATTAACTTAAAATTTGTATACTATTTCACAACAG
AGTCAGCATATACCACTTTCTTATAAAATTAGAAAGATCTAAAATTTTAGAGCTTATTTGGTGAAACAGGCATATT
GCTACATCTTTGTTTATAAATTATAATGTGCCTTTAGAGCCCAATAACAGATAACAAGATTTTGAAAATTCAGGTG
AATTAGAGTTATCAGAGGGAATGTTAATACACTCTATTCAAATACTATATGAGTAAGACATTTAAAATAGGAAACA
ATACTTTATATATTAAAAAAAATTAATCTTCCAGTCGATTTAATCCACTTTATGAATTCATTTAAATCGATTTAAA
TTCGAATTAATTAACTAGAGTACCCGGGGATCTTATTCCCTTTAACTAATAAAAAAAAAATAATAAAGCATCACTTA
CTTAAAATCAGTTAGCAAATTTCTGTCCAGTTTATTCAGCAGCACCTCCTTGCCCTCCTCCCAGCTCTGGTATTGC
AGCTTCCTCCTGGCTGCAAACTTTCTCCACAATCTAAATGGAATGTCAGTTTCCTCCTGTTCCTGTCCATCCGCAC
CCACTATCTTCATGTTGTTGCAGATGAAGCGCGCAAGACCGTCTGAAGATACCTTCAACCCCGTGTATCCATATGA
CACGGAAACCGGTCCTCCAACTGTGCCTTTTCTTACTCCTCCCTTTGTATCCCCCAATGGGTTTCAAGAGAGTCCC
CCTGGGGTACTCTCTTTGCGCCTATCCGAACCTCTAGTTACCTCCAATGGCATGCTTGCGCTCAAAATGGGCAACG
GCCTCTCTCTGGACGAGGCCGGCAACCTTACCTCCCAAAATGTAACCACTGTGAGCCCACCTCTCAAAAAAACCAA
GTCAAACATAAACCTGGAAATATCTGCACCCCTCACAGTTACCTCAGAAGCCCTAACTGTGGCTGCCGCCGCACCT
CTAATGGTCGCGGGCAACACACTCACCATGCAATCACAGGCCCCGCTAACCGTGCACGACTCCAAACTTAGCATTG
CCACCCAAGGACCCCTCACAGTGTCAGAAGGAAAGCTAGCCCTGCAAACATCAGGCCCCCTCACCACCACCGATAG
CAGTACCCTTACTATCACTGCCTCACCCCCTCTAACTACTGCCACTGGTAGCTTGGGCATTGACTTGAAAGAGCCC
ATTTATACACAAAATGGAAAACTAGGACTAAAGTACGGGGCTCCTTTGCATGTAACAGACGACCTAAACACTTTGA
CCGTAGCAACTGGTCCAGGTGTGACTATTAATAATACTTCCTTGCAAACTAAAGTTACTGGAGCCTTGGGTTTTGA
TTCACAAGGCAATATGCAACTTAATGTAGCAGGAGGACTAAGGATTGATTCTCAAAACAGACGCCTTATACTTGAT
GTTAGTTATCCGTTTGATGCTCAAAACCAACTAAATCTAAGACTAGGACAGGGCCCTCTTTTTATAAACTCAGCCC
ACAACTTGGATATTAACTACAACAAAGGCCTTTACTTGTTTACAGCTTCAAACAATTCCAAAAAGCTTGAGGTTAA
CCTAAGCACTGCCAAGGGGTTGATGTTTGACGCTACAGCCATAGCCATTAATGCAGGAGATGGGCTTGAATTTGGT
TCACCTAATGCACCAAACACAAATCCCCTCAAAACAAAAATTGGCCATGGCCTAGAATTTGATTCAAACAAGGCTA
TGGTTCCTAAACTAGGAACTGGCCTTAGTTTTGACAGCACAGGTGCCATTACAGTAGGAAACAAAAATAATGATAA
GCTAACTTTGTGGACCACACCAGCTCCATCTCCTAACTGTAGACTAAATGCAGAGAAAGATGCTAAACTCACTTTG
GTCTTAACAAAATGTGGCAGTCAAATACTTGCTACAGTTTCAGTTTTGGCTGTTAAAGGCAGTTTGGCTCCAATAT
CTGGAACAGTTCAAAGTGCTCATCTTATTATAAGATTTGACGAAAATGGAGTGCTACTAAACAATTCCTTCCTGGA
CCCAGAATATTGGAACTTTAGAAATGGAGATCTTACTGAAGGCACAGCCTATACAAACGCTGTTGGATTTATGCCT
AACCTATCAGCTTATCCAAAATCTCACGGTAAAACTGCCAAAAGTAACATTGTCAGTCAAGTTTACTTAAACGGAG
ACAAAACTAAACCTGTAACACTAACCATTACACTAAACGGTACACAGGAAACAGGAGACACAACTCCAAGTGCATA
CTCTATGTCATTTTCATGGGACTGGTCTGGCCACAACTACATTAATGAAATATTTGCCACATCCTCTTACACTTTT
TCATACATTGCCCAAGAATAAAGAATCGTTTGTGTTATGTTTCAACGTGTTTATTTTTCAATTGCAGAAAATTTCA

FIGURE 17 (cont.)

AGTCATTTTTCATTCAGTAGTATAGCCCCACCACCACATAGCTTATACAGATCACCGTACCTTAATCAAACTCACA
GAACCCTAGTATTCAACCTGCCACCTCCCTCCCAACACACAGAGTACACAGTCCTTTCTCCCCGGCTGGCCTTAAA
AAGCATCATATCATGGGTAACAGACATATTCTTAGGTGTTATATTCCACACGGTTTCCTGTCGAGCCAAACGCTCA
TCAGTGATATTAATAAACTCCCCGGGCAGCTCACTTAAGTTCATGTCGCTGTCCAGCTGCTGAGCCACAGGCTGCT
GTCCAACTTGCGGTTGCTTAACGGGCGGCGAAGGAGAAGTCCACGCCTACATGGGGGTAGAGTCATAATCGTGCAT
CAGGATAGGGCGGTGGTGCTGCAGCAGCGCGCGAATAAACTGCTGCCGCCGCCGCTCCGTCCTGCAGGAATACAAC
ATGGCAGTGGTCTCCTCAGCGATGATTCGCACCGCCCGCAGCATAAGGCGCCTTGTCCTCCGGGCACAGCAGCGCA
CCCTGATCTCACTTAAATCAGCACAGTAACTGCAGCACAGCACCACAATATTGTTCAAAATCCCACAGTGCAAGGC
GCTGTATCCAAAGCTCATGGCGGGGACCACAGAACCCACGTGGCCATCATACCACAAGCGCAGGTAGATTAAGTGG
CGACCCCTCATAAACACGCTGGACATAAACATTACCTCTTTTGGCATGTTGTAATTCACCACCTCCCGGTACCATA
TAAACCTCTGATTAAACATGGCGCCATCCACCACCATCCTAAACCAGCTGGCCAAAACCTGCCCGCCGGCTATACA
CTGCAGGGAACCGGGACTGGAACAATGACAGTGGAGAGCCCAGGACTCGTAACCATGGATCATCATGCTCGTCATG
ATATCAATGTTGGCACAACACAGGCACACGTGCATACACTTCCTCAGGATTACAAGCTCCTCCCGCGTTAGAACCA
TATCCCAGGGAACAACCCATTCCTGAATCAGCGTAAATCCCACACTGCAGGGAAGACCTCGCACGTAACTCACGTT
GTGCATTGTCAAAGTGTTACATTCGGGCAGCAGCGGATGATCCTCCAGTATGGTAGCGCGGGTTTCTGTCTCAAAA
GGAGGTAGACGATCCCTACTGTACGGAGTGCGCCGAGACAACCGAGATCGTGTTGGTCGTAGTGTCATGCCAAATG
GAACGCCGGACGTAGTCATATTTCCTGAAGCAAAACCAGGTGCGGGCGTGACAAACAGATCTGCGTCTCCGGTCTC
GCCGCTTAGATCGCTCTGTGTAGTAGTTGTAGTATATCCACTCTCTCAAAGCATCCAGGCGCCCCCTGGCTTCGGG
TTCTATGTAAACTCCTTCATGCGCCGCTGCCCTGATAACATCCACCACCGCAGAATAAGCCACACCCAGCCAACCT
ACACATTCGTTCTGCGAGTCACACACGGGAGGAGCGGGAAGAGCTGGAAGAACCATGTTTTTTTTTTTATTCCAAA
AGATTATCCAAAACCTCAAAATGAAGATCTATTAAGTGAACGCGCTCCCCTCCGGTGGCGTGGTCAAACTCTACAG
CCAAAGAACAGATAATGGCATTTGTAAGATGTTGCACAATGGCTTCCAAAAGGCAAACGGCCCTCACGTCCAAGTG
GACGTAAAGGCTAAACCCTTCAGGGTGAATCTCCTCTATAAACATTCCAGCACCTTCAACCATGCCCAAATAATTC
TCATCTCGCCACCTTCTCAATATATCTCTAAGCAAATCCCGAATATTAAGTCCGGCCATTGTAAAAATCTGCTCCA
GAGCGCCCTCCACCTTCAGCCTCAAGCAGCGAATCATGATTGCAAAAATTCAGGTTCCTCACAGACCTGTATAAGA
TTCAAAAGCGGAACATTAACAAAAATACCGCGATCCCGTAGGTCCCTTCGCAGGGCCAGCTGAACATAATCGTGCA
GGTCTGCACGGACCAGCGCGGCCACTTCCCCGCCAGGAACCTTGACAAAAGAACCCACACTGATTATGACACGCAT
ACTCGGAGCTATGCTAACCAGCGTAGCCCCGATGTAAGCTTTGTTGCATGGGCGGCGATATAAAATGCAAGGTGCT
GCTCAAAAAATCAGGCAAAGCCTCGCGCAAAAAAGAAAGCACATCGTAGTCATGCTCATGCAGATAAAGGCAGGTA
AGCTCCGGAACCACCACAGAAAAAGACACCATTTTTCTCTCAAACATGTCTGCGGGTTTCTGCATAAACACAAAAT
AAAATAACAAAAAAACATTTAAACATTAGAAGCCTGTCTTACAACAGGAAAAACAACCCTTATAAGCATAAGACGG
ACTACGGCCATGCCGGCGTGACCGTAAAAAAACTGGTCACCGTGATTAAAAAGCACCACCGACAGCTCCTCGGTCA
TGTCCGGAGTCATAATGTAAGACTCGGTAAACACATCAGGTTGATTCATCGGTCAGTGCTAAAAAGCGACCGAAAT
AGCCCGGGGGAATACATACCCGCAGGCGTAGAGACAACATTACAGCCCCCATAGGAGGTATAACAAAATTAATAGG
AGAGAAAAACACATAAACACCTGAAAAACCCTCCTGCCTAGGCAAAATAGCACCCTCCCGCTCCAGAACAACATAC
AGCGCTTCACAGCGGCAGCCTAACAGTCAGCCTTACCAGTAAAAAAGAAAACCTATTAAAAAAACACCACTCGACA
CGGCACCAGCTCAATCAGTCACAGTGTAAAAAAGGGCCAAGTGCAGAGCGAGTATATATAGGACTAAAAAATGACG
TAACGGTTAAAGTCCACAAAAAACACCCAGAAAACCGCACGCGAACCTACGCCCAGAAACGAAAGCCAAAAAACCC
ACAACTTCCTCAAATCGTCACTTCCGTTTTCCCACGTTACGTAACTTCCCATTTTAAGAAAACTACAATTCCCAAC
ACATACAAGTTACTCCGCCCTAAAACCTACGTCACCCGCCCCGTTCCCACGCCCCGCGCCACGTCACAAACTCCAC
CCCCTCATTATCATATTGGCTTCAATCCAAAATAAGGTATATTATTGATGATGGCCGGCCGAATTGAATCAGGGGA
TAACGCAGGAAAGAACATGTGAGCAAAAGGCCAGCAAAAGGCCAGGAACCGTAAAAAGGCCGCGTTGCTGGCGTTT
TTCCATAGGCTCCGCCCCCCTGACGAGCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATCTCAGTTCGGTGTAG
GTCGTTCGCTCCAAGCTGGGCTGTGTGCACGAACCCCCCGTTCAGCCCGACCGCTGCGCCTTATCCGGTAACTATC
GTCTTGAGTCCAACCCGGTAAGACACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAGAAGGACAGTATTTGGTATC
TGCGCTCTGCTGAAGCCAGTTACCTTCGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGATCTCAAGAAGATCCTTTGATCTTTTC
TACGGGGTCTGACGCTCAGTGGAACGAAAACTCACGTTAAGGGATTTTGGTCATGAGATTATCAAAAAGGATCTTC
ACCTAGATCCTTTTAAATTAAAAATGAAGTTTTAAATCAATCTAAAGTATATATGAGTAAACTTGGTCTGACAGTT
ACCAATGCTTAATCAGTGAGGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGATACCGCGAGACCCACGCTCA
CCGGCTCCAGATTTATCAGCAATAAACCAGCCAGCCGGAAGGGCCGAGCGCAGAAGTGGTCCTGCAACTTTATCCG
CCTCCATCCAGTCTATTAATTGTTGCCGGGAAGCTAGAGTAAGTAGTTCGCCAGTTAATAGTTTGCGCAACGTTGT
TGCCATTGCTACAGGCATCGTGGTGTCACGCTCGTCGTTTGGTATGGCTTCATTCAGCTCCGGTTCCCAACGATCA
AGGCGAGTTACATGATCCCCCATGTTGTGCAAAAAAGCGGTTAGCTCCTTCGGTCCTCCGATCGTTGTCAGAAGTA
AGTTGGCCGCAGTGTTATCACTCATGGTTATGGCAGCACTGCATAATTCTCTTACTGTCATGCCATCCGTAAGATG
CTTTTCTGTGACTGGTGAGTACTCAACCAAGTCATTCTGAGAATAGTGTATGCGGCGACCGAGTTGCTCTTGCCCG
GCGTCAATACGGGATAATACCGCGCCACATAGCAGAACTTTAAAAGTGCTCATCATTGGAAAACGTTCTTCGGGGC

FIGURE 17 (cont.)

GAAAACTCTCAAGGATCTTACCGCTGTTGAGATCCAGTTCGATGTAACCCACTCGTGCACCCAACTGATCTTCAGC
ATCTTTTACTTTCACCAGCGTTTCTGGGTGAGCAAAAACAGGAAGGCAAAATGCCGCAAAAAAGGGAATAAGGGCG
ACACGGAAATGTTGAATACTCATACTCTTCCTTTTTCAATATTATTGAAGCATTTATCAGGGTTATTGTCTCATGA
GCGGATACATATTTGAATGTATTTAGAAAAATAAACAAATAGGGGTTCCGCGCACATTTCCCCGAAAAGTGCCAC

FIGURE 18

SEQ ID NO:17 (Ad2 preterminal protein)
MALSVNDCARLTGQSVPTMEHFLPLRNIWNRVRDFPRASTTAAGITWMSRYIYGYHRLMLEDLA
PGAPATLRWPLYRQPPPHFLVGYQYLVRTCNDYVFDSRAYSRLRYTELSQPGHQTVNWSVMANC
TYTINTGAYHRFVDMDDFQSTLTQVQQAILAERVVADLALLQPMRGFGVTRMGGRGRHLRPNSA
AAVAIDARDAGQEEGEEEVPVERLMQDYYKDLRRCQNEAWGMADRLRIQQAGPKDMVLLSTIR
RLKTAYFNYIISSTSARNNPDRHPLPPATVLSLPCDCDWLDAFLERFSDPVDADSLRSLGGGVPTQQ
LLRCIVSAVSLPHGSPPPTHNRDMTGGVFQLRPRENGRAVTETMRRRRGEMIERFVDRLPVRRRRR
RVPPPPPPPEEEEEGEALMEEEIEEEEAPVAFEREVRDTVAELIRLLEEELTVSARNSQFFNFAVDFY
EAMERLEALGDINESTLRRWVMYFFVAEHTATTLNYLFQRLRNYAVFARHVELNLAQVVMRAR
DAEGGVVYSRVWNEGGLNAFSQLMARISNDLAATVERAGRGDLQEEEIEQFMAEIAYQDNSGDV
QEILRQAAVNDTEIDSVELSFRFKLTGPVVFTQRRQIQEINRRVVAFASNLRAQHQLLPARGADVPL
PPLPAGPEPPLPPGARPRHRF*

SEQ ID NO:18 (Ad2 terminal protein)
VFQLRPRENGRAVTETMRRRRGEMIERFVDRLPVRRRRRRVPPPPPPPEEEEEGEALMEEEIEEEEA
PVAFEREVRDTVAELIRLLEEELTVSARNSQFFNFAVDFYEAMERLEALGDINESTLRRWVMYFFV
AEHTATTLNYLFQRLRNYAVFARHVELNLAQVVMRARDAEGGVVYSRVWNEGGLNAFSQLMA
RISNDLAATVERAGRGDLQEEEIEQFMAEIAYQDNSGDVQEILRQAAVNDTEIDSVELSFRFKLTGP
VVFTQRRQIQEINRRVVAFASNLRAQHQLLPARGADVPLPPLPAGPEPPLPPGARPRHRF*

SEQ ID NO:19 (Ad5 preterminal protein)
MALSVNDCARLTGQSVPTMEHFLPLRNIWNRVRDFPRASTTAAGITWMSRYIYGYHRLMLEDLA
PGAPATLRWPLYRQPPPHFLVGYQYLVRTCNDYVFDSRAYSRLRYTELSQPGHQTVNWSVMANC
TYTINTGAYHRFVDMDDFQSTLTQVQQAILAERVVADLALLQPMRGFGVTRMGGRGRHLRPNSA
AAAAIDARDAGQEEGEEEVPVERLMQDYYKDLRRCQNEAWGMADRLRIQQAGPKDMVLLSTIR
RLKTAYFNYIISSTSARNNPDRRPLPPATVLSLPCDCDWLDAFLERFSDPVDADSLRSLGGGVPTQQ
LLRCIVSAVSLPHGSPPPTHNRDMTGGVFQLRPRENGRAVTETMRRRRGEMIERFVDRLPVRRRRR
RVPPPPPPPEEEEGEALMEEEIEEEEEAPVAFEREVRDTVAELIRLLEEELTVSARNSQFFNFAVDFY
EAMERLEALGDINESTLRRWVMYFFVAEHTATTLNYLFQRLRNYAVFARHVELNLAQVVMRAR
DAEGGVVYSRVWNEGGLNAFSQLMARISNDLAATVERAGRGDLQEEEIEQFMAEIAYQDNSGDV
QEILRQAAVNDTEIDSVELSFRLKLTGPVVFTQRRQIQEINRRVVAFASNLRAQHQLLPARGADVP
LPPLPAGPEPPLPPGARPRHRF*

SEQ ID NO:20 (Ad5 terminal protein)
VFQLRPRENGRAVTETMRRRRGEMIERFVDRLPVRRRRRRVPPPPPPPEEEEGEALMEEEIEEEEEA
PVAFEREVRDTVAELIRLLEEELTVSARNSQFFNFAVDFYEAMERLEALGDINESTLRRWVMYFFV
AEHTATTLNYLFQRLRNYAVFARHVELNLAQVVMRARDAEGGVVYSRVWNEGGLNAFSQLMA
RISNDLAATVERAGRGDLQEEEIEQFMAEIAYQDNSGDVQEILRQAAVNDTEIDSVELSFRLKLTGP
VVFTQRRQIQEINRRVVAFASNLRAQHQLLPARGADVPLPPLPAGPEPPLPPGARPRHRF*

PRODUCTION OF VIRAL VECTORS

This application is a continuation of application Ser. No. 10/381,153, filed on Oct. 9, 2003 and now U.S. Pat. No. 7,820,441 issued on Oct. 26, 2010, which is a 371 filing of PCT/US2001/029496 filed on Sep. 21, 2001 which claims priority to 60/235,060 filed on Sep. 25, 2000.

This invention was made with Government support under contract NIH P01A6015434. The government has certain rights in this invention.

A Sequence Listing has been submitted in an ASCII text file named "07763.ST25.txt" created on Jan. 3, 2007, consisting of 218 kilo bytes, the entire content of which is herein incorporated by reference.

FIELD OF THE INVENTION

The present invention relates to methods and compositions for the production of viral vectors. In particular, the present invention provides methods and compositions for faster, higher titer and higher purity production of adenovirus vectors.

BACKGROUND OF THE INVENTION

Conventional adenovirus (Ad) gene-delivery vectors are based on replacement of early regions of the viral genome with an expression cassette coding for a gene of interest. Unfortunately, Ad vectors have drawbacks that limit their usefulness for many applications. First, the cloning capacity of these vectors is limited to 8-10 kb. Second, despite deletion of the E1 region, leaky expression of immunogenic viral proteins occurs in vivo, which leads to a host immune response and elimination of gene expression from transduced tissues. Gutted, or helper-dependent, adenoviral vectors may overcome these drawbacks. Gutted vectors contain cis-acting DNA sequences necessary for viral replication and packaging, but usually do not contain viral coding sequences (See U.S. Pat. No. 6,083,750, incorporated by reference). These vectors can accommodate up to 36 kb of exogenous DNA and are unable to express viral proteins. Gutted vectors are produced by replication in the presence of a helper virus, which provides all necessary viral proteins in trans. Since the viral proteins act to replicate both gutted and helper genomes, gutted adenovirus particles are prepared as a mixture with helper virions, though selection against helper virus packaging can reduce this contamination. Particles containing gutted viral genomes, rather than helper genomes, are subsequently purified on the basis of their lower density.

Generally, the starting point for production of a gutted virus is plasmid DNA. The plasmid contains the viral inverted terminal repeats (ITRs), the viral packaging signal, and exogenous DNA to be carried by the gutted virus. To increase production of gutted virus, most investigators linearize the gutted viral plasmid (some systems require the ligation of viral ITRs after linearization). The plasmid DNA is co-introduced with helper sequences into a cell line that can replicate the helper virus, normally 293 cells. Replication of the helper virus eventually causes lysis of the cells with the lysate containing a large number of helper virions and a comparatively small number of gutted virions.

To increase the number and proportion of gutted virions in the lysate, the initial mixture is generally serially passaged. Helper-dependent Ad vectors are usually propagated with constant selective pressure against helper virus packaging. During early passages, selection allows for gradual improvement in the ratio of gutted to helper virus. At the last passage selection removes the majority of helper virus before further purification. Unfortunately, growth of vector stocks under selective pressure can lead to rearrangement of helper and gutted viruses.

The production of gutted virus particles from plasmid DNA in the first step of gutted vector production is so inefficient that titers of less than 100 particles per milliliter have been reported. In some cases no gutted virions can be detected until at least one serial passage has been performed. What is needed is methods and compositions for faster, higher titer and higher purity production of adenovirus vectors.

SUMMARY OF THE INVENTION

The present invention relates to methods and compositions for the production of viral vectors. In particular, the present invention provides methods and compositions for faster, higher titer and higher purity production of viral vectors (e.g. adenoviral vectors). In some embodiments, the present invention provides gutted and helper viruses with corresponding termini. In other embodiments, the present invention provides terminal protein linked adenoviral DNA. In other embodiments, the present invention provides template extended adenoviral DNA (e.g. for increased viral production/recovery and plaquing efficiency). In additional embodiments, the present invention provides methods and compositions for culturing gutted and helper adenoviruses (e.g. with similar or identical termini). For example, the present invention provides compositions and methods for regulated expression of site specific recombinases. In another example, the present invention provides compositions (e.g. cell lines) and methods for culturing adenoviral vectors with adenoviral protein IX.

In some embodiments, the present invention provides methods for producing helper-dependent viral vectors comprising: a) providing; i) helper-dependent viral DNA comprising a first origin of replication, ii) helper viral DNA comprising a second origin of replication, wherein the second origin of replication has similar activity level in a replication assay as the first origin of replication, and iii) target cells; and b) transfecting the target cells with the helper-dependent viral DNA and the helper viral DNA under conditions such that helper-dependent viral vectors are produced. In particular embodiments, the present invention provides compositions comprising the helper-dependent viral vectors produced with the methods of the present invention. In certain embodiments, the helper-dependent viral DNA comprises adenoviral DNA. In particular embodiments, the helper-dependent viral DNA comprises a heterologous gene sequence. In some embodiments, the helper-dependent viral DNA comprises the left and right inverted terminal repeats (ITRs) of adenovirus, the adenoviral packaging sequence (e.g. linked to one of the ITRs), and a heterologous gene sequence.

In preferred embodiments, the first origin of replication and the second origin of replication have nucleic acid sequences that are identical. In some embodiments, the first and/or second origin of replication lie near the terminus of the viral DNA. In other embodiments, the helper-dependent viral DNA has been released from a plasmid backbone by restriction enzyme digestion. In some embodiments, the helper viral DNA has been released from a plasmid backbone. In preferred embodiments, the helper-dependent viral DNA is at least partially linear (in some cases, entirely linear). In other embodiments, the helper viral DNA is at least partially linear (in some cases, entirely linear). In certain embodiments, both the helper-viral DNA and the helper viral DNA lack internal FseI restriction sites (e.g. so plasmids containing both kinds of viral DNA may be digested with FseI to release the viral DNA without cutting viral coding sequences).

In certain embodiments, the first origin of replication and the second origin of replication have nucleic acid sequences that are similar (e.g. they differ by one base, two bases, or three bases). In additional embodiments, the origins are similar and one of the origins is the natural origin and the other is unnatural (e.g. it has additional sequences attached). In some embodiments, the helper viral DNA is adenoviral helper viral DNA. In preferred embodiments, the first origin of replication and the second origin of replication are not linked to terminal protein or any terminal protein remnant.

In some embodiments, the helper viral DNA comprises a crippling sequence. In preferred embodiments, the crippling sequence comprises recognition sites for site-specific recombinases (e.g. loxP and Frt). In some embodiments, the target cells express adenoviral DNA polymerase and preterminal protein. In other embodiments, the target cells express adenoviral factor IX.

In some embodiments, the present invention provides methods for producing helper-dependent viral vectors comprising: a) providing; i) helper-dependent viral DNA comprising a first origin of replication, ii) helper viral DNA comprising a crippling sequence and a second origin of replication, wherein the second origin of replication has similar activity level in a replication assay as the first origin of replication, iii) target cells, and iv) a vector encoding a site-specific recombinase; and b) transfecting the target cells with the helper-dependent viral DNA, the helper viral DNA, and the vector encoding a site-specific recombinase under conditions such that helper-dependent viral vectors are produced. In preferred embodiments, the transfection of the helper-dependent viral DNA, the helper viral DNA, and the vector encoding a site-specific recombinase all occur at approximately the same time. In particularly preferred embodiments, the transfection of the helper-dependent viral DNA, the helper viral DNA, and the vector encoding a site-specific recombinase all occur at approximately the same time such that the vector expresses the recombinase in a regulated manner (e.g. the amount of recombinase in the transfected cells builds up slowly over time). In some embodiments, the transfection of the helper-dependent viral DNA, the helper viral DNA, and the vector encoding a site-specific recombinase occur at different time (e.g. the helper-dependent viral DNA is transfected before the helper viral DNA, or vice versa). In particular embodiments, the transfecting is accomplished by a method selected from calcium phosphate-DNA co-precipitation, DEAE-dextran-mediated transfection, polybrene-mediated transfection, electroporation, microinjection, liposome fusion, lipofection, and biolistics.

In some embodiments, the present invention provides methods for producing helper-dependent viral vectors comprising: a) providing; i) helper-dependent viral DNA comprising a first origin of replication, ii) helper viral DNA comprising a second origin of replication, wherein the second origin of replication has a similar activity level in a replication assay as the first origin of replication, and iii) target cells; b) transfecting the target cells with the helper-dependent viral DNA and the helper viral DNA under conditions such that helper-dependent viral vectors are produced; and c) recovering the helper-dependent vectors. In preferred embodiments, the recovering step yields a helper-dependent titer of up to approximately 30 fold increase compared to transfection/infection protocols in cells expressing adenoviral DNA polymerase and preterminal protein (e.g., at least a 10 fold, at least a 15 fold, at least a 20 fold, or at least 25 fold increase). In particularly preferred embodiments, the recovering step yields a helper-dependent titer of up to approximately 60 fold increase compared to transfection/infection protocols in cells expressing adenoviral DNA polymerase and preterminal protein (e.g., at least 40 fold, at least 50 fold, or at least 55 fold increase).

In some embodiments, the present invention provides compositions comprising; a) helper-dependent viral DNA comprising a first origin of replication, and b) helper viral DNA comprising a second origin of replication, wherein the second origin of replication has a similar activity level in a replication assay as the first origin of replication. In certain embodiments, the helper-dependent viral DNA comprises adenoviral DNA. In particular embodiments, the helper-dependent viral DNA comprises a heterologous gene sequence. In some embodiments, the helper-dependent viral DNA comprises the left and right inverted terminal repeats (ITRs) of adenovirus, the adenoviral packaging sequence (e.g. linked to one of the ITRs), and a heterologous gene sequence. In preferred embodiments, the first origin of replication and the second origin of replication have nucleic acid sequences that are identical. In certain embodiments, the first origin of replication and the second origin of replication have nucleic acid sequences that are similar (e.g. they differ by one base, two bases, or three bases). In additional embodiments, the origins are similar and one of the origins is the natural origin and the other is unnatural (e.g. it has additional sequences attached). In some embodiments, the helper viral DNA is adenoviral helper viral DNA. In preferred embodiments, the first origin of replication and the second origin of replication are not linked to terminal protein or any terminal protein remnant.

In some embodiments, the present invention provides kits and systems comprising; i) helper-dependent viral DNA comprising a first origin of replication, and ii) helper viral DNA comprising a second origin of replication, wherein the second origin of replication has similar activity level in a replication assay as the first origin of replication. In preferred embodiments, the kits and systems of the present invention further comprise target cells (e.g., cells expressing adenoviral DNA polymerase and preterminal protein). In other embodiments, the kits and systems of the present invention comprise the helper-dependent viral vectors produced by the methods of the present invention, and one additional component (e.g., an insert component with written instructions for using the components of the kit and system). The kits and systems of the present invention may comprise any of the components listed herein (e.g., helper-dependent viral DNA, helper viral DNA, target cells, insert component, etc.). In particular embodiments, the kits and systems of the present invention comprise a host cell and one additional component, wherein the host cell comprises a) helper-dependent viral DNA comprising a first origin of replication, and b) helper viral DNA comprising a second origin of replication, wherein the second origin of replication has a similar activity level in a replication assay as the first origin of replication.

In some embodiments, the present invention provides methods for producing helper-dependent viral vectors comprising: a) providing; i) helper-dependent viral DNA comprising an origin of replication linked to a replication-promoting agent, and ii) target cells; and b) transfecting the target cells with the helper-dependent viral DNA under conditions such that helper-dependent viral vectors are produced. In particular embodiments, the present invention provides methods for producing helper-dependent viral vectors comprising: a) providing; i) helper-dependent viral DNA comprising an origin of replication linked to a replication-promoting agent, ii) helper viral DNA, and iii) target cells; and b) transfecting the target cells with the helper-dependent viral DNA and the helper viral DNA under conditions such that helper-dependent viral vectors are produced. In certain embodiments, the present invention provides compositions comprising the helper-dependent viral vectors produced with the methods of the present invention. In preferred embodiments, the replication-promoting agent is selected from Ad2 preterminal protein, Ad2 terminal protein, Ad5 preterminal protein, and Ad5 terminal protein. In other embodiments, replication-promoting agent is selected from at least a portion of Ad2 preterminal protein, Ad2 terminal protein, Ad5 preterminal protein, and Ad5 terminal protein. In preferred embodiments, the replication-promoting agent is Ad5 terminal protein.

In some embodiments, the helper-dependent viral DNA comprises adenoviral DNA. In other embodiments, the helper-dependent viral DNA comprises a heterologous gene sequence. In some embodiments, the helper-dependent viral DNA comprises the left and right inverted terminal repeats (ITRs) of adenovirus, the adenoviral packaging sequence (e.g. linked to one of the ITRs), and a heterologous gene sequence. In some embodiments, the helper viral DNA is linked to adenoviral terminal protein. In additional embodiments, the helper viral DNA is adenoviral helper viral DNA. In preferred embodiments, the helper viral DNA comprises a crippling sequence (e.g. loxP). In particular embodiments, the helper viral DNA comprises recognition sites for site-specific recombinases. In certain embodiments, the target cells express adenoviral DNA polymerase and preterminal protein. In other embodiments, the target cells express adenoviral protein IX. In certain embodiments, the target cells express adenoviral DNA polymerase, preterminal protein, and adenoviral protein IX. In some embodiments, the method further comprises recovering the helper-dependent vectors. In particular embodiments, the recovering yields a helper-dependent titer of up to approximately 85 fold increase compared to transfection/infection protocols in cells expressing adenoviral DNA polymerase and preterminal protein (e.g., at least a 40 fold, 55 fold, 70 fold, or 80 fold increase). In preferred embodiments, the recovering yields a helper-dependent titer of up to 170 fold increase compared to transfection/infection protocols in cells expressing adenoviral DNA polymerase and preterminal protein (e.g., at least 100 fold, 120 fold, 140 fold, 150 fold, or 160 fold increase).

In particular embodiments, the present invention provides methods for producing helper-dependent viral vectors comprising: a) providing; i) helper-dependent viral DNA comprising an origin of replication linked to a replication-promoting agent, ii) helper viral DNA comprising a crippling sequence, and iii) target cells; and b) transfecting the target cells with the helper-dependent viral DNA and the helper viral DNA under conditions such that helper-dependent viral vectors are produced. In preferred embodiments, the transfection of the helper-dependent viral DNA, the helper viral DNA, and the vector encoding a site-specific recombinase all occur at approximately the same time. In particularly preferred embodiments, the transfection of the helper-dependent viral DNA, the helper viral DNA, and the vector encoding a site-specific recombinase all occur at approximately the same time such that the vector expresses the recombinase in a regulated manner (e.g. the amount of recombinase in the transfected cells builds up slowly over time). In some embodiments, the transfection of the helper-dependent viral DNA, the helper viral DNA, and the vector encoding a site-specific recombinase occur at different time (e.g. the helper-dependent viral DNA is transfected before the helper viral DNA, or vice versa). In particular embodiments, the transfecting is accomplished by a method selected from calcium phosphate-DNA co-precipitation, DEAE-dextran-mediated transfection, polybrene-mediated transfection, electroporation, microinjection, liposome fusion, lipofection, and biolistics.

In some embodiments, the present invention provides compositions comprising helper-dependent viral DNA comprising an origin of replication linked a replication-promoting agent. In preferred embodiments, the replication-promoting agent is selected from Ad2 preterminal protein, Ad2 terminal protein, Ad5 preterminal protein, and Ad5 terminal protein. In other embodiments, replication-promoting agent is selected from at least a portion of Ad2 preterminal protein, Ad2 terminal protein, Ad5 preterminal protein, and Ad5 terminal protein. In preferred embodiments, the replication-promoting agent is Ad5 terminal protein.

In some embodiments, the present invention provides kits and systems comprising i) helper-dependent viral DNA comprising an origin of replication linked to a replication-promoting agent, and ii) target cells. In preferred embodiments, the kits and systems of the present invention further comprise helper viral DNA. In other embodiments, the kits and systems of the present invention comprise the helper-dependent viral vectors produced by the methods of the present invention, and one additional component (e.g., an insert component with written instructions). The kits and systems of the present invention may comprise any of the components listed herein (e.g., helper-dependent viral DNA, helper viral DNA, target cells, insert component, etc.).

In certain embodiments, the present invention provides methods comprising: a) providing; i) a first helper-dependent viral DNA comprising a first origin of replication capable of promoting a first activity level in a replication assay, ii) an agent capable of extending the first origin of replication, and b) contacting the helper-dependent viral DNA with the agent for a period of time sufficient to generate a second helper-dependent viral DNA with an second origin of replication capable of promoting a second activity level in a replication assay, wherein the second activity level in a replication assay is greater than the first activity level in a replication assay. In other embodiments, the present invention provides methods comprising: a) providing; i) a first helper-dependent viral DNA comprising a first origin of replication capable of promoting a first activity level in a replication assay, ii) an agent capable of extending the first origin of replication, iii) helper viral DNA, and iv) target cells; b) contacting the helper-dependent viral DNA with the agent for a period of time sufficient to generate a second helper-dependent viral DNA with an second origin of replication capable of promoting a second activity level in a replication assay, wherein the second activity level in a replication assay is greater than the first activity level in a replication assay; and c) transfecting the target cells with the second helper-dependent viral DNA and the helper viral DNA under conditions such that helper-dependent viral vectors are produced.

In certain embodiments, the first origin of replication is natural. In some embodiments, the first origin of replication is non-natural (e.g. it has one, two, or three bases added onto the natural origin of replication). In other embodiments, the agent is selected from the group of terminal transferase, T4 DNA ligase, and T4 RNA ligase. In preferred embodiments, the agent is terminal transferase. In some embodiments, the helper-dependent viral DNA comprises adenoviral DNA. In other embodiments, the helper-dependent viral DNA comprises a heterologous gene sequence. In still other embodiments, the helper-dependent viral DNA comprises the left and right inverted terminal repeats (ITRs) of adenovirus, the adenoviral packaging sequence (e.g. linked to of the ITRs), and a heterologous gene sequence. In particular embodiments, the helper viral DNA is adenoviral helper viral DNA. In preferred embodiments, the helper viral DNA comprises a crippling sequence (e.g. a site specific recombinase). In some embodiments, the crippling sequence is loxP. In some embodiments, the target cells express adenoviral DNA polymerase and preterminal protein. In other embodiments, the target cells express adenoviral factor IX. In certain embodiments, the method further comprises recovering the helper-dependent vectors. In preferred embodiments, the second activity level in a replication assay is approximately 2-2.5 fold greater than the first activity level in a replication assay.

In other embodiments, the present invention provides methods comprising: a) providing; i) a first helper-dependent viral DNA comprising a first origin of replication capable of promoting a first activity level in a replication assay, ii) an agent capable of extending the first origin of replication, iii) helper viral DNA, iv) target cells and v) a vector encoding a site-specific recombinase; b) contacting the helper-dependent viral DNA with the agent for a period of time sufficient to generate a second helper-dependent viral DNA with an second origin of replication capable of promoting a second activity level in a replication assay, wherein the second activity level in a replication assay is greater than the first activity level in a replication assay; and c) transfecting the target cells with the second helper-dependent viral DNA, the helper viral DNA, and the vector encoding a site-specific recombinase under conditions such that helper-dependent viral vectors are produced. In certain embodiments, the present invention provides compositions comprising the helper-dependent viral vectors produced with the methods of the present invention. In preferred embodiments, the transfection of the helper-dependent viral DNA, the helper viral DNA, and the vector encoding a site-specific recombinase all occur at approximately the same time. In particularly preferred embodiments, the transfection of the helper-dependent viral DNA, the helper viral DNA, and the vector encoding a site-specific recombinase all occur at approximately the same time such that the vector expresses the recombinase in a regulated manner (e.g. the amount of recombinase in the transfected cells builds up slowly over time). In some embodiments, the transfection of the helper-dependent viral DNA, the helper viral DNA, and the vector encoding a site-specific recombinase occur at different time (e.g. the helper-dependent viral DNA is transfected before the helper viral DNA, or vice versa). In particular embodiments, the transfecting is accomplished by a method selected from calcium phosphate-DNA co-precipitation, DEAE-dextran-mediated transfection, polybrene-mediated transfection, electroporation, microinjection, liposome fusion, lipofection, retroviral infection and biolistics.

In some embodiments, the present invention provides kits and systems comprising i) a first helper-dependent viral DNA comprising a first origin of replication capable of promoting a first activity level in a replication assay, and an agent capable of extending the first origin of replication. In other embodiments, the kits and systems further comprise helper viral DNA and/or target cells. In other embodiments, the kits and systems of the present invention comprise the helper-dependent viral vectors produced by the methods of the present invention, and one additional component (e.g., an insert component with written instructions). The kits and systems of the present invention may comprise any of the components listed herein (e.g., helper-dependent viral DNA, helper viral DNA, target cells, insert component, etc.). In particular embodiments, the kits and systems of the present invention comprise a host cell and one additional component, wherein the host cell (e.g., mammalian) stably and constitutively expresses adenovirus preterminal protein, adenovirus DNA polymerase, and adenovirus protein IX.

In some embodiments the present invention provides mammalian cell lines stably and constitutively expressing adenovirus preterminal protein, adenovirus DNA polymerase, and adenovirus protein IX. In some embodiments, the cell line is D2104#10.

DESCRIPTION OF THE FIGURES

FIG. 4 shows that conversion of plasmid-derived gutted virus to a natural, TP-linked structure facilitates gutted virus rescue.

FIG. 8 shows the nucleic acid sequence of (+)lox(+)pol helper virus (SEQ ID NO:1).

FIG. 9 shows the nucleic acid sequence of pBSX (SEQ ID NO:12).

FIG. 11 shows the nucleic acid sequence of ΔFseI.4 helper virus (SEQ ID NO:9).

FIG. 14 shows the nucleic acid sequence of pD1940 (SEQ ID NO:13).

FIG. 15 shows the nucleic acid sequence of pD1962delBbsI-pIX (SEQ ID NO:14).

FIG. 17 shows the nucleic acid sequence of ΔHIX#3 (SEQ ID NO:15).

FIG. 18 shows the nucleic acid sequence for: Ad2 preterminal protein (SEQ ID NO:17); Ad2 terminal protein (SEQ ID NO:18); Ad5 preterminal protein (SEQ ID NO:19); and Ad5 terminal protein (SEQ ID NO:20).

DEFINITIONS

Figure 1:
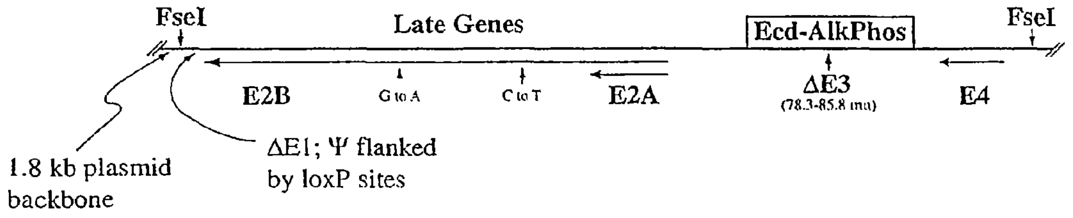
FIG. 1 shows: A) (SEQ ID NOS:21-26) the structure of viral origins of replication (both natural and non-natural origins that result when particular restriction enzymes are employed); B) (SEQ ID NOS:27-30) points where viral genome is mutated to remove FseI restriction sites; and C) partial structure of pD1940#3 and pD1940#6.

To facilitate an understanding of the present invention, a number of terms and phrases are defined below:

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. Oligonucleotide may be generated in any manner, including chemical synthesis, DNA replication, reverse transcription, or a combination thereof.

As used herein, the term “helper dependent viral DNA” or “gutted viral DNA” refers to viral DNA that codes for viral vectors that contain cis-acting DNA sequences necessary for viral replication and packaging, but generally no viral coding sequences (See U.S. Pat. No. 6,083,750, incorporated by reference). These vectors can accommodate up to about 36 kb of exogenous DNA and are unable to express viral proteins sufficient for replication. Helper-dependent viral vectors are produced by replication of the helper dependent viral DNA in the presence of a helper adenovirus, which alone or with a packaging cell line, supplies necessary viral proteins in trans such that the helper-dependent viral DNA is able to be replicated. Gutted vectors may be constructed as described in U.S. Pat. No. 6,083,750.

As used herein the term “helper viral DNA” refers to viral DNA encoding helper viral vectors, that are capable of providing, alone or with a packaging cell line, viral proteins in trans such that a gutted virus is able to replicate. A “helper adenovirus” or “helper virus” refers to an adenovirus which is replication-competent in a particular host cell. The host may provide, for example, Ad gene products such as E1 proteins. The ‘helper virus’ is used to supply in trans functions (e.g., proteins) which are lacking in a second replication-incompetent virus (e.g. a gutted viral vector). Therefore, the first replication-competent virus is said to “help” the second replication-incompetent virus thereby permitting the propagation of the second viral genome in the cell containing the helper and second viruses. Helper virus may include a sequence capable, of crippling helper virus replication in the presence of certain crippling agents. An example of a helper virus with a crippling sequence is the (+)lox(+)pol helper virus (SEQ ID NO:1). The (+)lox(+)pol helper virus is an E1-, E3-deleted virus that can be negatively selected using Cre recombinase and carries an alkaline phosphatase reporter gene in its E3 region. The packaging signal, which consists of packaging elements I-V, is flanked by loxP sites in direct repeat orientation, allowing removal of the packaging signal in the presence of Cre (a crippling agent).

The term “bacteria” refers to any bacterial species including eubacterial and archaebacterial species.

The term “virus” refers to obligate, ultramicroscopic, intracellular parasites incapable of autonomous replication (i.e., replication requires the use of the host cell’s machinery). Adenoviruses are double-stranded DNA viruses. The left and right inverted terminal repeats (ITRs) are short elements located at the 5' and 3' termini of the linear Ad genome, respectively, and are required for replication of the viral DNA. The left ITR is located between 1-130 bp in the Ad genome (also referred to as 0-0.5 mu). The right ITR is located from ~35,800 bp to the end of the genome (also referred to as 99.5-100 mu). The two ITRs are inverted repeats of each other.

The term “transfection” as used herein refers to the introduction of foreign DNA into eukaryotic cells. Transfection may be accomplished by a variety of means known to the art including, but not limited to, calcium phosphate-DNA co-precipitation, DEAE-dextran-mediated transfection, polybrene-mediated transfection, electroporation, microinjection, liposome fusion, lipofection and biolistics.

The term “stable transfection” or “stably transfected” refers to the introduction and integration of foreign DNA into the genome of the transfected cell. The term “stable transfectant” refers to a cell which has stably integrated foreign DNA into the genomic DNA.

As used herein, the term “gene of interest” or “heterologous gene sequence” refers to a gene inserted into a vector or plasmid whose expression is desired in a host cell. Genes of interest include genes having therapeutic value as well as reporter genes. A variety of such genes are contemplated, including genes of interest encoding proteins which provide a therapeutic function (such as the dystrophin gene, which is capable of correcting the defect seen in the muscle of MD patients), the utrophin gene, the CFTR gene (capable of correcting the defect seen in cystic fibrosis patients), etc.

The term “reporter gene” indicates a gene sequence that encodes a reporter molecule (including an enzyme). A “reporter molecule” is detectable in detection systems, including, but not limited to enzyme (e.g., ELISA, as well as enzyme-based histochemical assays), fluorescent, radioactive, and luminescent systems. Examples of reporter molecules include, but are not limited to, beta-galactosidase gene (available from Pharmacia Biotech, Pistacataway, N.J.), green fluorescent protein (GFP) (commercially available from Clontech, Palo Alto, Calif.), the human placental alkaline phosphatase gene, and the chloramphenicol acetyltransferase (CAT) gene. Other reporter genes are known to the art and may be employed.

As used herein, the term “activity level in a replication assay” refers to the level of activity observed for a particular type of viral origin of replication as measured in a replication assay. Examples of replication assays include, but are not limited to, plaque assays, rate of initiation of DNA replication assays, and replication factor affinity assays.

As used herein, the term “plaque assay” refers to a means for measuring the frequency with which virus or viral DNA can replicate productively (See, Graham, F. L. and Prevec, L. *Manipulation of Adenovirus Vectors in Gene Transfer and Expression Protocols*, Clifton: The Humana Press, Inc., 1991, hereby incorporated by reference). The assay may be performed, for example, by using either virus (by infection) or viral DNA (by transfection). For purposes of measuring the activity of an origin of replication the assay is performed using viral DNA. When viral DNA is introduced into cells by transfection, some transfected cells allow replication of the genome and progeny virions are produced. If the cells have been overlayed with agarose, the progeny virions diffuse to and infect only nearby cells. Thus, after several rounds of replication, foci of dead cells are observed (e.g. their presence may be highlighted through use of dyes like neutral red). These foci of dead cells are referred to as “plaques”. To measure the activity of an origin of replication in this assay, the origin is linked to helper-independent viral DNA and transfected into cells which support growth of the virus. The cells are overlayed with agarose, and the investigator waits for the appearance of plaques (e.g. 3-14 days). After plaques have appeared, their appearance may be highlighted with dye, and their number counted. The higher the number of plaques, the more often the viral DNA has been converted into replicating virus, and the higher the activity of the origin of replication is found to be. The number of plaques observed is also correlated with the amount of DNA transfected, so the results of a plaque assay may be expressed as “specific activity”; that is, the number of plaques observed per weight of DNA transfected. An origin of replication that is more active than a second origin will tend to display more plaques in the plaque assay.

As used herein, the term “rate of initiation of DNA replication assays” refers to methods for determining the rate of initiation of DNA replication on a given origin (See, Challberg M D., Rawlins Dr., *P. N. A. S.,* 81(1):100-4, 1984, herein incorporated by reference). The rate of initiation of DNA replication on a given origin may be measured, for example, by incubating the origin together with all the viral and cellular factors required for initiation, and then noting the rate with which new copies of the non-template strand appear. Generally, the steps in such an assay include: isolation of cellular and viral factors from infected cells; incubation of the isolated factors with origin fragments and radioactive nucleotides; observation of new DNA copies using an assay method such as gel electrophoresis followed by autoradiography. For each origin, the analysis is usually performed at several time points, so that the appearance of new DNA copies may be charted over time. Using this information, the rate of their appearance can be calculated. An origin of replication that is more active than a second origin will tend to cause the rate of appearance of new DNA copies to be more rapid in this assay.

As used herein, the term "replication factor affinity assays" refers to methods for determining the ability of viral DNA to attract viral replication factors (e.g. adenovirus DNA polymerase, adenovirus preterminal protein, NFI, and NFIII, See Pronlc et al, *Nucleic Acids Research,* 25(10):2293-300, 1993, herein incorporated by reference). The affinity of a replication factor for an origin of replication may be measured, for example, by incubating the two together at a variety of concentrations and then determining, at each concentration, the amount of origin DNA that was bound by factor. One example of a method used to determine the amount of bound origin DNA is an "electrophoretic mobility shift assay" (EMSA). In this assay, the presence of factor bound to DNA causes the mobility of the origin-containing DNA to be reduced in polyacrylamide gels. Using radioactive origin DNA, the amount of DNA bound by factor can therefore be determined by measuring the amount of radioactivity found in an electrophoretic band of reduced mobility—the larger the amount of radioactivity, the larger the amount of DNA bound by factor. The affinity of an origin of replication for a replication factor is indicated by the concentration levels at which substantial binding can occur: the lower the concentration at which binding occurs, the higher the affinity is said to be. The relative affinities of two origins for a replication factor could be compared by incubating radioactive samples of each origin together with different concentrations of replication factor, usually in the presence of random DNA fragments to inhibit non-specific interactions. If the first origin has a higher affinity for factor than the second origin, a lesser concentration of factor will be required to bind a given amount of origin DNA. For example, a lesser concentration of factor will be required to retard the migration of a certain proportion of DNA sequences containing the first origin than DNA sequences containing the second, as determined by EMSA.

As used herein, the term "target cells" refers to any cells that may be transfected with viral DNA. Target cells include, but are not limited to, bacterial cells, mammalian cells, and insect cells. Target cells may from any source including, but not limited to, bacterial colonies, cell lines, tissue samples, and blood samples.

As used herein the term "expresses said recombinase in a regulated manner" refers to the expression of recombinase in a target cell such that the level of recombinase in the cell gradually increases over time. This gradual increase in expression allows the helper viral DNA to replicate at a greater rate initially after transfection (when the level of recombinase is lower), and slows the replication rate of the helper virus as the level of recombinase increases. One example expression of recombinase in a regulated manner is provided in Example 6.

As used herein, the term "similar activity level in a replication assay" refers to the situation where two origins of replication have about the same activity level in a replication assay (e.g. plaque assay, replication factor affinity assay, or rate of initiation of DNA replication assay). For example, similar activity level includes a difference of 20 fold or less, preferably 10 fold or less, more preferably 5 fold or less, and most preferably 2 fold or less.

As used herein, the phrase "wherein said second activity level in a replication assay is greater than said first activity level in a replication assay" refers to a second activity level of at least 5% greater, preferably 10%, more preferably 20% greater, most preferably 50% greater, than said first activity level.

As used herein the phrase "at about the same time" refers to transfection steps that occur within approximately one hour of each other.

As used herein, the term "under conditions such that helper-dependent viral vectors are produced" refers to conditions such that help dependent viral DNA is able to replicate inside a cell (e.g. may require helper viral DNA) such that helper-dependent viral vectors (particles) are produced.

As used herein, the term "origin of replication" refers to the DNA sequence elements that are necessary and sufficient to direct replication of a DNA molecule to which they are attached. Generally, the sequence elements include binding sites for replication factors and usually span the points at which the synthesis of new DNA strand begin. Origins of replication can often be identified by the fact that their mutation or removal prevents replication of DNA molecules to which they had been attached and which had formerly replicated in a given system. In addition, the attachment of an origin of replication to a formerly inert molecule should be sufficient to cause its replication in a given system. For example, the origin of replication for adenoviral DNA has been identified as including at least the first 50 base pairs of the adenoviral genome and commonly refers to approximately the first 100 base pairs of the adenoviral genome also known as the inverted terminal repeat (ITR). Removal of the ITRs from adenoviral genome prevents its replication; the addition of ITRs to most DNA molecules is sufficient to allow their replication in cells that have been infected by helper independent adenovirals, which provides viral replication factors.

As used herein the term "viral recovery" refers to collection and storage of progeny virions produced by cells (e.g. infected by helper-dependent and helper viral DNA). This can be accomplished with or without purification of the virions to remove cellular contaminants. For example, a simple method for viral recovery is to collect lysed cells and store them in the freezer. The presence of virions may be revealed through an examination of the lysate by any of several methods including, but not limited to, plaque assay, a transduction assay that reveals the presence of a marker genes like beta-galactosidase, or physical methods such as chromatography followed by spectroscopy.

As used herein, the term "transfection/infection protocol" refers to the standard protocol where helper-dependent viral DNA is introduced into cells by a transfection method at approximately the same time (e.g. plus or minus 24 hours) that intact helper independent viral particles (e.g. contain adenoviral terminal protein linked to the origin of replication) are allowed to contact the cells and infect them. After a variable period of time the cells lyse due to replication of the virus. At that point, the progeny viral particles are collected.

As used herein, the term "replication-promoting agent" refers to a compound or molecule that may be ligated to viral DNA terminus such that the activity level in a replication assay of such viral DNA is increased (compared to not having the replication-promoting agent ligated to the viral terminus). Examples of replication-promoting agents include, but are not limited to, Ad5 adnenoviral preterminal protein, Ad5 adenoviral protein, Ad2 preterminal protein, and Ad2 terminal protein.

As used herein, the term “agent capable of extending said first origin of replication” refers to any agent that is capable of adding single nucleotides, or oligonucleotides (e.g. 10 mers) to the terminal end of viral DNA. Examples of such agents include, but are not limited to, terminal transferase, T4 DNA ligase, and T4 RNA ligase.

As used herein, the phrase “contacting said helper-dependent viral DNA with said agent for a period of time sufficient to generate”, in regards to time, refers to the length of time required to expose viral DNA origins (natural or un-natural) to an agent capable of extending such origins, such that the activity level in a replication assay of such extended origin is increased (as compared to not extended origins). This time period may vary according to the agent employed and other conditions (e.g. type and concentrations of nucleotides). One example of determining the appropriate length of time is provided in Example 5.

As used herein, the phrase “said first origin of replication and said second origin of replication have nucleic acid sequences that are substantially similar” refers to the situation where the first and second origins, while not identical, have origins of replication that are similar in nature (e.g. they both have additional nucleotides added to the natural origin of replication such that the ability). One example of substantially similar origins is provided in FIG. 1A, comparing the structure of the PacI digested viral DNA origin to the FseI digested viral DNA origin.

DESCRIPTION OF THE INVENTION

The present invention relates to methods and compositions for the production of viral vectors. In particular, the present invention provides methods and compositions for faster, higher titer and higher purity production of viral vectors (e.g. adenoviral vectors). In some embodiments, the present invention provides gutted and helper viruses with corresponding termini. In other embodiments, the present invention provides terminal protein linked adenoviral DNA. In other embodiments, the present invention provides template extended adenoviral DNA (e.g. for increased viral production/recovery and plaquing efficiency). In additional embodiments, the present invention provides methods and compositions for culturing gutted and helper adenoviruses (e.g. with similar or identical termini). For example, the present invention provides compositions and methods for regulated expression of site specific recombinases. In another example, the present invention provides compositions (e.g. cell lines) and methods for culturing adenoviral vectors with adenoviral protein IX.

I. Gutted and Helper Viruses with Similar or Identical Termini

In typical gutted virus-helper virus rescue production methods, the helper virus eventually comes to dominate the contents of the packaging cell (to the detriment of the gutted adenovirus). The number and proportion of gutted virions is small because plasmid DNA, whether circular (with fused ITRs) or linear, is a poor substrate for initiation of adenoviral DNA replication. As a result, replication of the helper virus occurs in many cells without concomitant production of gutted virus, despite the presence of gutted viral plasmid substrate.

As mentioned above, to increase the number and proportion of gutted virions in the lysate, the initial mixture is generally serially passaged. Helper-dependent Ad vectors are usually propagated with constant selective pressure against helper virus packaging. During early passages, selection allows for gradual improvement in the ratio of gutted to helper virus. Unfortunately, growth of vector stocks under selective pressure can lead to rearrangement of helper and gutted viruses. In addition, serial passage is time consuming.

Published protocols for rescue of helper-dependent Ad vectors employ gutted viral DNA derived from plasmids and helper viral DNA derived from replicating virus. Most investigators transfect gutted viral DNA and then infect with replication-competent helper virus the “transfection/infection” protocol. Others have compared transfection/infection to co-transfection of gutted viral DNA from plasmids and helper viral DNA prepared from replicating virus and found that co-transfection is more efficient. In these protocols, the helper and gutted viral DNAs have different structures at their origins of replication.

The present invention provides gutted and helper viral DNA with similar corresponding termini or linked to terminal protein, thus alleviating some of the problems of normal viral rescue protocols. While not limited to any mechanism, providing gutted and viral DNA that are substantially similar at the origin of replication allows parallel amplification of both types of vectors, thus preventing the helper viruses production from dominating over gutted virus production. Again, while not limited to any mechanism, it is believed that substantially similar termini or origins of replication (or identical termini or origins of replication) allow parallel amplification of both types of vectors because neither type of virus has a competitive advantage for attracting replication factors (such as adenoviral polymerase, transcription factors, etc.).

The present invention provides gutted and helper viruses with corresponding termini, and methods of employing such vectors for increased production yields (and faster production) of adenoviral vectors (which, may then be used, for example, for gene therapy applications). In some embodiments, gutted adenoviral DNA and helper adenoviral DNA (e.g. both located on plasmids) are released from their plasmids with the same restriction enzyme (cutting at the termini) such that the termini of the linearized DNA are the same (i.e. the gutted and helper adenoviral DNA have corresponding termini). Any type of restriction enzyme (or other enzyme that will cut DNA) may be used, as long as at least one viral terminus is released from its host vector or the ends of the DNA are able to be cut, leaving corresponding termini on both the gutted and helper DNA. In particular embodiments, different restriction enzymes are employed. In such embodiments, the ends of the viral DNA may not be identical, but the ability of the ends to promote replication in cells is approximately the same (e.g. neither type of DNA has a substantial competitive advantage after transfection, such that replication of both types of viruses proceeds at approximately the same pace). In preferred embodiments, the same restriction enzyme is used to generate the termini of both the gutted and helper viral DNA.

Preferably, restriction enzymes are employed that cut close to or at the termini of helper and gutted viral DNA. In some embodiments, creating gutted and helper adenoviral DNA with identical or similar termini requires that particular restriction sites be removed from one or both types of DNA (to prevent the digestion of the viral DNA). An example of removing unwanted restriction sites (FseI sites) from viral DNA (the Ad5 genome) is provided in Example 1. A similar procedure can be employed to remove other types of unwanted restriction sites from viral DNA. In this regard, any restriction enzyme could be employed to create identical (or similar) termini if the suitable modification are made (if necessary) in the viral DNA.

To confirm that the restriction enzyme employed is capable of releasing replication-competent viral DNA from flanking DNA sequences (e.g. plasmid DNA), an assay similar to Example 2 may be employed (transfecting gutted and helper DNA into cells known to replicate adenoviral DNA). Such a technique may also be employed to test the relative efficiency of production of viral particles from viral DNA with various termini.

In certain embodiments, neither the gutted or the helper viral DNA contain terminal protein, and both types are transfected into a cell line as DNA (e.g. the helper DNA is transfected as DNA, instead of a viral particle). In such embodiments, the identity of the termini of the helper and gutted viral DNA is not critical, as long as the termini both do not contain terminal protein or any terminal protein remnant (e.g. one serine residue). In certain embodiments, the gutted and helper viral DNA are co-transfected into a packaging cell line.

II. Replication-Promoting Agent Linked Adenoviral DNA

Another method for increasing viral production is linking gutted adenoviral DNA (e.g. the adenoviral origin) to a replication-promoting agent (e.g. adenoviral preterminal protein or adenoviral terminal protein). The normal substrate for initiation of adenoviral DNA replication is terminal protein-DNA complex. Plasmid-based substrates propagated in, for example, *E. coli*, normally lack terminal protein. As such, replication is greatly increased by linking gutted adenoviral DNA (and, in some embodiments, helper viral DNA) to adenoviral terminal protein.

In the transfection/infection protocol, or when helper virus terminal protein-DNA complex is used for co-transfection, the helper virus DNA is already attached to adenoviral terminal protein. While not limited to any mechanism, it is believed that linking the gutted adenoviral DNA termini to a replication-promoting agent (e.g. adenoviral terminal protein) reduces the competitive advantage helper virus has when supplied as viral particles (or DNA) that is already attached to terminal protein. In this regard, both types of viral DNA have a similar ability to attract replication factors and replicate into viral particles. Again, while not limited to any mechanism, it is believed that the presence of a replication-promoting agent (e.g. adenoviral preterminal protein) bound to the template confers higher affinity for incoming Ad polymerase-preterminal protein complex, an essential viral replication factor.

One method for preparing gutted viral genomes linked to adenoviral terminal protein (i.e. terminal protein serves as the replication-promoting agent) involves purifying terminal protein-containing fragments. Terminal protein-containing fragments (e.g. isolated from intact virus), can be purified away from other viral DNA fragments before ligation. It is desired that such purification be employed as the presence of other viral fragments would tend to inhibit the desired ligation reaction, since both partners in the desired ligation (gutted viral genomes and terminal protein-containing fragments) would likely be ligated to contaminating, more numerous random viral fragments in a mixed reaction. A second purification step may be performed after ligation, when unligated terminal protein-DNA fragments are removed. As these fragments contain natural Ad origins, failure to remove them could reduce the yield of gutted virus by inhibiting viral replication. Another method for obtaining terminal protein is purification of terminal protein-gutted genome complex from gutted virus preparations.

In a preferred embodiments, gutted Ad genomes are linked to normal Ad origins (FIG. 4). This method requires relatively small amounts of terminal protein DNA-complex (e.g. 2-4 moles of terminal protein-DNA complex are sufficient to convert approximately 1 mole of gutted viral genomes to the natural, terminal protein-containing form). Conveniently, the reaction can be performed without purification of the terminal protein-DNA reagent either before or after origin conversion (See Example 3).

In some embodiments, the compound used in the conversion process is terminal protein linked to single-stranded DNA (e.g. from the non-template strand of an Ad ITR). Another term for terminal protein linked to single-stranded DNA is "TP-primer". Example 3 provides one example of the preparation of TP-primer, employing a restriction enzyme digest of viral TP-DNA complex (employing Bsh1236I, AluI, and HinfI) followed by 2 exonuclease treatment. Other restriction enzymes may be employed in this process. Preferably, restriction enzymes are chosen that leave a substantial length of nucleic acid (i.e. 'primer') on the TP-primer reagent. For example, Bsh1236I, employed in Example 3, is known to cut between base pairs 73 and 74 of the Ad5 ITR, so this type of digestion results in terminal protein linked to a 73-bp, double stranded DNA molecule. This method may also employ other exonucleases (i.e. besides λ exonuclease), preferably 5' to 3' exonucleases (e.g. T7 gene 6 exonuclease).

In some embodiments, the TP-primer reagent is purified after it is constructed (e.g. to remove any mononucleotides or oligonucleotides created as a result of the enzyme digests). For example, as the TP-primer contains single-stranded DNA, any type of solid-phase purification strategy may be used (e.g. paramagnetic beads linked to single-stranded DNA that is complementary to the DNA in the TP-primer reagent—after binding of TP-primer to the beads, the beads could be collected and the TP-primer reagent released through heating). Other suitable purification/collection techniques are known in the art.

TP-primer may also be constructed synthetically. Such a synthetic reagent would contain, for example, a peptide fragment (or entire protein) of the Ad terminal protein linked to any number of bases from an adenovirus ITR. Synthesis techniques for polypeptides and nucleic acid are well known in the art.

A natural or synthetic "primer" sequence, for generating a TP-primer molecule, is selected to be substantially or completely complementary to a strand of specific sequence of the gutted viral template. A primer must be sufficiently complementary to hybridize with a template strand (e.g. such that primer elongation can occur). A primer sequence need not reflect the exact sequence of the template. Non-complementary bases or longer sequences can be interspersed into the primer, provided that the primer sequence has sufficient complementarity with the sequence of the template to hybridize and thereby form a template primer complex. Complementarity need not be perfect, stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

TP-primer molecules (or similar molecules) are used to convert viral origins to "natural" viral origins of replication. In a preferred embodiment, TP-primer is used to convert plasmid derived gutted viral genomes to natural adenoviral origins by attaching TP-primer to the terminus of adenoviral DNA. Any type of method may be employed. For example, gutted viral genomic DNA (flanked by restriction enzyme sites) may be digested with the appropriate restriction enzyme to release the gutted viral DNA. The products of this are then subjected to limited digestion with a 5' to 3' exonuclease (limited digestion with this type of enzyme exposes single-stranded regions near the gutted vector genomic termini, see FIG. 3B). Any type of 5' to 3' exonuclease may be employed (e.g. T7-gene-6 exonuclease, exonuclease, etc.). Digestion with the 5' to 3' nuclease is for a limited time (e.g. about 1-2 minutes), such that enough single strand template is exposed to hybridize to the nucleic acid in the TP-primer, but not so much that the entire strand is digested. The longer the single-stranded nucleic acid is on the TP-primer compound, the more 5' to 3' digestion is needed to expose a single-stranded template for hybridization. The exonuclease is preferably inactivated (e.g. by heating) prior to the introduction of the TP-primer.

TP-primer is then added to the digested product that is created after exonuclease digestion. The nucleic acid portion of the TP-primer (i.e. the 'primer' portion) will hybridize to its complement on the partially digested viral DNA. In preferred embodiments, the nucleic acid portion of the TP-primer is relatively long (e.g. 25 or more bases) such that the TP-primer reagent can bind efficiently to the exonuclease digest gutted DNA, even at low molar ratios. However, any length of 'primer' nucleic acid capable of hybridizing to the exonuclease digested viral DNA may be employed (see discussion above). Once the TP-primer reagent is added to the digested viral DNA, the mixture may be subjected to conditions that promote rapid hybridization. For example, the temperature of the mixture may be raised (e.g. to 75° C.) and allowed to cool (e.g. the temperature is allowed to fall slowly over 2-3 hours to room temperature).

Hybridized TP-primer molecules are then extended (e.g. using T4 DNA polymerase, Taq polymerase, etc.) and nicks are repaired (e.g. using T4 DNA ligase) in the presence of dNTPs. In some embodiments, products of the extension and nick repair are incubated for a period of time (e.g. 5 minutes) at 0°, then a period of time (e.g. 5 minutes) at room temperature, and then a period of time (e.g. 2 hours) at 37° C. In certain embodiments, EDTA is then added to this mixture, and the mixture is stored on ice. In particular embodiments, the reaction products are dialyzed against transfection buffer before being used (e.g. before being used to transfect cells).

In particular embodiments, the successful addition of TP-primer to the origin of replication (e.g. of gutted adenoviral DNA) is confirmed. Confirmation may be performed by any method. For example, a restriction digestion may be performed on the TP-primer-viral DNA molecules followed by agarose gel electrophoresis (See FIG. 4A, and Example 3). Another example of a method that may be employed to confirm the successful addition of TP-primer to the origin of replication is determining if these molecules have increased specific activity of these molecules (e.g. Example 4).

Linking gutted viral DNA to adenoviral terminal protein (e.g. by attaching TP-primer) increased the yield of gutted virus produced in a gutted viral rescue procedure. In some embodiments, co-transfection of terminal protein linked gutted DNA with terminal protein DNA complex from helper virus results in an 85 fold increase in virus production, when compared to transfection/infection protocols using C7 cells without linking the gutted viral DNA to adenoviral terminal protein. In other embodiments, co-transfection of adenoviral terminal linked gutted and helper adenoviral DNA results in greater than a 2.5 fold increase in adenoviral production (e.g. 2.7 fold increase), compared to not linking either viral DNA to adenoviral terminal protein.

The replication-promoting agent may be adenoviral terminal protein. Viral DNA may also be linked to adenoviral preterminal protein. Any source of terminal or preterminal protein (e.g. natural or synthetic) from any type of adenovirus (e.g. Ad5 and Ad2). The terminal protein or preterminal protein may be made synthetically by, for example, transfecting cells with an expression vector (e.g. plasmid) with a gene sequence encoding a least a portion of adenoviral terminal, or preterminal, protein. Examples of such nucleic acid sequences that may be express in such a recombinant fashion include, but are not limited to, SEQ ID NO:18 (Ad2 terminal protein, FIG. 18) and SEQ ID NO:20 (Ad5 terminal protein, FIG. 18). Examples of preterminal protein nucleic acid sequences include, but are not limited to, SEQ ID NO:17 (Ad2 preterminal protein, FIG. 18) and SEQ ID NO:19 (Ad5 preterminal protein). The sequences, or portions thereof, may linked to viral DNA as described above. The present invention also contemplates other replication promoting agents, including lipids, other proteins, carbohydrates, and nucleic acids, as long as they are capable of promoting the replication of viral DNA when linked to the origin of the viral DNA.

Another method for creating terminal protein-linked viral DNA is by the use of Cre recombinase to transfer a segment of DNA linked to terminal protein. For example, gutted viral plasmid DNA containing a loxP site near at least one terminus is incubated with terminal protein-DNA complex from a helper virus whose genome contains a loxP site. Cre is then added to the reaction to facilitate intermolecular exchange.

The present invention contemplates terminal protein linked gutted adenoviral DNA that is transfected with helper viral DNA that is either linked to terminal protein (e.g. natural adenoviral DNA), or not linked to helper viral DNA (e.g. deproteinized helper viral DNA). For example, terminal protein linked gutted viral DNA may be used in conjunction with adenovirus (e.g. transfection/infection protocol), deproteinized viral DNA or terminal transferase treated (see below) helper viral DNA. In some embodiments, the helper virus does not contain terminal protein. In other embodiments, the helper virus does not contain terminal protein and is used at a higher concentration than the gutted viral DNA. These sequence may also be mutated (e.g. directed evolution) to increase their ability to promote replication (See, e.g. U.S. Pat. No. 5,811,238, hereby incorporated by reference).

III. Template Strand Extended Adenoviral DNA

Figure 5:
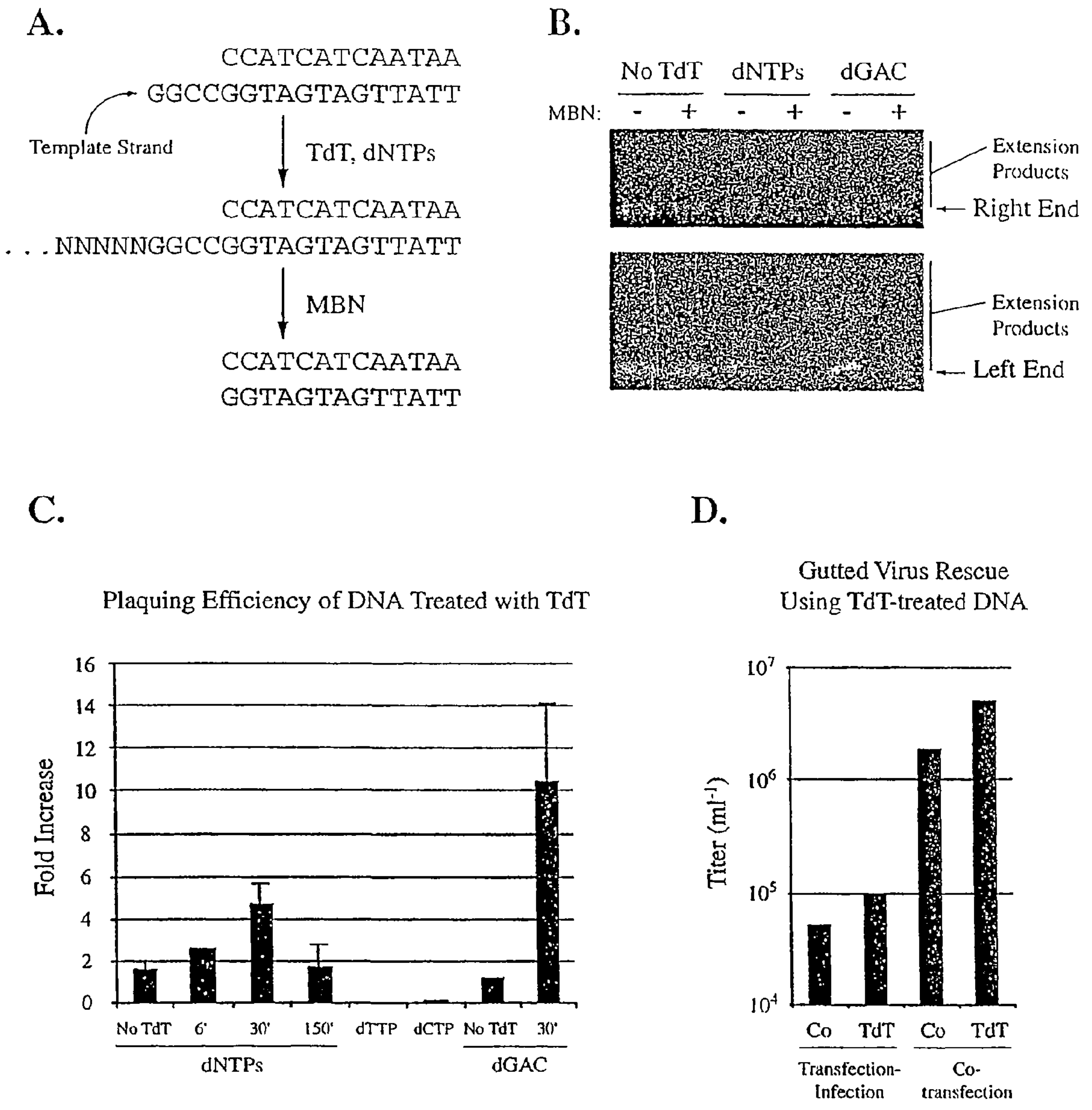
FIG. 5 (SEQ ID NOS:31-34) shows limited extension of template strand of the Ad origin increases plaquing efficiency and gutted virus recovery.

The present invention provides a further method for increasing gutted virus production (and recovery), as well as methods for increasing the plaquing efficiency of adenoviral DNA after transfection into cells. In particular, limited extension of adenoviral DNA termini (e.g. gutted adenoviral termini) increases plaquing efficiency (e.g. approximately 10 fold increase in efficiency, see Example 5 and FIG. 5) as well as increasing gutted virus recovery (e.g. an increase of 2.5 fold gutted viral recovery).

In preferred embodiments, the terminus of an adenoviral DNA is extended for a time sufficient to allow increased plaquing efficiency and/or gutted virus recovery. As demonstrated in Example 5, various time points may be tested to determine the appropriate limited template extension (e.g. in Example 5, approximately 30 minutes of extension in the presence of terminal transferase was optimal, with 6 minutes being less than optimal and 150 minutes being worse than no template extension). In some embodiments, adenoviral template DNA is extended from approximately 6 minutes to approximately 100 minutes. In preferred embodiments, the adenoviral DNA is extended for approximately 20 minutes to approximately 40 minutes. In particularly preferred embodiments, the adenoviral DNA is extended for approximately 30 minutes (e.g. 25-35 minutes). The time required to achieve a successful limited extension may be determined empirically employing methods similar to Example 5 and will vary depending on the conditions used (e.g. extending enzymes employed, concentrations of dNTPs, etc.).

Any type of enzyme capable of extending viral template DNA may be employed. For example, Taq polymerase, T4 polymerase, T4 DNA or RNA ligase, or terminal transferase may be used. In preferred embodiments, terminal transferase is employed. In some embodiments, the viral template DNA sequence is linearized by digesting with restriction enzyme(s) before template strand extension.

Template strand extension of viral DNA templates (e.g. gutted adenoviral DNA) employs molecule(s) capable of adding deoxyribonucleotide triphosphates (dNTPs) to the viral template DNA. In some embodiments, all four dNTPs are provided in the reaction mixture (i.e guanine, cytosine, adenine, thymine). In other embodiments, only two or three of the dNTPs are provided (e.g. guanine and adenine, or guanine, adenine, and cytosine). In preferred embodiments, only guanine, adenine, and cytosine are supplied to the reaction mixture (i.e. not thymine).

Limited template extension of viral DNA increases plaquing efficiency and gutted virus recovery. In certain embodiments, the plaquing efficiency is increased two fold (i.e. the plaquing efficiency is double compared to controls that do not have limited extension of the template DNA). In preferred embodiments, the plaquing efficiency is more than doubled (e.g. 3 fold, 4 fold, and 5 fold increased efficiency). In particularly preferred embodiments, the plaquing efficiency is increased approximately 10 fold. In some embodiments, the recovery of gutted virus is increased two fold. In preferred embodiments, the recovery of gutted virus is increased more than two fold (e.g. 2.5 fold). In some embodiments, template extended gutted viral DNA is transfected into cells, followed later by infection by helper virus (i.e. a transfection/infection protocol is employed). In preferred embodiments, helper and gutted viral DNA are co-transfected into cells (See Example 5, and FIG. 5D).

Extensions of viral DNA may also be accomplished by ligating various length oligos to the viral origin (i.e. ligation of oligonucleotides is employed instead of or in addition to the methods described above). For example, T4 DNA ligase may be used to ligate various oligonucleotides (e.g. ranging from 2-100 base pairs in length, and mixtures of various lengths) to viral origins in order to increase the activity of these origins. Again, assays may be employed to determine the optimal length of oligonucleotides to employ and the amount of time ligation is allowed to proceed.

IV. Culturing Gutted and Helper Adenoviruses

Methods and compositions are also provided by the present invention to increase viral recovery. In particular, improved selection strategies are provided (particularly well suited for gutted and helper adenoviral DNA with identical or similar termini). The present invention also provides cells lines expressing protein IX (and methods for allowing cells to express factor IX) to increase viral recovery.

A. Regulated Expression of Site-Specific Recombinases

Site-specific recombinases have been used to reduce helper contamination and improve gutted virus titer during serial passage. In these systems, the packaging element of the helper virus is flanked by recognition sites for site-specific recombinases like Cre or Flp. In these systems, the yield of gutted virus after rescue from plasmid is low, so improvement in gutted virus titer during serial passage is paramount. Use of a site-specific recombinase improves gutted virus titer by improving the gutted:helper ratio after lysis of a plate, so that a higher percentage of particles produced contain gutted viral genomes. This method results in a higher gutted virus titer at the following passage, since each infected cell contains a higher proportion of gutted genomes.

Such systems are typically designed for infection of each producer cell by at least one helper virus particle. This protocol typically allows for complete lysis of the plate despite the action of recombinase, which acts to prevent packaging and spread of helper virus, but does not prevent death of infected cells. In these systems, high-level production of the site-specific recombinase is desirable. Since each cell is infected by helper virus, viral spread is not necessary; higher production of recombinase leads to lower contamination with helper virus but does not compromise gutted virus production.

As described above, gutted virus rescue is most efficient when gutted and helper viral genomes with identical origin structure are co-transfected into producer cells (see also, Example 2). Employing gutted and helper viral genomes with identical (or similar) origin structure, however, a smaller fraction of transfected cells convert the helper virus DNA into replicating virus. This fact is confirmed by the observation that lysis of transfected plates takes about a week, although the time for a single round of viral replication is on the order of 24 hours. Virus produced by those few cells that converted transfected DNA to replicating virus must spread through the plate before complete lysis occurs. Under these conditions, constitutive, high-level expression of recombinase is not appropriate (See Example 6). In the presence of high levels of recombinase, the few cells that can produce virus produce very little, which often is not sufficient to lyse the plate, typically a requirement for high titers of gutted virus.

Regulated expression of site specific recombinase is provided by the present invention in order to take advantage of the beneficial activity of site specific recombinases, yet avoid the detrimental results evidenced in cells expressing site specific recombinase constitutively. Site specific recombinase may be regulated in time, with minimal to no expression at early times after transfection and high expression at later time points. While not limited to any mechanism, it is believed that the expression of a site-specific recombinase is detrimental at early times after transfection, when transfected helper genomes are being converted to replicating virus, thus providing helper particles that should spread through the plate. At later time points, however, when helper and gutted virus particles are replicating in tandem, expression of site-specific recombinase could increase the proportion of viral particles that contain gutted genomes, thereby assisting in gutted virus recovery. One example of providing such temporal expression employs co-transfection of site specific expression vectors (e.g. Cre recombinase expression vector) with viral genomes (e.g. gutted and helper viral genomes with identical origins of replication) (See Example 6). In this manner, transfected cells are not expressing Cre at the time of transfection, and after transfection, some time will pass before the appearance of the first molecules of Cre protein, since RNA and then protein must be synthesized. Finally, the level of Cre will increase to some equilibrium level on a time scale that depends on the half life of the RNA, the half life of the protein, and the strength of the promoter used to drive Cre recombinase expression.

The amount of the recombinase expression vector employed will depend on many factors. Importantly, transfecting cells with a level of recombinase expression vector that is too high to allow the helper virus DNA to replicate at a high enough level to infect most of the cells, and lyse the plate is to be avoided (See Example 6, where 176 ng of pOG231 is less effective than providing no Cre at all). Likewise, transfecting cells with a level of recombinase expression vector that is too low to prevent the helper virus from dominating the type of virus being expressed is also to be avoided (See Example 6, where 1.41 ng of pOG231 was no more effective than providing no Cre at all). Determining the appropriate level of recombinase expression level to employ for a given type of cell type, recombinase, promoters employed, etc., is within the skill in the art. For example, a concentration type assay may be employed as exemplified in Example 6. As demonstrated in this example, various levels of recombinase expression vector may be tested to determine the optimal levels of starting recombinase expression vector that should be employed. Examples of appropriate levels of recombinase expression level are provided in Example 6 (for the types of conditions employed in this assay). For example, appropriate levels of pOG231, as determined in example 6 include approximately 5-37 ng of expression vector, preferably 7-36 ng of expression vector, more preferably 16-35 ng of expression vector. Of course, altering the type of vector, cells, conditions, etc., may change the appropriate level as described above.

B. Culturing Adenovirus in Cells Expressing Adenoviral Protein IX

In order to improve production, gutted and helper adenovirus are co-transfected in cells expressing adenoviral protein IX (pIX). The protein IX gene of the adenoviruses encodes a minor component of the outer adenoviral capsid which stabilizes the group-of-nine hexons which compose the majority of the viral capsid (See U.S. Pat. Nos. 5,932,210 and 5,824,544, hereby incorporated by reference). Based upon study of adenovirus deletion mutants, protein IX initially was thought to be a non-essential component of the adenovirus, although its absence was associated with greater heat lability than observed with wild-type virus. More recently it was discovered that protein IX is essential for packaging full length viral DNA into capsids and that in the absence of protein IX, only genomes at least 1 kb smaller than wild-type could be propagated as recombinant viruses.

In one embodiment, an expression vector encoding protein IX is co-transfected with the gutted and helper adenovirus. In some embodiments, gutted and helper adenovirus are transfected in a cell line that expresses adenoviral protein IX. In preferred embodiments, the cell stably and constitutively expresses adenoviral protein IX. In particularly preferred embodiments, the cell line also expresses E2B proteins. One example of a cell line expressing E2B proteins (adenoviral DNA polymerase and preterminal protein) is the C7 cell line (See, U.S. Pat. No. 6,083,750). Creating a cell line that stably and constitutively expresses adenoviral protein IX, in addition to adenoviral DNA polymerase and preterminal protein, may be accomplished, for example by stably transfecting C7 cells (or other cells expressing E2B proteins) with a vector expressing adenoviral protein IX (See Example 7, creating the D2104#10 cell line).

Additional cell lines that stably and constitutely expresses adenoviral protein IX, in addition to adenoviral DNA polymerase and preterminal protein are contemplated. For example, any type of cell known to effectively allow adenoviral replication may be transfected with an expression vector encoding adenoviral protein IX (preferably with a selectable marker). Preferably, the cells also express preterminal protein and adenoviral DNA polymerase. Transfected cells may be grown on selective media. Clones are then screened for expression by transfection with an adenoviral protein IX negative genome, and clones producing virus after transfection are isolated.

V. Heterologous Gene Sequences

As described above, the present invention is useful for the production of adenoviral vectors (e.g. helper-dependent adenoviral vectors). The adenoviral vectors produced, in preferred embodiments, comprise a heterologous gene sequence, such that the vectors may be useful for various applications (protein expression in vitro, therapeutic applications, etc). Suitable heterologous DNA sequences include, for example, nucleic acid sequences that encode a protein that is defective or missing in a recipient subject, or a heterologous gene that encodes a protein having a desired biological or therapeutic effect (e.g. an antibacterial, antiviral, or antitumor function). Other suitable heterologous nucleic acids include, but are not limited to, those encoding for proteins used for the treatment of endocrine, metaloic, hematologic, cardiovascular, neurologic, musculoskeletal, urologic, pulmonary, and immune disorders, including such disorders as inflammatory diseases, autoimmune disease, chronic and infectious diseases, such as AIDS, cancer, hypercholestemia, insulin disorders such as diabetes, growth disorders, various blood disorders including various enemias, thalassemias, and hemophilia; genetic defects such as cystic fibrosis, Gaucher's disease, Hurler's disease, adenosine deaminase (ADA) deficiency, and emphysema.

The therapeutic or diagnostic nucleic acid sequence, in some embodiments, will code for a protein antigen. The antigen may include a native protein or protein fragment, or a synthetic protein or protein fragment or peptide. Examples of antigens include, but are not limited to, those that are capable of eliciting an immune response against viral or bacterial hepatitis, influenza, diphtheria, tetanus, pertussis, measles, mumps, rubella, polio, pneumococcus, herpes, respiratory syncytial virus, hemophilus influenza type b, chlamydia, varicella-zoster virus or rabies. The nucleic acid sequence may also be a normal muscle gene that is effected in a muscle disease (e.g. muscular dystrophies like Duchenne muscular dystrophy, limb-girdle muscular dystrophy, Landouzy-Dejerine muscular dystrophy, Becker's muscular dystrophy, ocular myopathy, and myotonic muscular dystrophy). For such muscular dystrophies, the nucleic acid may be a heterologous gene encoding the full length dystrophin gene (or cDNA sequence), BMD-minigene, ΔH2-R19 minigene, Laminin-α2, utrophin, α-sarcoglycan, and emerin. BMD mini-gene refers to dystrophin cDNAs containing internal truncations corresponding to specific exons of the gene, in particular, a deletion of the sequences encoded on exons 17-48 [Amalfitano et al., in Lucy J, and Brown S. (eds): Dystrophin: Gene, Protein, and Cell Biology (Cambridge University Press, 1997), Chpt. 1, 1-26, herein incorporated by reference]. ΔH2-R19 refers to a specific dystrophin cDNA containing internal deletions corresponding to specific functional domains of the gene, in particular, a deletion of the sequences that encode 'hinge 2' through 'spectrin-like repeat' 19 [See Amalfitano et al.].

Nucleic acid sequences may also be antisense molecules (e.g. for blocking the expression of an abnormal muscle gene). The nucleic acid sequence may also code for proteins that circulate in mammalian blood or lymphatic systems. Examples of circulating proteins include, but are not limited to, insulin, peptide hormones, hemoglobin, growth factors, liver enzymes, clotting factors and enzymes, complement factors, cytokines, tissue necrosis factor and erythropoietin. Heterologous genes may also include gene encoding proteins that are to be produced (e.g. commercially produced) in muscle cells in vitro or in vivo. For example, the improved expressions systems of the present invention may be applied to preexisting, working muscle expression systems to improve the level of expression of protein product from a gene of interest. The present invention also contemplates employing any gene of interest (heterologous or endogenous).

VI. Using Adenoviral Vectors

The adenoviral vectors produced as described above may be used, for example, in drug screen or in gene therapy methods. In one screening method, an adenoviral vector (e.g. helper-dependent adenoviral vector, produced according to the above methods) contain adenoviral DNA operably linked to a heterologous gene encoding an factor (e.g. enzyme, protein, antisense molecule) with a known function (e.g. alcohol dehydrogenase), is contacted in vitro with a tissue culture sample (e.g. a muscle cell containing tissue culture) such that the heterologous gene is expressed. A candidate compound is added along with a substrate for the enzyme (e.g. ethanol), and a parallel assay is run without the candidate compound. The level of enzyme activity is detected (e.g. amount of substrate remaining over time) in each assay. The results of both assays are compared in order to determine the affect of the candidate compound on the activity of the enzyme. In other embodiments, the candidate compound many comprise a factor suspected of altering gene expression of the heterologous gene and the assay detects that degree and/or ability of the candidate compound to reduce the activity of the expressed factor. One of ordinary skill in the art will appreciate that many other screening methods can be used. The adenoviral vectors may also be used advantageously in gene therapy to replace a defective gene in subject with a heterologous gene.

EXPERIMENTAL

The following examples are provided in order to demonstrate and further illustrate certain preferred embodiments and aspects of the present invention and are not to be construed as limiting the scope thereof. In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); Sigma (Sigma Chemical Co., St. Louis, Mo.); and

Example 1

Generating Gutted and Helper Virus with Identical Termini

This example describes the deletion of internal FseI sites in the nucleic acid sequence of an Ad5-based helper virus, and insertion of this nucleic acid sequence into a plasmid such that it is removable with FseI.

The FseI recognition sequence, "GGCCGGCC", contains cytosine residues and can be arranged to overlap with the first nucleotide of viral DNA so that only one additional base pair is attached to viral DNA removed from plasmid vectors with this enzyme (FIG. 1A). In addition, FseI is rare in cloning vector polylinkers and mammalian sequences, so it is ideal for removal of gutted viral genomes from plasmid vectors. FseI has been used previously for linearization of viral shuttle vectors, which contain a portion of the Ad genome; however, it could not be used to liberate the entire Ad5 genome from plasmid DNA, because the Ad5 genome contains two FseI sites.

Figure 10:
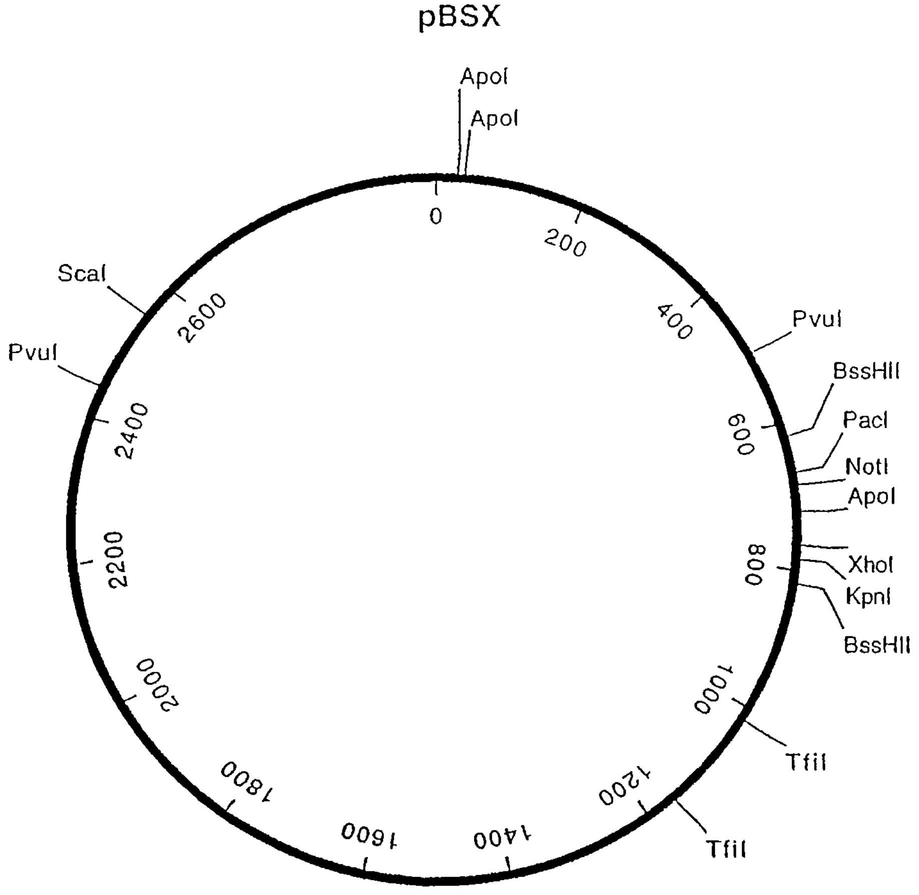
FIG. 10 show a restriction map of pBSX.

In order to remove the FseI sites in the (+)lox(+)pol helper virus DNA sequence (SEQ ID NO:1), mutations were created that destroy both FseI sites while maintaining the ability of the virus to replicate (transitions were made at nucleotides 12587 and 17756, creating SEQ ID NO:9, FIG. 11, see also FIG. 1B). The mutation at nucleotide 12587 was chosen so as to preserve the amino acid sequence of capsid protein IIIa. Primers 92521, CGGAATTCGGATCCAGCGACCGC-GAGCTGAT (SEQ ID NO:2) and 92531, CGGAAT-TCAGCCGGCTTCGTCGGGCCGGATGGC (SEQ ID NO:3) were used in a PCR reaction to simultaneously amplify approximately 540 base pairs of the Ad5 sequence, to introduce the G to A transition at nucleotide 12587, and to flank the resulting DNA sequence with EcoRI sites. The product was digested with EcoRI and ligated to the large, approximately 2.2 kb ApoI fragment of pBSX (pBSX—SEQ ID NO:12, FIG. 9, which is a minor modification of a Bluescript vector, with alterations to the polylinker sequence, See FIG. 10) to yield pD1858#7. Primers 92541, CGCGGATCCGCCGGCTACG-GCCTGACGGGCGG (SEQ ID NO:4) and 92551, CGGAATTCACACACATACGACACGTTAG (SEQ ID NO:5) were used to amplify approximately 1 kb of Ad5 sequence, to introduce the C to T transition at nucleotide 17756, and to append an EcoRI site to the rightmost end of the resulting DNA fragment. The product was digested with EcoRI and NgoMI, then ligated to EcoRI-, NgoMI-digested pD1858#7 to yield pD1863#4. This plasmid was digested with NgoMI and ligated to the 5162-bp NgoMI fragment from the Ad5 genome, resulting in pD1866#17, which contains both transitions mentioned above. To create a virus lacking FseI sites, pD1866#17 was digested with EcoRI and co-transfected with FseI-digested terminal protein-DNA complex from (+)lox(+)pol Ecd-AP helper virus. The sequence for (+)lox(+)pol Ecd-AP is SEQ ID NO:1, FIG. 8. After one week of incubation, the transfected cells showed evidence of viral cytopathic effect, indicating that they contained replicating virus, designated ΔFseI.4 (SEQ ID NO:9, FIG. 1B). The DNA was extracted from these cells by Hirt prep (DNA episomal extraction method employing lysis in 0.6% SDS/10 mM EDTA, followed by addition of salt, incubation at 4° C., and centrifugation to remove contaminants, Hirt, B., *J. Mol. Biol.* 26:365 [1967]) and shown not to contain FseI sites by restriction digest.

To confirm that FseI could be used to release replication-competent viral DNA from flanking DNA sequences, ΔFseI.4 genomic DNA was cloned into a plasmid vector, where it was flanked by FseI sites (FIG. 1C). Primers 82701, CGGAAT-TCGGCCGGCCATCATCAATAATATAC (SEQ ID NO:6) and 82741, CGGTCGATTCAATTGCTGGCAAGCTTCG-GCCCTAGACAAATAT (SEQ ID NO:7) were used in a PCR reaction to amplify approximately 400 bp from the left end of (+)lox(+)pol Ecd-AP helper virus and to introduce flanking restriction sites: EcoRI and FseI at the left end of the fragment and HindIII, MfeI, and TfiI at the right end. The product was digested with EcoRI and TfiI and cloned into the 1.86 kb ApoI/TfiI fragment of pBSX (See, FIG. 9), generating pD1812#1. Primers 82701 (SEQ ID NO:6) and 82731, CTAT-GCTAACCAGCGTAGC (SEQ ID NO:8) were used to amplify approximately 1 kb from the right end of (+)lox(+) pol Ecd-AP helper virus and to add FseI and EcoRI sites at the right end of the fragment. The product was digested with HindIII and EcoRI and cloned into HindIII-, MfeI-digested pD1812#1, generating pD1821#8. To clone ΔFseI.4 viral genomic DNA into pD1821#8, the plasmid was digested with HindIII and recombined with ΔFseI.4 Hirt prep DNA in BJ5183 bacterial cells (BJ5183 bacterial cells, see Hanahan, D., *J. Mol. Biol.,* 166:557 [1983]). The resulting plasmids, including pD1940#3 and pD1940#6, were shown by restriction digest to contain the entire ΔFseI.4 genome flanked by FseI sites (FIG. 1C). No internal FseI sites were detected, confirming that virus ΔFseI.4 contains mutations that destroy these sites.

To show that FseI digestion could release replication-competent Ad DNA from plasmids, pD1940#3 and pD1940#6 were digested with FseI and transfected into C7 cells (C7 cells express both Ad DNA polymerase and preterminal protein, see U.S. Pat. No. 6,083,750, hereby incorporated by reference). Plasmid pFG140 [See, Graham, F. L., *The EMBO J.,* 3:2917 (1984)] known to produce replicating adenovirus after transfection, was used as a control. Both sets of transfected cells were overlaid with agarose after transfection and stained with neutral red 10 days after overlay. It was determined that FseI-digested pD1940#3 and pD1940#6 produced 36 and 56 plaques per microgram, respectively; pFG140 produced 38 plaques per microgram. This result indicates that mutation of internal FseI sites did not prevent replication of adenovirus and that FseI is an appropriate enzyme for release of viral DNA from plasmids.

Example 2

Figure 2:
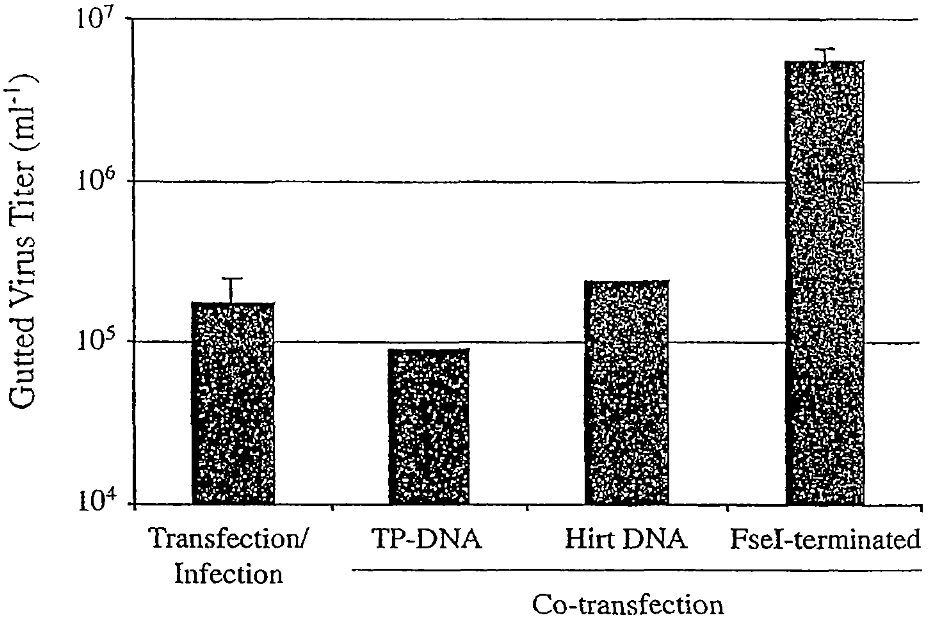
FIG. 2 shows improved gutted virus rescue that is achieved by co-transfection of matching plasmid-derived gutted and helper virus DNAs.
Figure 12:
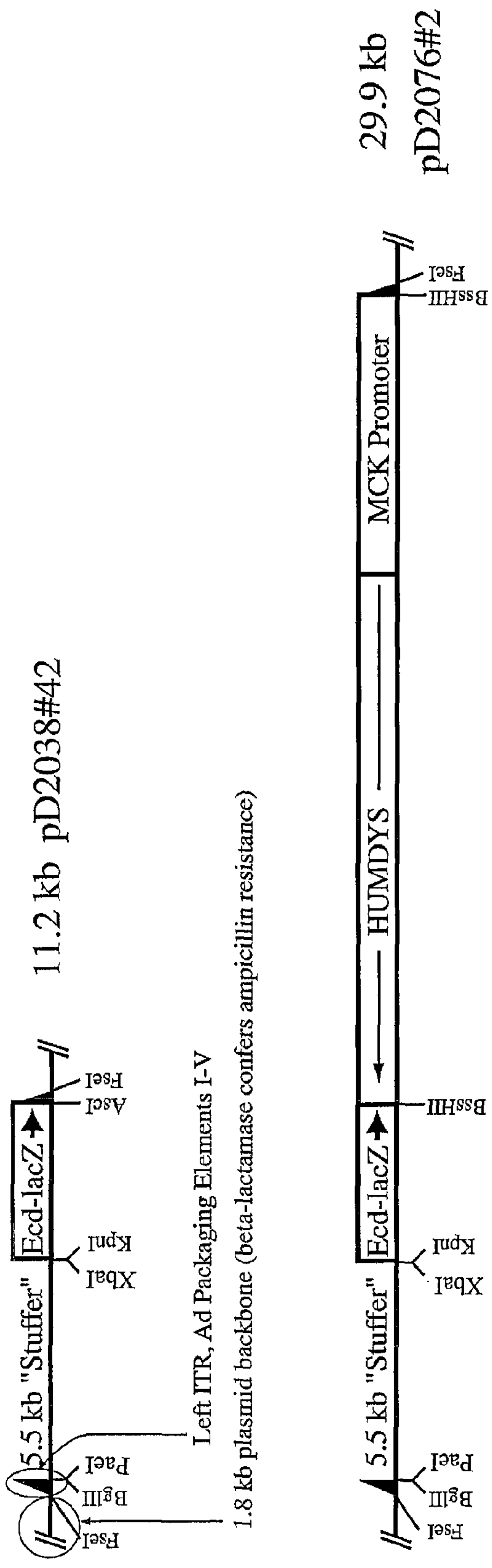
FIG. 12 shows pD2076#2.

Rescue of Helper-Dependent Ad Vectors Using Plasmid-Derived Substrates with Corresponding Termini This example describes the rescue of helper-dependent Ad vectors using plasmid-derived substrates with corresponding termini. To demonstrate that efficient gutted virus rescue depends on the relative specific activities of gutted and helper viral DNA, a FseI-terminated gutted virus was co-transfected with various forms of helper virus DNA or transfection/infection was performed (FIG. 2). The gutted adenovirus DNA employed was pD2076#2, which contains a gutted Ad genome flanked by FseI recognition sites and carries an inducible beta-galactosidase expression cassette (FIG. 12). This plasmid was digested with FseI, and 4.4 micrograms of digested DNA were transfected into C7 cells.

Figure 13:
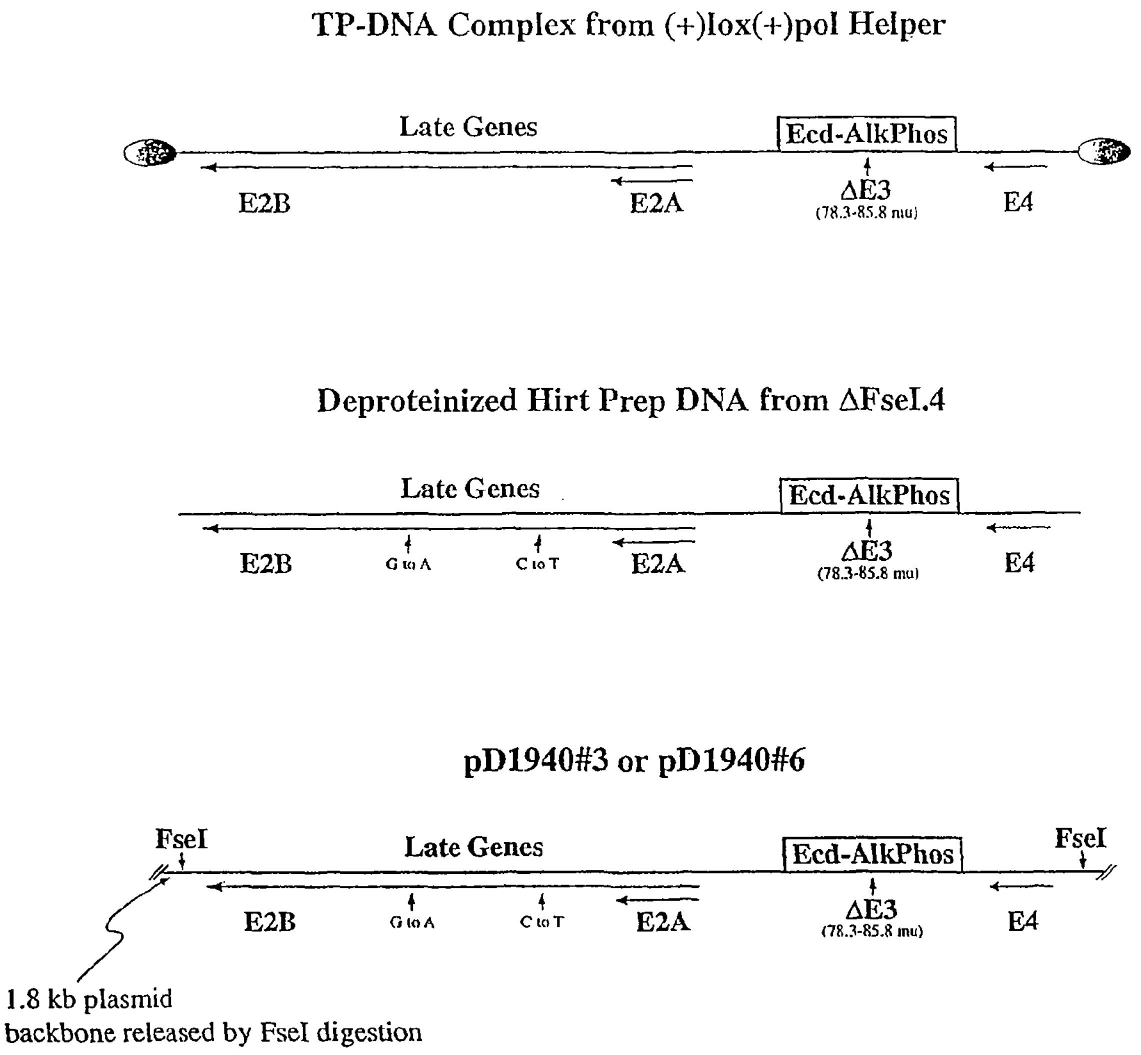
FIG. 13 shows TP-DNA complex from (+)lox(+)pol helper viral DNA; deproteinized Hirt prep DNA from ΔFseI.4; and pD1940#3 and pD1940#6.

For co-transfection assays, 4.4. micrograms of helper viral DNA (either TP-DNA, Hirt DNA, or FseI-terminated DNA) were co-transfected with pD2076#2 DNA. For transfection/infection, helper virus particles were added immediately following transfection at an MOI of 10 transducing units per cell. For the TP-DNA complex co-transfection, terminal protein-DNA complex was isolated from (+)lox(+)pol helper virus (SEQ ID NO:1) was isolated and transfected into cells to provide helper activity (FIG. 13). For the Hirt DNA samples, ΔFseI.4 DNA (SEQ ID NO:9) was isolated from infected cells and deproteinized (FIG. 13). For FseI-terminated samples, pD1940#3 or pD1940#6 (See FIG. 13) was digested with FseI and the released DNA was used to provide helper activity (SEQ ID NO:13, FIG. 14). Digestion with FseI releases what is essentially ΔFseI.4 (SEQ ID NO:9), except with a couple of extra nucleotides at the end (as shown in FIG. 1).

Transfection/infection was found to be very inefficient (See FIG. 2), although it is the method most frequently reported in the literature. In co-transfections, an inverse correlation was observed between the specific activity of the helper virus DNA from and the yield of gutted virus produced. Co-transfection of gutted viral DNA with plasmid-derived helper viral DNA, carrying a physically identical origin of replication (constructed as described in Example 1), was by far the most efficient method for rescue of gutted adenovirus (See, FIG. 2). After co-transfection of plasmid-derived, FseI-terminated genomes, the average gutted viral titer observed was $5.6\times10^{6}$ $ml^{-1}$. This yield represents an improvement of approximately 30 fold over typical titers obtained by transfection/infection into C7 cells and 300 fold over typical titers obtained by transfection/infection into 293 cells.

Example 3

Figure 3:
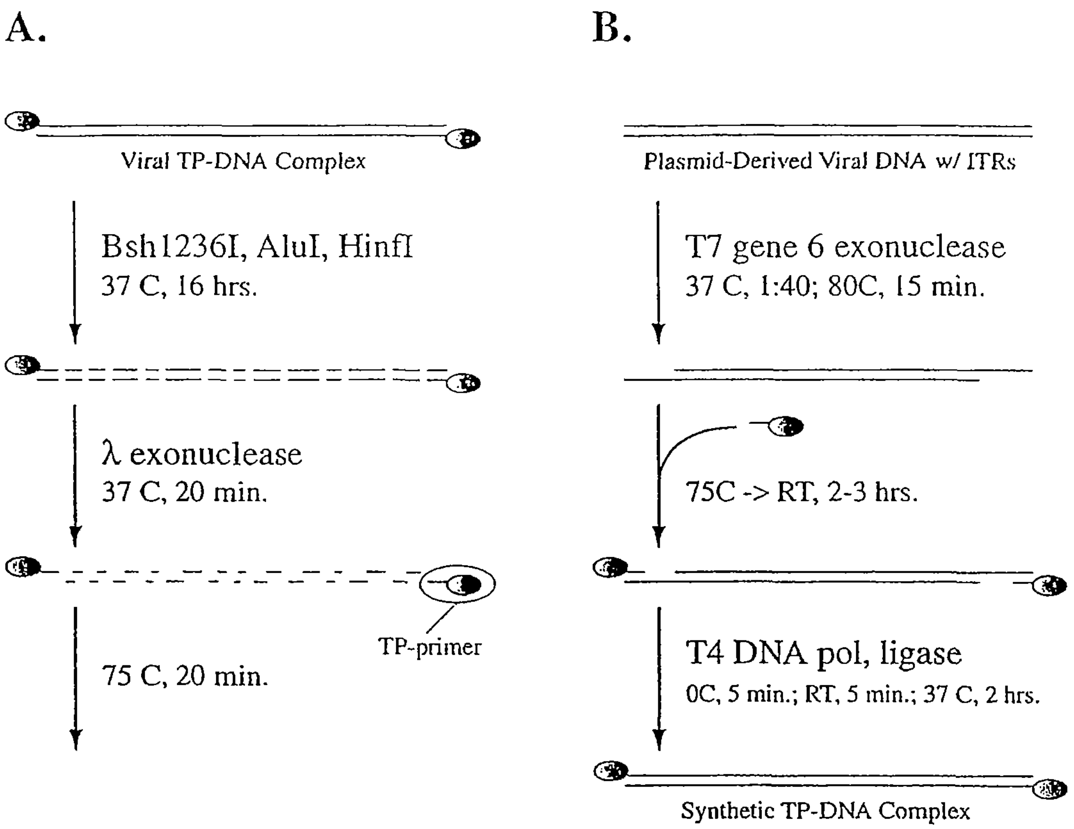
FIG. 3 shows a method for conversion of plasmid-derived Ad origins to natural form (creating TP-primer and ligating it to plasmid derived viral DNA).

Conversion of Plasmid-Derived Viral Replication Origins to Natural, Terminal Protein-Linked Origins This example describes the conversion of plasmid derived viral replication origins to natural, terminal protein-linked origins. This conversion employs "TP-primer", which is terminal protein DNA linked to single-stranded DNA from the non-template strand of an Ad ITR (FIG. 3A). TP Primer was prepared in the following manner. Terminal protein-DNA complex prepared from (+)lox(+)pol Ecd-AP virus was digested for at least 16 hours at 37° C. with 2.5 U/μg Bsh12361, 1.33 U/μg AluI, and 0.69 U/μg HinfI. Bsh12361 cuts between base pairs 73 and 74 of the Ad5 ITR (CATCATCAATAATATACCTTATTTTGGATTGAAGCCAATATGATAATGAGGG GGTGGAGTTTGTGACGTGGCGCGGGGCGTGGGAACGGGGCGGGTGACGTAG, SEQ ID NO:10), so this digestion results in terminal protein linked to a 73-bp, double-stranded DNA molecule (one of the two strands is as follows, CATCATCAATAATATACCTTATTTTGGATTGAAGCCAATATGATAATGAGGG GGTGGAGTTTGTGACGTGGCG, SEQ ID NO:11). The products of restriction digestion were then treated with 2.5 U/μg DNA of lambda exonuclease for 20 minutes at 37° C. This enzyme catalyzes the removal of 5' mononucleotides from duplex DNA. Since the enzyme acts in a 5' to 3' direction, strands linked to terminal protein are not degraded; all other strands are degraded until a single-stranded region is reached.

The products of this digestion, therefore, include: 1) terminal protein linked to 73 unpaired bases (SEQ ID NO:11) of the non-template strand of the Ad5 ITR (TP-primer); 2) many random, small, single-stranded DNA molecules resulting from the degradation of approximately half of the restriction fragments present in the reaction; and 3) mononucleotides. The first of these is the desired and useful product; however, the other products do not interfere with subsequent steps. The enzymes in the reaction were then inactivated by incubation at 75° C. for 20 minutes.

TP-primer was then used to convert plasmid-derived gutted viral genomes to natural Ad origins by the following method (FIG. 3B). First, a plasmid containing gutted viral genomic DNA (pD2076#2), flanked by FseI sites, was digested with FseI to release gutted viral DNA. The products were subjected to very limited digestion with T7 gene 6 exonuclease (0.76 U/μg for 1 minute, 40 seconds) and the exonuclease was inactivated by incubation at 80° C. for 15 minutes. T7 gene 6 exonuclease, like lambda exonuclease, is a 5' to 3' exonuclease, so limited digestion with this enzyme exposes single-stranded regions near the gutted vector genomic termini. These regions are complementary to the single-stranded DNA found in the TP-primer reagent. Due to the long (73 bp) stretch of complementary DNA sequence and the absence of competing binding partners, the TP-primer reagent can bind efficiently to T7 gene 6-digested gutted DNA even at low molar ratios.

We added TP-primer reagent, prepared as described above, to the digested gutted DNA, raised the temperature of the mixture to 75° C., and allowed the temperature to fall slowly (over 2-3 hours) to room temperature. Hybridized TP-primer molecules were then extended using T4 DNA polymerase and nicks were repaired using T4 DNA ligase. This was accomplished by addition of 0.5 mM each dNTP, 1 mM ATP, 2.5 units T4 polymerase per μg DNA, and 2 Weiss units T4 ligase per μg DNA. A small amount of buffer (10 mM Tris-HCl, 10 mM $MgCl_2$, 50 mM NaCl, and 1mM DTT, pH 7.9 at 25 C) was also added such that the final concentration of gutted vector genomic DNA was 0.04 μg/μL when a 2:1 (TP-primer: gutted genome) ratio was used or 0.029 μg/μL when a 4:1 ratio was used. The reaction was then incubated for 5 minutes at 0° C., 5 minutes at room temperature, and 2 hours at 37° C. EDTA was added to a final concentration of 15 mM and the reaction was stored on ice.

An assay was performed to confirm the successful addition of terminal protein to the origin of replication of the gutted virus. Specifically, a restriction digest employing NotI was performed on circular pD2076#2, the TP-primer linked pD2076#2 (FseI digested), and FseI digested pD2076#2 (negative control). This digestion was followed by agarose gel electrophoresis (FIG. 4A). The results confirmed the successful addition of the TP-primer as approximately two-thirds of the gutted DNA terminal fragments were retained in the wells of the agarose gel, behavior that is typical of protein-linked DNA (FIG. 4A).

Example 4

TP-Primer Increases the Specific Activity of Plasmid-Derived Ad DNA

This example describes the ability of TP-primer to increase the specific activity of plasmid derived Ad DNA. In particular, replication-competent helper virus genomes were excised from plasmids pD1940#3 or pD1940#6 and the origins of DNA replication were modified as described above (See Example 3, adding TP-primer to Ad DNA). Reaction mixtures were then diluted into 0.1× TE such that transfection mixtures contained either one microgram or 0.1 micrograms of modified plasmid DNA. Parallel transfection mixtures were prepared using unmodified FseI-digested pD1940 plasmid (SEQ ID NO:13, FIG. 14). The DNA was co-precipitated with calcium phosphate, and added to plates of C7 cells. Plates were washed 16 hours after addition of precipitates and overlayed with noble agar (See, Graham, F. L. and Prevec, L. *Manipulation of Adenovirus Vectors in Gene Transfer and Expression Protocols*, Clifton: The Humana Press, Inc., 1991). Eight to ten days after overlay, the plates were stained with neutral red and plaques were counted. Specific activity was calculated as the number of plaques observed divided by the weight of transfected DNA.

It was found that the specific activity of treated genomes was increased by an average of 24 or 27 fold after treatment with a 2:1 or 4:1 molar ratio of TP-primer, respectively. We also examined the effect of TP-primer treatment on the rescue of gutted Ad vectors from their plasmid-derived precursors. For these experiments, since large amounts of DNA were transfected, reaction mixtures were dialyzed against 1× HBS to avoid dilution. Conversion of gutted vector origins to natural, TP-linked form resulted in improved competition with helper virus DNA (FIG. 4B). Strikingly, co-transfection of TP-gutted DNA and untreated, FseI-terminated helper virus DNA prevented lysis of the transfected cells, indicating that the specific activity of TP-gutted DNA is high enough to prevent robust helper replication.

Co-transfection of TP-gutted DNA with terminal protein-DNA complex from helper virus resulted in an average gutted viral titer of $1.5\times10^7$ per ml. This titer represents an improvement of approximately 85 fold over typical titers obtained by transfection/infection into C7 cells, 850 fold over titers obtained by transfection/infection into 293 cells, and 2.7 fold over titers obtained by co-transfection of plasmid-derived, FseI-liberated gutted and helper genomes (See FIG. 4B).

Example 5

Terminal Transferase Template Strand Extension of Adenoviral DNA

This example describes terminal transferase (TdT) template strand extension of adenoviral DNA, and how limited extensions increase the specific activity in plaque assays and allow for more efficient recovery of gutted adenovirus.

pD1940#3 or pD1940#6 viral DNA was digested to completion with FseI. The restriction enzyme reaction was diluted 3.125-fold into 1× TdT reaction buffer (Promega, Madison, Wis.) and supplemented with 80 micromolar dNTPs and 10 units TdT per picomole DNA termini. The reaction was mixed well, incubated for a variable length of time at 37° C., and the TdT was inactivated by incubation at 75° C. for 10 minutes. The reaction mixture was extracted with 0.5 volumes of phenol-chloroform and DNA was precipitated. Samples were resuspended in 0.1× TE and transfected into C7 cells using the calcium phosphate co-precipitation method.

To determine whether TdT treatment had improved the ability of viral DNA to replicate in cells, the specific activity of treated and untreated DNA in transfected cells was measured ('specific activity' was defined as the number of viral plaques observed per microgram of DNA transfected; higher specific activity indicates that a lesser weight of viral DNA must be transfected to produce actively replicating virus). The results of the this assay indicate that the specific activity of pD1940 DNA was increased by approximately 5 fold after 30 minutes of treatment but less so after 6 minutes or 2.5 hours (FIG. 5C). Control reactions lacking the TdT enzyme showed no evidence of increased plaquing efficiency (FIG. 5C).

To test whether the identity of added nucleotides is important for the observed effect, we supplemented individual TdT reactions with various single and mixed nucleotides. The various reactions were precipitated individually, transfected into cells, and developing viral plaques were counted after 7-10 days. The effectiveness of TdT treatment was found to vary with the identity of the nucleotides included in the reaction (FIG. 5C). It was determined that the addition of single nucleotides was not effective; in fact, addition of thymidine or cytosine residues alone markedly reduced plaquing efficiency. It was also determined that the most effective combination was addition of guanine, adenine, and cytosine (dGAC), which increased plaquing efficiency by approximately 10 fold (FIG. 5C and data not shown).

An assay was also conducted involving TdT treatment of gutted Ad virus, and rescue from bacterial plasmids. In this example, gutted Ad genomes excised from pD2076#2 with the restriction enzyme FseI were employed. These excised genomes were treated with the combination of guanine, adenine, and cytosine as described above. 8.8 micrograms of treated DNA were transfected into approximately 2 million C7 cells in a 60-mm plate. 16 hours later the cells were washed and then infected with 20 million transducing units of ΔFseI.4 helper virus (SEQ ID NO:9). Two to three days after this procedure, the plates displayed viral cytopathic effect and lysates were harvested. By measuring the titer of gutted virus in the recovered lysates, it was determined that TdT treatment of the gutted vector doubled the amount of gutted virus produced by the cells after rescue (FIG. 5D). By co-transfecting plasmid-derived helper and gutted DNAs, as described above, the baseline titer obtained without TdT treatment was increased (FIG. 5D). After treatment of gutted plasmid DNA with TdT, a further 2.5-fold increase in gutted virus titer was obtained (FIG. 5D).

Example 6

Regulated Expression of Site-Specific Recombinase Improves Gutted Virus Rescue

This example describes the use of regulated expression of Cre recombinase to improve gutted virus rescue when gutted and helper virus with identical ends are co-transfected. Initially, the effect of constitutive expression of Cre recombinase in packing cells co-transfected with gutted and helper viruses with identical ends was examined. ΔFseI.4 helper virus (SEQ ID NO:9) is an E1-, E3-deleted virus that can be negatively selected using Cre recombinase and carries an alkaline phosphatase reporter gene in its E3 region. The packaging signal, which consists of packaging elements I-V, is flanked by loxP sites in direct repeat orientation, allowing removal of the packaging signal in the presence of Cre. The E1 region (map units 1-9.2) has been removed. The E3 region (map units 78.3-85.8) has also been removed and replaced with an expression cassette, oriented from left to right in the viral genome, that consists of the inducible ecdysone promoter, the coding region for human placental alkaline phosphatase, polyadenylation sequences from SV40, and approximately 2 kb of "stuffer" DNA derived from an intron of the human dystrophin gene. For these experiments, ΔFseI.4 genomes were released from pD1940#3 or pD1940#6 by digestion with FseI.

Figure 6:
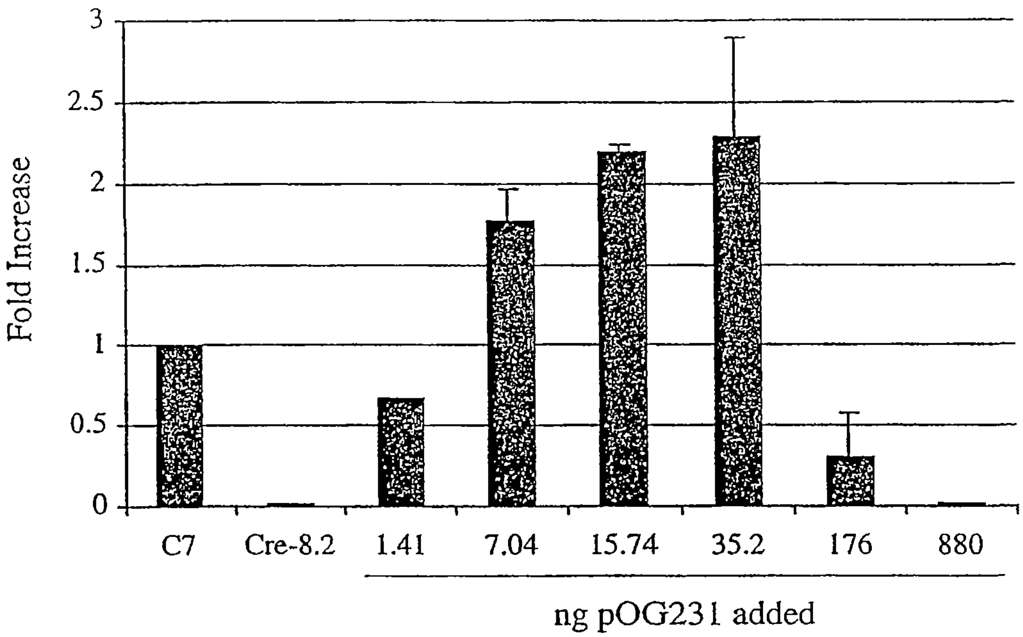
FIG. 6 shows that the regulated expression of Cre recombinase improves gutted virus recovery.

Specifically, FseI-terminated gutted and helper viral genomes were co-transfected into either C7 cells or C7-Cre-8.2 cells, which constitutively express Cre recombinase. The plate of transfected C7-Cre-8.2 cells showed no signs of lysis even after 12 days of incubation and the resulting titer of gutted virus was approximately 100 times lower than that observed in C7 cells (FIG. 6). This result indicates that when gutted and helper viral genomes with identical origin structures are co-transfected, constitutive expression Cre recombinase in the packaging cells is not desirable.

Cre recombinase, however, may still be employed to improve gutted virus recovery. Instead of constitutive expression of Cre recombinase, the recombinase expression is regulated over time. This was accomplished by co-transfection of a Cre recombinase expression vector (the level of Cre recombinase will increase gradually over time). Specifically, C7 cells were transfected with FseI-terminated gutted virus, FseI-terminated helper virus, and varying amounts of a Cre recombinase expression vector (pOG231). The results of this experiment show very low amounts of pOG231 had minimal effects on gutted virus production, with increasing amounts of pOG231, gutted virus production was improved (FIG. 6). The results also indicate that using the highest amounts of pOG231, little viral replication was observed and gutted virus titers were reduced (indicating that Cre protein levels increased to a level beyond which lysis could not proceed). Maximal improvement in gutted virus titers was observed using 16-35 ng of Cre expression vector, at which level average gutted titers more than doubled, to 1.3×107 ml-1 (FIG. 6). High levels of gutted virus were also observed using 7.04 ng of the Cre expression vector.

This selection strategy was also shown to be effective for gutted virus rescue from TdT-modified and TP-primer-modified genomes. For TdT-modified genomes, co-transfection with 35.2 ng Cre increased gutted virus production by an average of 3 fold. For TP-primer-modified genomes, use of 0.88 μg Cre approximately doubled gutted virus production, to 2.5×107 ml-1.

Example 7

Generating an Adenoviral Protein IX Expressing Cell Line

Figure 16:
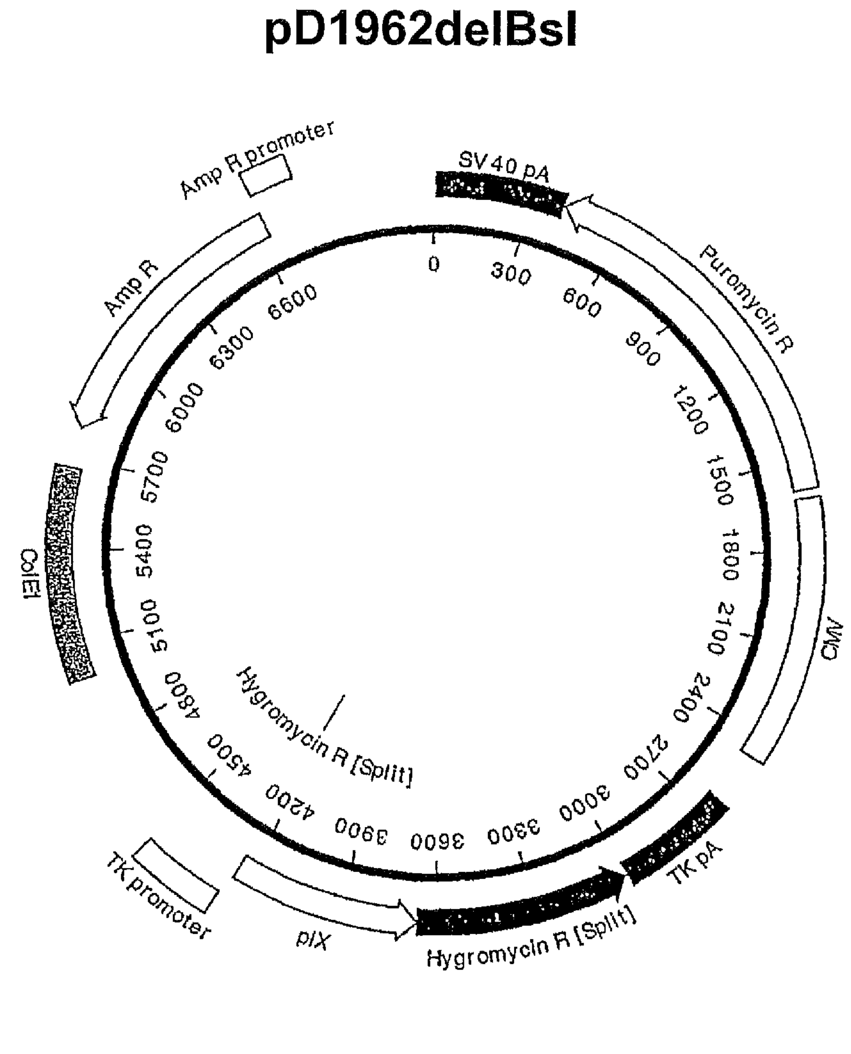
FIG. 16 shows a restriction map of pD1962delBsI.

This example describes the generation of a cell line expressing adenoviral protein IX (pIX), in addition to E2B proteins (adenoviral DNA polymerase and preterminal protein). C7 cells (that already express adenoviral DNA polymerase and preterminal protein) were transfected with PvuI-linearized pD1962delBbsI-pIX (SEQ ID NO:14, FIG. 15), a plasmid that contains expression cassettes directing expression of adenoviral protein IX and puromycin N-acetyl transferase (See FIG. 16). Positive clones were selected in the presence of 2 micrograms puromycin per milliliter of medium. Clones were screened for expression of pIX by transfection with FseI-digested HΔIX#3 (SEQ ID NO:15, FIG. 17), a plasmid that contains an E1-, E3-, and pIX-negative Ad genome of approximately 35.6 kb in size. Clone pD2104#10 produced virus after transfection with HΔIX#3.

Figure 7:
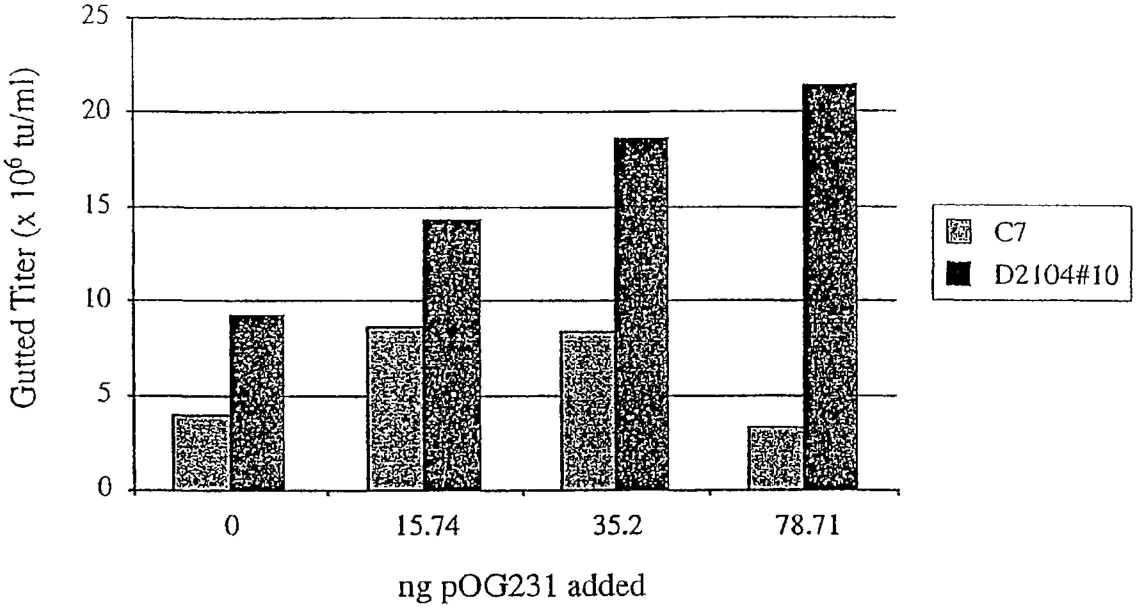
FIG. 7 shows the recovery of gutted virus in D2104#10 cells.

D2104#10 cells and C7 cells were then transfected with FseI-digested pD1940#6, which contains a pIX-positive Ad genome. The cells were then overlayed with agarose to allow for counting of plaques, each representing the successful conversion of a transfected genome to a replicating virus. It was determined that D2104#10 cells displayed three times as many plaques as C7 cells (FIG. 7). Additionally, plaques formed on D2104#10 cells were larger than those formed on C7 cells.

D2104#10 cells were then tested for the ability to rescue gutted virus from a plasmid-based precursor, either in the presence or absence of regulated Cre expression (FIG. 7). Plates of each cell type were transfected with FseI-terminated gutted and helper genomes at a 1:1 ratio, together with varying amounts (15.74 ng, 35.2 ng, and 78.71 ng) of the Cre expression plasmid pOG231. Plates of D2104#10 cells were found to lyse before plates of C7 cells that had been transfected under the same conditions, reflecting the higher proportion of transfected cells that initiated replication of the helper. The co-transfection of C7 cells in the presence of 79 ng of pOG231 failed to produce lysis even after 13 days, whereas D2104#10 cells lysed within 10 days. More gutted virus was produced in D2104#10 cells under all the conditions tested (FIG. 7). In the absence of Cre selection, D2104#10 cells produced twice as much virus as C7 cells. Examining the highest level of selection tested (79 ng), D2104#10 cells produced twice as much virus as C7 cells did under their highest selection conditions (16 ng).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in material science, chemistry, and molecular biology or related fields are intended to be within the scope of the following claims.

We claim:

1. A method for producing helper-dependent adenoviral vectors, said method comprising:

a) providing;

i) an isolated helper-dependent adenoviral DNA sequence comprising an origin of replication linked to a replication-promoting agent, ii) a helper viral DNA sequence, and iii) target cells; and b) transfecting said target cells with said helper-dependent adenoviral DNA sequence and with said helper viral DNA sequence under conditions such that helper-dependent adenoviral vectors are produced.

2. The method of claim 1, wherein said replication-promoting agent is selected from Ad2 preterminal protein, Ad2 terminal protein, Ad5 preterminal protein, and Ad5 terminal protein.

3. The method of claim 1, wherein said replication-promoting agent comprises adenoviral terminal protein.

4. The method of claim 1, wherein said helper-dependent adenoviral DNA sequence comprises a heterologous gene sequence.

5. The method of claim 1, wherein said helper viral DNA sequence comprises helper adenoviral DNA sequence.

6. A method for producing helper-dependent adenoviral vectors, said method comprising:

a) providing;

i) an isolated helper-dependent adenoviral DNA sequence comprising a first origin of replication and a second origin of replication, wherein each of the first and the second origin of replication is linked to a replication-promoting agent, ii) a helper viral DNA sequence, and iii) target cells; and b) transfecting said target cells with said helper-dependent adenoviral DNA sequence and with said helper viral DNA sequence under conditions such that helper-dependent adenoviral vectors are produced.

7. The method of claim 6, wherein said replication-promoting agent is selected from Ad2 preterminal protein, Ad2 terminal protein, Ad5 preterminal protein, and Ad5 terminal protein.

8. The method of claim 6, wherein said replication-promoting agent comprises adenoviral terminal protein.

9. The method of claim 6, wherein said helper-dependent adenoviral DNA sequence comprises a heterologous gene sequence.

10. The method of claim 6, wherein said helper viral DNA sequence comprises helper adenoviral DNA sequence.

11. A host cell comprising an isolated helper-dependent adenoviral DNA sequence comprising a first origin of replication and a second origin of replication, wherein each of the first and the second origin of replication is linked to a replication-promoting agent.

* * * * *

SEQUENCE LISTING

<160> NUMBER OF SEQ ID NOS: 34

<210> SEQ ID NO 1
<211> LENGTH: 36154
<212> TYPE: DNA
<213> ORGANISM: Artificial Sequence
<220> FEATURE:
<223> OTHER INFORMATION: Synthetic

<400> SEQUENCE: 1
catcatcaat aatatacctt attttggatt gaagccaata tgataatgag gggtggagt 60 ttgtgacgtg gcgcggggcg tgggaacggg gcgggtgacg tagtagtgtg gcggaagtgt 120
gatgttgcaa gtgtggcgga acacatgtat aacttcgtat aatgtatgct atacgaagtt 180
atacatgtaa gcgacggatg tggcaaaagt gacgtttttg gtgtgcgccg gtgtacacag 240
gaagtgacaa ttttcgcgcg gttttaggcg gatgttgtag taaatttggg cgtaaccgag 300
taagatttgg ccattttcgc gggaaaactg aataagagga agtgaaatct gaataatttt 360
gtgttactca tagcgcgtaa tatttgtcta gggagatcta taacttcgta taatgtatgc 420
tatacgaagt tattaccgaa gaaatggctc gagatctgga aggtgctgag gtacgatgag 480
acccgcacca ggtgcagacc ctgcgagtgt ggcggtaaac atattaggaa ccagcctgtg 540
atgctggatg tgaccgagga gctgaggccc gatcacttgg tgctggcctg cacccgcgct 600
gagtttggct ctagcgatga agatacagat tgaggtactg aaatgtgtgg gcgtggctta 660
agggtgggaa agaatatata aggtgggggt cttatgtagt tttgtatctg ttttgcagca 720
gccgccgccg ccatgagcac caactcgttt gatggaagca ttgtgagctc atatttgaca 780
acgcgcatgc ccccatgggc cggggtgcgt cagaatgtga tgggctccag cattgatggt 840
cgccccgtcc tgcccgcaaa ctctactacc ttgacctacg agaccgtgtc tggaacgccg 900
ttggagactg cagcctccgc cgccgcttca gccgctgcag ccaccgcccg cgggattgtg 960
actgactttg ctttcctgag cccgcttgca agcagtgcag cttcccgttc atccgcccgc 1020
gatgacaagt tgacggctct tttggcacaa ttggattctt tgacccggga acttaatgtc 1080
gtttctcagc agctgttgga tctgcgccag caggtttctg ccctgaaggc ttcctcccct 1140
cccaatgcgg tttaaaacat aaataaaaaa ccagactctg tttggatttg gatcaagcaa 1200
gtgtcttgct gtctttattt aggggttttg cgcgcgcggt aggcccggga ccagcggtct 1260
cggtcgttga gggtcctgtg tattttttcc aggacgtggt aaaggtgact ctggatgttc 1320
agatacatgg gcataagccc gtctctgggg tggaggtagc accactgcag agcttcatgc 1380
tgcggggtgg tgttgtagat gatccagtcg tagcaggagc gctgggcgtg gtgcctaaaa 1440
atgtctttca gtagcaagct gattgccagg ggcaggccct tggtgtaagt gtttacaaag 1500
cggttaagct gggatgggtg catacgtggg gatatgagat gcatcttgga ctgtattttt 1560
aggttggcta tgttcccagc catatccctc cggggattca tgttgtgcag aaccaccagc 1620
acagtgtatc cggtgcactt gggaaatttg tcatgtagct tagaaggaaa tgcgtggaag 1680
aacttggaga cgcccttgtg acctccaaga ttttccatgc attcgtccat aatgatggca 1740
atgggcccac gggcggcggc ctgggcgaag atatttctgg gatcactaac gtcatagttg 1800
tgttccagga tgagatcgtc ataggccatt tttacaaagc gcgggcggag ggtgccagac 1860
tgcggtataa tggttccatc cggcccaggg gcgtagttac cctcacagat ttgcatttcc 1920
cacgctttga gttcagatgg ggggatcatg tctacctgcg gggcgatgaa gaaaacggtt 1980

-continued

```
tccggggtag gggagatcag ctgggaagaa agcaggttcc tgagcagctg cgacttaccg   2040
cagccggtgg gcccgtaaat cacacctatt accgggtgca actggtagtt aagagagctg   2100
cagctgccgt catccctgag caggggggcc acttcgttaa gcatgtccct gactcgcatg   2160
ttttccctga ccaaatccgc cagaaggcgc tcgccgccca gcgatagcag ttcttgcaag   2220
gaagcaaagt ttttcaacgg tttgagaccg tccgccgtag gcatgctttt gagcgtttga   2280
ccaagcagtt ccaggcggtc ccacagctcg gtcacctgct ctacggcatc tcgatccagc   2340
atatctcctc gtttcgcggg ttggggcggc tttcgctgta cggcagtagt cggtgctcgt   2400
ccagacgggc cagggtcatg tctttccacg ggcgcagggt cctcgtcagc gtagtctggg   2460
tcacggtgaa ggggtgcgct ccgggctgcg cgctggccag ggtgcgcttg aggctggtcc   2520
tgctggtgct gaagcgctgc cggtcttcgc cctgcgcgtc ggccaggtag catttgacca   2580
tggtgtcata gtccagcccc tccgcggcgt ggcccttggc gcgcagcttg cccttggagg   2640
aggcgccgca cgaggggcag tgcagacttt tgagggcgta gagcttgggc gcgagaaata   2700
ccgattccgg ggagtaggca tccgcgccgc aggccccgca gacggtctcg cattccacga   2760
gccaggtgag ctctggccgt tcggggtcaa aaaccaggtt tcccccatgc tttttgatgc   2820
gtttcttacc tctggtttcc atgagccggt gtccacgctc ggtgacgaaa aggctgtccg   2880
tgtccccgta tacagacttg agaggcctgt cctcgagcgg tgttccgcgg tcctcctcgt   2940
atagaaactc ggaccactct gagacaaagg ctcgcgtcca ggccagcacg aaggaggcta   3000
agtgggaggg gtagcggtcg ttgtccacta gggggtccac tcgctccagg gtgtgaagac   3060
acatgtcgcc ctcttcggca tcaaggaagg tgattggttt gtaggtgtag gccacgtgac   3120
cgggtgttcc tgaagggggg ctataaaagg gggtgggggc gcgttcgtcc tcactctctt   3180
ccgcatcgct gtctgcgagg gccagctgtt ggggtgagta ctccctctga aaagcgggca   3240
tgacttctgc gctaagattg tcagtttcca aaaacgagga ggatttgata ttcacctggc   3300
ccgcggtgat gcctttgagg gtggccgcat ccatctggtc agaaaagaca atctttttgt   3360
tgtcaagctt ggtggcaaac gacccgtaga gggcgttgga cagcaacttg gcgatggagc   3420
gcagggtttg gtttttgtcg cgatcggcgc gctccttggc cgcgatgttt agctgcacgt   3480
attcgcgcgc aacgcaccgc cattcgggaa agacggtggt gcgctcgtcg ggcaccaggt   3540
gcacgcgcca accgcggttg tgcagggtga caaggtcaac gctggtggct acctctccgc   3600
gtaggcgctc gttggtccag cagaggcggc cgcccttgcg cgagcagaat ggcggtaggg   3660
ggtctagctg cgtctcgtcc ggggggtctg cgtccacggt aaagaccccg ggcagcaggc   3720
gcgcgtcgaa gtagtctatc ttgcatcctt gcaagtctag cgcctgctgc catgcgcggg   3780
cggcaagcgc gcgctcgtat gggttgagtg ggggacccca tggcatgggg tgggtgagcg   3840
cggaggcgta catgccgcaa atgtcgtaaa cgtagagggg ctctctgagt attccaagat   3900
atgtagggta gcatcttcca ccgcggatgc tggcgcgcac gtaatcgtat agttcgtgcg   3960
agggagcgag gaggtcggga ccgaggttgc tacgggcggg ctgctctgct cggaagacta   4020
tctgcctgaa gatggcatgt gagttggatg atatggttgg acgctggaag acgttgaagc   4080
tggcgtctgt gagacctacc gcgtcacgca cgaaggaggc gtaggagtcg cgcagcttgt   4140
tgaccagctc ggcggtgacc tgcacgtcta gggcgcagta gtccagggtt tccttgatga   4200
tgtcatactt atcctgtccc ttttttttcc acagctcgcg gttgaggaca aactcttcgc   4260
ggtctttcca gtactcttgg atcggaaacc cgtcggcctc cgaacggtaa gagcctagca   4320
tgtagaactg gttgacggcc tggtaggcgc agcatccctt ttctacgggt agcgcgtatg   4380
```

-continued

```
cctgcgcggc cttccggagc gaggtgtggg tgagcgcaaa ggtgtccctg accatgactt   4440
tgaggtactg gtatttgaag tcagtgtcgt cgcatccgcc ctgctcccag agcaaaaagt   4500
ccgtgcgctt tttggaacgc ggatttggca gggcgaaggt gacatcgttg aagagtatct   4560
ttcccgcgcg aggcataaag ttgcgtgtga tgcggaaggg tcccggcacc tcggaacggt   4620
tgttaattac ctgggcggcg agcacgatct cgtcaaagcc gttgatgttg tggcccacaa   4680
tgtaaagttc caagaagcgc gggatgccct tgatggaagg caattttta agttcctcgt   4740
aggtgagctc ttcaggggag ctgagcccgt gctctgaaag ggcccagtct gcaagatgag   4800
ggttggaagc gacgaatgag ctccacaggt cacgggccat tagcatttgc aggtggtcgc   4860
gaaaggtcct aaactggcga cctatggcca tttttctgg ggtgatgcag tagaaggtaa   4920
gcgggtcttg ttcccagcgg tcccatccaa ggttcgcggc taggtctcgc gcggcagtca   4980
ctagaggctc atctccgccg aacttcatga ccagcatgaa gggcacgagc tgcttcccaa   5040
aggcccccat ccaagtatag gtctctacat cgtaggtgac aaagagacgc tcggtgcgag   5100
gatgcgagcc gatcgggaag aactggatct cccgccacca attggaggag tggctattga   5160
tgtggtgaaa gtagaagtcc ctgcgacggg ccgaacactc gtgctggctt ttgtaaaaac   5220
gtgcgcagta ctggcagcgg tgcacgggct gtacatcctg cacgaggttg acctgacgac   5280
cgcgcacaag gaagcagagt gggaatttga gcccctcgcc tggcgggttt ggctggtggt   5340
cttctacttc ggctgcttgt ccttgaccgt ctggctgctc gaggggagtt acggtggatc   5400
ggaccaccac gccgcgcgag cccaaagtcc agatgtccgc gcgcggcggt cggagcttga   5460
tgacaacatc gcgcagatgg gagctgtcca tggtctggag ctcccgcggc gtcaggtcag   5520
gcgggagctc ctgcaggttt acctcgcata gacgggtcag ggcgcgggct agatccaggt   5580
gatacctaat ttccaggggc tggttggtgg cggcgtcgat ggcttgcaag aggccgcatc   5640
cccgcggcgc gactacggta ccgcgcggcg ggcggtgggc cgcgggggtg tccttggatg   5700
atgcatctaa aagcggtgac gcgggcgagc ccccggaggt aggggggct ccggacccgc   5760
cgggagaggg ggcaggggca cgtcggcgcc gcgcgcgggc aggagctggt gctgcgcgcg   5820
taggttgctg gcgaacgcga cgacgcggcg gttgatctcc tgaatctggc gcctctgcgt   5880
gaagacgacg ggcccggtga gcttgagcct gaaagagagt tcgacagaat caatttcggt   5940
gtcgttgacg gcggcctggc gcaaaatctc ctgcacgtct cctgagttgt cttgataggc   6000
gatctcggcc atgaactgct cgatctcttc ctcctggaga tctccgcgtc cggctcgctc   6060
cacggtggcg gcgaggtcgt tggaaatgcg ggccatgagc tgcgagaagg cgttgaggcc   6120
tccctcgttc cagacgcggc tgtagaccac gccccttcg gcatcgcggg cgcgcatgac   6180
cacctgcgcg agattgagct ccacgtgccg ggcgaagacg gcgtagtttc gcaggcgctg   6240
aaagaggtag ttgagggtgg tggcggtgtg ttctgccacg aagaagtaca taacccagcg   6300
tcgcaacgtg gattcgttga tatcccccaa ggcctcaagg cgctccatgg cctcgtagaa   6360
gtccacggcg aagttgaaaa actgggagtt gcgcgccgac acggttaact cctcctccag   6420
aagacggatg agctcggcga cagtgtcgcg cacctcgcgc tcaaaggcta caggggcctc   6480
ttcttcttct tcaatctcct cttccataag ggcctcccct tcttcttctt ctggcggcgg   6540
tgggggaggg gggacacggc ggcgacgacg gcgcaccggg aggcggtcga caaagcgctc   6600
gatcatctcc ccgcggcgac ggcgcatggt ctcggtgacg gcgcggccgt tctcgcgggg   6660
gcgcagttgg aagacgccgc ccgtcatgtc ccggttatgg gttggcgggg ggctgccatg   6720
cggcagggat acggcgctaa cgatgcatct caacaattgt tgtgtaggta ctccgccgcc   6780
```

-continued

```
gagggacctg agcgagtccg catcgaccgg atcggaaaac ctctcgagaa aggcgtctaa   6840
ccagtcacag tcgcaaggta ggctgagcac cgtggcgggc ggcagcgggc ggcggtcggg   6900
gttgtttctg gcggaggtgc tgctgatgat gtaattaaag taggcggtct tgagacggcg   6960
gatggtcgac agaagcacca tgtccttggg tccggcctgc tgaatgcgca ggcggtcggc   7020
catgccccag gcttcgtttt gacatcggcg caggtctttg tagtagtctt gcatgagcct   7080
ttctaccggc acttcttctt ctccttcctc ttgtcctgca tctcttgcat ctatcgctgc   7140
ggcggcggcg gagtttggcc gtaggtggcg ccctcttcct cccatgcgtg tgaccccgaa   7200
gcccctcatc ggctgaagca gggctaggtc ggcgacaacg cgctcggcta atatggcctg   7260
ctgcacctgc gtgagggtag actggaagtc atccatgtcc acaaagcggt ggtatgcgcc   7320
cgtgttgatg gtgtaagtgc agttggccat aacggaccag ttaacggtct ggtgacccgg   7380
ctgcgagagc tcggtgtacc tgagacgcga gtaagccctc gagtcaaata cgtagtcgtt   7440
gcaagtccgc accaggtact ggtatcccac caaaaagtgc ggcggcggct ggcggtagag   7500
gggccagcgt agggtggccg gggctccggg ggcgagatct tccaacataa ggcgatgata   7560
tccgtagatg tacctggaca tccaggtgat gccggcggcg gtggtggagg cgcgcggaaa   7620
gtcgcggacg cggttccaga tgttgcgcag cggcaaaaag tgctccatgg tcgggacgct   7680
ctggccggtc aggcgcgcgc aatcgttgac gctctaccgt gcaaaaggag agcctgtaag   7740
cgggcactct tccgtggtct ggtggataaa ttcgcaaggg tatcatggcg gacgaccggg   7800
gttcgagccc cgtatccggc cgtccgccgt gatccatgcg gttaccgccc gcgtgtcgaa   7860
cccaggtgtg cgacgtcaga caacggggga gtgctccttt tggcttcctt ccaggcgcgg   7920
cggctgctgc gctagctttt ttggccactg gccgcgcgca gcgtaagcgg ttaggctgga   7980
aagcgaaagc attaagtggc tcgctccctg tagccggagg gttattttcc aagggttgag   8040
tcgcgggacc cccggttcga gtctcggacc ggccggactg cggcgaacgg gggtttgcct   8100
ccccgtcatg caagaccccg cttgcaaatt cctccggaaa cagggacgag ccccttttt    8160
gcttttccca gatgcatccg gtgctgcggc agatgcgccc ccctcctcag cagcggcaag   8220
agcaagagca gcggcagaca tgcagggcac cctcccctcc tcctaccgcg tcaggagggg   8280
cgacatccgc ggttgacgcg gcagcagatg gtgattacga acccccgcgg cgccgggccc   8340
ggcactacct ggacttggag gagggcgagg gcctggcgcg gctaggagcg ccctctcctg   8400
agcggtaccc aagggtgcag ctgaagcgtg atacgcgtga ggcgtacgtg ccgcggcaga   8460
acctgtttcg cgaccgcgag ggagaggagc ccgaggagat gcgggatcga aagttccacg   8520
cagggcgcga gctgcggcat ggcctgaatc gcgagcggtt gctgcgcgag gaggactttg   8580
agcccgacgc gcgaaccggg attagtcccg cgcgcgcaca cgtggcggcc gccgacctgg   8640
taaccgcata cgagcagacg gtgaaccagg agattaactt tcaaaaaagc tttaacaacc   8700
acgtgcgtac gcttgtggcg cgcgaggagg tggctatagg actgatgcat ctgtgggact   8760
ttgtaagcgc gctggagcaa aacccaaata gcaagccgct catggcgcag ctgttcctta   8820
tagtgcagca cagcagggac aacgaggcat tcagggatgc gctgctaaac atagtagagc   8880
ccgagggccg ctggctgctc gatttgataa acatcctgca gagcatagtg gtgcaggagc   8940
gcagcttgag cctggctgac aaggtggccg ccatcaacta ttccatgctt agcctgggca   9000
agttttacgc ccgcaagata taccataccc cttacgttcc catagacaag gaggtaaaga   9060
tcgaggggtt ctacatgcgc atggcgctga aggtgcttac cttgagcgac gacctgggcg   9120
tttatcgcaa cgagcgcatc cacaaggccg tgagcgtgag ccggcggcgc gagctcagcg   9180
```

```
accgcgagct gatgcacagc ctgcaaaggg ccctggctgg cacgggcagc ggcgatagag   9240
aggccgagtc ctactttgac gcgggcgctg acctgcgctg ggccccaagc cgacgcgccc   9300
tggaggcagc tggggccgga cctgggctgg cggtggcacc cgcgcgcgct ggcaacgtcg   9360
gcggcgtgga ggaatatgac gaggacgatg agtacgagcc agaggacggc gagtactaag   9420
cggtgatgtt tctgatcaga tgatgcaaga cgcaacggac ccggcggtgc gggcggcgct   9480
gcagagccag ccgtccggcc ttaactccac ggacgactgg cgccaggtca tggaccgcat   9540
catgtcgctg actgcgcgca atcctgacgc gttccggcag cagccgcagg ccaaccggct   9600
ctccgcaatt ctggaagcgg tggtcccggc gcgcgcaaac cccacgcacg agaaggtgct   9660
ggcgatcgta aacgcgctgg ccgaaaacag ggccatccgg cccgacgagg ccggcctggt   9720
ctacgacgcg ctgcttcagc gcgtggctcg ttacaacagc ggcaacgtgc agaccaacct   9780
ggaccggctg gtgggggatg tgcgcgaggc cgtggcgcag cgtgagcgcg cgcagcagca   9840
gggcaacctg ggctccatgg ttgcactaaa cgccttcctg agtacacagc ccgccaacgt   9900
gccgcgggga caggaggact acaccaactt tgtgagcgca ctgcggctaa tggtgactga   9960
gacaccgcaa agtgaggtgt accagtctgg gccagactat tttttccaga ccagtagaca  10020
aggcctgcag accgtaaacc tgagccaggc tttcaaaaac ttgcaggggc tgtggggggt  10080
gcgggctccc acaggcgacc gcgcgaccgt gtctagcttg ctgacgccca actcgcgcct  10140
gttgctgctg ctaatagcgc ccttcacgga cagtggcagc gtgtcccggg acacatacct  10200
aggtcacttg ctgacactgt accgcgaggc cataggtcag gcgcatgtgg acgagcatac  10260
tttccaggag attacaagtg tcagccgcgc gctggggcag gaggacacgg gcagcctgga  10320
ggcaacccta aactacctgc tgaccaaccg gcggcagaag atcccctcgt tgcacagttt  10380
aaacagcgag gaggagcgca ttttgcgcta cgtgcagcag agcgtgagcc ttaacctgat  10440
gcgcgacggg gtaacgccca gcgtggcgct ggacatgacc gcgcgcaaca tggaaccggg  10500
catgtatgcc tcaaaccggc cgtttatcaa ccgcctaatg gactacttgc atcgcgcggc  10560
cgccgtgaac cccgagtatt tcaccaatgc catcttgaac ccgcactggc taccgccccc  10620
tggtttctac accgggggat tcgaggtgcc cgagggtaac gatggattcc tctgggacga  10680
catagacgac agcgtgtttt ccccgcaacc gcagaccctg ctagagttgc aacagcgcga  10740
gcaggcagag gcggcgctgc gaaaggaaag cttccgcagg ccaagcagct tgtccgatct  10800
aggcgctgcg gccccgcggt cagatgctag tagcccattt ccaagcttga tagggtctct  10860
taccagcact cgcaccaccc gcccgcgcct gctgggcgag gaggagtacc taaacaactc  10920
gctgctgcag ccgcagcgcg aaaaaaacct gcctccggca tttcccaaca acgggataga  10980
gagcctagtg gacaagatga gtagatggaa gacgtacgcg caggagcaca gggacgtgcc  11040
aggcccgcgc ccgcccaccc gtcgtcaaag gcacgaccgt cagcggggtc tggtgtggga  11100
ggacgatgac tcggcagacg acagcagcgt cctggatttg ggagggagtg gcaacccgtt  11160
tgcgcacctt cgccccaggc tggggagaat gttttaaaaa aaaaaaagca tgatgcaaaa  11220
taaaaaactc accaaggcca tggcaccgag cgttggtttt cttgtattcc ccttagtatg  11280
cggcgcgcgg cgatgtatga ggaaggtcct cctccctcct acgagagtgt ggtgagcgcg  11340
gcgccagtgg cggcggcgct gggttctccc ttcgatgctc ccctggaccc gccgtttgtg  11400
cctccgcggt acctgcggcc taccgggggg agaaacagca tccgttactc tgagttggca  11460
cccctattcg acaccacccg tgtgtacctg gtggacaaca agtcaacgga tgtggcatcc  11520
ctgaactacc agaacgacca cagcaacttt ctgaccacgg tcattcaaaa caatgactac  11580
```

-continued

```
agcccggggg aggcaagcac acagaccatc aatcttgacg accggtcgca ctggggcggc  11640
gacctgaaaa ccatcctgca taccaacatg ccaaatgtga acgagttcat gtttaccaat  11700
aagtttaagg cgcgggtgat ggtgtcgcgc ttgcctacta aggacaatca ggtggagctg  11760
aaatacgagt gggtggagtt cacgctgccc gagggcaact actccgagac catgaccata  11820
gaccttatga acaacgcgat cgtggagcac tacttgaaag tgggcagaca gaacggggtt  11880
ctggaaagcg acatcggggt aaagtttgac acccgcaact tcagactggg gtttgacccc  11940
gtcactggtc ttgtcatgcc tggggtatat acaaacgaag ccttccatcc agacatcatt  12000
ttgctgccag gatgcggggt ggacttcacc cacagccgcc tgagcaactt gttgggcatc  12060
cgcaagcggc aacccttcca ggagggcttt aggatcacct acgatgatct ggagggtggt  12120
aacattcccg cactgttgga tgtggacgcc taccaggcga gcttgaaaga tgacaccgaa  12180
cagggcgggg gtggcgcagg cggcagcaac agcagtggca gcggcgcgga agagaactcc  12240
aacgcggcag ccgcggcaat gcagccggtg gaggacatga acgatcatgc cattcgcggc  12300
gacacctttg ccacacgggc tgaggagaag cgcgctgagg ccgaagcagc ggccgaagct  12360
gccgcccccg ctgcgcaacc cgaggtcgag aagcctcaga agaaaccggt gatcaaaccc  12420
ctgacagagg acagcaagaa acgcagttac aacctaataa gcaatgacag caccttcacc  12480
cagtaccgca gctggtacct tgcatacaac tacggcgacc ctcagaccgg aatccgctca  12540
tggaccctgc tttgcactcc tgacgtaacc tgcggctcgg agcaggtcta ctggtcgttg  12600
ccagacatga tgcaagaccc cgtgaccttc cgctccacgc gccagatcag caactttccg  12660
gtggtgggcg ccgagctgtt gcccgtgcac tccaagagct tctacaacga ccaggccgtc  12720
tactcccaac tcatccgcca gtttacctct ctgacccacg tgttcaatcg ctttcccgag  12780
aaccagattt tggcgcgccc gccagccccc accatcacca ccgtcagtga aaacgttcct  12840
gctctcacag atcacgggac gctaccgctg cgcaacagca tcggaggagt ccagcgagtg  12900
accattactg acgccagacg ccgcacctgc ccctacgttt acaaggccct gggcatagtc  12960
tcgccgcgcg tcctatcgag ccgcactttt tgagcaagca tgtccatcct tatatcgccc  13020
agcaataaca caggctgggg cctgcgcttc ccaagcaaga tgtttggcgg ggccaagaag  13080
cgctccgacc aacacccagt gcgcgtgcgc gggcactacc gcgcgccctg gggcgcgcac  13140
aaacgcggcc gcactgggcg caccaccgtc gatgacgcca tcgacgcggt ggtggaggag  13200
gcgcgcaact acacgcccac gccgccacca gtgtccacag tggacgcggc cattcagacc  13260
gtggtgcgcg gagcccggcg ctatgctaaa atgaagagac ggcggaggcg cgtagcacgt  13320
cgccaccgcc gccgacccgg cactgccgcc caacgcgcgg cggcggccct gcttaaccgc  13380
gcacgtcgca ccggccgacg ggcggccatg cgggccgctc gaaggctggc cgcgggtatt  13440
gtcactgtgc ccccccaggtc caggcgacga gcggccgccg cagcagccgc ggccattagt  13500
gctatgactc agggtcgcag gggcaacgtg tattgggtgc gcgactcggt tagcggcctg  13560
cgcgtgcccg tgcgcacccg ccccccgcgc aactagattg caagaaaaaa ctacttagac  13620
tcgtactgtt gtatgtatcc agcggcggcg gcgcgcaacg aagctatgtc caagcgcaaa  13680
atcaaagaag agatgctcca ggtcatcgcg ccggagatct atggcccccc gaagaaggaa  13740
gagcaggatt acaagccccg aaagctaaag cgggtcaaaa agaaaaagaa agatgatgat  13800
gatgaacttg acgacgaggt ggaactgctg cacgctaccg cgcccaggcg acgggtacag  13860
tggaaaggtc gacgcgtaaa acgtgttttg cgacccggca ccaccgtagt ctttacgccc  13920
ggtgagcgct ccacccgcac ctacaagcgc gtgtatgatg aggtgtacgg cgacgaggac  13980
```

-continued

```
ctgcttgagc aggccaacga gcgcctcggg gagtttgcct acggaaagcg gcataaggac  14040
atgctggcgt tgccgctgga cgagggcaac ccaacaccta gcctaaagcc cgtaacactg  14100
cagcaggtgc tgcccgcgct tgcaccgtcc gaagaaaagc gcggcctaaa gcgcgagtct  14160
ggtgacttgg cacccaccgt gcagctgatg gtacccaagc gccagcgact ggaagatgtc  14220
ttggaaaaaa tgaccgtgga acctgggctg gagcccgagg tccgcgtgcg gccaatcaag  14280
caggtggcgc cgggactggg cgtgcagacc gtggacgttc agatacccac taccagtagc  14340
accagtattg ccaccgccac agagggcatg gagacacaaa cgtccccggt tgcctcagcg  14400
gtggcggatg ccgcggtgca ggcggtcgct gcggccgcgt ccaagacctc tacggaggtg  14460
caaacggacc cgtggatgtt tcgcgtttca gccccccggc gcccgcgcgg ttcgaggaag  14520
tacggcgccg ccagcgcgct actgcccgaa tatgccctac atccttccat tgcgcctacc  14580
cccggctatc gtggctacac ctaccgcccc agaagacgag caactacccg acgccgaacc  14640
accactggaa cccgccgccg ccgtcgccgt cgccagcccg tgctggcccc gatttccgtg  14700
cgcagggtgg ctcgcgaagg aggcaggacc ctggtgctgc caacagcgcg ctaccacccc  14760
agcatcgttt aaaagccggt ctttgtggtt cttgcagata tggccctcac ctgccgcctc  14820
cgtttcccgg tgccgggatt ccgaggaaga atgcaccgta ggaggggcat ggccggccac  14880
ggcctgacgg gcggcatgcg tcgtgcgcac caccggcggc ggcgcgcgtc gcaccgtcgc  14940
atgcgcggcg gtatcctgcc cctccttatt ccactgatcg ccgcggcgat tggcgccgtg  15000
cccggaattg catccgtggc cttgcaggcg cagagacact gattaaaaac aagttgcatg  15060
tggaaaaatc aaaataaaaa gtctggactc tcacgctcgc ttggtcctgt aactattttg  15120
tagaatggaa gacatcaact ttgcgtctct ggccccgcga cacggctcgc gcccgttcat  15180
gggaaactgg caagatatcg gcaccagcaa tatgagcggt ggcgccttca gctggggctc  15240
gctgtggagc ggcattaaaa atttcggttc caccgttaag aactatggca gcaaggcctg  15300
gaacagcagc acaggccaga tgctgaggga taagttgaaa gagcaaaatt tccaacaaaa  15360
ggtggtagat ggcctggcct ctggcattag cggggtggtg gacctggcca accaggcagt  15420
gcaaaataag attaacagta agcttgatcc ccgccctccc gtagaggagc ctccaccggc  15480
cgtggagaca gtgtctccag aggggcgtgg cgaaaagcgt ccgcgccccg acagggaaga  15540
aactctggtg acgcaaatag acgagcctcc ctcgtacgag gaggcactaa agcaaggcct  15600
gcccaccacc cgtcccatcg cgcccatggc taccggagtg ctgggccagc acacacccgt  15660
aacgctggac ctgcctcccc ccgccgacac ccagcagaaa cctgtgctgc caggcccgac  15720
cgccgttgtt gtaacccgtc ctagccgcgc gtccctgcgc cgcgccgcca gcggtccgcg  15780
atcgttgcgg cccgtagcca gtggcaactg gcaaagcaca ctgaacagca tcgtgggtct  15840
gggggtgcaa tccctgaagc gccgacgatg cttctgaata gctaacgtgt cgtatgtgtg  15900
tcatgtatgc gtccatgtcg ccgccagagg agctgctgag ccgccgcgcg cccgctttcc  15960
aagatggcta ccccttcgat gatgccgcag tggtcttaca tgcacatctc gggccaggac  16020
gcctcggagt acctgagccc cgggctggtg cagtttgccc gcgccaccga gacgtacttc  16080
agcctgaata acaagtttag aaaccccacg gtggcgccta cgcacgacgt gaccacagac  16140
cggtcccagc gtttgacgct gcggttcatc cctgtggacc gtgaggatac tgcgtactcg  16200
tacaaggcgc ggttcaccct agctgtgggt gataaccgtg tgctggacat ggcttccacg  16260
tactttgaca tccgcggcgt gctggacagg ggccctactt ttaagcccta ctctggcact  16320
gcctacaacg ccctggctcc caagggtgcc ccaaatcctt gcgaatggga tgaagctgct  16380
```

-continued

```
actgctcttg aaataaacct agaagaagag gacgatgaca acgaagacga agtagacgag  16440
caagctgagc agcaaaaaac tcacgtattt gggcaggcgc cttattctgg tataaatatt  16500
acaaaggagg gtattcaaat aggtgtcgaa ggtcaaacac ctaaatatgc cgataaaaca  16560
tttcaacctg aacctcaaat aggagaatct cagtggtacg aaactgaaat taatcatgca  16620
gctgggagag tccttaaaaa gactacccca atgaaaccat gttacggttc atatgcaaaa  16680
cccacaaatg aaaatggagg gcaaggcatt cttgtaaagc aacaaaatgg aaagctagaa  16740
agtcaagtgg aaatgcaatt tttctcaact actgaggcga ccgcaggcaa tggtgataac  16800
ttgactccta aagtggtatt gtacagtgaa gatgtagata tagaaacccc agacactcat  16860
atttcttaca tgcccactat taaggaaggt aactcacgag aactaatggg ccaacaatct  16920
atgcccaaca ggcctaatta cattgctttt agggacaatt ttattggtct aatgtattac  16980
aacagcacgg gtaatatggg tgttctggcg ggccaagcat cgcagttgaa tgctgttgta  17040
gatttgcaag acagaaacac agagctttca taccagcttt tgcttgattc cattggtgat  17100
agaaccaggt acttttctat gtggaatcag gctgttgaca gctatgatcc agatgttaga  17160
attattgaaa atcatggaac tgaagatgaa cttccaaatt actgctttcc actgggaggt  17220
gtgattaata cagagactct taccaaggta aaacctaaaa caggtcagga aaatggatgg  17280
gaaaaagatg ctacagaatt ttcagataaa aatgaaataa gagttggaaa taattttgcc  17340
atggaaatca atctaaatgc caacctgtgg agaaatttcc tgtactccaa catagcgctg  17400
tatttgcccg acaagctaaa gtacagtcct tccaacgtaa aaatttctga taacccaaac  17460
acctacgact acatgaacaa gcgagtggtg gctcccgggt tagtggactg ctacattaac  17520
cttggagcac gctggtccct tgactatatg gacaacgtca acccatttaa ccaccaccgc  17580
aatgctggcc tgcgctaccg ctcaatgttg ctgggcaatg gtcgctatgt gcccttccac  17640
atccaggtgc ctcagaagtt ctttgccatt aaaaacctcc ttctcctgcc gggctcatac  17700
acctacgagt ggaacttcag gaaggatgtt aacatggttc tgcagagctc cctaggaaat  17760
gacctaaggg ttgacggagc cagcattaag tttgatagca tttgccttta cgccaccttc  17820
ttccccatgg cccacaacac cgcctccacg cttgaggcca tgcttagaaa cgacaccaac  17880
gaccagtcct ttaacgacta tctctccgcc gccaacatgc tctaccctat acccgccaac  17940
gctaccaacg tgcccatatc catcccctcc cgcaactggg cggctttccg cggctgggcc  18000
ttcacgcgcc ttaagactaa ggaaacccca tcactgggct cgggctacga cccttattac  18060
acctactctg gctctatacc ctacctagat ggaacctttt acctcaacca cacctttaag  18120
aaggtggcca ttacctttga ctcttctgtc agctggcctg gcaatgaccg cctgcttacc  18180
cccaacgagt ttgaaattaa gcgctcagtt gacggggagg gttacaacgt tgcccagtgt  18240
aacatgacca aagactggtt cctggtacaa atgctagcta actacaacat tggctaccag  18300
ggcttctata tcccagagag ctacaaggac cgcatgtact ccttctttag aaacttccag  18360
cccatgagcc gtcaggtggt ggatgatact aaatacaagg actaccaaca ggtgggcatc  18420
ctacaccaac acaacaactc tggatttgtt ggctaccttg cccccaccat gcgcgaagga  18480
caggcctacc ctgctaactt ccccctatccg cttataggca agaccgcagt tgacagcatt  18540
acccagaaaa agtttctttg cgatcgcacc ctttggcgca tcccattctc cagtaacttt  18600
atgtccatgg gcgcactcac agacctgggc caaaaccttc tctacgccaa ctccgcccac  18660
gcgctagaca tgacttttga ggtggatccc atggacgagc ccacccttct ttatgttttg  18720
tttgaagtct ttgacgtggt ccgtgtgcac cggccgcacc gcggcgtcat cgaaaccgtg  18780
```

tacctgcgca cgcccttctc ggccggcaac gccacaacat aaagaagcaa gcaacatcaa 18840
caacagctgc cgccatgggc tccagtgagc aggaactgaa agccattgtc aaagatcttg 18900
gttgtgggcc atattttttg ggcacctatg acaagcgctt tccaggcttt gtttctccac 18960
acaagctcgc ctgcgccata gtcaatacgg ccggtcgcga gactgggggc gtacactgga 19020
tggcctttgc ctggaacccg cactcaaaaa catgctacct ctttgagccc tttggctttt 19080
ctgaccagcg actcaagcag gtttaccagt ttgagtacga gtcactcctg cgccgtagcg 19140
ccattgcttc ttcccccgac cgctgtataa cgctggaaaa gtccacccaa agcgtacagg 19200
ggcccaactc ggccgcctgt ggactattct gctgcatgtt tctccacgcc tttgccaact 19260
ggccccaaac tcccatggat cacaacccca ccatgaacct tattaccggg gtacccaact 19320
ccatgctcaa cagtccccag gtacagccca ccctgcgtcg caaccaggaa cagctctaca 19380
gcttcctgga gcgccactcg ccctacttcc gcagccacag tgcgcagatt aggagcgcca 19440
cttctttttg tcacttgaaa aacatgtaaa aataatgtac tagagacact ttcaataaag 19500
gcaaatgctt ttatttgtac actctcgggt gattatttac cccacccctt gccgtctgcg 19560
ccgtttaaaa atcaaagggg ttctgccgcg catcgctatg cgccactggc agggacacgt 19620
tgcgatactg gtgtttagtg ctccacttaa actcaggcac aaccatccgc ggcagctcgg 19680
tgaagttttc actccacagg ctgcgcacca tcaccaacgc gtttagcagg tcgggcgccg 19740
atatcttgaa gtcgcagttg gggcctccgc cctgcgcgcg cgagttgcga tacacagggt 19800
tgcagcactg gaacactatc agcgccgggt ggtgcacgct ggccagcacg ctcttgtcgg 19860
agatcagatc cgcgtccagg tcctccgcgt tgctcagggc gaacggagtc aactttggta 19920
gctgccttcc caaaaagggc gcgtgcccag gctttgagtt gcactcgcac cgtagtggca 19980
tcaaaaggtg accgtgcccg gtctgggcgt taggatacag cgcctgcata aaagccttga 20040
tctgcttaaa agccacctga gcctttgcgc cttcagagaa gaacatgccg caagacttgc 20100
cggaaaactg attggccgga caggccgcgt cgtgcacgca gcaccttgcg tcggtgttgg 20160
agatctgcac cacatttcgg ccccaccggt tcttcacgat cttggccttg ctagactgct 20220
ccttcagcgc gcgctgcccg ttttcgctcg tcacatccat ttcaatcacg tgctccttat 20280
ttatcataat gcttccgtgt agacacttaa gctcgccttc gatctcagcg cagcggtgca 20340
gccacaacgc gcagcccgtg ggctcgtgat gcttgtaggt cacctctgca aacgactgca 20400
ggtacgcctg caggaatcgc cccatcatcg tcacaaaggt cttgttgctg gtgaaggtca 20460
gctgcaaccc gcggtgctcc tcgttcagcc aggtcttgca tacggccgcc agagcttcca 20520
cttggtcagg cagtagtttg aagttcgcct ttagatcgtt atccacgtgg tacttgtcca 20580
tcagcgcgcg cgcagcctcc atgcccttct cccacgcaga cacgatcggc acactcagcg 20640
ggttcatcac cgtaatttca ctttccgctt cgctgggctc ttcctcttcc tcttgcgtcc 20700
gcataccacg cgccactggg tcgtcttcat tcagccgccg cactgtgcgc ttacctcctt 20760
tgccatgctt gattagcacc ggtgggttgc tgaaacccac catttgtagc gccacatctt 20820
ctctttcttc ctcgctgtcc acgattacct ctggtgatgg cgggcgctcg ggcttgggag 20880
aagggcgctt ctttttcttc ttgggcgcaa tggccaaatc cgccgccgag gtcgatggcc 20940
gcgggctggg tgtgcgcggc accagcgcgt cttgtgatga gtcttcctcg tcctcggact 21000
cgatacgccg cctcatccgc ttttttgggg gcgcccgggg aggcggcggc gacggggacg 21060
gggacgacac gtcctccatg gttgggggac gtcgcgccgc accgcgtccg cgctcggggg 21120
tggtttcgcg ctgctcctct tcccgactgg ccatttcctt ctcctatagg cagaaaaaga 21180

-continued

```
tcatggagtc agtcgagaag aaggacagcc taaccgcccc ctctgagttc gccaccaccg  21240
cctccaccga tgccgccaac gcgcctacca ccttccccgt cgaggcaccc ccgcttgagg  21300
aggaggaagt gattatcgag caggacccag gttttgtaag cgaagacgac gaggaccgct  21360
cagtaccaac agaggataaa aagcaagacc aggacaacgc agaggcaaac gaggaacaag  21420
tcgggcgggg ggacgaaagg catggcgact acctagatgt gggagacgac gtgctgttga  21480
agcatctgca gcgccagtgc gccattatct gcgacgcgtt gcaagagcgc agcgatgtgc  21540
ccctcgccat agcggatgtc agccttgcct acgaacgcca cctattctca ccgcgcgtac  21600
cccccaaacg ccaagaaaac ggcacatgcg agcccaaccc gcgcctcaac ttctaccccg  21660
tatttgccgt gccagaggtg cttgccacct atcacatctt tttccaaaac tgcaagatac  21720
ccctatcctg ccgtgccaac cgcagccgag cggacaagca gctggccttg cggcagggcg  21780
ctgtcatacc tgatatcgcc tcgctcaacg aagtgccaaa aatctttgag ggtcttggac  21840
gcgacgagaa gcgcgcggca aacgctctgc aacaggaaaa cagcgaaaat gaaagtcact  21900
ctggagtgtt ggtggaactc gagggtgaca acgcgcgcct agccgtacta aaacgcagca  21960
tcgaggtcac ccactttgcc tacccggcac ttaacctacc ccccaaggtc atgagcacag  22020
tcatgagtga gctgatcgtg cgccgtgcgc agcccctgga gagggatgca aatttgcaag  22080
aacaaacaga ggagggccta cccgcagttg gcgacgagca gctagcgcgc tggcttcaaa  22140
cgcgcgagcc tgccgacttg gaggagcgac gcaaactaat gatggccgca gtgctcgtta  22200
ccgtggagct tgagtgcatg cagcggttct ttgctgaccc ggagatgcag cgcaagctag  22260
aggaaacatt gcactacacc tttcgacagg gctacgtacg ccaggcctgc aagatctcca  22320
acgtggagct ctgcaacctg gtctcctacc ttggaatttt gcacgaaaac cgccttgggc  22380
aaaacgtgct tcattccacg ctcaagggcg aggcgcgccg cgactacgtc cgcgactgcg  22440
tttacttatt tctatgctac acctggcaga cggccatggg cgtttggcag cagtgcttgg  22500
aggagtgcaa cctcaaggag ctgcagaaac tgctaaagca aaacttgaag gacctatgga  22560
cggccttcaa cgagcgctcc gtggccgcgc acctggcgga catcattttc cccgaacgcc  22620
tgcttaaaac cctgcaacag ggtctgccag acttcaccag tcaaagcatg ttgcagaact  22680
ttaggaactt tatcctagag cgctcaggaa tcttgcccgc cacctgctgt gcacttccta  22740
gcgactttgt gcccattaag taccgcgaat gccctccgcc gctttggggc cactgctacc  22800
ttctgcagct agccaactac cttgcctacc actctgacat aatggaagac gtgagcggtg  22860
acggtctact ggagtgtcac tgtcgctgca acctatgcac cccgcaccgc tccctggttt  22920
gcaattcgca gctgcttaac gaaagtcaaa ttatcggtac ctttgagctg cagggtccct  22980
cgcctgacga aaagtccgcg gctccggggt tgaaactcac tccggggctg tggacgtcgg  23040
cttaccttcg caaatttgta cctgaggact accacgccca cgagattagg ttctacgaag  23100
accaatcccg cccgccaaat gcggagctta ccgcctgcgt cattacccag ggccacattc  23160
ttggccaatt gcaagccatc aacaaagccc gccaagagtt tctgctacga aagggacggg  23220
gggtttactt ggacccccag tccggcgagg agctcaaccc aatccccccg ccgccgcagc  23280
cctatcagca gcagccgcgg gcccttgctt cccaggatgg cacccaaaaa gaagctgcag  23340
ctgccgccgc cacccacgga cgaggaggaa tactgggaca gtcaggcaga ggaggttttg  23400
gacgaggagg aggaggacat gatggaagac tgggagagcc tagacgagga agcttccgag  23460
gtcgaagagg tgtcagacga aacaccgtca ccctcggtcg cattcccctc gccggcgccc  23520
cagaaatcgg caaccggttc cagcatggct acaacctccg ctcctcaggc gccgccggca  23580
```

-continued

```
ctgcccgttc gccgacccaa ccgtagatgg gacaccactg gaaccagggc cggtaagtcc  23640
aagcagccgc cgccgttagc ccaagagcaa caacagcgcc aaggctaccg ctcatggcgc  23700
gggcacaaga acgccatagt tgcttgcttg caagactgtg ggggcaacat ctccttcgcc  23760
cgccgctttc ttctctacca tcacggcgtg gccttccccc gtaacatcct gcattactac  23820
cgtcatctct acagcccata ctgcaccggc ggcagcggca gcggcagcaa cagcagcggc  23880
cacacagaag caaaggcgac cggatagcaa gactctgaca aagcccaaga aatccacagc  23940
ggcggcagca gcaggaggag gagcgctgcg tctggcgccc aacgaacccg tatcgacccg  24000
cgagcttaga aacaggattt ttcccactct gtatgctata tttcaacaga gcaggggcca  24060
agaacaagag ctgaaaataa aaaacaggtc tctgcgatcc ctcacccgca gctgcctgta  24120
tcacaaaagc gaagatcagc ttcggcgcac gctggaagac gcggaggctc tcttcagtaa  24180
atactgcgcg ctgactctta aggactagtt tcgcgccctt tctcaaattt aagcgcgaaa  24240
actacgtcat ctccagcggc cacacccggc gccagcacct gtcgtcagcg ccattatgag  24300
caaggaaatt cccacgccct acatgtggag ttaccagcca caaatgggac ttgcggctgg  24360
agctgcccaa gactactcaa cccgaataaa ctacatgagc gcgggacccc acatgatatc  24420
ccgggtcaac ggaatccgcg cccaccgaaa ccgaattctc ttggaacagg cggctattac  24480
caccacacct cgtaataacc ttaatccccg tagttggccc gctgccctgg tgtaccagga  24540
aagtcccgct cccaccactg tggtacttcc cagagacgcc caggccgaag ttcagatgac  24600
taactcaggg gcgcagcttg cgggcggctt tcgtcacagg gtgcggtcgc ccgggcaggg  24660
tataactcac ctgacaatca gagggcgagg tattcagctc aacgacgagt cggtgagctc  24720
ctcgcttggt ctccgtccgg acgggacatt tcagatcggc ggcgccggcc gtccttcatt  24780
cacgcctcgt caggcaatcc taactctgca gacctcgtcc tctgagccgc gctctggagg  24840
cattggaact ctgcaattta ttgaggagtt tgtgccatcg gtctacttta accccttctc  24900
gggacctccc ggccactatc cggatcaatt tattcctaac tttgacgcgg taaaggactc  24960
ggcggacggc tacgactgaa tgttaagtgg agaggcagag caactgcgcc tgaaacacct  25020
ggtccactgt cgccgccaca agtgctttgc ccgcgactcc ggtgagtttt gctactttga  25080
attgcccgag gatcatatcg agggcccggc gcacggcgtc cggcttaccg cccagggaga  25140
gcttgcccgt agcctgattc gggagtttac ccagcgcccc ctgctagttg agcgggacag  25200
gggaccctgt gttctcactg tgatttgcaa ctgtcctaac cttggattac atcaagatcc  25260
tctagttaat taacagcttg catgcctgca ggtcgacgga tcgggagatc tcggccgcat  25320
attaagtgca ttgttctcga taccgctaag tgcattgttc tcgttagctc gatggacaag  25380
tgcattgttc tcttgctgaa agctcgatgg acaagtgcat tgttctcttg ctgaaagctc  25440
gatggacaag tgcattgttc tcttgctgaa agctcagtac ccgggagtac cctcgaccgc  25500
cggagtataa atagaggcgc ttcgtctacg gagcgacaat tcaattcaaa caagcaaagt  25560
gaacacgtcg ctaagcgaaa gctaagcaaa taaacaagcg cagctgaaca agctaaacaa  25620
tctgcagtaa agtgcaagtt aaagtgaatc aattaaaagt aaccagcaac caagtaaatc  25680
aactgcaact actgaaatct gccaagaagt aattattgaa tacaagaaga gaactctgaa  25740
tactttcaac aagttaccga gaaagaagaa ctcacacaca gctagcgttt aaacttaagc  25800
ttcaccatgg tggggccctg catgctgctg ctgctgctgc tgctgggcct gaggctacag  25860
ctctccctgg gcatcatcct agttgaggag gagaacccgg acttctggaa ccgcgaggca  25920
gccgaggccc tgggtgccgc caagaagctg cagcctgcac agacagccgc caagaacctc  25980
```

-continued

```
atcatcttcc tgggcgatgg ggtgggggtg tctacggtga cagctgccag gatcctaaaa  26040
gggcagaaga aggacaaact ggggcctgag ataccccctgg ccatggaccg cttcccatat  26100
gtggctctgt ccaagacata caatgtagac aaacatgtgc cagacagtgg agccacagcc  26160
acggcctacc tgtgcggggt caagggcaac ttccagacca ttggcttgag tgcagccgcc  26220
cgctttaacc agtgcaacac gacacgcggc aacgaggtca tctccgtgat gaatcgggcc  26280
aagaaagcag ggaagtcagt gggagtggta accaccacac gagtgcagca cgcctcgcca  26340
gccggcacct acgcccacac ggtgaaccgc aactggtact cggacgccga cgtgcctgcc  26400
tcggcccgcc aggaggggtg ccaggacatc gctacgcagc tcatctccaa catggacatt  26460
gacgtgatcc taggtggggg ccgaaagtac atgtttcgca tgggaacccc agaccctgag  26520
tacccagatg actacagcca aggtgggacc aggctggacg ggaagaatct ggtgcaggaa  26580
tggctggcga agcaccaggg tgcccggtac gtgtggaacc gcactgagct catgcgggct  26640
tccctggacc cgtctgtggc ccatctcatg ggtctctttg agcctggaga catgaaatac  26700
gagatccacc gagactccac actggacccc tccctgatgg agatgacaga ggctgccctg  26760
cgcctgctga gcaggaaccc ccgcggcttc ttcctcttcg tggagggtgg tcgcatcgac  26820
catggtcatc atgaaagcag ggcttaccgg gcactgactg agacgatcat gttcgacgac  26880
gccattgaga gggcgggcca gctcaccagc gaggaggaca cgctgagcct cgtcactgcc  26940
gaccactccc acgtcttctc cttcggaggc tgccccctgc gagggggctc catcttcggg  27000
ctggcccctg gcaaggcccg ggacaggaag gcctacacgg tcctcctata cggaaacggt  27060
ccaggctatg tgctcaagga cggcgcccgg ccggatgtta ccgagagcga gagcgggagc  27120
cccgagtatc ggcagcagtc agcagtgccc ctggacgaag agacccacgc aggcgaggac  27180
gtggcggtgt tcgcgcgcgg cccgcaggcg cacctggttc acggcgtgca ggagcagacc  27240
ttcatagcgc acgtcatggc cttcgccgcc tgcctggagc cctacaccgc ctgcgacctg  27300
gcgccccccg ccggcaccac cgacgccgcg cacccggggc ggtccgtggt ccccgcgttg  27360
cttcctctgc tggccgggac cctgctgctg ctggagacgg ccactgctcc ctgagtgtcc  27420
cgtccctggg gctcctgctt ccccatcccg gagttctcct gctccccgcc tcctgtcgtc  27480
ctgcctggcc tccagcccga gtcgtcatcc ccggagtccc tatacagagg tcctgccatg  27540
gaaccttccc ctccccgtgc gctctgggga ctgagcccat gacaccaaac ctgccccttg  27600
gctgctctcg gactccctac cccaacccca gggacagatc tggccagatt tgtaaaacaa  27660
atagatttta ggcccaaaga ttatttaaag cattgcctgg aacgcagtga gtttttgtta  27720
gaaaagagaa taattcaaag tggcattgct ttgcttctta tgttaatttg gtacagacct  27780
gtggctgagt ttgctcaaag tattcagagc agaattgtgg agtggaaaga gagattggac  27840
aaagagttta gtttgtcagt gtatcaaaaa atgaagttta atgtggctat gggaattgga  27900
gttttagatt ggctaagaaa cagtgatgat gatgatgaag acagccagga aaatgctgat  27960
aaaaatgaag atggtgggga gaagaacatg gaagactcag ggcatgaaac aggcattgat  28020
tcacagtccc aaggctcatt tcaggcccct cagtcctcac agtctgttca tgatcataat  28080
cagccatacc acatttgtag aggttttact tgctttaaaa aacctcccac acctcccccct  28140
gaacctgaaa cataaaatga atgcaattgt tgttgttaac ttgtttattg cagcttataa  28200
tggttacaaa taaagcaata gcatcacaaa tttcacaaat aaagcatttt tttcactgca  28260
ttctagttgt ggtttgtcca aactcatcaa tgtatcttat catgtctgga tccccaggaa  28320
gctcctctgt gtcctcataa accctaacct cctctacttg agaggacatt ccaatcatag  28380
```

-continued gctgcccatc caccctctgt gtcctcctgt taattaggtc acttaacaaa aaggaaattg 28440
ggtaggggtt tttcacagac cgctttctaa gggtaatttt aaaatatctg ggaagtccct 28500
tccactgctg tgttccagaa gtgttggtaa acagcccaca aatgtcaaca gcagaaacat 28560
acaagctgtc agctttgcac aagggcccaa caccctgctc atcaagaagc actgtggttg 28620
ctgtgttagt aatgtgcaaa acaggaggca cattttcccc acctgtgtag gttccaaaat 28680
atctagtgtt ttcattttta cttggatcag gaacccagca ctccactgga taagcattat 28740
ccttatccaa aacagccttg tggtcagtgt tcatctgctg actgtcaact gtagcatttt 28800
ttggggttac agtttgagca ggatatttgg tcctgtagtt tgctaacaca ccctgcagct 28860
ccaaaggttc cccaccaaca gcaaaaaaat gaaaatttga cccttgaatg ggttttccag 28920 caccatttc atgagttttt tgtgtccctg aatgcaagtt taacatagca gttaccccaa 28980
taacctcagt tttaacagta acagcttccc acatcaaaat atttccacag gttaagtcct 29040
catttaaatt aggcaaagga attccacttc ccactgcctt gcttccgtct cccattcaaa 29100
cttttatcaa ctgacattat tctaagtaaa atcctcttca ttatgttgtc agcaatccat 29160
tgcttgaagg cctggctccc cagaacccct cgactggtat gtcttctcct agaatactcc 29220
agaagaaaag gagtgtatga agatagtgac tgcacattaa aatgactgaa accatagtaa 29280
attaggatga gattctgggc agataaacag acagctggct aggatcattt ttttatgcct 29340
tggacttctt tggcaatctg ttgaagcctg acattcctca gaataatgtt ttaaagccca 29400
acaataagac cctgtagcac atataataag tactgcagtt ttgaagtagt gataagcata 29460
aatgatattt tgatatattt attataactg taatgagatg tgtacatatc tgtgacttca 29520
taggtactga ttgtactact gtgatttttt tgcctacttt caaaatgaaa aggaatgctt 29580
aatttcagtt agaggttagt aaagacaaat aggtaatttt cttctccagt gaagagcatg 29640
gcgccccttg ctattcatgg acgcttgctt aaagacttgt acacaggctt gctttgtatc 29700
aacctatgac ttccccttac agccgatgat aggtttttat ttgcacctcc ttcgtgtaca 29760
aagacagttt tggtggctac gccatcatta aactcattat tatcatgctt aagcctatag 29820
atgtatccag ttcttctgtt acataattga agctgtagtg aattgtctat cttaaactgc 29880
atcgctaact gactacattt cacacttcat ttgcttccaa catagactaa ccttcttgga 29940
tgtccactat tatttgaact tttgagattt tttttcctat ttctaatatc ttaaaatttc 30000
agaagactta aagttttgca actacagggc tccatataga catctagctt gaatttatac 30060
actttctttc attgatgtcc ctggactaaa aaatgttaaa tatttctaac cgctgtactt 30120
aaagtccatt acaaacgaag actactgttg ttaagttgaa taggcatctt atatattttt 30180
caccggtgca ataaataact tctattccct tctaacatct gcttgcgttg cactgagagt 30240
acactattga ttagcaatag gttcgtgatt acagcccttc tataattaat tgttaggtta 30300
acatattatt cataaaatat tattttatta atttttactt gatttgctac tggatgctta 30360
gaaatagcta tgagtatatt ggtagaacca gtacttatat tttattacat ttttacattt 30420
cataaaattt aagtgatata aaaatcctga ggaagtatgc cacaaaagtg gtctcagtgg 30480
aaatttaaat atgttaacat ttatttttaa aatgtagcgt gaaatagaca actttaaaag 30540
ctcagcttaa aaaaaaaact caaggaagct gaacttgact ttttaaagca ctgaagtgca 30600
atatttaatg taggtcaaca tgtttaaatg ggaaaatttt tttcctaatt acagccaaat 30660
ccctagctgt aattaactta aaatttgtat actatttcac aacagagtca gcatatacca 30720
ctttcttata aaattagaaa gatctaaaat tttagagctt atttggtgaa acaggcatat 30780

-continued

```
tgctacatct ttgtttataa attataatgt gcctttagag cccaataaca gataacaaga  30840
ttttgaaaat tcaggtgaat tagagttatc agagggaatg ttaatacact ctattcaaat  30900
actatatgag taagacattt aaaataggaa acaatacttt atatattaaa aaaaattaat  30960
cttccagtcg atttaatcca ctttatgaat tcatttaaat cgatttaaat tcgaattaat  31020
taactagagt acccggggat cttattccct ttaactaata aaaaaaaata ataaagcatc  31080
acttacttaa aatcagttag caaatttctg tccagtttat tcagcagcac ctccttgccc  31140
tcctcccagc tctggtattg cagcttcctc ctggctgcaa actttctcca caatctaaat  31200
ggaatgtcag tttcctcctg ttcctgtcca tccgcaccca ctatcttcat gttgttgcag  31260
atgaagcgcg caagaccgtc tgaagatacc ttcaaccccg tgtatccata tgacacggaa  31320
accggtcctc caactgtgcc ttttcttact cctccctttg tatcccccaa tgggtttcaa  31380
gagagtcccc ctggggtact ctctttgcgc ctatccgaac ctctagttac ctccaatggc  31440
atgcttgcgc tcaaaatggg caacggcctc tctctggacg aggccggcaa ccttacctcc  31500
caaaatgtaa ccactgtgag cccacctctc aaaaaaacca agtcaaacat aaacctggaa  31560
atatctgcac ccctcacagt tacctcagaa gccctaactg tggctgccgc cgcacctcta  31620
atggtcgcgg gcaacacact caccatgcaa tcacaggccc cgctaaccgt gcacgactcc  31680
aaacttagca ttgccaccca aggacccctc acagtgtcag aaggaaagct agccctgcaa  31740
acatcaggcc ccctcaccac caccgatagc agtaccctta ctatcactgc ctcaccccct  31800
ctaactactg ccactggtag cttgggcatt gacttgaaag agcccattta tacacaaaat  31860
ggaaaactag gactaaagta cggggctcct ttgcatgtaa cagacgacct aaacactttg  31920
accgtagcaa ctggtccagg tgtgactatt aataatactt ccttgcaaac taaagttact  31980
ggagccttgg gttttgattc acaaggcaat atgcaactta atgtagcagg aggactaagg  32040
attgattctc aaaacagacg ccttatactt gatgttagtt atccgtttga tgctcaaaac  32100
caactaaatc taagactagg acagggccct ctttttataa actcagccca caacttggat  32160
attaactaca acaaaggcct ttacttgttt acagcttcaa acaattccaa aaagcttgag  32220
gttaacctaa gcactgccaa ggggttgatg tttgacgcta cagccatagc cattaatgca  32280
ggagatgggc ttgaatttgg ttcacctaat gcaccaaaca caaatcccct caaaacaaaa  32340
attggccatg gcctagaatt tgattcaaac aaggctatgg ttcctaaact aggaactggc  32400
cttagttttg acagcacagg tgccattaca gtaggaaaca aaaataatga taagctaact  32460
ttgtggacca caccagctcc atctcctaac tgtagactaa atgcagagaa agatgctaaa  32520
ctcactttgg tcttaacaaa atgtggcagt caaatacttg ctacagtttc agttttggct  32580
gttaaaggca gtttggctcc aatatctgga acagttcaaa gtgctcatct tattataaga  32640
tttgacgaaa atggagtgct actaaacaat tccttcctgg acccagaata ttggaacttt  32700
agaaatggag atcttactga aggcacagcc tatacaaacg ctgttggatt tatgcctaac  32760
ctatcagctt atccaaaatc tcacggtaaa actgccaaaa gtaacattgt cagtcaagtt  32820
tacttaaacg gagacaaaac taaacctgta acactaacca ttacactaaa cggtacacag  32880
gaaacaggag acacaactcc aagtgcatac tctatgtcat tttcatggga ctggtctggc  32940
cacaactaca ttaatgaaat atttgccaca tcctcttaca ctttttcata cattgcccaa  33000
gaataaagaa tcgtttgtgt tatgtttcaa cgtgtttatt tttcaattgc agaaaatttc  33060
aagtcatttt tcattcagta gtatagcccc accaccacat agcttataca gatcaccgta  33120
ccttaatcaa actcacagaa ccctagtatt caacctgcca cctccctccc aacacacaga  33180
```

-continued

```
gtacacagtc ctttctcccc ggctggcctt aaaaagcatc atatcatggg taacagacat  33240
attcttaggt gttatattcc acacggtttc ctgtcgagcc aaacgctcat cagtgatatt  33300
aataaactcc ccgggcagct cacttaagtt catgtcgctg tccagctgct gagccacagg  33360
ctgctgtcca acttgcggtt gcttaacggg cggcgaagga gaagtccacg cctacatggg  33420
ggtagagtca taatcgtgca tcaggatagg gcggtggtgc tgcagcagcg cgcgaataaa  33480
ctgctgccgc cgccgctccg tcctgcagga atacaacatg gcagtggtct cctcagcgat  33540
gattcgcacc gcccgcagca taaggcgcct tgtcctccgg gcacagcagc gcaccctgat  33600
ctcacttaaa tcagcacagt aactgcagca cagcaccaca atattgttca aaatcccaca  33660
gtgcaaggcg ctgtatccaa agctcatggc ggggaccaca gaacccacgt ggccatcata  33720
ccacaagcgc aggtagatta agtggcgacc cctcataaac acgctggaca taaacattac  33780
ctcttttggc atgttgtaat tcaccacctc ccggtaccat ataaacctct gattaaacat  33840
ggcgccatcc accaccatcc taaaccagct ggccaaaacc tgcccgccgg ctatacactg  33900
cagggaaccg ggactggaac aatgacagtg gagagcccag gactcgtaac catggatcat  33960
catgctcgtc atgatatcaa tgttggcaca acacaggcac acgtgcatac acttcctcag  34020
gattacaagc tcctcccgcg ttagaaccat atcccaggga acaacccatt cctgaatcag  34080
cgtaaatccc acactgcagg gaagacctcg cacgtaactc acgttgtgca ttgtcaaagt  34140
gttacattcg ggcagcagcg gatgatcctc cagtatggta gcgcgggttt ctgtctcaaa  34200
aggaggtaga cgatccctac tgtacggagt gcgccgagac aaccgagatc gtgttggtcg  34260
tagtgtcatg ccaaatggaa cgccggacgt agtcatattt cctgaagcaa aaccaggtgc  34320
gggcgtgaca aacagatctg cgtctccggt ctcgccgctt agatcgctct gtgtagtagt  34380
tgtagtatat ccactctctc aaagcatcca ggcgcccctt ggcttcgggt tctatgtaaa  34440
ctccttcatg cgccgctgcc ctgataacat ccaccaccgc agaataagcc acacccagcc  34500
aacctacaca ttcgttctgc gagtcacaca cgggaggagc gggaagagct ggaagaacca  34560
tgtttttttt tttattccaa aagattatcc aaaacctcaa aatgaagatc tattaagtga  34620
acgcgctccc ctccggtggc gtggtcaaac tctacagcca aagaacagat aatggcattt  34680
gtaagatgtt gcacaatggc ttccaaaagg caaacggccc tcacgtccaa gtggacgtaa  34740
aggctaaacc cttcagggtg aatctcctct ataaacattc cagcaccttc aaccatgccc  34800
aaataattct catctcgcca ccttctcaat atatctctaa gcaaatcccg aatattaagt  34860
ccggccattg taaaaatctg ctccagagcg ccctccacct tcagcctcaa gcagcgaatc  34920
atgattgcaa aaattcaggt tcctcacaga cctgtataag attcaaaagc ggaacattaa  34980
caaaaatacc gcgatcccgt aggtcccttc gcagggccag ctgaacataa tcgtgcaggt  35040
ctgcacggac cagcgcggcc acttccccgc caggaacctt gacaaaagaa cccacactga  35100
ttatgacacg catactcgga gctatgctaa ccagcgtagc cccgatgtaa gctttgttgc  35160
atgggcggcg atataaaatg caaggtgctg ctcaaaaaat caggcaaagc ctcgcgcaaa  35220
aaagaaagca catcgtagtc atgctcatgc agataaaggc aggtaagctc cggaaccacc  35280
acagaaaaag acaccatttt tctctcaaac atgtctgcgg gtttctgcat aaacacaaaa  35340
taaaataaca aaaaaacatt taaacattag aagcctgtct tacaacagga aaaacaaccc  35400
ttataagcat aagacggact acggccatgc cggcgtgacc gtaaaaaaac tggtcaccgt  35460
gattaaaaag caccaccgac agctcctcgg tcatgtccgg agtcataatg taagactcgg  35520
taaacacatc aggttgattc atcggtcagt gctaaaaagc gaccgaaata gcccgggga  35580
```

-continued

```
atacataccc gcaggcgtag agacaacatt acagccccca taggaggtat aacaaaatta  35640

ataggagaga aaaacacata aacacctgaa aaaccctcct gcctaggcaa aatagcaccc  35700

tcccgctcca gaacaacata cagcgcttca cagcggcagc ctaacagtca gccttaccag  35760

taaaaaagaa aacctattaa aaaaacacca ctcgacacgg caccagctca atcagtcaca  35820

gtgtaaaaaa gggccaagtg cagagcgagt atatatagga ctaaaaaatg acgtaacggt  35880

taaagtccac aaaaaacacc cagaaaaccg cacgcgaacc tacgcccaga aacgaaagcc  35940

aaaaaaccca caacttcctc aaatcgtcac ttccgttttc ccacgttacg tcacttccca  36000

ttttaagaaa actacaattc ccaacacata caagttactc cgccctaaaa cctacgtcac  36060

ccgccccgtt cccacgcccc gcgccacgtc acaaactcca ccccctcatt atcatattgg  36120

cttcaatcca aaataaggta tattattgat gatg                              36154


<210> SEQ ID NO 2
<211> LENGTH: 31
<212> TYPE: DNA
<213> ORGANISM: Artificial Sequence
<220> FEATURE:
<223> OTHER INFORMATION: Synthetic

<400> SEQUENCE: 2

cggaattcgg atccagcgac cgcgagctga t                                    31


<210> SEQ ID NO 3
<211> LENGTH: 33
<212> TYPE: DNA
<213> ORGANISM: Artificial Sequence
<220> FEATURE:
<223> OTHER INFORMATION: Synthetic

<400> SEQUENCE: 3

cggaattcag ccggcttcgt cgggccggat ggc                                  33


<210> SEQ ID NO 4
<211> LENGTH: 32
<212> TYPE: DNA
<213> ORGANISM: Artificial Sequence
<220> FEATURE:
<223> OTHER INFORMATION: Synthetic

<400> SEQUENCE: 4

cgcggatccg ccggctacgg cctgacgggc gg                                   32


<210> SEQ ID NO 5
<211> LENGTH: 28
<212> TYPE: DNA
<213> ORGANISM: Artificial Sequence
<220> FEATURE:
<223> OTHER INFORMATION: Synthetic

<400> SEQUENCE: 5

cggaattcac acacatacga cacgttag                                        28


<210> SEQ ID NO 6
<211> LENGTH: 32
<212> TYPE: DNA
<213> ORGANISM: Artificial Sequence
<220> FEATURE:
<223> OTHER INFORMATION: Synthetic

<400> SEQUENCE: 6

cggaattcgg ccggccatca tcaataatat ac                                   32
```

<210> SEQ ID NO 7
<211> LENGTH: 43
<212> TYPE: DNA
<213> ORGANISM: Artificial Sequence
<220> FEATURE:
<223> OTHER INFORMATION: Synthetic

<400> SEQUENCE: 7
cggtcgattc aattgctggc aagcttcggc cctagacaaa tat 43

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
ctatgctaac cagcgtagc 19

<210> SEQ ID NO 9
<211> LENGTH: 36154
<212> TYPE: DNA
<213> ORGANISM: Artificial Sequence
<220> FEATURE:
<223> OTHER INFORMATION: Synthetic

<400> SEQUENCE: 9
catcatcaat aatatacctt attttggatt gaagccaata tgataatgag gggtggagt 60 ttgtgacgtg gcgcggggcg tgggaacggg gcgggtgacg tagtagtgtg gcggaagtgt 120
gatgttgcaa gtgtggcgga acacatgtat aacttcgtat aatgtatgct atacgaagtt 180
atacatgtaa gcgacggatg tggcaaaagt gacgtttttg gtgtgcgccg gtgtacacag 240
gaagtgacaa ttttcgcgcg gttttaggcg gatgttgtag taaatttggg cgtaaccgag 300
taagatttgg ccattttcgc gggaaaactg aataagagga agtgaaatct gaataatttt 360
gtgttactca tagcgcgtaa tatttgtcta gggagatcta taacttcgta taatgtatgc 420
tatacgaagt tattaccgaa gaaatggctc gagatctgga aggtgctgag gtacgatgag 480
acccgcacca ggtgcagacc ctgcgagtgt ggcggtaaac atattaggaa ccagcctgtg 540
atgctggatg tgaccgagga gctgaggccc gatcacttgg tgctggcctg cacccgcgct 600
gagtttggct ctagcgatga agatacagat tgaggtactg aaatgtgtgg gcgtggctta 660
agggtgggaa agaatatata aggtgggggt cttatgtagt tttgtatctg ttttgcagca 720
gccgccgccg ccatgagcac caactcgttt gatggaagca ttgtgagctc atatttgaca 780
acgcgcatgc ccccatgggc cggggtgcgt cagaatgtga tgggctccag cattgatggt 840
cgccccgtcc tgcccgcaaa ctctactacc ttgacctacg agaccgtgtc tggaacgccg 900
ttggagactg cagcctccgc cgccgcttca gccgctgcag ccaccgcccg cgggattgtg 960
actgactttg ctttcctgag cccgcttgca agcagtgcag cttcccgttc atccgcccgc 1020
gatgacaagt tgacggctct tttggcacaa ttggattctt tgacccggga acttaatgtc 1080
gtttctcagc agctgttgga tctgcgccag caggtttctg ccctgaaggc ttcctcccct 1140
cccaatgcgg tttaaaacat aaataaaaaa ccagactctg tttggatttg gatcaagcaa 1200
gtgtcttgct gtctttattt aggggttttg cgcgcgcggt aggcccggga ccagcggtct 1260
cggtcgttga gggtcctgtg tattttttcc aggacgtggt aaaggtgact ctggatgttc 1320
agatacatgg gcataagccc gtctctgggg tggaggtagc accactgcag agcttcatgc 1380

-continued

```
tgcggggtgg tgttgtagat gatccagtcg tagcaggagc gctgggcgtg gtgcctaaaa   1440
atgtctttca gtagcaagct gattgccagg ggcaggccct tggtgtaagt gtttacaaag   1500
cggttaagct gggatgggtg catacgtggg gatatgagat gcatcttgga ctgtattttt   1560
aggttggcta tgttcccagc catatccctc cggggattca tgttgtgcag aaccaccagc   1620
acagtgtatc cggtgcactt gggaaatttg tcatgtagct tagaaggaaa tgcgtggaag   1680
aacttggaga cgcccttgtg acctccaaga ttttccatgc attcgtccat aatgatggca   1740
atgggcccac gggcggcggc ctgggcgaag atatttctgg gatcactaac gtcatagttg   1800
tgttccagga tgagatcgtc ataggccatt tttacaaagc gcgggcggag ggtgccagac   1860
tgcggtataa tggttccatc cggcccaggg gcgtagttac cctcacagat ttgcatttcc   1920
cacgctttga gttcagatgg ggggatcatg tctacctgcg gggcgatgaa gaaaacggtt   1980
tccggggtag gggagatcag ctgggaagaa agcaggttcc tgagcagctg cgacttaccg   2040
cagccggtgg gcccgtaaat cacacctatt accgggtgca actggtagtt aagagagctg   2100
cagctgccgt catccctgag caggggggcc acttcgttaa gcatgtccct gactcgcatg   2160
ttttccctga ccaaatccgc cagaaggcgc tcgccgccca gcgatagcag ttcttgcaag   2220
gaagcaaagt ttttcaacgg tttgagaccg tccgccgtag gcatgctttt gagcgtttga   2280
ccaagcagtt ccaggcggtc ccacagctcg gtcacctgct ctacggcatc tcgatccagc   2340
atatctcctc gtttcgcggg ttggggcggc tttcgctgta cggcagtagt cggtgctcgt   2400
ccagacgggc cagggtcatg tctttccacg ggcgcagggt cctcgtcagc gtagtctggg   2460
tcacggtgaa ggggtgcgct ccgggctgcg cgctggccag ggtgcgcttg aggctggtcc   2520
tgctggtgct gaagcgctgc cggtcttcgc cctgcgcgtc ggccaggtag catttgacca   2580
tggtgtcata gtccagcccc tccgcggcgt ggcccttggc gcgcagcttg cccttggagg   2640
aggcgccgca cgaggggcag tgcagacttt tgagggcgta gagcttgggc gcgagaaata   2700
ccgattccgg ggagtaggca tccgcgccgc aggccccgca gacggtctcg cattccacga   2760
gccaggtgag ctctggccgt tcggggtcaa aaaccaggtt tcccccatgc tttttgatgc   2820
gtttcttacc tctggtttcc atgagccggt gtccacgctc ggtgacgaaa aggctgtccg   2880
tgtccccgta tacagacttg agaggcctgt cctcgagcgg tgttccgcgg tcctcctcgt   2940
atagaaactc ggaccactct gagacaaagg ctcgcgtcca ggccagcacg aaggaggcta   3000
agtgggaggg gtagcggtcg ttgtccacta gggggtccac tcgctccagg gtgtgaagac   3060
acatgtcgcc ctcttcggca tcaaggaagg tgattggttt gtaggtgtag gccacgtgac   3120
cgggtgttcc tgaagggggg ctataaaagg gggtgggggc gcgttcgtcc tcactctctt   3180
ccgcatcgct gtctgcgagg gccagctgtt ggggtgagta ctccctctga aaagcgggca   3240
tgacttctgc gctaagattg tcagtttcca aaaacgagga ggatttgata ttcacctggc   3300
ccgcggtgat gcctttgagg gtggccgcat ccatctggtc agaaaagaca atctttttgt   3360
tgtcaagctt ggtggcaaac gacccgtaga gggcgttgga cagcaacttg gcgatggagc   3420
gcagggtttg gtttttgtcg cgatcggcgc gctccttggc cgcgatgttt agctgcacgt   3480
attcgcgcgc aacgcaccgc cattcgggaa agacggtggt gcgctcgtcg ggcaccaggt   3540
gcacgcgcca accgcggttg tgcagggtga caaggtcaac gctggtggct acctctccgc   3600
gtaggcgctc gttggtccag cagaggcggc cgcccttgcg cgagcagaat ggcggtaggg   3660
ggtctagctg cgtctcgtcc ggggggtctg cgtccacggt aaagaccccg ggcagcaggc   3720
gcgcgtcgaa gtagtctatc ttgcatcctt gcaagtctag cgcctgctgc catgcgcggg   3780
```

-continued

```
cggcaagcgc gcgctcgtat gggttgagtg ggggacccca tggcatgggg tgggtgagcg   3840
cggaggcgta catgccgcaa atgtcgtaaa cgtagagggg ctctctgagt attccaagat   3900
atgtagggta gcatcttcca ccgcggatgc tggcgcgcac gtaatcgtat agttcgtgcg   3960
agggagcgag gaggtcggga ccgaggttgc tacgggcggg ctgctctgct cggaagacta   4020
tctgcctgaa gatggcatgt gagttggatg atatggttgg acgctggaag acgttgaagc   4080
tggcgtctgt gagacctacc gcgtcacgca cgaaggaggc gtaggagtcg cgcagcttgt   4140
tgaccagctc ggcggtgacc tgcacgtcta gggcgcagta gtccagggtt tccttgatga   4200
tgtcatactt atcctgtccc ttttttttcc acagctcgcg gttgaggaca aactcttcgc   4260
ggtctttcca gtactcttgg atcggaaacc cgtcggcctc cgaacggtaa gagcctagca   4320
tgtagaactg gttgacggcc tggtaggcgc agcatccctt ttctacgggt agcgcgtatg   4380
cctgcgcggc cttccggagc gaggtgtggg tgagcgcaaa ggtgtccctg accatgactt   4440
tgaggtactg gtatttgaag tcagtgtcgt cgcatccgcc ctgctcccag agcaaaaagt   4500
ccgtgcgctt tttggaacgc ggatttggca gggcgaaggt gacatcgttg aagagtatct   4560
ttcccgcgcg aggcataaag ttgcgtgtga tgcggaaggg tcccggcacc tcggaacggt   4620
tgttaattac ctgggcggcg agcacgatct cgtcaaagcc gttgatgttg tggcccacaa   4680
tgtaaagttc caagaagcgc gggatgccct tgatggaagg caattttttta agttcctcgt   4740
aggtgagctc ttcaggggag ctgagcccgt gctctgaaag ggcccagtct gcaagatgag   4800
ggttggaagc gacgaatgag ctccacaggt cacgggccat tagcatttgc aggtggtcgc   4860
gaaaggtcct aaactggcga cctatggcca tttttctgg ggtgatgcag tagaaggtaa   4920
gcgggtcttg ttcccagcgg tcccatccaa ggttcgcggc taggtctcgc gcggcagtca   4980
ctagaggctc atctccgccg aacttcatga ccagcatgaa gggcacgagc tgcttcccaa   5040
aggcccccat ccaagtatag gtctctacat cgtaggtgac aaagagacgc tcggtgcgag   5100
gatgcgagcc gatcgggaag aactggatct cccgccacca attggaggag tggctattga   5160
tgtggtgaaa gtagaagtcc ctgcgacggg ccgaacactc gtgctggctt ttgtaaaaac   5220
gtgcgcagta ctggcagcgg tgcacgggct gtacatcctg cacgaggttg acctgacgac   5280
cgcgcacaag gaagcagagt gggaatttga gcccctcgcc tggcgggttt ggctggtggt   5340
cttctacttc ggctgcttgt ccttgaccgt ctggctgctc gaggggagtt acggtggatc   5400
ggaccaccac gccgcgcgag cccaaagtcc agatgtccgc gcgcggcggt cggagcttga   5460
tgacaacatc gcgcagatgg gagctgtcca tggtctggag ctcccgcggc gtcaggtcag   5520
gcgggagctc ctgcaggttt acctcgcata gacgggtcag ggcgcgggct agatccaggt   5580
gatacctaat ttccaggggc tggttggtgg cggcgtcgat ggcttgcaag aggccgcatc   5640
cccgcggcgc gactacggta ccgcgcggcg ggcggtgggc cgcgggggtg tccttggatg   5700
atgcatctaa aagcggtgac gcgggcgagc ccccggaggt aggggggggct ccggacccgc   5760
cgggagaggg ggcaggggca cgtcggcgcc gcgcgcgggc aggagctggt gctgcgcgcg   5820
taggttgctg gcgaacgcga cgacgcggcg gttgatctcc tgaatctggc gcctctgcgt   5880
gaagacgacg ggcccggtga gcttgagcct gaaagagagt tcgacagaat caatttcggt   5940
gtcgttgacg gcggcctggc gcaaaatctc ctgcacgtct cctgagttgt cttgataggc   6000
gatctcggcc atgaactgct cgatctcttc ctcctggaga tctccgcgtc cggctcgctc   6060
cacggtggcg gcgaggtcgt tggaaatgcg ggccatgagc tgcgagaagg cgttgaggcc   6120
tccctcgttc cagacgcggc tgtagaccac gccccccttcg gcatcgcggg cgcgcatgac   6180
```

-continued

```
cacctgcgcg agattgagct ccacgtgccg ggcgaagacg gcgtagtttc gcaggcgctg   6240
aaagaggtag ttgagggtgg tggcggtgtg ttctgccacg aagaagtaca taacccagcg   6300
tcgcaacgtg gattcgttga tatcccccaa ggcctcaagg cgctccatgg cctcgtagaa   6360
gtccacggcg aagttgaaaa actgggagtt gcgcgccgac acggttaact cctcctccag   6420
aagacggatg agctcggcga cagtgtcgcg cacctcgcgc tcaaaggcta caggggcctc   6480
ttcttcttct tcaatctcct cttccataag ggcctcccct tcttcttctt ctggcggcgg   6540
tgggggaggg gggacacggc ggcgacgacg gcgcaccggg aggcggtcga caaagcgctc   6600
gatcatctcc ccgcggcgac ggcgcatggt ctcggtgacg gcgcggccgt tctcgcgggg   6660
gcgcagttgg aagacgccgc ccgtcatgtc ccggttatgg gttggcgggg ggctgccatg   6720
cggcagggat acggcgctaa cgatgcatct caacaattgt tgtgtaggta ctccgccgcc   6780
gagggacctg agcgagtccg catcgaccgg atcggaaaac ctctcgagaa aggcgtctaa   6840
ccagtcacag tcgcaaggta ggctgagcac cgtggcgggc ggcagcgggc ggcggtcggg   6900
gttgtttctg gcggaggtgc tgctgatgat gtaattaaag taggcggtct tgagacggcg   6960
gatggtcgac agaagcacca tgtccttggg tccggcctgc tgaatgcgca ggcggtcggc   7020
catgccccag gcttcgtttt gacatcggcg caggtctttg tagtagtctt gcatgagcct   7080
ttctaccggc acttcttctt ctccttcctc ttgtcctgca tctcttgcat ctatcgctgc   7140
ggcggcggcg gagtttggcc gtaggtggcg ccctcttcct cccatgcgtg tgaccccgaa   7200
gcccctcatc ggctgaagca gggctaggtc ggcgacaacg cgctcggcta atatggcctg   7260
ctgcacctgc gtgagggtag actggaagtc atccatgtcc acaaagcggt ggtatgcgcc   7320
cgtgttgatg gtgtaagtgc agttggccat aacggaccag ttaacggtct ggtgacccgg   7380
ctgcgagagc tcggtgtacc tgagacgcga gtaagccctc gagtcaaata cgtagtcgtt   7440
gcaagtccgc accaggtact ggtatcccac caaaaagtgc ggcggcggct ggcggtagag   7500
gggccagcgt agggtggccg gggctccggg ggcgagatct tccaacataa ggcgatgata   7560
tccgtagatg tacctggaca tccaggtgat gccggcggcg gtggtggagg cgcgcggaaa   7620
gtcgcggacg cggttccaga tgttgcgcag cggcaaaaag tgctccatgg tcgggacgct   7680
ctggccggtc aggcgcgcgc aatcgttgac gctctaccgt gcaaaaggag agcctgtaag   7740
cgggcactct tccgtggtct ggtggataaa ttcgcaaggg tatcatggcg gacgaccggg   7800
gttcgagccc cgtatccggc cgtccgccgt gatccatgcg gttaccgccc gcgtgtcgaa   7860
cccaggtgtg cgacgtcaga caacggggga gtgctccttt tggcttcctt ccaggcgcgg   7920
cggctgctgc gctagctttt ttggccactg gccgcgcgca gcgtaagcgg ttaggctgga   7980
aagcgaaagc attaagtggc tcgctccctg tagccggagg gttatttttcc aagggttgag   8040
tcgcgggacc cccggttcga gtctcggacc ggccggactg cggcgaacgg gggtttgcct   8100
ccccgtcatg caagaccccg cttgcaaatt cctccggaaa cagggacgag ccccttttttt   8160
gcttttccca gatgcatccg gtgctgcggc agatgcgccc ccctcctcag cagcggcaag   8220
agcaagagca gcggcagaca tgcagggcac cctcccctcc tcctaccgcg tcaggagggg   8280
cgacatccgc ggttgacgcg gcagcagatg gtgattacga acccccgcgg cgccgggccc   8340
ggcactacct ggacttggag gagggcgagg gcctggcgcg gctaggagcg ccctctcctg   8400
agcggtaccc aagggtgcag ctgaagcgtg atacgcgtga ggcgtacgtg ccgcggcaga   8460
acctgtttcg cgaccgcgag ggagaggagc ccgaggagat gcgggatcga aagttccacg   8520
cagggcgcga gctgcggcat ggcctgaatc gcgagcggtt gctgcgcgag gaggactttg   8580
```

-continued agcccgacgc gcgaaccggg attagtcccg cgcgcgcaca cgtggcggcc gccgacctgg 8640
taaccgcata cgagcagacg gtgaaccagg agattaactt tcaaaaaagc tttaacaacc 8700
acgtgcgtac gcttgtggcg cgcgaggagg tggctatagg actgatgcat ctgtgggact 8760
ttgtaagcgc gctggagcaa aacccaaata gcaagccgct catggcgcag ctgttcctta 8820
tagtgcagca cagcagggac aacgaggcat tcagggatgc gctgctaaac atagtagagc 8880
ccgagggccg ctggctgctc gatttgataa acatcctgca gagcatagtg gtgcaggagc 8940
gcagcttgag cctggctgac aaggtggccg ccatcaacta ttccatgctt agcctgggca 9000
agttttacgc ccgcaagata taccataccc cttacgttcc catagacaag gaggtaaaga 9060
tcgaggggtt ctacatgcgc atggcgctga aggtgcttac cttgagcgac gacctgggcg 9120
tttatcgcaa cgagcgcatc cacaaggccg tgagcgtgag ccggcggcgc gagctcagcg 9180
accgcgagct gatgcacagc ctgcaaaggg ccctggctgg cacgggcagc ggcgatagag 9240
aggccgagtc ctactttgac gcgggcgctg acctgcgctg ggccccaagc cgacgcgccc 9300
tggaggcagc tggggccgga cctgggctgg cggtggcacc cgcgcgcgct ggcaacgtcg 9360
gcggcgtgga ggaatatgac gaggacgatg agtacgagcc agaggacggc gagtactaag 9420
cggtgatgtt tctgatcaga tgatgcaaga cgcaacggac ccggcggtgc gggcggcgct 9480
gcagagccag ccgtccggcc ttaactccac ggacgactgg cgccaggtca tggaccgcat 9540
catgtcgctg actgcgcgca atcctgacgc gttccggcag cagccgcagg ccaaccggct 9600
ctccgcaatt ctggaagcgg tggtcccggc gcgcgcaaac cccacgcacg agaaggtgct 9660
ggcgatcgta aacgcgctgg ccgaaaacag ggccatccgg cccgacgaag ccggcctggt 9720
ctacgacgcg ctgcttcagc gcgtggctcg ttacaacagc ggcaacgtgc agaccaacct 9780
ggaccggctg gtgggggatg tgcgcgaggc cgtggcgcag cgtgagcgcg cgcagcagca 9840
gggcaacctg ggctccatgg ttgcactaaa cgccttcctg agtacacagc ccgccaacgt 9900
gccgcgggga caggaggact acaccaactt tgtgagcgca ctgcggctaa tggtgactga 9960
gacaccgcaa agtgaggtgt accagtctgg gccagactat tttttccaga ccagtagaca 10020
aggcctgcag accgtaaacc tgagccaggc tttcaaaaac ttgcaggggc tgtggggggt 10080
gcgggctccc acaggcgacc gcgcgaccgt gtctagcttg ctgacgccca actcgcgcct 10140
gttgctgctg ctaatagcgc ccttcacgga cagtggcagc gtgtcccggg acacatacct 10200
aggtcacttg ctgacactgt accgcgaggc cataggtcag gcgcatgtgg acgagcatac 10260
tttccaggag attacaagtg tcagccgcgc gctggggcag gaggacacgg gcagcctgga 10320
ggcaacccta aactacctgc tgaccaaccg gcggcagaag atcccctcgt tgcacagttt 10380
aaacagcgag gaggagcgca ttttgcgcta cgtgcagcag agcgtgagcc ttaacctgat 10440
gcgcgacggg gtaacgccca gcgtggcgct ggacatgacc gcgcgcaaca tggaaccggg 10500
catgtatgcc tcaaaccggc cgtttatcaa ccgcctaatg gactacttgc atcgcgcggc 10560
cgccgtgaac cccgagtatt tcaccaatgc catcttgaac ccgcactggc taccgccccc 10620
tggtttctac accgggggat tcgaggtgcc cgagggtaac gatggattcc tctgggacga 10680
catagacgac agcgtgtttt ccccgcaacc gcagaccctg ctagagttgc aacagcgcga 10740
gcaggcagag gcggcgctgc gaaaggaaag cttccgcagg ccaagcagct tgtccgatct 10800
aggcgctgcg gccccgcggt cagatgctag tagcccattt ccaagcttga tagggtctct 10860
taccagcact cgcaccaccc gcccgcgcct gctgggcgag gaggagtacc taaacaactc 10920
gctgctgcag ccgcagcgcg aaaaaaacct gcctccggca tttcccaaca acgggataga 10980

-continued

```
gagcctagtg gacaagatga gtagatggaa gacgtacgcg caggagcaca gggacgtgcc  11040
aggcccgcgc ccgcccaccc gtcgtcaaag gcacgaccgt cagcggggtc tggtgtggga  11100
ggacgatgac tcggcagacg acagcagcgt cctggatttg ggagggagtg gcaacccgtt  11160
tgcgcacctt cgccccaggc tggggagaat gttttaaaaa aaaaaaagca tgatgcaaaa  11220
taaaaaactc accaaggcca tggcaccgag cgttggtttt cttgtattcc ccttagtatg  11280
cggcgcgcgg cgatgtatga ggaaggtcct cctccctcct acgagagtgt ggtgagcgcg  11340
gcgccagtgg cggcggcgct gggttctccc ttcgatgctc ccctggaccc gccgtttgtg  11400
cctccgcggt acctgcggcc taccgggggg agaaacagca tccgttactc tgagttggca  11460
cccctattcg acaccacccg tgtgtacctg gtggacaaca agtcaacgga tgtggcatcc  11520
ctgaactacc agaacgacca cagcaacttt ctgaccacgg tcattcaaaa caatgactac  11580
agcccggggg aggcaagcac acagaccatc aatcttgacg accggtcgca ctggggcggc  11640
gacctgaaaa ccatcctgca taccaacatg ccaaatgtga acgagttcat gtttaccaat  11700
aagtttaagg cgcgggtgat ggtgtcgcgc ttgcctacta aggacaatca ggtggagctg  11760
aaatacgagt gggtggagtt cacgctgccc gagggcaact actccgagac catgaccata  11820
gaccttatga acaacgcgat cgtggagcac tacttgaaag tgggcagaca gaacggggtt  11880
ctggaaagcg acatcggggt aaagtttgac acccgcaact tcagactggg gtttgacccc  11940
gtcactggtc ttgtcatgcc tggggtatat acaaacgaag ccttccatcc agacatcatt  12000
ttgctgccag gatgcggggt ggacttcacc cacagccgcc tgagcaactt gttgggcatc  12060
cgcaagcggc aacccttcca ggagggcttt aggatcacct acgatgatct ggagggtggt  12120
aacattcccg cactgttgga tgtggacgcc taccaggcga gcttgaaaga tgacaccgaa  12180
cagggcgggg gtggcgcagg cggcagcaac agcagtggca gcggcgcgga agagaactcc  12240
aacgcggcag ccgcggcaat gcagccggtg gaggacatga acgatcatgc cattcgcggc  12300
gacacctttg ccacacgggc tgaggagaag cgcgctgagg ccgaagcagc ggccgaagct  12360
gccgcccccg ctgcgcaacc cgaggtcgag aagcctcaga agaaaccggt gatcaaaccc  12420
ctgacagagg acagcaagaa acgcagttac aacctaataa gcaatgacag caccttcacc  12480
cagtaccgca gctggtacct tgcatacaac tacggcgacc ctcagaccgg aatccgctca  12540
tggaccctgc tttgcactcc tgacgtaacc tgcggctcgg agcaggtcta ctggtcgttg  12600
ccagacatga tgcaagaccc cgtgaccttc cgctccacgc gccagatcag caactttccg  12660
gtggtgggcg ccgagctgtt gcccgtgcac tccaagagct tctacaacga ccaggccgtc  12720
tactcccaac tcatccgcca gtttacctct ctgacccacg tgttcaatcg ctttcccgag  12780
aaccagattt tggcgcgccc gccagccccc accatcacca ccgtcagtga aaacgttcct  12840
gctctcacag atcacgggac gctaccgctg cgcaacagca tcggaggagt ccagcgagtg  12900
accattactg acgccagacg ccgcacctgc ccctacgttt acaaggccct gggcatagtc  12960
tcgccgcgcg tcctatcgag ccgcactttt tgagcaagca tgtccatcct tatatcgccc  13020
agcaataaca caggctgggg cctgcgcttc ccaagcaaga tgtttggcgg ggccaagaag  13080
cgctccgacc aacacccagt gcgcgtgcgc gggcactacc gcgcgccctg gggcgcgcac  13140
aaacgcggcc gcactgggcg caccaccgtc gatgacgcca tcgacgcggt ggtggaggag  13200
gcgcgcaact acacgcccac gccgccacca gtgtccacag tggacgcggc cattcagacc  13260
gtggtgcgcg gagcccggcg ctatgctaaa atgaagagac ggcggaggcg cgtagcacgt  13320
cgccaccgcc gccgacccgg cactgccgcc caacgcgcgg cggcggccct gcttaaccgc  13380
```

-continued

```
gcacgtcgca ccggccgacg ggcggccatg cgggccgctc gaaggctggc cgcgggtatt  13440
gtcactgtgc cccccaggtc caggcgacga gcggccgccg cagcagccgc ggccattagt  13500
gctatgactc agggtcgcag gggcaacgtg tattgggtgc gcgactcggt tagcggcctg  13560
cgcgtgcccg tgcgcacccg ccccccgcgc aactagattg caagaaaaaa ctacttagac  13620
tcgtactgtt gtatgtatcc agcggcggcg gcgcgcaacg aagctatgtc caagcgcaaa  13680
atcaaagaag agatgctcca ggtcatcgcg ccggagatct atggcccccc gaagaaggaa  13740
gagcaggatt acaagccccg aaagctaaag cgggtcaaaa agaaaaagaa agatgatgat  13800
gatgaacttg acgacgaggt ggaactgctg cacgctaccg cgcccaggcg acgggtacag  13860
tggaaaggtc gacgcgtaaa acgtgttttg cgacccggca ccaccgtagt ctttacgccc  13920
ggtgagcgct ccacccgcac ctacaagcgc gtgtatgatg aggtgtacgg cgacgaggac  13980
ctgcttgagc aggccaacga gcgcctcggg gagtttgcct acggaaagcg gcataaggac  14040
atgctggcgt tgccgctgga cgagggcaac ccaacaccta gcctaaagcc cgtaacactg  14100
cagcaggtgc tgcccgcgct tgcaccgtcc gaagaaaagc gcggcctaaa gcgcgagtct  14160
ggtgacttgg cacccaccgt gcagctgatg gtacccaagc gccagcgact ggaagatgtc  14220
ttggaaaaaa tgaccgtgga acctgggctg gagcccgagg tccgcgtgcg gccaatcaag  14280
caggtggcgc cgggactggg cgtgcagacc gtggacgttc agatacccac taccagtagc  14340
accagtattg ccaccgccac agagggcatg gagacacaaa cgtccccggt tgcctcagcg  14400
gtggcggatg ccgcggtgca ggcggtcgct gcggccgcgt ccaagacctc tacggaggtg  14460
caaacggacc cgtggatgtt tcgcgtttca gccccccggc gcccgcgcgg ttcgaggaag  14520
tacggcgccg ccagcgcgct actgcccgaa tatgccctac atccttccat tgcgcctacc  14580
cccggctatc gtggctacac ctaccgcccc agaagacgag caactacccg acgccgaacc  14640
accactggaa cccgccgccg ccgtcgccgt cgccagcccg tgctggcccc gatttccgtg  14700
cgcagggtgg ctcgcgaagg aggcaggacc ctggtgctgc caacagcgcg ctaccacccc  14760
agcatcgttt aaaagccggt ctttgtggtt cttgcagata tggccctcac ctgccgcctc  14820
cgtttcccgg tgccgggatt ccgaggaaga atgcaccgta ggaggggcat ggccggctac  14880
ggcctgacgg gcggcatgcg tcgtgcgcac caccggcggc ggcgcgcgtc gcaccgtcgc  14940
atgcgcggcg gtatcctgcc cctccttatt ccactgatcg ccgcggcgat tggcgccgtg  15000
cccggaattg catccgtggc cttgcaggcg cagagacact gattaaaaac aagttgcatg  15060
tggaaaaatc aaaataaaaa gtctggactc tcacgctcgc ttggtcctgt aactattttg  15120
tagaatggaa gacatcaact ttgcgtctct ggccccgcga cacggctcgc gcccgttcat  15180
gggaaactgg caagatatcg gcaccagcaa tatgagcggt ggcgccttca gctggggctc  15240
gctgtggagc ggcattaaaa atttcggttc caccgttaag aactatggca gcaaggcctg  15300
gaacagcagc acaggccaga tgctgaggga taagttgaaa gagcaaaatt tccaacaaaa  15360
ggtggtagat ggcctggcct ctggcattag cggggtggtg gacctggcca accaggcagt  15420
gcaaaataag attaacagta agcttgatcc ccgccctccc gtagaggagc ctccaccggc  15480
cgtggagaca gtgtctccag aggggcgtgg cgaaaagcgt ccgcgccccg acagggaaga  15540
aactctggtg acgcaaatag acgagcctcc ctcgtacgag gaggcactaa agcaaggcct  15600
gcccaccacc cgtcccatcg cgcccatggc taccggagtg ctgggccagc acacacccgt  15660
aacgctggac ctgcctcccc ccgccgacac ccagcagaaa cctgtgctgc caggcccgac  15720
cgccgttgtt gtaacccgtc ctagccgcgc gtccctgcgc cgcgccgcca gcggtccgcg  15780
```

-continued atcgttgcgg cccgtagcca gtggcaactg gcaaagcaca ctgaacagca tcgtgggtct 15840
gggggtgcaa tccctgaagc gccgacgatg cttctgaata gctaacgtgt cgtatgtgtg 15900
tcatgtatgc gtccatgtcg ccgccagagg agctgctgag ccgccgcgcg cccgctttcc 15960
aagatggcta ccccttcgat gatgccgcag tggtcttaca tgcacatctc gggccaggac 16020
gcctcggagt acctgagccc cgggctggtg cagtttgccc gcgccaccga gacgtacttc 16080
agcctgaata acaagtttag aaaccccacg gtggcgccta cgcacgacgt gaccacagac 16140
cggtcccagc gtttgacgct gcggttcatc cctgtggacc gtgaggatac tgcgtactcg 16200
tacaaggcgc ggttcaccct agctgtgggt gataaccgtg tgctggacat ggcttccacg 16260
tactttgaca tccgcggcgt gctggacagg ggccctactt ttaagcccta ctctggcact 16320
gcctacaacg ccctggctcc caagggtgcc ccaaatcctt gcgaatggga tgaagctgct 16380
actgctcttg aaataaacct agaagaagag gacgatgaca acgaagacga agtagacgag 16440
caagctgagc agcaaaaaac tcacgtattt gggcaggcgc cttattctgg tataaatatt 16500
acaaaggagg gtattcaaat aggtgtcgaa ggtcaaacac ctaaatatgc cgataaaaca 16560
tttcaacctg aacctcaaat aggagaatct cagtggtacg aaactgaaat taatcatgca 16620
gctgggagag tccttaaaaa gactacccca atgaaaccat gttacggttc atatgcaaaa 16680
cccacaaatg aaaatggagg gcaaggcatt cttgtaaagc aacaaaatgg aaagctagaa 16740
agtcaagtgg aaatgcaatt tttctcaact actgaggcga ccgcaggcaa tggtgataac 16800
ttgactccta aagtggtatt gtacagtgaa gatgtagata tagaaacccc agacactcat 16860
atttcttaca tgcccactat taaggaaggt aactcacgag aactaatggg ccaacaatct 16920
atgcccaaca ggcctaatta cattgctttt agggacaatt ttattggtct aatgtattac 16980
aacagcacgg gtaatatggg tgttctggcg ggccaagcat cgcagttgaa tgctgttgta 17040
gatttgcaag acagaaacac agagctttca taccagcttt tgcttgattc cattggtgat 17100
agaaccaggt acttttctat gtggaatcag gctgttgaca gctatgatcc agatgttaga 17160
attattgaaa atcatggaac tgaagatgaa cttccaaatt actgctttcc actgggaggt 17220
gtgattaata cagagactct taccaaggta aaacctaaaa caggtcagga aaatggatgg 17280
gaaaaagatg ctacagaatt ttcagataaa aatgaaataa gagttggaaa taattttgcc 17340
atggaaatca atctaaatgc caacctgtgg agaaatttcc tgtactccaa catagcgctg 17400
tatttgcccg acaagctaaa gtacagtcct tccaacgtaa aaatttctga taacccaaac 17460
acctacgact acatgaacaa gcgagtggtg gctcccgggt tagtggactg ctacattaac 17520
cttggagcac gctggtccct tgactatatg gacaacgtca acccatttaa ccaccaccgc 17580
aatgctggcc tgcgctaccg ctcaatgttg ctgggcaatg gtcgctatgt gcccttccac 17640
atccaggtgc ctcagaagtt ctttgccatt aaaaacctcc ttctcctgcc gggctcatac 17700
acctacgagt ggaacttcag gaaggatgtt aacatggttc tgcagagctc cctaggaaat 17760
gacctaaggg ttgacggagc cagcattaag tttgatagca tttgccttta cgccaccttc 17820
ttccccatgg cccacaacac cgcctccacg cttgaggcca tgcttagaaa cgacaccaac 17880
gaccagtcct ttaacgacta tctctccgcc gccaacatgc tctaccctat acccgccaac 17940
gctaccaacg tgcccatatc catcccctcc cgcaactggg cggctttccg cggctgggcc 18000
ttcacgcgcc ttaagactaa ggaaacccca tcactgggct cgggctacga cccttattac 18060
acctactctg gctctatacc ctacctagat ggaacctttt acctcaacca cacctttaag 18120
aaggtggcca ttacctttga ctcttctgtc agctggcctg gcaatgaccg cctgcttacc 18180

-continued cccaacgagt ttgaaattaa gcgctcagtt gacggggagg gttacaacgt tgcccagtgt 18240
aacatgacca aagactggtt cctggtacaa atgctagcta actacaacat tggctaccag 18300
ggcttctata tcccagagag ctacaaggac cgcatgtact ccttctttag aaacttccag 18360
cccatgagcc gtcaggtggt ggatgatact aaatacaagg actaccaaca ggtgggcatc 18420
ctacaccaac acaacaactc tggatttgtt ggctaccttg cccccaccat gcgcgaagga 18480
caggcctacc ctgctaactt cccctatccg cttataggca agaccgcagt tgacagcatt 18540
acccagaaaa agtttctttg cgatcgcacc ctttggcgca tcccattctc cagtaacttt 18600
atgtccatgg gcgcactcac agacctgggc caaaaccttc tctacgccaa ctccgcccac 18660
gcgctagaca tgacttttga ggtggatccc atggacgagc ccacccttct ttatgttttg 18720
tttgaagtct ttgacgtggt ccgtgtgcac cggccgcacc gcggcgtcat cgaaaccgtg 18780
tacctgcgca cgcccttctc ggccggcaac gccacaacat aaagaagcaa gcaacatcaa 18840
caacagctgc cgccatgggc tccagtgagc aggaactgaa agccattgtc aaagatcttg 18900
gttgtgggcc atatttttg ggcacctatg acaagcgctt tccaggcttt gtttctccac 18960
acaagctcgc ctgcgccata gtcaatacgg ccggtcgcga gactgggggc gtacactgga 19020
tggcctttgc ctggaacccg cactcaaaaa catgctacct ctttgagccc tttggctttt 19080
ctgaccagcg actcaagcag gtttaccagt ttgagtacga gtcactcctg cgccgtagcg 19140
ccattgcttc ttcccccgac cgctgtataa cgctggaaaa gtccacccaa agcgtacagg 19200
ggcccaactc ggccgcctgt ggactattct gctgcatgtt tctccacgcc tttgccaact 19260
ggccccaaac tcccatggat cacaacccca ccatgaacct tattaccggg gtacccaact 19320
ccatgctcaa cagtccccag gtacagccca ccctgcgtcg caaccaggaa cagctctaca 19380
gcttcctgga gcgccactcg ccctacttcc gcagccacag tgcgcagatt aggagcgcca 19440
cttctttttg tcacttgaaa aacatgtaaa aataatgtac tagagacact ttcaataaag 19500
gcaaatgctt ttatttgtac actctcgggt gattatttac cccacccctt gccgtctgcg 19560
ccgtttaaaa atcaaagggg ttctgccgcg catcgctatg cgccactggc agggacacgt 19620
tgcgatactg gtgtttagtg ctccacttaa actcaggcac aaccatccgc ggcagctcgg 19680
tgaagttttc actccacagg ctgcgcacca tcaccaacgc gtttagcagg tcgggcgccg 19740
atatcttgaa gtcgcagttg gggcctccgc cctgcgcgcg cgagttgcga tacacagggt 19800
tgcagcactg gaacactatc agcgccgggt ggtgcacgct ggccagcacg ctcttgtcgg 19860
agatcagatc cgcgtccagg tcctccgcgt tgctcagggc gaacggagtc aactttggta 19920
gctgccttcc caaaaagggc gcgtgcccag gctttgagtt gcactcgcac cgtagtggca 19980
tcaaaaggtg accgtgcccg gtctgggcgt taggatacag cgcctgcata aaagccttga 20040
tctgcttaaa agccacctga gcctttgcgc cttcagagaa gaacatgccg caagacttgc 20100
cggaaaactg attggccgga caggccgcgt cgtgcacgca gcaccttgcg tcggtgttgg 20160
agatctgcac cacatttcgg ccccaccggt tcttcacgat cttggccttg ctagactgct 20220
ccttcagcgc gcgctgcccg ttttcgctcg tcacatccat ttcaatcacg tgctccttat 20280
ttatcataat gcttccgtgt agacacttaa gctcgccttc gatctcagcg cagcggtgca 20340
gccacaacgc gcagcccgtg ggctcgtgat gcttgtaggt cacctctgca aacgactgca 20400
ggtacgcctg caggaatcgc cccatcatcg tcacaaaggt cttgttgctg gtgaaggtca 20460
gctgcaaccc gcggtgctcc tcgttcagcc aggtcttgca tacggccgcc agagcttcca 20520
cttggtcagg cagtagtttg aagttcgcct ttagatcgtt atccacgtgg tacttgtcca 20580

-continued

```
tcagcgcgcg cgcagcctcc atgcccttct cccacgcaga cacgatcggc acactcagcg  20640
ggttcatcac cgtaatttca ctttccgctt cgctgggctc ttcctcttcc tcttgcgtcc  20700
gcataccacg cgccactggg tcgtcttcat tcagccgccg cactgtgcgc ttacctcctt  20760
tgccatgctt gattagcacc ggtgggttgc tgaaacccac catttgtagc gccacatctt  20820
ctctttcttc ctcgctgtcc acgattacct ctggtgatgg cgggcgctcg ggcttgggag  20880
aagggcgctt ctttttcttc ttgggcgcaa tggccaaatc cgccgccgag gtcgatggcc  20940
gcgggctggg tgtgcgcggc accagcgcgt cttgtgatga gtcttcctcg tcctcggact  21000
cgatacgccg cctcatccgc ttttttgggg gcgcccgggg aggcggcggc gacggggacg  21060
gggacgacac gtcctccatg gttgggggac gtcgcgccgc accgcgtccg cgctcggggg  21120
tggtttcgcg ctgctcctct tcccgactgg ccatttcctt ctcctatagg cagaaaaaga  21180
tcatggagtc agtcgagaag aaggacagcc taaccgcccc ctctgagttc gccaccaccg  21240
cctccaccga tgccgccaac gcgcctacca ccttccccgt cgaggcaccc ccgcttgagg  21300
aggaggaagt gattatcgag caggacccag gttttgtaag cgaagacgac gaggaccgct  21360
cagtaccaac agaggataaa aagcaagacc aggacaacgc agaggcaaac gaggaacaag  21420
tcgggcgggg ggacgaaagg catggcgact acctagatgt gggagacgac gtgctgttga  21480
agcatctgca gcgccagtgc gccattatct gcgacgcgtt gcaagagcgc agcgatgtgc  21540
ccctcgccat agcggatgtc agccttgcct acgaacgcca cctattctca ccgcgcgtac  21600
cccccaaacg ccaagaaaac ggcacatgcg agcccaaccc gcgcctcaac ttctaccccg  21660
tatttgccgt gccagaggtg cttgccacct atcacatctt tttccaaaac tgcaagatac  21720
ccctatcctg ccgtgccaac cgcagccgag cggacaagca gctggccttg cggcagggcg  21780
ctgtcatacc tgatatcgcc tcgctcaacg aagtgccaaa aatctttgag ggtcttggac  21840
gcgacgagaa gcgcgcggca aacgctctgc aacaggaaaa cagcgaaaat gaaagtcact  21900
ctggagtgtt ggtggaactc gagggtgaca acgcgcgcct agccgtacta aaacgcagca  21960
tcgaggtcac ccactttgcc tacccggcac ttaacctacc ccccaaggtc atgagcacag  22020
tcatgagtga gctgatcgtg cgccgtgcgc agcccctgga gagggatgca aatttgcaag  22080
aacaaacaga ggagggccta cccgcagttg gcgacgagca gctagcgcgc tggcttcaaa  22140
cgcgcgagcc tgccgacttg gaggagcgac gcaaactaat gatggccgca gtgctcgtta  22200
ccgtggagct tgagtgcatg cagcggttct ttgctgaccc ggagatgcag cgcaagctag  22260
aggaaacatt gcactacacc tttcgacagg gctacgtacg ccaggcctgc aagatctcca  22320
acgtggagct ctgcaacctg gtctcctacc ttggaatttt gcacgaaaac cgccttgggc  22380
aaaacgtgct tcattccacg ctcaagggcg aggcgcgccg cgactacgtc cgcgactgcg  22440
tttacttatt tctatgctac acctggcaga cggccatggg cgtttggcag cagtgcttgg  22500
aggagtgcaa cctcaaggag ctgcagaaac tgctaaagca aaacttgaag gacctatgga  22560
cggccttcaa cgagcgctcc gtggccgcgc acctggcgga catcattttc cccgaacgcc  22620
tgcttaaaac cctgcaacag ggtctgccag acttcaccag tcaaagcatg ttgcagaact  22680
ttaggaactt tatcctagag cgctcaggaa tcttgcccgc cacctgctgt gcacttccta  22740
gcgactttgt gcccattaag taccgcgaat gccctccgcc gctttggggc cactgctacc  22800
ttctgcagct agccaactac cttgcctacc actctgacat aatggaagac gtgagcggtg  22860
acggtctact ggagtgtcac tgtcgctgca acctatgcac cccgcaccgc tccctggttt  22920
gcaattcgca gctgcttaac gaaagtcaaa ttatcggtac ctttgagctg cagggtccct  22980
```

-continued

```
cgcctgacga aaagtccgcg gctccggggt tgaaactcac tccggggctg tggacgtcgg  23040
cttaccttcg caaatttgta cctgaggact accacgccca cgagattagg ttctacgaag  23100
accaatcccg cccgccaaat gcggagctta ccgcctgcgt cattacccag ggccacattc  23160
ttggccaatt gcaagccatc aacaaagccc gccaagagtt tctgctacga aagggacggg  23220
gggtttactt ggacccccag tccggcgagg agctcaaccc aatccccccg ccgccgcagc  23280
cctatcagca gcagccgcgg gcccttgctt cccaggatgg cacccaaaaa gaagctgcag  23340
ctgccgccgc cacccacgga cgaggaggaa tactgggaca gtcaggcaga ggaggttttg  23400
gacgaggagg aggaggacat gatggaagac tgggagagcc tagacgagga agcttccgag  23460
gtcgaagagg tgtcagacga aacaccgtca ccctcggtcg cattcccctc gccggcgccc  23520
cagaaatcgg caaccggttc cagcatggct acaacctccg ctcctcaggc gccgccggca  23580
ctgcccgttc gccgacccaa ccgtagatgg gacaccactg gaaccagggc cggtaagtcc  23640
aagcagccgc cgccgttagc ccaagagcaa caacagcgcc aaggctaccg ctcatggcgc  23700
gggcacaaga acgccatagt tgcttgcttg caagactgtg ggggcaacat ctccttcgcc  23760
cgccgctttc ttctctacca tcacggcgtg gccttccccc gtaacatcct gcattactac  23820
cgtcatctct acagcccata ctgcaccggc ggcagcggca gcggcagcaa cagcagcggc  23880
cacacagaag caaaggcgac cggatagcaa gactctgaca aagcccaaga aatccacagc  23940
ggcggcagca gcaggaggag gagcgctgcg tctggcgccc aacgaacccg tatcgacccg  24000
cgagcttaga aacaggattt ttcccactct gtatgctata tttcaacaga gcaggggcca  24060
agaacaagag ctgaaaataa aaaacaggtc tctgcgatcc ctcacccgca gctgcctgta  24120
tcacaaaagc gaagatcagc ttcggcgcac gctggaagac gcggaggctc tcttcagtaa  24180
atactgcgcg ctgactctta aggactagtt tcgcgccctt tctcaaattt aagcgcgaaa  24240
actacgtcat ctccagcggc cacacccggc gccagcacct gtcgtcagcg ccattatgag  24300
caaggaaatt cccacgccct acatgtggag ttaccagcca caaatgggac ttgcggctgg  24360
agctgcccaa gactactcaa cccgaataaa ctacatgagc gcgggacccc acatgatatc  24420
ccgggtcaac ggaatccgcg cccaccgaaa ccgaattctc ttggaacagg cggctattac  24480
caccacacct cgtaataacc ttaatccccg tagttggccc gctgccctgg tgtaccagga  24540
aagtcccgct cccaccactg tggtacttcc cagagacgcc caggccgaag ttcagatgac  24600
taactcaggg gcgcagcttg cgggcggctt tcgtcacagg gtgcggtcgc ccgggcaggg  24660
tataactcac ctgacaatca gagggcgagg tattcagctc aacgacgagt cggtgagctc  24720
ctcgcttggt ctccgtccgg acgggacatt tcagatcggc ggcgccggcc gtccttcatt  24780
cacgcctcgt caggcaatcc taactctgca gacctcgtcc tctgagccgc gctctggagg  24840
cattggaact ctgcaattta ttgaggagtt tgtgccatcg gtctacttta accccttctc  24900
gggacctccc ggccactatc cggatcaatt tattcctaac tttgacgcgg taaaggactc  24960
ggcggacggc tacgactgaa tgttaagtgg agaggcagag caactgcgcc tgaaacacct  25020
ggtccactgt cgccgccaca agtgctttgc ccgcgactcc ggtgagtttt gctactttga  25080
attgcccgag gatcatatcg agggcccggc gcacggcgtc cggcttaccg cccagggaga  25140
gcttgcccgt agcctgattc gggagtttac ccagcgcccc ctgctagttg agcgggacag  25200
gggaccctgt gttctcactg tgatttgcaa ctgtcctaac cttggattac atcaagatcc  25260
tctagttaat taacagcttg catgcctgca ggtcgacgga tcgggagatc tcggccgcat  25320
attaagtgca ttgttctcga taccgctaag tgcattgttc tcgttagctc gatggacaag  25380
```

```
tgcattgttc tcttgctgaa agctcgatgg acaagtgcat tgttctcttg ctgaaagctc  25440
gatggacaag tgcattgttc tcttgctgaa agctcagtac ccgggagtac cctcgaccgc  25500
cggagtataa atagaggcgc ttcgtctacg gagcgacaat tcaattcaaa caagcaaagt  25560
gaacacgtcg ctaagcgaaa gctaagcaaa taaacaagcg cagctgaaca agctaaacaa  25620
tctgcagtaa agtgcaagtt aaagtgaatc aattaaaagt aaccagcaac caagtaaatc  25680
aactgcaact actgaaatct gccaagaagt aattattgaa tacaagaaga gaactctgaa  25740
tactttcaac aagttaccga gaaagaagaa ctcacacaca gctagcgttt aaacttaagc  25800
ttcaccatgg tggggccctg catgctgctg ctgctgctgc tgctgggcct gaggctacag  25860
ctctccctgg gcatcatcct agttgaggag gagaacccgg acttctggaa ccgcgaggca  25920
gccgaggccc tgggtgccgc caagaagctg cagcctgcac agacagccgc caagaacctc  25980
atcatcttcc tgggcgatgg ggtgggggtg tctacggtga cagctgccag gatcctaaaa  26040
gggcagaaga aggacaaact ggggcctgag ataccccctgg ccatggaccg cttcccatat  26100
gtggctctgt ccaagacata caatgtagac aaacatgtgc cagacagtgg agccacagcc  26160
acggcctacc tgtgcggggt caagggcaac ttccagacca ttggcttgag tgcagccgcc  26220
cgctttaacc agtgcaacac gacacgcggc aacgaggtca tctccgtgat gaatcgggcc  26280
aagaaagcag ggaagtcagt gggagtggta accaccacac gagtgcagca cgcctcgcca  26340
gccggcacct acgcccacac ggtgaaccgc aactggtact cggacgccga cgtgcctgcc  26400
tcggcccgcc aggaggggtg ccaggacatc gctacgcagc tcatctccaa catggacatt  26460
gacgtgatcc taggtggggg ccgaaagtac atgtttcgca tgggaacccc agaccctgag  26520
tacccagatg actacagcca aggtgggacc aggctggacg ggaagaatct ggtgcaggaa  26580
tggctggcga agcaccaggg tgcccggtac gtgtggaacc gcactgagct catgcgggct  26640
tccctggacc cgtctgtggc ccatctcatg ggtctctttg agcctggaga catgaaatac  26700
gagatccacc gagactccac actggacccc tccctgatgg agatgacaga ggctgccctg  26760
cgcctgctga gcaggaaccc ccgcggcttc ttcctcttcg tggagggtgg tcgcatcgac  26820
catggtcatc atgaaagcag ggcttaccgg gcactgactg agacgatcat gttcgacgac  26880
gccattgaga gggcgggcca gctcaccagc gaggaggaca cgctgagcct cgtcactgcc  26940
gaccactccc acgtcttctc cttcggaggc tgccccctgc gagggggctc catcttcggg  27000
ctggcccctg gcaaggcccg ggacaggaag gcctacacgg tcctcctata cggaaacggt  27060
ccaggctatg tgctcaagga cggcgcccgg ccggatgtta ccgagagcga gagcgggagc  27120
cccgagtatc ggcagcagtc agcagtgccc ctggacgaag agacccacgc aggcgaggac  27180
gtggcggtgt tcgcgcgcgg cccgcaggcg cacctggttc acggcgtgca ggagcagacc  27240
ttcatagcgc acgtcatggc cttcgccgcc tgcctggagc cctacaccgc ctgcgacctg  27300
gcgcccccccg ccggcaccac cgacgccgcg cacccggggc ggtccgtggt ccccgcgttg  27360
cttcctctgc tggccgggac cctgctgctg ctggagacgg ccactgctcc ctgagtgtcc  27420
cgtccctggg gctcctgctt ccccatcccg gagttctcct gctccccgcc tcctgtcgtc  27480
ctgcctggcc tccagcccga gtcgtcatcc ccggagtccc tatacagagg tcctgccatg  27540
gaaccttccc ctccccgtgc gctctgggga ctgagcccat gacaccaaac ctgccccttg  27600
gctgctctcg gactccctac cccaacccca gggacagatc tggccagatt tgtaaaacaa  27660
atagatttta ggcccaaaga ttatttaaag cattgcctgg aacgcagtga gtttttgtta  27720
gaaaagagaa taattcaaag tggcattgct ttgcttctta tgttaatttg gtacagacct  27780
```

-continued

```
gtggctgagt ttgctcaaag tattcagagc agaattgtgg agtggaaaga gagattggac  27840
aaagagttta gtttgtcagt gtatcaaaaa atgaagttta atgtggctat gggaattgga  27900
gttttagatt ggctaagaaa cagtgatgat gatgatgaag acagccagga aaatgctgat  27960
aaaaatgaag atggtgggga gaagaacatg gaagactcag ggcatgaaac aggcattgat  28020
tcacagtccc aaggctcatt tcaggcccct cagtcctcac agtctgttca tgatcataat  28080
cagccatacc acatttgtag aggttttact tgctttaaaa aacctcccac acctccccct  28140
gaacctgaaa cataaaatga atgcaattgt tgttgttaac ttgtttattg cagcttataa  28200
tggttacaaa taaagcaata gcatcacaaa tttcacaaat aaagcatttt tttcactgca  28260
ttctagttgt ggtttgtcca aactcatcaa tgtatcttat catgtctgga tccccaggaa  28320
gctcctctgt gtcctcataa accctaacct cctctacttg agaggacatt ccaatcatag  28380
gctgcccatc caccctctgt gtcctcctgt taattaggtc acttaacaaa aaggaaattg  28440
ggtaggggtt tttcacagac cgctttctaa gggtaatttt aaaatatctg ggaagtccct  28500
tccactgctg tgttccagaa gtgttggtaa acagcccaca aatgtcaaca gcagaaacat  28560
acaagctgtc agctttgcac aagggcccaa caccctgctc atcaagaagc actgtggttg  28620
ctgtgttagt aatgtgcaaa acaggaggca catttcccc acctgtgtag gttccaaaat  28680
atctagtgtt ttcattttta cttggatcag gaacccagca ctccactgga taagcattat  28740
ccttatccaa aacagccttg tggtcagtgt tcatctgctg actgtcaact gtagcatttt  28800
ttggggttac agtttgagca ggatatttgg tcctgtagtt tgctaacaca ccctgcagct  28860
ccaaaggttc cccaccaaca gcaaaaaaat gaaaatttga cccttgaatg ggttttccag  28920
caccattttc atgagttttt tgtgtccctg aatgcaagtt taacatagca gttaccccaa  28980
taacctcagt tttaacagta acagcttccc acatcaaaat atttccacag gttaagtcct  29040
catttaaatt aggcaaagga attccacttc ccactgcctt gcttccgtct cccattcaaa  29100
cttttatcaa ctgacattat tctaagtaaa atcctcttca ttatgttgtc agcaatccat  29160
tgcttgaagg cctggctccc cagaacccct cgactggtat gtcttctcct agaatactcc  29220
agaagaaaag gagtgtatga agatagtgac tgcacattaa aatgactgaa accatagtaa  29280
attaggatga gattctgggc agataaacag acagctggct aggatcattt ttttatgcct  29340
tggacttctt tggcaatctg ttgaagcctg acattcctca gaataatgtt ttaaagccca  29400
acaataagac cctgtagcac atataataag tactgcagtt ttgaagtagt gataagcata  29460
aatgatattt tgatatattt attataactg taatgagatg tgtacatatc tgtgacttca  29520
taggtactga ttgtactact gtgatttttt tgcctacttt caaaatgaaa aggaatgctt  29580
aatttcagtt agaggttagt aaagacaaat aggtaatttt cttctccagt gaagagcatg  29640
gcgccccttg ctattcatgg acgcttgctt aaagacttgt acacaggctt gctttgtatc  29700
aacctatgac ttccccttac agccgatgat aggtttttat ttgcacctcc ttcgtgtaca  29760
aagacagttt tggtggctac gccatcatta aactcattat tatcatgctt aagcctatag  29820
atgtatccag ttcttctgtt acataattga agctgtagtg aattgtctat cttaaactgc  29880
atcgctaact gactacattt cacacttcat ttgcttccaa catagactaa ccttcttgga  29940
tgtccactat tatttgaact tttgagattt tttttcctat ttctaatatc ttaaaatttc  30000
agaagactta aagttttgca actacagggc tccatataga catctagctt gaatttatac  30060
actttctttc attgatgtcc ctggactaaa aaatgttaaa tatttctaac cgctgtactt  30120
aaagtccatt acaaacgaag actactgttg ttaagttgaa taggcatctt atatattttt  30180
```

-continued caccggtgca ataaataact tctattccct tctaacatct gcttgcgttg cactgagagt 30240
acactattga ttagcaatag gttcgtgatt acagcccttc tataattaat tgttaggtta 30300
acatattatt cataaaatat tattttatta atttttactt gatttgctac tggatgctta 30360
gaaatagcta tgagtatatt ggtagaacca gtacttatat tttattacat ttttacattt 30420
cataaaattt aagtgatata aaaatcctga ggaagtatgc cacaaaagtg gtctcagtgg 30480
aaatttaaat atgttaacat ttatttttaa aatgtagcgt gaaatagaca actttaaaag 30540
ctcagcttaa aaaaaaaact caaggaagct gaacttgact ttttaaagca ctgaagtgca 30600
atatttaatg taggtcaaca tgtttaaatg ggaaaatttt tttcctaatt acagccaaat 30660
ccctagctgt aattaactta aaatttgtat actatttcac aacagagtca gcatatacca 30720
ctttcttata aaattagaaa gatctaaaat tttagagctt atttggtgaa acaggcatat 30780
tgctacatct ttgtttataa attataatgt gcctttagag cccaataaca gataacaaga 30840
ttttgaaaat tcaggtgaat tagagttatc agagggaatg ttaatacact ctattcaaat 30900
actatatgag taagacattt aaaataggaa acaatacttt atatattaaa aaaaattaat 30960
cttccagtcg atttaatcca ctttatgaat tcatttaaat cgatttaaat tcgaattaat 31020
taactagagt acccggggat cttattccct ttaactaata aaaaaaaata ataaagcatc 31080
acttacttaa aatcagttag caaatttctg tccagtttat tcagcagcac ctccttgccc 31140
tcctcccagc tctggtattg cagcttcctc ctggctgcaa actttctcca caatctaaat 31200
ggaatgtcag tttcctcctg ttcctgtcca tccgcaccca ctatcttcat gttgttgcag 31260
atgaagcgcg caagaccgtc tgaagatacc ttcaaccccg tgtatccata tgacacggaa 31320
accggtcctc caactgtgcc ttttcttact cctccctttg tatcccccaa tgggtttcaa 31380
gagagtcccc ctggggtact ctctttgcgc ctatccgaac ctctagttac ctccaatggc 31440
atgcttgcgc tcaaaatggg caacggcctc tctctggacg aggccggcaa ccttacctcc 31500
caaaatgtaa ccactgtgag cccacctctc aaaaaaacca agtcaaacat aaacctggaa 31560
atatctgcac ccctcacagt tacctcagaa gccctaactg tggctgccgc cgcacctcta 31620
atggtcgcgg gcaacacact caccatgcaa tcacaggccc cgctaaccgt gcacgactcc 31680
aaacttagca ttgccaccca aggacccctc acagtgtcag aaggaaagct agccctgcaa 31740
acatcaggcc ccctcaccac caccgatagc agtaccctta ctatcactgc ctcaccccct 31800
ctaactactg ccactggtag cttgggcatt gacttgaaag agcccattta tacacaaaat 31860
ggaaaactag gactaaagta cggggctcct ttgcatgtaa cagacgacct aaacactttg 31920
accgtagcaa ctggtccagg tgtgactatt aataatactt ccttgcaaac taaagttact 31980
ggagccttgg gttttgattc acaaggcaat atgcaactta atgtagcagg aggactaagg 32040
attgattctc aaaacagacg ccttatactt gatgttagtt atccgtttga tgctcaaaac 32100
caactaaatc taagactagg acagggccct ctttttataa actcagccca caacttggat 32160
attaactaca acaaaggcct ttacttgttt acagcttcaa acaattccaa aaagcttgag 32220
gttaacctaa gcactgccaa ggggttgatg tttgacgcta cagccatagc cattaatgca 32280
ggagatgggc ttgaatttgg ttcacctaat gcaccaaaca caaatcccct caaaacaaaa 32340
attggccatg gcctagaatt tgattcaaac aaggctatgg ttcctaaact aggaactggc 32400
cttagttttg acagcacagg tgccattaca gtaggaaaca aaaataatga taagctaact 32460
ttgtggacca caccagctcc atctcctaac tgtagactaa atgcagagaa agatgctaaa 32520
ctcactttgg tcttaacaaa atgtggcagt caaatacttg ctacagtttc agttttggct 32580

-continued

```
gttaaaggca gtttggctcc aatatctgga acagttcaaa gtgctcatct tattataaga  32640
tttgacgaaa atggagtgct actaaacaat tccttcctgg acccagaata ttggaacttt  32700
agaaatggag atcttactga aggcacagcc tatacaaacg ctgttggatt tatgcctaac  32760
ctatcagctt atccaaaatc tcacggtaaa actgccaaaa gtaacattgt cagtcaagtt  32820
tacttaaacg gagacaaaac taaacctgta acactaacca ttacactaaa cggtacacag  32880
gaaacaggag acacaactcc aagtgcatac tctatgtcat tttcatggga ctggtctggc  32940
cacaactaca ttaatgaaat atttgccaca tcctcttaca ctttttcata cattgcccaa  33000
gaataaagaa tcgtttgtgt tatgtttcaa cgtgtttatt tttcaattgc agaaaatttc  33060
aagtcatttt tcattcagta gtatagcccc accaccacat agcttataca gatcaccgta  33120
ccttaatcaa actcacagaa ccctagtatt caacctgcca cctccctccc aacacacaga  33180
gtacacagtc ctttctcccc ggctggcctt aaaaagcatc atatcatggg taacagacat  33240
attcttaggt gttatattcc acacggtttc ctgtcgagcc aaacgctcat cagtgatatt  33300
aataaactcc ccgggcagct cacttaagtt catgtcgctg tccagctgct gagccacagg  33360
ctgctgtcca acttgcggtt gcttaacggg cggcgaagga gaagtccacg cctacatggg  33420
ggtagagtca taatcgtgca tcaggatagg gcggtggtgc tgcagcagcg cgcgaataaa  33480
ctgctgccgc cgccgctccg tcctgcagga atacaacatg gcagtggtct cctcagcgat  33540
gattcgcacc gcccgcagca taaggcgcct tgtcctccgg gcacagcagc gcaccctgat  33600
ctcacttaaa tcagcacagt aactgcagca cagcaccaca atattgttca aaatcccaca  33660
gtgcaaggcg ctgtatccaa agctcatggc ggggaccaca gaacccacgt ggccatcata  33720
ccacaagcgc aggtagatta agtggcgacc cctcataaac acgctggaca taaacattac  33780
ctcttttggc atgttgtaat tcaccacctc ccggtaccat ataaacctct gattaaacat  33840
ggcgccatcc accaccatcc taaaccagct ggccaaaacc tgcccgccgg ctatacactg  33900
cagggaaccg ggactggaac aatgacagtg gagagcccag gactcgtaac catggatcat  33960
catgctcgtc atgatatcaa tgttggcaca acacaggcac acgtgcatac acttcctcag  34020
gattacaagc tcctcccgcg ttagaaccat atcccaggga acaacccatt cctgaatcag  34080
cgtaaatccc acactgcagg gaagacctcg cacgtaactc acgttgtgca ttgtcaaagt  34140
gttacattcg ggcagcagcg gatgatcctc cagtatggta gcgcgggttt ctgtctcaaa  34200
aggaggtaga cgatccctac tgtacggagt gcgccgagac aaccgagatc gtgttggtcg  34260
tagtgtcatg ccaaatggaa cgccggacgt agtcatattt cctgaagcaa aaccaggtgc  34320
gggcgtgaca aacagatctg cgtctccggt ctcgccgctt agatcgctct gtgtagtagt  34380
tgtagtatat ccactctctc aaagcatcca ggcgccccct ggcttcgggt tctatgtaaa  34440
ctccttcatg cgccgctgcc ctgataacat ccaccaccgc agaataagcc acacccagcc  34500
aacctacaca ttcgttctgc gagtcacaca cgggaggagc gggaagagct ggaagaacca  34560
tgtttttttt tttattccaa aagattatcc aaaacctcaa aatgaagatc tattaagtga  34620
acgcgctccc ctccggtggc gtggtcaaac tctacagcca aagaacagat aatggcattt  34680
gtaagatgtt gcacaatggc ttccaaaagg caaacggccc tcacgtccaa gtggacgtaa  34740
aggctaaacc cttcagggtg aatctcctct ataaacattc cagcaccttc aaccatgccc  34800
aaataattct catctcgcca ccttctcaat atatctctaa gcaaatcccg aatattaagt  34860
ccggccattg taaaaatctg ctccagagcg ccctccacct tcagcctcaa gcagcgaatc  34920
atgattgcaa aaattcaggt tcctcacaga cctgtataag attcaaaagc ggaacattaa  34980
```

-continued caaaaatacc gcgatcccgt aggtcccttc gcagggccag ctgaacataa tcgtgcaggt 35040
ctgcacggac cagcgcggcc acttccccgc caggaacctt gacaaaagaa cccacactga 35100
ttatgacacg catactcgga gctatgctaa ccagcgtagc cccgatgtaa gctttgttgc 35160
atgggcggcg atataaaatg caaggtgctg ctcaaaaaat caggcaaagc ctcgcgcaaa 35220
aaagaaagca catcgtagtc atgctcatgc agataaaggc aggtaagctc cggaaccacc 35280
acagaaaaag acaccatttt tctctcaaac atgtctgcgg gtttctgcat aaacacaaaa 35340
taaaataaca aaaaaacatt taaacattag aagcctgtct tacaacagga aaaacaaccc 35400
ttataagcat aagacggact acggccatgc cggcgtgacc gtaaaaaaac tggtcaccgt 35460
gattaaaaag caccaccgac agctcctcgg tcatgtccgg agtcataatg taagactcgg 35520
taaacacatc aggttgattc atcggtcagt gctaaaaagc gaccgaaata gcccggggga 35580
atacataccc gcaggcgtag agacaacatt acagccccca taggaggtat aacaaaatta 35640
ataggagaga aaaacacata aacacctgaa aaaccctcct gcctaggcaa aatagcaccc 35700
tcccgctcca gaacaacata cagcgcttca cagcggcagc ctaacagtca gccttaccag 35760
taaaaaagaa aacctattaa aaaaacacca ctcgacacgg caccagctca atcagtcaca 35820
gtgtaaaaaa gggccaagtg cagagcgagt atatatagga ctaaaaaatg acgtaacggt 35880
taaagtccac aaaaaacacc cagaaaaccg cacgcgaacc tacgcccaga aacgaaagcc 35940
aaaaaaccca caacttcctc aaatcgtcac ttccgttttc ccacgttacg taacttccca 36000
ttttaagaaa actacaattc ccaacacata caagttactc cgccctaaaa cctacgtcac 36060
ccgccccgtt cccacgcccc gcgccacgtc acaaactcca ccccctcatt atcatattgg 36120
cttcaatcca aaataaggta tattattgat gatg 36154

<210> SEQ ID NO 10
<211> LENGTH: 103
<212> TYPE: DNA
<213> ORGANISM: Artificial Sequence
<220> FEATURE:
<223> OTHER INFORMATION: Synthetic

<400> SEQUENCE: 10
catcatcaat aatatacctt attttggatt gaagccaata tgataatgag ggggtggagt 60
ttgtgacgtg gcgcggggcg tgggaacggg gcgggtgacg tag 103

<210> SEQ ID NO 11
<211> LENGTH: 73
<212> TYPE: DNA
<213> ORGANISM: Artificial Sequence
<220> FEATURE:
<223> OTHER INFORMATION: Synthetic

<400> SEQUENCE: 11
catcatcaat aatatacctt attttggatt gaagccaata tgataatgag ggggtggagt 60
ttgtgacgtg gcg 73

<210> SEQ ID NO 12
<211> LENGTH: 2989
<212> TYPE: DNA
<213> ORGANISM: Artificial Sequence
<220> FEATURE:
<223> OTHER INFORMATION: Synthetic

<400> SEQUENCE: 12
ctaaattgta agcgttaata ttttgttaaa attcgcgtta aatttttgtt aaatcagctc 60

-continued

```
atttttaac caataggccg aaatcggcaa aatcccttat aaatcaaaag aatagaccga    120
gatagggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt tttttggggt cgaggtgccg taaagcacta aatcggaacc ctaaagggag   300
cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgagc gcgcgtaata cgactcacta tagggcgaat tggagcttac   660
gtattaatta aggcgccgcg gtggcggccg ctctagaact agtggatccc ccgggctgca   720
ggaattcggc cgcctaggcc acgcgtaagc ttatcgatac cgtcgacctc gagggggggc   780
ccggtaccca gcttttgttc cctttagtga gggttaattg cgcgcttggc gtaatcatgg   840
tcatagctgt ttcctgtgtg aaattgttat ccgctcacaa ttccacacaa catacgagcc   900
ggaagcataa agtgtaaagc ctggggtgcc taatgagtga gctaactcac attaattgcg   960
ttgcgctcac tgcccgcttt ccagtcggga aacctgtcgt gccagctgca ttaatgaatc  1020
ggccaacgcg cggggagagg cggtttgcgt attgggcgct cttccgcttc ctcgctcact  1080
gactcgctgc gctcggtcgt tcggctgcgg cgagcggtat cagctcactc aaaggcggta  1140
atacggttat ccacagaatc aggggataac gcaggaaaga acatgtgagc aaaaggccag  1200
caaaaggcca ggaaccgtaa aaaggccgcg ttgctggcgt ttttccatag gctccgcccc  1260
cctgacgagc atcacaaaaa tcgacgctca agtcagaggt ggcgaaaccc gacaggacta  1320
taaagatacc aggcgtttcc ccctggaagc tccctcgtgc gctctcctgt tccgaccctg  1380
ccgcttaccg gatacctgtc cgcctttctc ccttcgggaa gcgtggcgct ttctcatagc  1440
tcacgctgta ggtatctcag ttcggtgtag gtcgttcgct ccaagctggg ctgtgtgcac  1500
gaaccccccg ttcagcccga ccgctgcgcc ttatccggta actatcgtct tgagtccaac  1560
ccggtaagac acgacttatc gccactggca gcagccactg gtaacaggat tagcagagcg  1620
aggtatgtag gcggtgctac agagttcttg aagtggtggc ctaactacgg ctacactaga  1680
aggacagtat ttggtatctg cgctctgctg aagccagtta ccttcggaaa aagagttggt  1740
agctcttgat ccggcaaaca aaccaccgct ggtagcggtg gtttttttgt ttgcaagcag  1800
cagattacgc gcagaaaaaa aggatctcaa gaagatcctt tgatcttttc tacggggtct  1860
gacgctcagt ggaacgaaaa ctcacgttaa gggattttgg tcatgagatt atcaaaaagg  1920
atcttcacct agatcctttt aaattaaaaa tgaagtttta aatcaatcta aagtatatat  1980
gagtaaactt ggtctgacag ttaccaatgc ttaatcagtg aggcacctat ctcagcgatc  2040
tgtctatttc gttcatccat agttgcctga ctccccgtcg tgtagataac tacgatacgg  2100
gagggcttac catctggccc cagtgctgca atgataccgc gagacccacg ctcaccggct  2160
ccagatttat cagcaataaa ccagccagcc ggaagggccg agcgcagaag tggtcctgca  2220
actttatccg cctccatcca gtctattaat tgttgccggg aagctagagt aagtagttcg  2280
ccagttaata gtttgcgcaa cgttgttgcc attgctacag gcatcgtggt gtcacgctcg  2340
tcgtttggta tggcttcatt cagctccggt tcccaacgat caaggcgagt tacatgatcc  2400
cccatgttgt gcaaaaaagc ggttagctcc ttcggtcctc cgatcgttgt cagaagtaag  2460
```

-continued

```
ttggccgcag tgttatcact catggttatg gcagcactgc ataattctct tactgtcatg   2520

ccatccgtaa gatgcttttc tgtgactggt gagtactcaa ccaagtcatt ctgagaatag   2580

tgtatgcggc gaccgagttg ctcttgcccg gcgtcaatac gggataatac cgcgccacat   2640

agcagaactt taaaagtgct catcattgga aaacgttctt cggggcgaaa actctcaagg   2700

atcttaccgc tgttgagatc cagttcgatg taacccactc gtgcacccaa ctgatcttca   2760

gcatctttta ctttcaccag cgtttctggg tgagcaaaaa caggaaggca aaatgccgca   2820

aaaaagggaa taagggcgac acggaaatgt tgaatactca tactcttcct ttttcaatat   2880

tattgaagca tttatcaggg ttattgtctc atgagcggat acatatttga atgtatttag   2940

aaaaataaac aaataggggt tccgcgcaca tttccccgaa aagtgccac              2989
```

<210> SEQ ID NO 13
<211> LENGTH: 38041
<212> TYPE: DNA
<213> ORGANISM: Artificial Sequence
<220> FEATURE:
<223> OTHER INFORMATION: Synthetic

<400> SEQUENCE: 13

```
ctaaattgta agcgttaata ttttgttaaa attcggccgg ccatcatcaa taatatacct     60

tattttggat tgaagccaat atgataatga gggggtggag tttgtgacgt ggcgcggggc    120

gtgggaacgg ggcgggtgac gtagtagtgt ggcggaagtg tgatgttgca agtgtggcgg    180

aacacatgta taacttcgta taatgtatgc tatacgaagt tatacatgta agcgacggat    240

gtggcaaaag tgacgttttt ggtgtgcgcc ggtgtacaca ggaagtgaca attttcgcgc    300

ggttttaggc ggatgttgta gtaaatttgg gcgtaaccga gtaagatttg gccattttcg    360

cgggaaaact gaataagagg aagtgaaatc tgaataattt tgtgttactc atagcgcgta    420

atatttgtct agggagatct ataacttcgt ataatgtatg ctatacgaag ttattaccga    480

agaaatggct cgagatctgg aaggtgctga ggtacgatga gacccgcacc aggtgcagac    540

cctgcgagtg tggcggtaaa catattagga accagcctgt gatgctggat gtgaccgagg    600

agctgaggcc cgatcacttg gtgctggcct gcacccgcgc tgagtttggc tctagcgatg    660

aagatacaga ttgaggtact gaaatgtgtg ggcgtggctt aagggtggga aagaatatat    720

aaggtggggg tcttatgtag ttttgtatct gttttgcagc agccgccgcc gccatgagca    780

ccaactcgtt tgatggaagc attgtgagct catatttgac aacgcgcatg cccccatggg    840

ccggggtgcg tcagaatgtg atgggctcca gcattgatgg tcgccccgtc ctgcccgcaa    900

actctactac cttgacctac gagaccgtgt ctggaacgcc gttggagact gcagcctccg    960

ccgccgcttc agccgctgca gccaccgccc gcgggattgt gactgacttt gctttcctga   1020

gcccgcttgc aagcagtgca gcttcccgtt catccgcccg cgatgacaag ttgacggctc   1080

ttttggcaca attggattct ttgacccggg aacttaatgt cgtttctcag cagctgttgg   1140

atctgcgcca gcaggtttct gccctgaagg cttcctcccc tcccaatgcg gtttaaaaca   1200

taaataaaaa accagactct gtttggattt ggatcaagca agtgtcttgc tgtctttatt   1260

taggggtttt gcgcgcgcgg taggcccggg accagcggtc tcggtcgttg agggtcctgt   1320

gtattttttc caggacgtgg taaaggtgac tctggatgtt cagatacatg ggcataagcc   1380

cgtctctggg gtggaggtag caccactgca gagcttcatg ctgcggggtg gtgttgtaga   1440

tgatccagtc gtagcaggag cgctgggcgt ggtgcctaaa aatgtctttc agtagcaagc   1500

tgattgccag ggcaggcccc ttggtgtaag tgtttacaaa gcggttaagc tgggatgggt   1560
```

```
gcatacgtgg ggatatgaga tgcatcttgg actgtatttt taggttggct atgttcccag   1620
ccatatccct ccggggattc atgttgtgca gaaccaccag cacagtgtat ccggtgcact   1680
tgggaaattt gtcatgtagc ttagaaggaa atgcgtggaa gaacttggag acgcccttgt   1740
gacctccaag attttccatg cattcgtcca taatgatggc aatgggccca cgggcggcgg   1800
cctgggcgaa gatatttctg ggatcactaa cgtcatagtt gtgttccagg atgagatcgt   1860
cataggccat ttttacaaag cgcgggcgga gggtgccaga ctgcggtata atggttccat   1920
ccggcccagg ggcgtagtta ccctcacaga tttgcatttc ccacgctttg agttcagatg   1980
gggggatcat gtctacctgc ggggcgatga agaaaacggt ttccggggta ggggagatca   2040
gctgggaaga aagcaggttc ctgagcagct gcgacttacc gcagccggtg ggcccgtaaa   2100
tcacacctat taccgggtgc aactggtagt taagagagct gcagctgccg tcatccctga   2160
gcaggggggc cacttcgtta agcatgtccc tgactcgcat gttttccctg accaaatccg   2220
ccagaaggcg ctcgccgccc agcgatagca gttcttgcaa ggaagcaaag tttttcaacg   2280
gtttgagacc gtccgccgta ggcatgcttt tgagcgtttg accaagcagt tccaggcggt   2340
cccacagctc ggtcacctgc tctacggcat ctcgatccag catatctcct cgtttcgcgg   2400
gttggggcgg ctttcgctgt acggcagtag tcggtgctcg tccagacggg ccagggtcat   2460
gtctttccac gggcgcaggg tcctcgtcag cgtagtctgg gtcacggtga aggggtgcgc   2520
tccgggctgc gcgctggcca gggtgcgctt gaggctggtc ctgctggtgc tgaagcgctg   2580
ccggtcttcg ccctgcgcgt cggccaggta gcatttgacc atggtgtcat agtccagccc   2640
ctccgcggcg tggcccttgg cgcgcagctt gcccttggag gaggcgccgc acgaggggca   2700
gtgcagactt ttgagggcgt agagcttggg cgcgagaaat accgattccg gggagtaggc   2760
atccgcgccg caggccccgc agacggtctc gcattccacg agccaggtga gctctggccg   2820
ttcggggtca aaaaccaggt ttcccccatg ctttttgatg cgtttcttac ctctggtttc   2880
catgagccgg tgtccacgct cggtgacgaa aaggctgtcc gtgtccccgt atacagactt   2940
gagaggcctg tcctcgagcg gtgttccgcg gtcctcctcg tatagaaact cggaccactc   3000
tgagacaaag gctcgcgtcc aggccagcac gaaggaggct aagtgggagg ggtagcggtc   3060
gttgtccact agggggtcca ctcgctccag ggtgtgaaga cacatgtcgc cctcttcggc   3120
atcaaggaag gtgattggtt tgtaggtgta ggccacgtga ccgggtgttc ctgaaggggg   3180
gctataaaag ggggtggggg cgcgttcgtc ctcactctct tccgcatcgc tgtctgcgag   3240
ggccagctgt tggggtgagt actccctctg aaaagcgggc atgacttctg cgctaagatt   3300
gtcagtttcc aaaaacgagg aggatttgat attcacctgg cccgcggtga tgcctttgag   3360
ggtggccgca tccatctggt cagaaaagac aatctttttg ttgtcaagct tggtggcaaa   3420
cgacccgtag agggcgttgg acagcaactt ggcgatggag cgcagggttt ggtttttgtc   3480
gcgatcggcg cgctccttgg ccgcgatgtt tagctgcacg tattcgcgcg caacgcaccg   3540
ccattcggga aagacggtgg tgcgctcgtc gggcaccagg tgcacgcgcc aaccgcggtt   3600
gtgcagggtg acaaggtcaa cgctggtggc tacctctccg cgtaggcgct cgttggtcca   3660
gcagaggcgg ccgcccttgc gcgagcagaa tggcggtagg gggtctagct gcgtctcgtc   3720
cggggggtct gcgtccacgg taaagacccc gggcagcagg cgcgcgtcga agtagtctat   3780
cttgcatcct tgcaagtcta gcgcctgctg ccatgcgcgg gcggcaagcg cgcgctcgta   3840
tgggttgagt gggggacccc atggcatggg gtgggtgagc gcggaggcgt acatgccgca   3900
aatgtcgtaa acgtagaggg gctctctgag tattccaaga tatgtagggt agcatcttcc   3960
```

-continued accgcggatg ctggcgcgca cgtaatcgta tagttcgtgc gagggagcga ggaggtcggg 4020
accgaggttg ctacgggcgg gctgctctgc tcggaagact atctgcctga agatggcatg 4080
tgagttggat gatatggttg gacgctggaa gacgttgaag ctggcgtctg tgagacctac 4140
cgcgtcacgc acgaaggagg cgtaggagtc gcgcagcttg ttgaccagct cggcggtgac 4200
ctgcacgtct agggcgcagt agtccagggt ttccttgatg atgtcatact tatcctgtcc 4260
cttttttttc cacagctcgc ggttgaggac aaactcttcg cggtctttcc agtactcttg 4320
gatcggaaac ccgtcggcct ccgaacggta agagcctagc atgtagaact ggttgacggc 4380
ctggtaggcg cagcatccct tttctacggg tagcgcgtat gcctgcgcgg ccttccggag 4440
cgaggtgtgg gtgagcgcaa aggtgtccct gaccatgact ttgaggtact ggtatttgaa 4500
gtcagtgtcg tcgcatccgc cctgctccca gagcaaaaag tccgtgcgct ttttggaacg 4560
cggatttggc agggcgaagg tgacatcgtt gaagagtatc tttcccgcgc gaggcataaa 4620
gttgcgtgtg atgcggaagg gtcccggcac ctcggaacgg ttgttaatta cctgggcggc 4680
gagcacgatc tcgtcaaagc cgttgatgtt gtggcccaca atgtaaagtt ccaagaagcg 4740
cgggatgccc ttgatggaag gcaatttttt aagttcctcg taggtgagct cttcagggga 4800
gctgagcccg tgctctgaaa gggcccagtc tgcaagatga gggttggaag cgacgaatga 4860
gctccacagg tcacgggcca ttagcatttg caggtggtcg cgaaaggtcc taaactggcg 4920
acctatggcc atttttctg gggtgatgca gtagaaggta agcgggtctt gttcccagcg 4980
gtcccatcca aggttcgcgg ctaggtctcg cgcggcagtc actagaggct catctccgcc 5040
gaacttcatg accagcatga agggcacgag ctgcttccca aaggccccca tccaagtata 5100
ggtctctaca tcgtaggtga caaagagacg ctcggtgcga ggatgcgagc cgatcgggaa 5160
gaactggatc tcccgccacc aattggagga gtggctattg atgtggtgaa agtagaagtc 5220
cctgcgacgg gccgaacact cgtgctggct tttgtaaaaa cgtgcgcagt actggcagcg 5280
gtgcacgggc tgtacatcct gcacgaggtt gacctgacga ccgcgcacaa ggaagcagag 5340
tgggaatttg agcccctcgc ctggcgggtt tggctggtgg tcttctactt cggctgcttg 5400
tccttgaccg tctggctgct cgaggggagt tacggtggat cggaccacca cgccgcgcga 5460
gcccaaagtc cagatgtccg cgcgcggcgg tcggagcttg atgacaacat cgcgcagatg 5520
ggagctgtcc atggtctgga gctcccgcgg cgtcaggtca ggcgggagct cctgcaggtt 5580
tacctcgcat agacgggtca gggcgcgggc tagatccagg tgatacctaa tttccagggg 5640
ctggttggtg gcggcgtcga tggcttgcaa gaggccgcat ccccgcggcg cgactacggt 5700
accgcgcggc gggcggtggg ccgcgggggt gtccttggat gatgcatcta aaagcggtga 5760
cgcgggcgag cccccggagg taggggggc tccggacccg ccgggagagg gggcaggggc 5820
acgtcggcgc cgcgcgcggg caggagctgg tgctgcgcgc gtaggttgct ggcgaacgcg 5880
acgacgcggc ggttgatctc ctgaatctgg cgcctctgcg tgaagacgac gggcccggtg 5940
agcttgagcc tgaaagagag ttcgacagaa tcaatttcgg tgtcgttgac ggcggcctgg 6000
cgcaaaatct cctgcacgtc tcctgagttg tcttgatagg cgatctcggc catgaactgc 6060
tcgatctctt cctcctggag atctccgcgt ccggctcgct ccacggtggc ggcgaggtcg 6120
ttggaaatgc gggccatgag ctgcgagaag gcgttgaggc ctccctcgtt ccagacgcgg 6180
ctgtagacca cgcccccttc ggcatcgcgg gcgcgcatga ccacctgcgc gagattgagc 6240
tccacgtgcc gggcgaagac ggcgtagttt cgcaggcgct gaaagaggta gttgagggtg 6300
gtggcggtgt gttctgccac gaagaagtac ataacccagc gtcgcaacgt ggattcgttg 6360

-continued

```
atatccccca aggcctcaag gcgctccatg gcctcgtaga agtccacggc gaagttgaaa   6420
aactgggagt tgcgcgccga cacggttaac tcctcctcca gaagacggat gagctcggcg   6480
acagtgtcgc gcacctcgcg ctcaaaggct acaggggcct cttcttcttc ttcaatctcc   6540
tcttccataa gggcctcccc ttcttcttct tctggcggcg gtgggggagg ggggacacgg   6600
cggcgacgac ggcgcaccgg gaggcggtcg acaaagcgct cgatcatctc cccgcggcga   6660
cggcgcatgg tctcggtgac ggcgcggccg ttctcgcggg ggcgcagttg gaagacgccg   6720
cccgtcatgt cccggttatg ggttggcggg gggctgccat gcggcaggga tacggcgcta   6780
acgatgcatc tcaacaattg ttgtgtaggt actccgccgc cgagggacct gagcgagtcc   6840
gcatcgaccg gatcggaaaa cctctcgaga aaggcgtcta accagtcaca gtcgcaaggt   6900
aggctgagca ccgtggcggg cggcagcggg cggcggtcgg ggttgtttct ggcggaggtg   6960
ctgctgatga tgtaattaaa gtaggcggtc ttgagacggc ggatggtcga cagaagcacc   7020
atgtccttgg gtccggcctg ctgaatgcgc aggcggtcgg ccatgcccca ggcttcgttt   7080
tgacatcggc gcaggtcttt gtagtagtct tgcatgagcc tttctaccgg cacttcttct   7140
tctccttcct cttgtcctgc atctcttgca tctatcgctg cggcggcggc ggagtttggc   7200
cgtaggtggc gccctcttcc tcccatgcgt gtgaccccga agcccctcat cggctgaagc   7260
agggctaggt cggcgacaac gcgctcggct aatatggcct gctgcacctg cgtgagggta   7320
gactggaagt catccatgtc cacaaagcgg tggtatgcgc ccgtgttgat ggtgtaagtg   7380
cagttggcca taacggacca gttaacggtc tggtgacccg gctgcgagag ctcggtgtac   7440
ctgagacgcg agtaagccct cgagtcaaat acgtagtcgt tgcaagtccg caccaggtac   7500
tggtatccca ccaaaaagtg cggcggcggc tggcggtaga ggggccagcg tagggtggcc   7560
ggggctccgg gggcgagatc ttccaacata aggcgatgat atccgtagat gtacctggac   7620
atccaggtga tgccggcggc ggtggtggag gcgcgcggaa agtcgcggac gcggttccag   7680
atgttgcgca gcggcaaaaa gtgctccatg gtcgggacgc tctggccggt caggcgcgcg   7740
caatcgttga cgctctaccg tgcaaaagga gagcctgtaa gcgggcactc ttccgtggtc   7800
tggtggataa attcgcaagg gtatcatggc ggacgaccgg ggttcgagcc ccgtatccgg   7860
ccgtccgccg tgatccatgc ggttaccgcc cgcgtgtcga acccaggtgt gcgacgtcag   7920
acaacggggg agtgctcctt ttggcttcct tccaggcgcg gcggctgctg cgctagcttt   7980
tttggccact ggccgcgcgc agcgtaagcg gttaggctgg aaagcgaaag cattaagtgg   8040
ctcgctccct gtagccggag ggttattttc caagggttga gtcgcgggac ccccggttcg   8100
agtctcggac cggccggact gcggcgaacg gggggtttgcc tccccgtcat gcaagacccc   8160
gcttgcaaat tcctccggaa acagggacga gccccttttt tgcttttccc agatgcatcc   8220
ggtgctgcgg cagatgcgcc cccctcctca gcagcggcaa gagcaagagc agcggcagac   8280
atgcagggca ccctcccctc ctcctaccgc gtcaggaggg gcgacatccg cggttgacgc   8340
ggcagcagat ggtgattacg aaccccccgcg gcgccgggcc cggcactacc tggacttgga   8400
ggagggcgag ggcctggcgc ggctaggagc gccctctcct gagcggtacc caagggtgca   8460
gctgaagcgt gatacgcgtg aggcgtacgt gccgcggcag aacctgtttc gcgaccgcga   8520
gggagaggag cccgaggaga tgcgggatcg aaagttccac gcagggcgcg agctgcggca   8580
tggcctgaat cgcgagcggt tgctgcgcga ggaggacttt gagcccgacg cgcgaaccgg   8640
gattagtccc gcgcgcgcac acgtggcggc cgccgacctg gtaaccgcat acgagcagac   8700
ggtgaaccag gagattaact ttcaaaaaag ctttaacaac cacgtgcgta cgcttgtggc   8760
```

-continued

```
gcgcgaggag gtggctatag gactgatgca tctgtgggac tttgtaagcg cgctggagca   8820
aaacccaaat agcaagccgc tcatggcgca gctgttcctt atagtgcagc acagcaggga   8880
caacgaggca ttcagggatg cgctgctaaa catagtagag cccgagggcc gctggctgct   8940
cgatttgata aacatcctgc agagcatagt ggtgcaggag cgcagcttga gcctggctga   9000
caaggtggcc gccatcaact attccatgct tagcctgggc aagttttacg cccgcaagat   9060
ataccatacc ccttacgttc ccatagacaa ggaggtaaag atcgaggggt tctacatgcg   9120
catggcgctg aaggtgctta ccttgagcga cgacctgggc gtttatcgca acgagcgcat   9180
ccacaaggcc gtgagcgtga gccggcggcg cgagctcagc gaccgcgagc tgatgcacag   9240
cctgcaaagg gccctggctg gcacgggcag cggcgataga gaggccgagt cctactttga   9300
cgcgggcgct gacctgcgct gggccccaag ccgacgcgcc ctggaggcag ctggggccgg   9360
acctgggctg gcggtggcac ccgcgcgcgc tggcaacgtc ggcggcgtgg aggaatatga   9420
cgaggacgat gagtacgagc cagaggacgg cgagtactaa gcggtgatgt ttctgatcag   9480
atgatgcaag acgcaacgga cccggcggtg cgggcggcgc tgcagagcca gccgtccggc   9540
cttaactcca cggacgactg gcgccaggtc atggaccgca tcatgtcgct gactgcgcgc   9600
aatcctgacg cgttccggca gcagccgcag gccaaccggc tctccgcaat tctggaagcg   9660
gtggtcccgg cgcgcgcaaa ccccacgcac gagaaggtgc tggcgatcgt aaacgcgctg   9720
gccgaaaaca gggccatccg gcccgacgaa gccggcctgg tctacgacgc gctgcttcag   9780
cgcgtggctc gttacaacag cggcaacgtg cagaccaacc tggaccggct ggtgggggat   9840
gtgcgcgagg ccgtggcgca gcgtgagcgc gcgcagcagc agggcaacct gggctccatg   9900
gttgcactaa acgccttcct gagtacacag cccgccaacg tgccgcgggg acaggaggac   9960
tacaccaact ttgtgagcgc actgcggcta atggtgactg agacaccgca aagtgaggtg  10020
taccagtctg ggccagacta ttttttccag accagtagac aaggcctgca gaccgtaaac  10080
ctgagccagg ctttcaaaaa cttgcagggg ctgtgggggg tgcgggctcc cacaggcgac  10140
cgcgcgaccg tgtctagctt gctgacgccc aactcgcgcc tgttgctgct gctaatagcg  10200
cccttcacgg acagtggcag cgtgtcccgg gacacatacc taggtcactt gctgacactg  10260
taccgcgagg ccataggtca ggcgcatgtg gacgagcata ctttccagga gattacaagt  10320
gtcagccgcg cgctggggca ggaggacacg ggcagcctgg aggcaaccct aaactacctg  10380
ctgaccaacc ggcggcagaa gatcccctcg ttgcacagtt taaacagcga ggaggagcgc  10440
attttgcgct acgtgcagca gagcgtgagc cttaacctga tgcgcgacgg ggtaacgccc  10500
agcgtggcgc tggacatgac cgcgcgcaac atggaaccgg gcatgtatgc ctcaaaccgg  10560
ccgtttatca accgcctaat ggactacttg catcgcgcgg ccgccgtgaa ccccgagtat  10620
ttcaccaatg ccatcttgaa cccgcactgg ctaccgcccc ctggtttcta caccggggga  10680
ttcgaggtgc ccgagggtaa cgatggattc ctctgggacg acatagacga cagcgtgttt  10740
tccccgcaac cgcagaccct gctagagttg caacagcgcg agcaggcaga ggcggcgctg  10800
cgaaaggaaa gcttccgcag gccaagcagc ttgtccgatc taggcgctgc ggccccgcgg  10860
tcagatgcta gtagcccatt tccaagcttg atagggtctc ttaccagcac tcgcaccacc  10920
cgcccgcgcc tgctgggcga ggaggagtac ctaaacaact cgctgctgca gccgcagcgc  10980
gaaaaaaacc tgcctccggc atttcccaac aacgggatag agagcctagt ggacaagatg  11040
agtagatgga agacgtacgc gcaggagcac agggacgtgc caggcccgcg cccgcccacc  11100
cgtcgtcaaa ggcacgaccg tcagcggggt ctggtgtggg aggacgatga ctcggcagac  11160
```

-continued

```
gacagcagcg tcctggattt gggagggagt ggcaacccgt ttgcgcacct tcgccccagg  11220
ctggggagaa tgttttaaaa aaaaaaaagc atgatgcaaa ataaaaaact caccaaggcc  11280
atggcaccga gcgttggttt tcttgtattc cccttagtat gcggcgcgcg gcgatgtatg  11340
aggaaggtcc tcctccctcc tacgagagtg tggtgagcgc ggcgccagtg gcggcggcgc  11400
tgggttctcc cttcgatgct cccctggacc cgccgtttgt gcctccgcgg tacctgcggc  11460
ctaccggggg gagaaacagc atccgttact ctgagttggc acccctattc gacaccaccc  11520
gtgtgtacct ggtggacaac aagtcaacgg atgtggcatc cctgaactac cagaacgacc  11580
acagcaactt tctgaccacg gtcattcaaa acaatgacta cagcccgggg gaggcaagca  11640
cacagaccat caatcttgac gaccggtcgc actggggcgg cgacctgaaa accatcctgc  11700
ataccaacat gccaaatgtg aacgagttca tgtttaccaa taagtttaag gcgcgggtga  11760
tggtgtcgcg cttgcctact aaggacaatc aggtggagct gaaatacgag tgggtggagt  11820
tcacgctgcc cgagggcaac tactccgaga ccatgaccat agaccttatg aacaacgcga  11880
tcgtggagca ctacttgaaa gtgggcagac agaacggggt tctggaaagc gacatcgggg  11940
taaagtttga cacccgcaac ttcagactgg ggtttgaccc cgtcactggt cttgtcatgc  12000
ctggggtata tacaaacgaa gccttccatc cagacatcat tttgctgcca ggatgcgggg  12060
tggacttcac ccacagccgc ctgagcaact tgttgggcat ccgcaagcgg caacccttcc  12120
aggagggctt taggatcacc tacgatgatc tggagggtgg taacattccc gcactgttgg  12180
atgtggacgc ctaccaggcg agcttgaaag atgacaccga acagggcggg ggtggcgcag  12240
gcggcagcaa cagcagtggc agcggcgcgg aagagaactc caacgcggca gccgcggcaa  12300
tgcagccggt ggaggacatg aacgatcatg ccattcgcgg cgacaccttt gccacacggg  12360
ctgaggagaa gcgcgctgag gccgaagcag cggccgaagc tgccgccccc gctgcgcaac  12420
ccgaggtcga gaagcctcag aagaaaccgg tgatcaaacc cctgacagag gacagcaaga  12480
aacgcagtta caacctaata agcaatgaca gcaccttcac ccagtaccgc agctggtacc  12540
ttgcatacaa ctacggcgac cctcagaccg gaatccgctc atggaccctg ctttgcactc  12600
ctgacgtaac ctgcggctcg gagcaggtct actggtcgtt gccagacatg atgcaagacc  12660
ccgtgacctt ccgctccacg cgccagatca gcaactttcc ggtggtgggc gccgagctgt  12720
tgcccgtgca ctccaagagc ttctacaacg accaggccgt ctactcccaa ctcatccgcc  12780
agtttacctc tctgacccac gtgttcaatc gctttcccga gaaccagatt ttggcgcgcc  12840
cgccagcccc caccatcacc accgtcagtg aaaacgttcc tgctctcaca gatcacggga  12900
cgctaccgct gcgcaacagc atcggaggag tccagcgagt gaccattact gacgccagac  12960
gccgcacctg cccctacgtt tacaaggccc tgggcatagt ctcgccgcgc gtcctatcga  13020
gccgcacttt ttgagcaagc atgtccatcc ttatatcgcc cagcaataac acaggctggg  13080
gcctgcgctt cccaagcaag atgtttggcg gggccaagaa gcgctccgac caacacccag  13140
tgcgcgtgcg cgggcactac cgcgcgccct ggggcgcgca caaacgcggc cgcactgggc  13200
gcaccaccgt cgatgacgcc atcgacgcgg tggtggagga ggcgcgcaac tacacgccca  13260
cgccgccacc agtgtccaca gtggacgcgg ccattcagac cgtggtgcgc ggagcccggc  13320
gctatgctaa aatgaagaga cggcggaggc gcgtagcacg tcgccaccgc cgccgacccg  13380
gcactgccgc ccaacgcgcg gcggcggccc tgcttaaccg cgcacgtcgc accggccgac  13440
gggcggccat gcgggccgct cgaaggctgg ccgcgggtat tgtcactgtg ccccccaggt  13500
ccaggcgacg agcggccgcc gcagcagccg cggccattag tgctatgact cagggtcgca  13560
```

-continued

```
ggggcaacgt gtattgggtg cgcgactcgg ttagcggcct gcgcgtgccc gtgcgcaccc  13620
gcccccgcg caactagatt gcaagaaaaa actacttaga ctcgtactgt tgtatgtatc  13680
cagcggcggc ggcgcgcaac gaagctatgt ccaagcgcaa aatcaaagaa gagatgctcc  13740
aggtcatcgc gccggagatc tatggccccc cgaagaagga agagcaggat tacaagcccc  13800
gaaagctaaa gcgggtcaaa aagaaaaaga aagatgatga tgatgaactt gacgacgagg  13860
tggaactgct gcacgctacc gcgcccaggc gacgggtaca gtggaaaggt cgacgcgtaa  13920
aacgtgtttt gcgacccggc accaccgtag tctttacgcc cggtgagcgc tccacccgca  13980
cctacaagcg cgtgtatgat gaggtgtacg gcgacgagga cctgcttgag caggccaacg  14040
agcgcctcgg ggagtttgcc tacggaaagc ggcataagga catgctggcg ttgccgctgg  14100
acgagggcaa cccaacacct agcctaaagc ccgtaacact gcagcaggtg ctgcccgcgc  14160
ttgcaccgtc cgaagaaaag cgcggcctaa agcgcgagtc tggtgacttg gcacccaccg  14220
tgcagctgat ggtacccaag cgccagcgac tggaagatgt cttggaaaaa atgaccgtgg  14280
aacctgggct ggagcccgag gtccgcgtgc ggccaatcaa gcaggtggcg ccgggactgg  14340
gcgtgcagac cgtggacgtt cagataccca ctaccagtag caccagtatt gccaccgcca  14400
cagagggcat ggagacacaa acgtccccgg ttgcctcagc ggtggcggat gccgcggtgc  14460
aggcggtcgc tgcggccgcg tccaagacct ctacggaggt gcaaacggac ccgtggatgt  14520
ttcgcgtttc agccccccgg cgcccgcgcg gttcgaggaa gtacggcgcc gccagcgcgc  14580
tactgcccga atatgcccta catccttcca ttgcgcctac ccccggctat cgtggctaca  14640
cctaccgccc cagaagacga gcaactaccc gacgccgaac caccactgga acccgccgcc  14700
gccgtcgccg tcgccagccc gtgctggccc cgatttccgt gcgcagggtg gctcgcgaag  14760
gaggcaggac cctggtgctg ccaacagcgc gctaccaccc cagcatcgtt taaaagccgg  14820
tctttgtggt tcttgcagat atggccctca cctgccgcct ccgtttcccg gtgccgggat  14880
tccgaggaag aatgcaccgt aggaggggca tggccggcta cggcctgacg ggcggcatgc  14940
gtcgtgcgca ccaccggcgg cggcgcgcgt cgcaccgtcg catgcgcggc ggtatcctgc  15000
ccctccttat tccactgatc gccgcggcga ttggcgccgt gcccggaatt gcatccgtgg  15060
ccttgcaggc gcagagacac tgattaaaaa caagttgcat gtggaaaaat caaaataaaa  15120
agtctggact ctcacgctcg cttggtcctg taactatttt gtagaatgga agacatcaac  15180
tttgcgtctc tggccccgcg acacggctcg cgcccgttca tgggaaactg gcaagatatc  15240
ggcaccagca atatgagcgg tggcgccttc agctggggct cgctgtggag cggcattaaa  15300
aatttcggtt ccaccgttaa gaactatggc agcaaggcct ggaacagcag cacaggccag  15360
atgctgaggg ataagttgaa agagcaaaat ttccaacaaa aggtggtaga tggcctggcc  15420
tctggcatta gcggggtggt ggacctggcc aaccaggcag tgcaaaataa gattaacagt  15480
aagcttgatc cccgccctcc cgtagaggag cctccaccgg ccgtggagac agtgtctcca  15540
gaggggcgtg gcgaaaagcg tccgcgcccc gacagggaag aaactctggt gacgcaaata  15600
gacgagcctc cctcgtacga ggaggcacta aagcaaggcc tgcccaccac ccgtcccatc  15660
gcgcccatgg ctaccggagt gctgggccag cacacacccg taacgctgga cctgcctccc  15720
cccgccgaca cccagcagaa acctgtgctg ccaggcccga ccgccgttgt tgtaacccgt  15780
cctagccgcg cgtccctgcg ccgcgccgcc agcggtccgc gatcgttgcg gcccgtagcc  15840
agtggcaact ggcaaagcac actgaacagc atcgtgggtc tgggggtgca atccctgaag  15900
cgccgacgat gcttctgaat agctaacgtg tcgtatgtgt gtcatgtatg cgtccatgtc  15960
```

-continued

```
gccgccagag gagctgctga gccgccgcgc gcccgctttc caagatggct accccttcga  16020
tgatgccgca gtggtcttac atgcacatct cgggccagga cgcctcggag tacctgagcc  16080
ccgggctggt gcagtttgcc cgcgccaccg agacgtactt cagcctgaat aacaagttta  16140
gaaaccccac ggtggcgcct acgcacgacg tgaccacaga ccggtcccag cgtttgacgc  16200
tgcggttcat ccctgtggac cgtgaggata ctgcgtactc gtacaaggcg cggttcaccc  16260
tagctgtggg tgataaccgt gtgctggaca tggcttccac gtactttgac atccgcggcg  16320
tgctggacag gggccctact tttaagccct actctggcac tgcctacaac gccctggctc  16380
ccaagggtgc cccaaatcct tgcgaatggg atgaagctgc tactgctctt gaaataaacc  16440
tagaagaaga ggacgatgac aacgaagacg aagtagacga gcaagctgag cagcaaaaaa  16500
ctcacgtatt tgggcaggcg ccttattctg gtataaatat tacaaaggag ggtattcaaa  16560
taggtgtcga aggtcaaaca cctaaatatg ccgataaaac atttcaacct gaacctcaaa  16620
taggagaatc tcagtggtac gaaactgaaa ttaatcatgc agctgggaga gtccttaaaa  16680
agactacccc aatgaaacca tgttacggtt catatgcaaa acccacaaat gaaaatggag  16740
ggcaaggcat tcttgtaaag caacaaaatg gaaagctaga aagtcaagtg gaaatgcaat  16800
ttttctcaac tactgaggcg accgcaggca atggtgataa cttgactcct aaagtggtat  16860
tgtacagtga agatgtagat atagaaaccc cagacactca tatttcttac atgcccacta  16920
ttaaggaagg taactcacga gaactaatgg gccaacaatc tatgcccaac aggcctaatt  16980
acattgcttt tagggacaat tttattggtc taatgtatta caacagcacg ggtaatatgg  17040
gtgttctggc gggccaagca tcgcagttga atgctgttgt agatttgcaa gacagaaaca  17100
cagagctttc ataccagctt ttgcttgatt ccattggtga tagaaccagg tacttttcta  17160
tgtggaatca ggctgttgac agctatgatc cagatgttag aattattgaa aatcatggaa  17220
ctgaagatga acttccaaat tactgctttc cactgggagg tgtgattaat acagagactc  17280
ttaccaaggt aaaacctaaa acaggtcagg aaaatggatg ggaaaaagat gctacagaat  17340
tttcagataa aaatgaaata agagttggaa ataattttgc catggaaatc aatctaaatg  17400
ccaacctgtg gagaaatttc ctgtactcca acatagcgct gtatttgccc gacaagctaa  17460
agtacagtcc ttccaacgta aaaatttctg ataacccaaa cacctacgac tacatgaaca  17520
agcgagtggt ggctcccggg ttagtggact gctacattaa ccttggagca cgctggtccc  17580
ttgactatat ggacaacgtc aacccattta accaccaccg caatgctggc ctgcgctacc  17640
gctcaatgtt gctgggcaat ggtcgctatg tgcccttcca catccaggtg cctcagaagt  17700
tctttgccat taaaaacctc cttctcctgc cgggctcata cacctacgag tggaacttca  17760
ggaaggatgt taacatggtt ctgcagagct ccctaggaaa tgacctaagg gttgacggag  17820
ccagcattaa gtttgatagc atttgccttt acgccacctt cttccccatg gcccacaaca  17880
ccgcctccac gcttgaggcc atgcttagaa acgacaccaa cgaccagtcc tttaacgact  17940
atctctccgc cgccaacatg ctctacccta tacccgccaa cgctaccaac gtgcccatat  18000
ccatcccctc ccgcaactgg gcggctttcc gcggctgggc cttcacgcgc cttaagacta  18060
aggaaacccc atcactgggc tcgggctacg acccttatta cacctactct ggctctatac  18120
cctacctaga tggaaccttt tacctcaacc acacctttaa gaaggtggcc attacctttg  18180
actcttctgt cagctggcct ggcaatgacc gcctgcttac ccccaacgag tttgaaatta  18240
agcgctcagt tgacggggag ggttacaacg ttgcccagtg taacatgacc aaagactggt  18300
tcctggtaca aatgctagct aactacaaca ttggctacca gggcttctat atcccagaga  18360
```

-continued

```
gctacaagga ccgcatgtac tccttcttta gaaacttcca gcccatgagc cgtcaggtgg  18420
tggatgatac taaatacaag gactaccaac aggtgggcat cctacaccaa cacaacaact  18480
ctggatttgt tggctacctt gcccccacca tgcgcgaagg acaggcctac cctgctaact  18540
tcccctatcc gcttataggc aagaccgcag ttgacagcat tacccagaaa aagtttcttt  18600
gcgatcgcac cctttggcgc atcccattct ccagtaactt tatgtccatg ggcgcactca  18660
cagacctggg ccaaaacctt ctctacgcca actccgccca cgcgctagac atgacttttg  18720
aggtggatcc catggacgag cccacccttc tttatgtttt gtttgaagtc tttgacgtgg  18780
tccgtgtgca ccggccgcac cgcggcgtca tcgaaaccgt gtacctgcgc acgcccttct  18840
cggccggcaa cgccacaaca taaagaagca agcaacatca acaacagctg ccgccatggg  18900
ctccagtgag caggaactga aagccattgt caaagatctt ggttgtgggc catatttttt  18960
gggcacctat gacaagcgct ttccaggctt tgtttctcca cacaagctcg cctgcgccat  19020
agtcaatacg gccggtcgcg agactggggg cgtacactgg atggcctttg cctggaaccc  19080
gcactcaaaa acatgctacc tctttgagcc ctttggcttt tctgaccagc gactcaagca  19140
ggtttaccag tttgagtacg agtcactcct gcgccgtagc gccattgctt cttcccccga  19200
ccgctgtata acgctggaaa agtccaccca aagcgtacag gggcccaact cggccgcctg  19260
tggactattc tgctgcatgt ttctccacgc ctttgccaac tggccccaaa ctcccatgga  19320
tcacaacccc accatgaacc ttattaccgg ggtacccaac tccatgctca acagtcccca  19380
ggtacagccc accctgcgtc gcaaccagga acagctctac agcttcctgg agcgccactc  19440
gccctacttc cgcagccaca gtgcgcagat taggagcgcc acttcttttt gtcacttgaa  19500
aaacatgtaa aaataatgta ctagagacac tttcaataaa ggcaaatgct tttatttgta  19560
cactctcggg tgattattta cccccaccct tgccgtctgc gccgtttaaa aatcaaaggg  19620
gttctgccgc gcatcgctat gcgccactgg cagggacacg ttgcgatact ggtgtttagt  19680
gctccactta aactcaggca caaccatccg cggcagctcg gtgaagtttt cactccacag  19740
gctgcgcacc atcaccaacg cgtttagcag gtcgggcgcc gatatcttga agtcgcagtt  19800
ggggcctccg ccctgcgcgc gcgagttgcg atacacaggg ttgcagcact ggaacactat  19860
cagcgccggg tggtgcacgc tggccagcac gctcttgtcg gagatcagat ccgcgtccag  19920
gtcctccgcg ttgctcaggg cgaacggagt caactttggt agctgccttc ccaaaaaggg  19980
cgcgtgccca ggctttgagt tgcactcgca ccgtagtggc atcaaaaggt gaccgtgccc  20040
ggtctgggcg ttaggataca gcgcctgcat aaaagccttg atctgcttaa aagccacctg  20100
agcctttgcg ccttcagaga agaacatgcc gcaagacttg ccggaaaact gattggccgg  20160
acaggccgcg tcgtgcacgc agcaccttgc gtcggtgttg gagatctgca ccacatttcg  20220
gccccaccgg ttcttcacga tcttggcctt gctagactgc tccttcagcg cgcgctgccc  20280
gttttcgctc gtcacatcca tttcaatcac gtgctcctta tttatcataa tgcttccgtg  20340
tagacactta agctcgcctt cgatctcagc gcagcggtgc agccacaacg cgcagcccgt  20400
gggctcgtga tgcttgtagg tcacctctgc aaacgactgc aggtacgcct gcaggaatcg  20460
ccccatcatc gtcacaaagg tcttgttgct ggtgaaggtc agctgcaacc cgcggtgctc  20520
ctcgttcagc caggtcttgc atacggccgc cagagcttcc acttggtcag gcagtagttt  20580
gaagttcgcc tttagatcgt tatccacgtg gtacttgtcc atcagcgcgc gcgcagcctc  20640
catgcccttc tcccacgcag acacgatcgg cacactcagc gggttcatca ccgtaatttc  20700
actttccgct tcgctgggct cttcctcttc ctcttgcgtc cgcataccac gcgccactgg  20760
```

-continued

```
gtcgtcttca ttcagccgcc gcactgtgcg cttacctcct ttgccatgct tgattagcac  20820
cggtgggttg ctgaaaccca ccatttgtag cgccacatct tctctttctt cctcgctgtc  20880
cacgattacc tctggtgatg gcgggcgctc gggcttggga gaagggcgct tctttttctt  20940
cttgggcgca atggccaaat ccgccgccga ggtcgatggc cgcgggctgg gtgtgcgcgg  21000
caccagcgcg tcttgtgatg agtcttcctc gtcctcggac tcgatacgcc gcctcatccg  21060
ctttttttggg ggcgcccggg gaggcggcgg cgacggggac ggggacgaca cgtcctccat  21120
ggttggggga cgtcgcgccg caccgcgtcc gcgctcgggg gtggtttcgc gctgctcctc  21180
ttcccgactg gccatttcct tctcctatag gcagaaaaag atcatggagt cagtcgagaa  21240
gaaggacagc ctaaccgccc cctctgagtt cgccaccacc gcctccaccg atgccgccaa  21300
cgcgcctacc accttccccg tcgaggcacc cccgcttgag gaggaggaag tgattatcga  21360
gcaggaccca ggttttgtaa gcgaagacga cgaggaccgc tcagtaccaa cagaggataa  21420
aaagcaagac caggacaacg cagaggcaaa cgaggaacaa gtcgggcggg gggacgaaag  21480
gcatggcgac tacctagatg tgggagacga cgtgctgttg aagcatctgc agcgccagtg  21540
cgccattatc tgcgacgcgt tgcaagagcg cagcgatgtg cccctcgcca tagcggatgt  21600
cagccttgcc tacgaacgcc acctattctc accgcgcgta ccccccaaac gccaagaaaa  21660
cggcacatgc gagcccaacc cgcgcctcaa cttctacccc gtatttgccg tgccagaggt  21720
gcttgccacc tatcacatct ttttccaaaa ctgcaagata cccctatcct gccgtgccaa  21780
ccgcagccga gcggacaagc agctggcctt gcggcagggc gctgtcatac ctgatatcgc  21840
ctcgctcaac gaagtgccaa aaatctttga gggtcttgga cgcgacgaga agcgcgcggc  21900
aaacgctctg caacaggaaa acagcgaaaa tgaaagtcac tctggagtgt tggtggaact  21960
cgagggtgac aacgcgcgcc tagccgtact aaaacgcagc atcgaggtca cccactttgc  22020
ctacccggca cttaacctac cccccaaggt catgagcaca gtcatgagtg agctgatcgt  22080
gcgccgtgcg cagcccctgg agagggatgc aaatttgcaa gaacaaacag aggagggcct  22140
acccgcagtt ggcgacgagc agctagcgcg ctggcttcaa acgcgcgagc ctgccgactt  22200
ggaggagcga cgcaaactaa tgatggccgc agtgctcgtt accgtggagc ttgagtgcat  22260
gcagcggttc tttgctgacc cggagatgca gcgcaagcta gaggaaacat tgcactacac  22320
ctttcgacag ggctacgtac gccaggcctg caagatctcc aacgtggagc tctgcaacct  22380
ggtctcctac cttggaattt tgcacgaaaa ccgccttggg caaaacgtgc ttcattccac  22440
gctcaagggc gaggcgcgcc gcgactacgt ccgcgactgc gtttacttat ttctatgcta  22500
cacctggcag acggccatgg gcgtttggca gcagtgcttg gaggagtgca acctcaagga  22560
gctgcagaaa ctgctaaagc aaaacttgaa ggacctatgg acggccttca acgagcgctc  22620
cgtggccgcg cacctggcgg acatcatttt ccccgaacgc ctgcttaaaa ccctgcaaca  22680
gggtctgcca gacttcacca gtcaaagcat gttgcagaac tttaggaact ttatcctaga  22740
gcgctcagga atcttgcccg ccacctgctg tgcacttcct agcgactttg tgcccattaa  22800
gtaccgcgaa tgccctccgc cgctttgggg ccactgctac cttctgcagc tagccaacta  22860
ccttgcctac cactctgaca taatggaaga cgtgagcggt gacggtctac tggagtgtca  22920
ctgtcgctgc aacctatgca ccccgcaccg ctccctggtt tgcaattcgc agctgcttaa  22980
cgaaagtcaa attatcggta cctttgagct gcagggtccc tcgcctgacg aaaagtccgc  23040
ggctccgggg ttgaaactca ctccggggct gtggacgtcg gcttaccttc gcaaatttgt  23100
acctgaggac taccacgccc acgagattag gttctacgaa gaccaatccc gcccgccaaa  23160
```

```
tgcggagctt accgcctgcg tcattaccca gggccacatt cttggccaat tgcaagccat  23220
caacaaagcc cgccaagagt ttctgctacg aaagggacgg ggggtttact tggacccccca  23280
gtccggcgag gagctcaacc caatcccccc gccgccgcag ccctatcagc agcagccgcg  23340
ggcccttgct tcccaggatg gcacccaaaa agaagctgca gctgccgccg ccacccacgg  23400
acgaggagga atactgggac agtcaggcag aggaggtttt ggacgaggag gaggaggaca  23460
tgatggaaga ctgggagagc ctagacgagg aagcttccga ggtcgaagag gtgtcagacg  23520
aaacaccgtc accctcggtc gcattcccct cgccggcgcc ccagaaatcg gcaaccggtt  23580
ccagcatggc tacaacctcc gctcctcagg cgccgccggc actgcccgtt cgccgaccca  23640
accgtagatg ggacaccact ggaaccaggg ccggtaagtc caagcagccg ccgccgttag  23700
cccaagagca acaacagcgc caaggctacc gctcatggcg cgggcacaag aacgccatag  23760
ttgcttgctt gcaagactgt gggggcaaca tctccttcgc ccgccgcttt cttctctacc  23820
atcacggcgt ggccttcccc cgtaacatcc tgcattacta ccgtcatctc tacagcccat  23880
actgcaccgg cggcagcggc agcggcagca acagcagcgg ccacacagaa gcaaaggcga  23940
ccggatagca agactctgac aaagcccaag aaatccacag cggcggcagc agcaggagga  24000
ggagcgctgc gtctggcgcc caacgaaccc gtatcgaccc gcgagcttag aaacaggatt  24060
tttcccactc tgtatgctat atttcaacag agcaggggcc aagaacaaga gctgaaaata  24120
aaaaacaggt ctctgcgatc cctcacccgc agctgcctgt atcacaaaag cgaagatcag  24180
cttcggcgca cgctggaaga cgcggaggct ctcttcagta aatactgcgc gctgactctt  24240
aaggactagt ttcgcgccct ttctcaaatt taagcgcgaa aactacgtca tctccagcgg  24300
ccacacccgg cgccagcacc tgtcgtcagc gccattatga gcaaggaaat tcccacgccc  24360
tacatgtgga gttaccagcc acaaatggga cttgcggctg gagctgccca agactactca  24420
acccgaataa actacatgag cgcgggaccc cacatgatat cccgggtcaa cggaatccgc  24480
gcccaccgaa accgaattct cttggaacag gcggctatta ccaccacacc tcgtaataac  24540
cttaatcccc gtagttggcc cgctgccctg gtgtaccagg aaagtcccgc tcccaccact  24600
gtggtacttc ccagagacgc ccaggccgaa gttcagatga ctaactcagg ggcgcagctt  24660
gcgggcggct ttcgtcacag ggtgcggtcg cccgggcagg gtataactca cctgacaatc  24720
agagggcgag gtattcagct caacgacgag tcggtgagct cctcgcttgg tctccgtccg  24780
gacgggacat ttcagatcgg cggcgccggc cgtccttcat tcacgcctcg tcaggcaatc  24840
ctaactctgc agacctcgtc ctctgagccg cgctctggag gcattggaac tctgcaattt  24900
attgaggagt ttgtgccatc ggtctacttt aacccctttct cgggacctcc cggccactat  24960
ccggatcaat ttattcctaa ctttgacgcg gtaaaggact cggcggacgg ctacgactga  25020
atgttaagtg gagaggcaga gcaactgcgc ctgaaacacc tggtccactg tcgccgccac  25080
aagtgctttg cccgcgactc cggtgagttt tgctactttg aattgcccga ggatcatatc  25140
gagggcccgg cgcacggcgt ccggcttacc gcccagggag agcttgcccg tagcctgatt  25200
cgggagttta cccagcgccc cctgctagtt gagcgggaca ggggaccctg tgttctcact  25260
gtgatttgca actgtcctaa ccttggatta catcaagatc ctctagttaa ttaacagctt  25320
gcatgcctgc aggtcgacgg atcgggagat ctcggccgca tattaagtgc attgttctcg  25380
ataccgctaa gtgcattgtt ctcgttagct cgatggacaa gtgcattgtt ctcttgctga  25440
aagctcgatg gacaagtgca ttgttctctt gctgaaagct cgatggacaa gtgcattgtt  25500
ctcttgctga aagctcagta cccgggagta ccctcgaccg ccggagtata aatagaggcg  25560
```

-continued

```
cttcgtctac ggagcgacaa ttcaattcaa acaagcaaag tgaacacgtc gctaagcgaa  25620
agctaagcaa ataaacaagc gcagctgaac aagctaaaca atctgcagta aagtgcaagt  25680
taaagtgaat caattaaaag taaccagcaa ccaagtaaat caactgcaac tactgaaatc  25740
tgccaagaag taattattga atacaagaag agaactctga atactttcaa caagttaccg  25800
agaaagaaga actcacacac agctagcgtt taaacttaag cttcaccatg gtggggccct  25860
gcatgctgct gctgctgctg ctgctgggcc tgaggctaca gctctccctg ggcatcatcc  25920
tagttgagga ggagaacccg gacttctgga accgcgaggc agccgaggcc ctgggtgccg  25980
ccaagaagct gcagcctgca cagacagccg ccaagaacct catcatcttc ctgggcgatg  26040
gggtgggggt gtctacggtg acagctgcca ggatcctaaa agggcagaag aaggacaaac  26100
tggggcctga gatacccctg gccatggacc gcttcccata tgtggctctg tccaagacat  26160
acaatgtaga caaacatgtg ccagacagtg gagccacagc cacggcctac ctgtgcgggg  26220
tcaagggcaa cttccagacc attggcttga gtgcagccgc ccgctttaac cagtgcaaca  26280
cgacacgcgg caacgaggtc atctccgtga tgaatcgggc caagaaagca gggaagtcag  26340
tgggagtggt aaccaccaca cgagtgcagc acgcctcgcc agccggcacc tacgcccaca  26400
cggtgaaccg caactggtac tcggacgccg acgtgcctgc ctcggcccgc caggaggggt  26460
gccaggacat cgctacgcag ctcatctcca acatggacat tgacgtgatc ctaggtgggg  26520
gccgaaagta catgtttcgc atgggaaccc cagaccctga gtacccagat gactacagcc  26580
aaggtgggac caggctggac gggaagaatc tggtgcagga atggctggcg aagcaccagg  26640
gtgcccggta cgtgtggaac cgcactgagc tcatgcgggc ttccctggac ccgtctgtgg  26700
cccatctcat gggtctcttt gagcctggag acatgaaata cgagatccac cgagactcca  26760
cactggaccc ctccctgatg gagatgacag aggctgccct gcgcctgctg agcaggaacc  26820
cccgcggctt cttcctcttc gtggagggtg gtcgcatcga ccatggtcat catgaaagca  26880
gggcttaccg ggcactgact gagacgatca tgttcgacga cgccattgag agggcgggcc  26940
agctcaccag cgaggaggac acgctgagcc tcgtcactgc cgaccactcc cacgtcttct  27000
ccttcggagg ctgccccctg cgagggggct ccatcttcgg gctggcccct ggcaaggccc  27060
gggacaggaa ggcctacacg gtcctcctat acggaaacgg tccaggctat gtgctcaagg  27120
acggcgcccg gccggatgtt accgagagcg agagcgggag ccccgagtat cggcagcagt  27180
cagcagtgcc cctggacgaa gagacccacg caggcgagga cgtggcggtg ttcgcgcgcg  27240
gcccgcaggc gcacctggtt cacggcgtgc aggagcagac cttcatagcg cacgtcatgg  27300
ccttcgccgc ctgcctggag ccctacaccg cctgcgacct ggcgcccccc gccggcacca  27360
ccgacgccgc gcacccgggg cggtccgtgg tccccgcgtt gcttcctctg ctggccggga  27420
ccctgctgct gctggagacg gccactgctc cctgagtgtc ccgtccctgg ggctcctgct  27480
tccccatccc ggagttctcc tgctccccgc ctcctgtcgt cctgcctggc ctccagcccg  27540
agtcgtcatc cccggagtcc ctatacagag gtcctgccat ggaaccttcc cctccccgtg  27600
cgctctgggg actgagccca tgacaccaaa cctgcccctt ggctgctctc ggactcccta  27660
ccccaacccc agggacagat ctggccagat ttgtaaaaca aatagatttt aggcccaaag  27720
attatttaaa gcattgcctg gaacgcagtg agtttttgtt agaaaagaga ataattcaaa  27780
gtggcattgc tttgcttctt atgttaattt ggtacagacc tgtggctgag tttgctcaaa  27840
gtattcagag cagaattgtg gagtggaaag agagattgga caaagagttt agtttgtcag  27900
tgtatcaaaa aatgaagttt aatgtggcta tgggaattgg agttttagat tggctaagaa  27960
```

-continued

```
acagtgatga tgatgatgaa gacagccagg aaaatgctga taaaaatgaa gatggtgggg  28020
agaagaacat ggaagactca gggcatgaaa caggcattga ttcacagtcc caaggctcat  28080
ttcaggcccc tcagtcctca cagtctgttc atgatcataa tcagccatac cacatttgta  28140
gaggttttac ttgctttaaa aaacctccca cacctccccc tgaacctgaa acataaaatg  28200
aatgcaattg ttgttgttaa cttgtttatt gcagcttata atggttacaa ataaagcaat  28260
agcatcacaa atttcacaaa taaagcattt ttttcactgc attctagttg tggtttgtcc  28320
aaactcatca atgtatctta tcatgtctgg atccccagga agctcctctg tgtcctcata  28380
aaccctaacc tcctctactt gagaggacat tccaatcata ggctgcccat ccaccctctg  28440
tgtcctcctg ttaattaggt cacttaacaa aaaggaaatt gggtaggggt ttttcacaga  28500
ccgctttcta agggtaattt taaaatatct gggaagtccc ttccactgct gtgttccaga  28560
agtgttggta aacagcccac aaatgtcaac agcagaaaca tacaagctgt cagctttgca  28620
caagggccca acaccctgct catcaagaag cactgtggtt gctgtgttag taatgtgcaa  28680
aacaggaggc acattttccc cacctgtgta ggttccaaaa tatctagtgt tttcattttt  28740
acttggatca ggaacccagc actccactgg ataagcatta tccttatcca aaacagcctt  28800
gtggtcagtg ttcatctgct gactgtcaac tgtagcattt tttggggtta cagtttgagc  28860
aggatatttg gtcctgtagt ttgctaacac accctgcagc tccaaaggtt ccccaccaac  28920
agcaaaaaaa tgaaaatttg acccttgaat gggttttcca gcaccatttt catgagtttt  28980
ttgtgtccct gaatgcaagt ttaacatagc agttacccca ataacctcag ttttaacagt  29040
aacagcttcc cacatcaaaa tatttccaca ggttaagtcc tcatttaaat taggcaaagg  29100
aattccactt cccactgcct tgcttccgtc tcccattcaa acttttatca actgacatta  29160
ttctaagtaa aatcctcttc attatgttgt cagcaatcca ttgcttgaag gcctggctcc  29220
ccagaacccc tcgactggta tgtcttctcc tagaatactc cagaagaaaa ggagtgtatg  29280
aagatagtga ctgcacatta aaatgactga aaccatagta aattaggatg agattctggg  29340
cagataaaca gacagctggc taggatcatt tttttatgcc ttggacttct ttggcaatct  29400
gttgaagcct gacattcctc agaataatgt tttaaagccc aacaataaga ccctgtagca  29460
catataataa gtactgcagt tttgaagtag tgataagcat aaatgatatt ttgatatatt  29520
tattataact gtaatgagat gtgtacatat ctgtgacttc ataggtactg attgtactac  29580
tgtgattttt ttgcctactt tcaaaatgaa aaggaatgct taatttcagt tagaggttag  29640
taaagacaaa taggtaattt tcttctccag tgaagagcat ggcgcccctt gctattcatg  29700
gacgcttgct taaagacttg tacacaggct tgctttgtat caacctatga cttcccctta  29760
cagccgatga taggttttta tttgcacctc cttcgtgtac aaagacagtt ttggtggcta  29820
cgccatcatt aaactcatta ttatcatgct taagcctata gatgtatcca gttcttctgt  29880
tacataattg aagctgtagt gaattgtcta tcttaaactg catcgctaac tgactacatt  29940
tcacacttca tttgcttcca acatagacta accttcttgg atgtccacta ttatttgaac  30000
ttttgagatt ttttttccta tttctaatat cttaaaattt cagaagactt aaagttttgc  30060
aactacaggg ctccatatag acatctagct tgaatttata cactttcttt cattgatgtc  30120
cctggactaa aaaatgttaa atatttctaa ccgctgtact taaagtccat tacaaacgaa  30180
gactactgtt gttaagttga ataggcatct tatatatttt tcaccggtgc aataaataac  30240
ttctattccc ttctaacatc tgcttgcgtt gcactgagag tacactattg attagcaata  30300
ggttcgtgat tacagccctt ctataattaa ttgttaggtt aacatattat tcataaaata  30360
```

-continued

```
ttattttatt aatttttact tgatttgcta ctggatgctt agaaatagct atgagtatat  30420
tggtagaacc agtacttata ttttattaca tttttacatt tcataaaatt taagtgatat  30480
aaaaatcctg aggaagtatg ccacaaaagt ggtctcagtg gaaatttaaa tatgttaaca  30540
tttattttta aaatgtagcg tgaaatagac aactttaaaa gctcagctta aaaaaaaaac  30600
tcaaggaagc tgaacttgac tttttaaagc actgaagtgc aatatttaat gtaggtcaac  30660
atgtttaaat gggaaaattt ttttcctaat tacagccaaa tccctagctg taattaactt  30720
aaaatttgta tactatttca caacagagtc agcatatacc actttcttat aaaattagaa  30780
agatctaaaa ttttagagct tatttggtga aacaggcata ttgctacatc tttgtttata  30840
aattataatg tgcctttaga gcccaataac agataacaag attttgaaaa ttcaggtgaa  30900
ttagagttat cagagggaat gttaatacac tctattcaaa tactatatga gtaagacatt  30960
taaaatagga aacaatactt tatatattaa aaaaaattaa tcttccagtc gatttaatcc  31020
actttatgaa ttcatttaaa tcgatttaaa ttcgaattaa ttaactagag tacccgggga  31080
tcttattccc tttaactaat aaaaaaaaat aataaagcat cacttactta aaatcagtta  31140
gcaaatttct gtccagttta ttcagcagca cctccttgcc ctcctcccag ctctggtatt  31200
gcagcttcct cctggctgca aactttctcc acaatctaaa tggaatgtca gtttcctcct  31260
gttcctgtcc atccgcaccc actatcttca tgttgttgca gatgaagcgc gcaagaccgt  31320
ctgaagatac cttcaacccc gtgtatccat atgacacgga aaccggtcct ccaactgtgc  31380
cttttcttac tcctcccttt gtatccccca atgggtttca agagagtccc cctggggtac  31440
tctctttgcg cctatccgaa cctctagtta cctccaatgg catgcttgcg ctcaaaatgg  31500
gcaacggcct ctctctggac gaggccggca accttacctc ccaaaatgta accactgtga  31560
gcccacctct caaaaaaacc aagtcaaaca taaacctgga aatatctgca cccctcacag  31620
ttacctcaga agccctaact gtggctgccg ccgcacctct aatggtcgcg ggcaacacac  31680
tcaccatgca atcacaggcc ccgctaaccg tgcacgactc caaacttagc attgccaccc  31740
aaggacccct cacagtgtca gaaggaaagc tagccctgca aacatcaggc cccctcacca  31800
ccaccgatag cagtaccctt actatcactg cctcaccccc tctaactact gccactggta  31860
gcttgggcat tgacttgaaa gagcccattt atacacaaaa tggaaaacta ggactaaagt  31920
acggggctcc tttgcatgta acagacgacc taaacacttt gaccgtagca actggtccag  31980
gtgtgactat taataatact tccttgcaaa ctaaagttac tggagccttg ggttttgatt  32040
cacaaggcaa tatgcaactt aatgtagcag gaggactaag gattgattct caaaacagac  32100
gccttatact tgatgttagt tatccgtttg atgctcaaaa ccaactaaat ctaagactag  32160
gacagggccc tctttttata aactcagccc acaacttgga tattaactac aacaaaggcc  32220
tttacttgtt tacagcttca aacaattcca aaaagcttga ggttaaccta agcactgcca  32280
aggggttgat gtttgacgct acagccatag ccattaatgc aggagatggg cttgaatttg  32340
gttcacctaa tgcaccaaac acaaatcccc tcaaaacaaa aattggccat ggcctagaat  32400
ttgattcaaa caaggctatg gttcctaaac taggaactgg ccttagtttt gacagcacag  32460
gtgccattac agtaggaaac aaaaataatg ataagctaac tttgtggacc acaccagctc  32520
catctcctaa ctgtagacta aatgcagaga aagatgctaa actcactttg gtcttaacaa  32580
aatgtggcag tcaaatactt gctacagttt cagttttggc tgttaaaggc agtttggctc  32640
caatatctgg aacagttcaa agtgctcatc ttattataag atttgacgaa aatggagtgc  32700
tactaaacaa ttccttcctg gacccagaat attggaactt tagaaatgga gatcttactg  32760
```

aaggcacagc ctatacaaac gctgttggat ttatgcctaa cctatcagct tatccaaaat 32820
ctcacggtaa aactgccaaa agtaacattg tcagtcaagt ttacttaaac ggagacaaaa 32880
ctaaacctgt aacactaacc attacactaa acggtacaca ggaaacagga gacacaactc 32940
caagtgcata ctctatgtca ttttcatggg actggtctgg ccacaactac attaatgaaa 33000
tatttgccac atcctcttac actttttcat acattgccca agaataaaga atcgtttgtg 33060
ttatgtttca acgtgtttat ttttcaattg cagaaaattt caagtcattt ttcattcagt 33120
agtatagccc caccaccaca tagcttatac agatcaccgt accttaatca aactcacaga 33180
accctagtat tcaacctgcc acctccctcc caacacacag agtacacagt cctttctccc 33240
cggctggcct taaaaagcat catatcatgg gtaacagaca tattcttagg tgttatattc 33300
cacacggttt cctgtcgagc caaacgctca tcagtgatat taataaactc cccgggcagc 33360
tcacttaagt tcatgtcgct gtccagctgc tgagccacag gctgctgtcc aacttgcggt 33420
tgcttaacgg gcggcgaagg agaagtccac gcctacatgg gggtagagtc ataatcgtgc 33480
atcaggatag ggcggtggtg ctgcagcagc gcgcgaataa actgctgccg ccgccgctcc 33540
gtcctgcagg aatacaacat ggcagtggtc tcctcagcga tgattcgcac cgcccgcagc 33600
ataaggcgcc ttgtcctccg ggcacagcag cgcaccctga tctcacttaa atcagcacag 33660
taactgcagc acagcaccac aatattgttc aaaatcccac agtgcaaggc gctgtatcca 33720
aagctcatgg cggggaccac agaacccacg tggccatcat accacaagcg caggtagatt 33780
aagtggcgac ccctcataaa cacgctggac ataaacatta cctcttttgg catgttgtaa 33840
ttcaccacct cccggtacca tataaacctc tgattaaaca tggcgccatc caccaccatc 33900
ctaaaccagc tggccaaaac ctgcccgccg gctatacact gcagggaacc gggactggaa 33960
caatgacagt ggagagccca ggactcgtaa ccatggatca tcatgctcgt catgatatca 34020
atgttggcac aacacaggca cacgtgcata cacttcctca ggattacaag ctcctcccgc 34080
gttagaacca tatcccaggg aacaacccat tcctgaatca gcgtaaatcc cacactgcag 34140
ggaagacctc gcacgtaact cacgttgtgc attgtcaaag tgttacattc gggcagcagc 34200
ggatgatcct ccagtatggt agcgcgggtt tctgtctcaa aaggaggtag acgatcccta 34260
ctgtacggag tgcgccgaga caaccgagat cgtgttggtc gtagtgtcat gccaaatgga 34320
acgccggacg tagtcatatt tcctgaagca aaaccaggtg cgggcgtgac aaacagatct 34380
gcgtctccgg tctcgccgct tagatcgctc tgtgtagtag ttgtagtata tccactctct 34440
caaagcatcc aggcgccccc tggcttcggg ttctatgtaa actccttcat gcgccgctgc 34500
cctgataaca tccaccaccg cagaataagc cacacccagc caacctacac attcgttctg 34560
cgagtcacac acgggaggag cgggaagagc tggaagaacc atgttttttt ttttattcca 34620
aaagattatc caaaacctca aaatgaagat ctattaagtg aacgcgctcc cctccggtgg 34680
cgtggtcaaa ctctacagcc aaagaacaga taatggcatt tgtaagatgt tgcacaatgg 34740
cttccaaaag gcaaacggcc ctcacgtcca agtggacgta aaggctaaac ccttcagggt 34800
gaatctcctc tataaacatt ccagcacctt caaccatgcc caaataattc tcatctcgcc 34860
accttctcaa tatatctcta agcaaatccc gaatattaag tccggccatt gtaaaaatct 34920
gctccagagc gccctccacc ttcagcctca agcagcgaat catgattgca aaaattcagg 34980
ttcctcacag acctgtataa gattcaaaag cggaacatta acaaaaatac cgcgatcccg 35040
taggtccctt cgcagggcca gctgaacata atcgtgcagg tctgcacgga ccagcgcggc 35100
cacttccccg ccaggaacct tgacaaaaga acccacactg attatgacac gcatactcgg 35160

-continued

```
agctatgcta accagcgtag ccccgatgta agctttgttg catgggcggc gatataaaat  35220
gcaaggtgct gctcaaaaaa tcaggcaaag cctcgcgcaa aaaagaaagc acatcgtagt  35280
catgctcatg cagataaagg caggtaagct ccggaaccac cacagaaaaa gacaccattt  35340
ttctctcaaa catgtctgcg ggtttctgca taaacacaaa ataaaataac aaaaaaacat  35400
ttaaacatta gaagcctgtc ttacaacagg aaaaacaacc cttataagca taagacggac  35460
tacggccatg ccggcgtgac cgtaaaaaaa ctggtcaccg tgattaaaaa gcaccaccga  35520
cagctcctcg gtcatgtccg gagtcataat gtaagactcg gtaaacacat caggttgatt  35580
catcggtcag tgctaaaaag cgaccgaaat agcccggggg aatacatacc cgcaggcgta  35640
gagacaacat tacagccccc ataggaggta taacaaaatt aataggagag aaaaacacat  35700
aaacacctga aaaaccctcc tgcctaggca aaatagcacc ctcccgctcc agaacaacat  35760
acagcgcttc acagcggcag cctaacagtc agccttacca gtaaaaaaga aaacctatta  35820
aaaaaacacc actcgacacg gcaccagctc aatcagtcac agtgtaaaaa agggccaagt  35880
gcagagcgag tatatatagg actaaaaaat gacgtaacgg ttaaagtcca caaaaaacac  35940
ccagaaaacc gcacgcgaac ctacgcccag aaacgaaagc caaaaaaccc acaacttcct  36000
caaatcgtca cttccgtttt cccacgttac gtaacttccc atttaagaa aactacaatt  36060
cccaacacat acaagttact ccgccctaaa acctacgtca cccgccccgt tcccacgccc  36120
cgcgccacgt cacaaactcc accccctcat tatcatattg gcttcaatcc aaaataaggt  36180
atattattga tgatggccgg ccgaattgaa tcaggggata acgcaggaaa gaacatgtga  36240
gcaaaaggcc agcaaaaggc caggaaccgt aaaaaggccg cgttgctggc gtttttccat  36300
aggctccgcc cccctgacga gcatcacaaa aatcgacgct caagtcagag gtggcgaaac  36360
ccgacaggac tataaagata ccaggcgttt ccccctggaa gctccctcgt gcgctctcct  36420
gttccgaccc tgccgcttac cggatacctg tccgcctttc tcccttcggg aagcgtggcg  36480
ctttctcata gctcacgctg taggtatctc agttcggtgt aggtcgttcg ctccaagctg  36540
ggctgtgtgc acgaaccccc cgttcagccc gaccgctgcg ccttatccgg taactatcgt  36600
cttgagtcca acccggtaag acacgactta tcgccactgg cagcagccac tggtaacagg  36660
attagcagag cgaggtatgt aggcggtgct acagagttct tgaagtggtg gcctaactac  36720
ggctacacta gaaggacagt atttggtatc tgcgctctgc tgaagccagt taccttcgga  36780
aaaagagttg gtagctcttg atccggcaaa caaaccaccg ctggtagcgg tggttttttt  36840
gtttgcaagc agcagattac gcgcagaaaa aaaggatctc aagaagatcc tttgatcttt  36900
tctacggggt ctgacgctca gtggaacgaa aactcacgtt aagggatttt ggtcatgaga  36960
ttatcaaaaa ggatcttcac ctagatcctt ttaaattaaa aatgaagttt taaatcaatc  37020
taaagtatat atgagtaaac ttggtctgac agttaccaat gcttaatcag tgaggcacct  37080
atctcagcga tctgtctatt tcgttcatcc atagttgcct gactccccgt cgtgtagata  37140
actacgatac gggagggctt accatctggc cccagtgctg caatgatacc gcgagaccca  37200
cgctcaccgg ctccagattt atcagcaata aaccagccag ccggaagggc cgagcgcaga  37260
agtggtcctg caactttatc cgcctccatc cagtctatta attgttgccg ggaagctaga  37320
gtaagtagtt cgccagttaa tagtttgcgc aacgttgttg ccattgctac aggcatcgtg  37380
gtgtcacgct cgtcgtttgg tatggcttca ttcagctccg gttcccaacg atcaaggcga  37440
gttacatgat cccccatgtt gtgcaaaaaa gcggttagct ccttcggtcc tccgatcgtt  37500
gtcagaagta agttggccgc agtgttatca ctcatggtta tggcagcact gcataattct  37560
```

cttactgtca tgccatccgt aagatgcttt tctgtgactg gtgagtactc aaccaagtca 37620
ttctgagaat agtgtatgcg gcgaccgagt tgctcttgcc cggcgtcaat acgggataat 37680
accgcgccac atagcagaac tttaaaagtg ctcatcattg gaaaacgttc ttcggggcga 37740
aaactctcaa ggatcttacc gctgttgaga tccagttcga tgtaacccac tcgtgcaccc 37800
aactgatctt cagcatcttt tactttcacc agcgtttctg ggtgagcaaa aacaggaagg 37860
caaaatgccg caaaaaaggg aataagggcg acacggaaat gttgaatact catactcttc 37920
ctttttcaat attattgaag catttatcag ggttattgtc tcatgagcgg atacatattt 37980
gaatgtattt agaaaaataa acaaataggg gttccgcgca catttccccg aaaagtgcca 38040
c 38041

<210> SEQ ID NO 14
<211> LENGTH: 7180
<212> TYPE: DNA
<213> ORGANISM: Artificial Sequence
<220> FEATURE:
<223> OTHER INFORMATION: Synthetic

<400> SEQUENCE: 14
tctagagtcg accggtcatg gctgcgcccc gacacccgcc aacacccgct gacgcgccct 60
gacgggcttg tctgctcccg gcatccgctt acagacaagc tgtgaccgtc tccgggagct 120
gcatgtgtca gaggttttca ccgtcatcac cgaaacgcgc gaggcagccg gatcataatc 180
agccatacca catttgtaga ggttttactt gctttaaaaa acctccccac ctcccccctga 240 acctgaaaca taaaatgaat gcaattgttg ttgttaactt gtttattgca gcttataatg 300
gttacaaata aagcaatagc atcacaaatt tcacaaataa agcatttttt tcactgcatt 360
ctagttgtgg tttgtccaaa ctcatcaatg tatcttatca tgtctggatc cagttcgatg 420
taacccactc gtgcacccaa ctgatcttca gcatctttta ctttcaccag cgtttctggg 480
tgagcaaaaa caggaaggca aaatgccgca aaaaagggaa taagggcgac acggaaatgt 540
tgaatactca tactcttcct ttttcaatat tattgaagca tttatcaggg ttattgtctc 600
atgagcggat acatatttga atgtatttag aaaaataaac aaataggggt tccgcgcaca 660
tttccccgaa aagtgccacc tgacgtccat tgttcattcc acggacaaaa acagagaaag 720
gaaacgacag aggccaaaaa gcctcgcttt cagcacctgt cgtttccttt cttttcagag 780
ggtattttaa ataaaaacat taagttatga cgaagaagaa cggaaacgcc ttaaaccgga 840
aaattttcat aaatagcgaa aacccgcgag gtcgccgccc cgtaacctgt cggatcaccg 900
gaaaggaccc gtaaagtgat aatgattatc atctagacta catcgatggg tcgtgcgctc 960
ctttcggtcg ggcgctgcgg gtcgtggggc gggcgtcagg caccgggctt gcgggtcatg 1020
caccaggtcg cgcggtcctt cgggcactcg acgtcggcgg tgacggtgaa gccgagccgc 1080
tcgtagaagg ggaggttgcg gggcgcggag gtctccagga aggcgggcac cccggcgcgc 1140
tcggccgcct ccactccggg gagcacgacg gcgctgccca gacccttgcc ctggtggtcg 1200
ggcgagacgc cgacggtggc caggaaccac gcgggctcct tgggccggtg cggcgccagg 1260
aggccttcca tctgttgctg cgcggccagc cgggaaccgc tcaactcggc catgcgcggg 1320
ccgatctcgg cgaacaccgc ccccgcttcg acgctctccg gcgtggtcca gaccgccacc 1380
gcggcgccgt cgtccgcgac ccacaccttg ccgatgtcga gcccgacgcg cgtgaggaag 1440
agttcttgca gctcggtgac ccgctcgatg tggcggtccg gatcgacggt gtggcgcgtg 1500
gcggggtagt cggcgaacgc ggcggcgagg gtgcgtacgg ccctggggac gtcgtcgcgg 1560

-continued

```
gtggcgaggc gcaccgtggg cttgtactcg gtcatggtaa gcttgctagc agctggtacc   1620
cagcttctag agatctgacg gttcactaaa cgagctctgc ttatatagac ctcccaccgt   1680
acacgcctac cgcccatttg cgtcaacggg gcggggttat tacgacattt tggaaagtcc   1740
cgttgatttt ggtgccaaaa caaactccca ttgacgtcaa tggggtggag acttggaaat   1800
ccccgtgagt caaaccgcta tccacgccca ttggtgtact gccaaaaccg catcaccatg   1860
gtaatagcga tgactaatac gtagatgtac tgccaagtag gaaagtcccg taaggtcatg   1920
tactgggcat aatgccaggc gggccattta ccgtcattga cgtcaatagg gggcggactt   1980
ggcatatgat acacttgatg tactgccaag tgggcagttt accgtaaata ctccacccat   2040
tgacgtcaat ggaaagtccc tattggcgtt actatgggaa catacgtcat tattgacgtc   2100
aatgggcggg ggtcgttggg cggtcagcca ggcgggccat ttaccgtaag ttatgtaacg   2160
cggaactcca tatatgggct atgaactaat gaccccgtaa ttgattacta ttaataacta   2220
gtcaataatc aatgtcaaca tggcggtcat attggacatg agccaatata aatgtacata   2280
ttatgatata gatacaacgt atgcaatggc caatagccaa tattgattta tgctatataa   2340
ccaatgacta atatggctaa ttgccaatat tgattcaatg tatagatctt ccatacctac   2400
cagttctgcg cctgcagcaa tgcaacaacg ttgcccggat ctgcgatgat aagctgtcaa   2460
acatgagaat tggtcgacta gcttggcacg ccagaaatcc gcgcggtggt ttttgggggt   2520
cgggggtgtt tggcagccac agacgcccgg tgttcgtgtc gcgccagtac atgcggtcca   2580
tgcccaggcc atccaaaaac catgggtctg tctgctcagt ccagtcgtgg accagacccc   2640
acgcaacgcc caaaataata acccccacga accataaacc attccccatg ggggaccccg   2700
tccctaaccc acggggccag tggctatggc agggcctgcc gccccgacgt tggctgcgag   2760
ccctgggcct tcacccgaac ttgggggggtg gggtggggaa aaggaagaaa cgcgggcgta   2820
ttggccccaa tggggtctcg gtggggtatc gacagagtgc cagccctggg accgaacccc   2880
gcgtttatga acaaacgacc caacacccgt gcgttttatt ctgtcttttt attgccgtca   2940
tagcgcgggt tccttccggt attgtctcct tccgtgtttc agttagcctc cccatctcc    3000
cctattcctt tgccctcgga cgagtgctgg ggcgtcggtt tccactatcg gcgagtactt   3060
ctacacagcc atcggtccag acggccgcgc ttctgcgggc gatttgtgta cgcccgacag   3120
tcccggctcc ggatcggacg attgcgtcgc atcgaccctg cgcccaagct gcatcatcga   3180
aattgccgtc aaccaagctc tgatagagtt ggtcaagacc aatgcggagc atatacgccc   3240
ggagccgcgg cgatcctgca agctccggat gcctccgctc gaagtagcgc gtctgctgct   3300
ccatacaagc caaccacggc ctccagaaga agatgttggc gacctcgtat tgggaatccc   3360
cgaacatcgc ctcgctccag tcaatgaccg ctgttatgcg gccattgtcc gtcaggacat   3420
tgttggagcc gaaatccgcg tgcacgaggt gccggacttc ggggcagtcc tcggcccaaa   3480
gcatcagctc atcgagagcc tgcgcgacgg acgcactgac ggtgtcgtcc atcacagttt   3540
gccagtgata cacatgggga tcagcaatcg cgcatatgaa atcacgccat gtagtgtatt   3600
gaccgattcc ttgcggtccg aatgggccga acccgctcgt ctggctaaga tcggccgcag   3660
cgcgcgcaaa accccctaaat aaagacagca agacacttgc ttgatccaaa tccaaacaga   3720
gtctggtttt ttatttatgt tttaaaccgc attgggaggg gaggaagcct tcagggcaga   3780
aacctgctgg cgcagatcca acagctgctg agaaacgaca ttaagttccc gggtcaaaga   3840
atccaattgt gccaaaagag ccgtcaactt gtcatcgcgg gcggatgaac gggaagctgc   3900
actgcttgca agcgggctca ggaaagcaaa gtcagtcaca atcccgcggg cggtggctgc   3960
```

-continued

```
agcggctgaa gcggcggcgg aggctgcagt ctccaacggc gttccagaca cggtctcgta   4020
ggtcaaggta gtagagtttg cgggcaggac ggggcgacca tcaatgctgg agcccatcac   4080
attctgacgc accccggccc atgggggcat gcgcgttgtc aaatatgagc tcacaatgct   4140
tccatcaaac gagttggtgc tcatggcggc ggcggctgct gcaaaacaga tacaaaacta   4200
cataagaccc ccaccttata tattctttcc cacccgggat ctgcggcacg ctgttgacgc   4260
tgttaagcgg gtcgctgcag ggtcgctcgg tgttcgaggc cacacgcgtc accttaatat   4320
gcgaagtgga cctgggaccg cgccgccccg actgcatctg cgtgttcgaa ttcgccaatg   4380
acaagacgct gggcggggtt tgtgtcatca tagaactaaa gacatgcaaa tatatttctt   4440
ccggggacac cgccagcaaa cgcgagcaac gggccacggg gatgaagcag ggcatggcgg   4500
ccgacgcgct gggctacgtc ttgctggcgt tcgcgacgcg aggctggatg gccttcccca   4560
ttatgattct tctcgcttcc ggcggcatcg ggatgcccgc gttgcaggcc atgctgtcca   4620
ggcaggtaga tgacgaccat cagggacagc ttcaaggatc gctcgcggct cttaccagcc   4680
taacttcgat cactggaccg ctgatcgtca cggcgattta tgccgcctcg gcgagcacat   4740
ggaacgggtt ggcatggatt gtaggcgccg ccctatacct tgtctgcctc cccgcgttgc   4800
gtcgcggtgc atggagccgg gccacctcga cctgaatgga agccggcggc acctcgctaa   4860
cggattcacc actccaagaa ttggagccaa tcaattcttg cggagaactg tgaatgcgca   4920
aaccaaccct tggcagaaca tatccatcgc gtccgccatc tccagcagcc gcacgcggcg   4980
cagcaaaagg ccaggaaccg taaaaaggcc gcgttgctgg cgtttttcca taggctccgc   5040
ccccctgacg agcatcacaa aaatcgacgc tcaagtcaga ggtggcgaaa cccgacagga   5100
ctataaagat accaggcgtt tccccctgga agctccctcg tgcgctctcc tgttccgacc   5160
ctgccgctta ccggatacct gtccgccttt ctcccttcgg gaagcgtggc gctttctcat   5220
agctcacgct gtaggtatct cagttcggtg taggtcgttc gctccaagct gggctgtgtg   5280
cacgaacccc ccgttcagcc cgaccgctgc gccttatccg gtaactatcg tcttgagtcc   5340
aacccggtaa gacacgactt atcgccactg gcagcagcca ctggtaacag gattagcaga   5400
gcgaggtatg taggcggtgc tacagagttc ttgaagtggt ggcctaacta cggctacact   5460
agaaggacag tatttggtat ctgcgctctg ctgaagccag ttaccttcgg aaaaagagtt   5520
ggtagctctt gatccggcaa acaaaccacc gctggtagcg gtggtttttt tgtttgcaag   5580
cagcagatta cgcgcagaaa aaaaggatct caagaagatc ctttgatctt ttctacgggg   5640
tctgacgctc agtggaacga aaactcacgt taagggattt tggtcatgag attatcaaaa   5700
aggatcttca cctagatcct tttaaattaa aaatgaagtt ttaaatcaat ctaaagtata   5760
tatgagtaaa cttggtctga cagttaccaa tgcttaatca gtgaggcacc tatctcagcg   5820
atctgtctat ttcgttcatc catagttgcc tgactccccg tcgtgtagat aactacgata   5880
cgggagggct taccatctgg ccccagtgct gcaatgatac cgcgagaccc acgctcaccg   5940
gctccagatt tatcagcaat aaaccagcca gccggaaggg ccgagcgcag aagtggtcct   6000
gcaactttat ccgcctccat ccagtctatt aattgttgcc gggaagctag agtaagtagt   6060
tcgccagtta atagtttgcg caacgttgtt gccattgctg caggcatcgt ggtgtcacgc   6120
tcgtcgtttg gtatggcttc attcagctcc ggttcccaac gatcaaggcg agttacatga   6180
tcccccatgt tgtgcaaaaa agcggttagc tccttcggtc ctccgatcgt tgtcagaagt   6240
aagttggccg cagtgttatc actcatggtt atggcagcac tgcataattc tcttactgtc   6300
atgccatccg taagatgctt ttctgtgact ggtgagtact caaccaagtc attctgagaa   6360
```

-continued tagtgtatgc ggcgaccgag ttgctcttgc ccggcgtcaa cacgggataa taccgcgcca 6420
catagcagaa ctttaaaagt gctcatcatt ggaaaacgtt cttcggggcg aaaactctca 6480
aggatcttac cgctgttgag atccagttcg atgtaaccca ctcgtgcacc caactgatct 6540
tcagcatctt ttactttcac cagcgtttct gggtgagcaa aaacaggaag gcaaaatgcc 6600
gcaaaaaagg gaataagggc gacacggaaa tgttgaatac tcatactctt cctttttcaa 6660
tattattgaa gcatttatca gggttattgt ctcatgagcg gatacatatt tgaatgtatt 6720
tagaaaaata aacaaatagg ggttccgcgc acatttcccc gaaaagtgcc acctgacgtc 6780
taagaaacca ttattatcat gacattaacc tataaaaata ggcgtatcac gaggcccttc 6840
ccgtagtctt cctgggcccc tgggaggtac atgtccccca gcattggtgt aagagcttca 6900
gccaagagtt acacataaag gcaatgttgt gttgcagtcc acagactgca aagtctgctc 6960
caggatgaaa gccactcagt gttggcaaat gtgcacatcc atttataagg atgtcaacta 7020
cagtcagaga accccttgt gtttggtccc cccccgtgtc acatgtggaa cagggcccag 7080
ttggcaagtt gtaccaacca actgaaggga ttacatgcac tgccccgcga agaaggggca 7140
gagatgccgt agtcaggttt agttcgtccg gcggcggggc 7180

<210> SEQ ID NO 15
<211> LENGTH: 37391
<212> TYPE: DNA
<213> ORGANISM: Artificial Sequence
<220> FEATURE:
<223> OTHER INFORMATION: Synthetic

<400> SEQUENCE: 15
ctaaattgta agcgttaata ttttgttaaa attcggccgg ccatcatcaa taatatacct 60
tattttggat tgaagccaat atgataatga gggggtggag tttgtgacgt ggcgcggggc 120
gtgggaacgg ggcgggtgac gtagtagtgt ggcggaagtg tgatgttgca agtgtggcgg 180
aacacatgta taacttcgta taatgtatgc tatacgaagt tatacatgta agcgacggat 240
gtggcaaaag tgacgttttt ggtgtgcgcc ggtgtacaca ggaagtgaca attttcgcgc 300
ggttttaggc ggatgttgta gtaaatttgg gcgtaaccga gtaagatttg gccattttcg 360
cgggaaaact gaataagagg aagtgaaatc tgaataattt tgtgttactc atagcgcgta 420
atatttgtct agggagatca attggattct ttgacccggg aacttaatgt cgtttctcag 480
cagctgttgg atctgcgcca gcaggtttct gccctgaagg cttcctcccc tcccaatgcg 540
gtttaaaaca taaataaaaa accagactct gtttggattt ggatcaagca agtgtcttgc 600
tgtctttatt taggggtttt gcgcgcgcgg taggcccggg accagcggtc tcggtcgttg 660
agggtcctgt gtattttttc caggacgtgg taaaggtgac tctggatgtt cagatacatg 720
ggcataagcc cgtctctggg gtggaggtag caccactgca gagcttcatg ctgcggggtg 780
gtgttgtaga tgatccagtc gtagcaggag cgctgggcgt ggtgcctaaa aatgtctttc 840
agtagcaagc tgattgccag gggcaggccc ttggtgtaag tgtttacaaa gcggttaagc 900
tgggatgggt gcatacgtgg ggatatgaga tgcatcttgg actgtatttt taggttggct 960
atgttcccag ccatatccct ccggggattc atgttgtgca gaaccaccag cacagtgtat 1020
ccggtgcact tgggaaattt gtcatgtagc ttagaaggaa atgcgtggaa gaacttggag 1080
acgcccttgt gacctccaag attttccatg cattcgtcca taatgatggc aatgggccca 1140
cgggcggcgg cctgggcgaa gatatttctg ggatcactaa cgtcatagtt gtgttccagg 1200
atgagatcgt cataggccat ttttacaaag cgcgggcgga gggtgccaga ctgcggtata 1260

-continued

```
atggttccat ccggcccagg ggcgtagtta ccctcacaga tttgcatttc ccacgctttg   1320
agttcagatg gggggatcat gtctacctgc ggggcgatga agaaaacggt ttccggggta   1380
ggggagatca gctgggaaga aagcaggttc ctgagcagct gcgacttacc gcagccggtg   1440
ggcccgtaaa tcacacctat taccgggtgc aactggtagt taagagagct gcagctgccg   1500
tcatccctga gcagggggc cacttcgtta agcatgtccc tgactcgcat gttttccctg   1560
accaaatccg ccagaaggcg ctcgccgccc agcgatagca gttcttgcaa ggaagcaaag   1620
tttttcaacg gtttgagacc gtccgccgta ggcatgcttt tgagcgtttg accaagcagt   1680
tccaggcggt cccacagctc ggtcacctgc tctacggcat ctcgatccag catatctcct   1740
cgtttcgcgg gttggggcgg ctttcgctgt acggcagtag tcggtgctcg tccagacggg   1800
ccagggtcat gtctttccac gggcgcaggg tcctcgtcag cgtagtctgg gtcacggtga   1860
aggggtgcgc tccgggctgc gcgctggcca gggtgcgctt gaggctggtc ctgctggtgc   1920
tgaagcgctg ccggtcttcg ccctgcgcgt cggccaggta gcatttgacc atggtgtcat   1980
agtccagccc ctccgcggcg tggcccttgg cgcgcagctt gcccttggag gaggcgccgc   2040
acgaggggca gtgcagactt ttgagggcgt agagcttggg cgcgagaaat accgattccg   2100
gggagtaggc atccgcgccg caggccccgc agacggtctc gcattccacg agccaggtga   2160
gctctggccg ttcggggtca aaaaccaggt ttcccccatg ctttttgatg cgtttcttac   2220
ctctggtttc catgagccgg tgtccacgct cggtgacgaa aaggctgtcc gtgtccccgt   2280
atacagactt gagaggcctg tcctcgagcg gtgttccgcg gtcctcctcg tatagaaact   2340
cggaccactc tgagacaaag gctcgcgtcc aggccagcac gaaggaggct aagtgggagg   2400
ggtagcggtc gttgtccact agggggtcca ctcgctccag ggtgtgaaga cacatgtcgc   2460
cctcttcggc atcaaggaag gtgattggtt tgtaggtgta ggccacgtga ccgggtgttc   2520
ctgaaggggg gctataaaag gggtgggggg cgcgttcgtc ctcactctct tccgcatcgc   2580
tgtctgcgag ggccagctgt tggggtgagt actccctctg aaaagcgggc atgacttctg   2640
cgctaagatt gtcagtttcc aaaaacgagg aggatttgat attcacctgg cccgcggtga   2700
tgcctttgag ggtggccgca tccatctggt cagaaaagac aatctttttg ttgtcaagct   2760
tggtggcaaa cgacccgtag agggcgttgg acagcaactt ggcgatggag cgcagggttt   2820
ggtttttgtc gcgatcggcg cgctccttgg ccgcgatgtt tagctgcacg tattcgcgcg   2880
caacgcaccg ccattcggga aagacggtgg tgcgctcgtc gggcaccagg tgcacgcgcc   2940
aaccgcggtt gtgcagggtg acaaggtcaa cgctggtggc tacctctccg cgtaggcgct   3000
cgttggtcca gcagaggcgg ccgcccttgc gcgagcagaa tggcggtagg gggtctagct   3060
gcgtctcgtc cggggggtct gcgtccacgg taaagacccc gggcagcagg cgcgcgtcga   3120
agtagtctat cttgcatcct tgcaagtcta gcgcctgctg ccatgcgcgg gcggcaagcg   3180
cgcgctcgta tgggttgagt gggggacccc atggcatggg gtgggtgagc gcggaggcgt   3240
acatgccgca aatgtcgtaa acgtagaggg gctctctgag tattccaaga tatgtagggt   3300
agcatcttcc accgcggatg ctggcgcgca cgtaatcgta tagttcgtgc gagggagcga   3360
ggaggtcggg accgaggttg ctacgggcgg gctgctctgc tcggaagact atctgcctga   3420
agatggcatg tgagttggat gatatggttg gacgctggaa gacgttgaag ctggcgtctg   3480
tgagacctac cgcgtcacgc acgaaggagg cgtaggagtc gcgcagcttg ttgaccagct   3540
cggcggtgac ctgcacgtct agggcgcagt agtccagggt ttccttgatg atgtcatact   3600
tatcctgtcc cttttttttc cacagctcgc ggttgaggac aaactcttcg cggtctttcc   3660
```

-continued

```
agtactcttg gatcggaaac ccgtcggcct ccgaacggta agagcctagc atgtagaact   3720
ggttgacggc ctggtaggcg cagcatccct tttctacggg tagcgcgtat gcctgcgcgg   3780
ccttccggag cgaggtgtgg gtgagcgcaa aggtgtccct gaccatgact ttgaggtact   3840
ggtatttgaa gtcagtgtcg tcgcatccgc cctgctccca gagcaaaaag tccgtgcgct   3900
ttttggaacg cggatttggc agggcgaagg tgacatcgtt gaagagtatc tttcccgcgc   3960
gaggcataaa gttgcgtgtg atgcggaagg gtcccggcac ctcggaacgg ttgttaatta   4020
cctgggcggc gagcacgatc tcgtcaaagc cgttgatgtt gtggcccaca atgtaaagtt   4080
ccaagaagcg cgggatgccc ttgatggaag gcaatttttt aagttcctcg taggtgagct   4140
cttcagggga gctgagcccg tgctctgaaa gggcccagtc tgcaagatga gggttggaag   4200
cgacgaatga gctccacagg tcacgggcca ttagcatttg caggtggtcg cgaaaggtcc   4260
taaactggcg acctatggcc atttttttctg ggtgatgca gtagaaggta agcgggtctt   4320
gttcccagcg gtcccatcca aggttcgcgg ctaggtctcg cgcggcagtc actagaggct   4380
catctccgcc gaacttcatg accagcatga agggcacgag ctgcttccca aaggccccca   4440
tccaagtata ggtctctaca tcgtaggtga caaagagacg ctcggtgcga ggatgcgagc   4500
cgatcgggaa gaactggatc tcccgccacc aattggagga gtggctattg atgtggtgaa   4560
agtagaagtc cctgcgacgg gccgaacact cgtgctggct tttgtaaaaa cgtgcgcagt   4620
actggcagcg gtgcacgggc tgtacatcct gcacgaggtt gacctgacga ccgcgcacaa   4680
ggaagcagag tgggaatttg agcccctcgc ctggcgggtt tggctggtgg tcttctactt   4740
cggctgcttg tccttgaccg tctggctgct cgaggggagt tacggtggat cggaccacca   4800
cgccgcgcga gcccaaagtc cagatgtccg cgcgcggcgg tcggagcttg atgacaacat   4860
cgcgcagatg ggagctgtcc atggtctgga gctcccgcgg cgtcaggtca ggcgggagct   4920
cctgcaggtt tacctcgcat agacgggtca gggcgcgggc tagatccagg tgatacctaa   4980
tttccagggg ctggttggtg gcggcgtcga tggcttgcaa gaggccgcat ccccgcggcg   5040
cgactacggt accgcgcggc gggcggtggg ccgcgggggt gtccttggat gatgcatcta   5100
aaagcggtga cgcgggcgag cccccggagg taggggggc tccggacccg ccgggagagg   5160
gggcaggggc acgtcggcgc cgcgcgcggg caggagctgg tgctgcgcgc gtaggttgct   5220
ggcgaacgcg acgacgcggc ggttgatctc ctgaatctgg cgcctctgcg tgaagacgac   5280
gggcccggtg agcttgagcc tgaaagagag ttcgacagaa tcaatttcgg tgtcgttgac   5340
ggcggcctgg cgcaaaatct cctgcacgtc tcctgagttg tcttgatagg cgatctcggc   5400
catgaactgc tcgatctctt cctcctggag atctccgcgt ccggctcgct ccacggtggc   5460
ggcgaggtcg ttggaaatgc gggccatgag ctgcgagaag gcgttgaggc ctccctcgtt   5520
ccagacgcgg ctgtagacca cgcccccttc ggcatcgcgg gcgcgcatga ccacctgcgc   5580
gagattgagc tccacgtgcc gggcgaagac ggcgtagttt cgcaggcgct gaaagaggta   5640
gttgagggtg gtggcggtgt gttctgccac gaagaagtac ataacccagc gtcgcaacgt   5700
ggattcgttg atatccccca aggcctcaag gcgctccatg gcctcgtaga agtccacggc   5760
gaagttgaaa aactgggagt tgcgcgccga cacggttaac tcctcctcca gaagacggat   5820
gagctcggcg acagtgtcgc gcacctcgcg ctcaaaggct acaggggcct cttcttcttc   5880
ttcaatctcc tcttccataa gggcctcccc ttcttcttct tctggcggcg gtgggggagg   5940
ggggacacgg cggcgacgac ggcgcaccgg gaggcggtcg acaaagcgct cgatcatctc   6000
cccgcggcga cggcgcatgg tctcggtgac ggcgcggccg ttctcgcggg ggcgcagttg   6060
```

-continued

```
gaagacgccg cccgtcatgt cccggttatg ggttggcggg gggctgccat gcggcaggga   6120
tacggcgcta acgatgcatc tcaacaattg ttgtgtaggt actccgccgc cgagggacct   6180
gagcgagtcc gcatcgaccg gatcggaaaa cctctcgaga aaggcgtcta accagtcaca   6240
gtcgcaaggt aggctgagca ccgtggcggg cggcagcggg cggcggtcgg ggttgtttct   6300
ggcggaggtg ctgctgatga tgtaattaaa gtaggcggtc ttgagacggc ggatggtcga   6360
cagaagcacc atgtccttgg gtccggcctg ctgaatgcgc aggcggtcgg ccatgcccca   6420
ggcttcgttt tgacatcggc gcaggtcttt gtagtagtct tgcatgagcc tttctaccgg   6480
cacttcttct tctccttcct cttgtcctgc atctcttgca tctatcgctg cggcggcggc   6540
ggagtttggc cgtaggtggc gccctcttcc tcccatgcgt gtgaccccga agcccctcat   6600
cggctgaagc agggctaggt cggcgacaac gcgctcggct aatatggcct gctgcacctg   6660
cgtgagggta gactggaagt catccatgtc cacaaagcgg tggtatgcgc ccgtgttgat   6720
ggtgtaagtg cagttggcca taacggacca gttaacggtc tggtgacccg gctgcgagag   6780
ctcggtgtac ctgagacgcg agtaagccct cgagtcaaat acgtagtcgt tgcaagtccg   6840
caccaggtac tggtatccca ccaaaaagtg cggcggcggc tggcggtaga ggggccagcg   6900
tagggtggcc ggggctccgg gggcgagatc ttccaacata aggcgatgat atccgtagat   6960
gtacctggac atccaggtga tgccggcggc ggtggtggag gcgcgcggaa agtcgcggac   7020
gcggttccag atgttgcgca gcggcaaaaa gtgctccatg gtcgggacgc tctggccggt   7080
caggcgcgcg caatcgttga cgctctaccg tgcaaaagga gagcctgtaa gcgggcactc   7140
ttccgtggtc tggtggataa attcgcaagg gtatcatggc ggacgaccgg ggttcgagcc   7200
ccgtatccgg ccgtccgccg tgatccatgc ggttaccgcc cgcgtgtcga acccaggtgt   7260
gcgacgtcag acaacggggg agtgctcctt ttggcttcct tccaggcgcg gcggctgctg   7320
cgctagcttt tttggccact ggccgcgcgc agcgtaagcg gttaggctgg aaagcgaaag   7380
cattaagtgg ctcgctccct gtagccggag ggttattttc caagggttga gtcgcgggac   7440
ccccggttcg agtctcggac cggccggact gcggcgaacg gggggtttgcc tccccgtcat   7500
gcaagacccc gcttgcaaat tcctccggaa acagggacga gccccttttt tgcttttccc   7560
agatgcatcc ggtgctgcgg cagatgcgcc cccctcctca gcagcggcaa gagcaagagc   7620
agcggcagac atgcagggca ccctcccctc ctcctaccgc gtcaggaggg gcgacatccg   7680
cggttgacgc ggcagcagat ggtgattacg aacccccgcg gcgccgggcc cggcactacc   7740
tggacttgga ggagggcgag ggcctggcgc ggctaggagc gccctctcct gagcggtacc   7800
caagggtgca gctgaagcgt gatacgcgtg aggcgtacgt gccgcggcag aacctgtttc   7860
gcgaccgcga gggagaggag cccgaggaga tgcgggatcg aaagttccac gcagggcgcg   7920
agctgcggca tggcctgaat cgcgagcggt tgctgcgcga ggaggacttt gagcccgacg   7980
cgcgaaccgg gattagtccc gcgcgcgcac acgtggcggc cgccgacctg gtaaccgcat   8040
acgagcagac ggtgaaccag gagattaact ttcaaaaaag ctttaacaac cacgtgcgta   8100
cgcttgtggc gcgcgaggag gtggctatag gactgatgca tctgtgggac tttgtaagcg   8160
cgctggagca aaacccaaat agcaagccgc tcatggcgca gctgttcctt atagtgcagc   8220
acagcaggga caacgaggca ttcagggatg cgctgctaaa catagtagag cccgagggcc   8280
gctggctgct cgatttgata aacatcctgc agagcatagt ggtgcaggag cgcagcttga   8340
gcctggctga caaggtggcc gccatcaact attccatgct tagcctgggc aagttttacg   8400
cccgcaagat ataccatacc ccttacgttc ccatagacaa ggaggtaaag atcgaggggt   8460
```

-continued

```
tctacatgcg catggcgctg aaggtgctta ccttgagcga cgacctgggc gtttatcgca   8520
acgagcgcat ccacaaggcc gtgagcgtga gccggcggcg cgagctcagc gaccgcgagc   8580
tgatgcacag cctgcaaagg gccctggctg gcacgggcag cggcgataga gaggccgagt   8640
cctactttga cgcgggcgct gacctgcgct gggccccaag ccgacgcgcc ctggaggcag   8700
ctggggccgg acctgggctg gcggtggcac ccgcgcgcgc tggcaacgtc ggcggcgtgg   8760
aggaatatga cgaggacgat gagtacgagc cagaggacgg cgagtactaa gcggtgatgt   8820
ttctgatcag atgatgcaag acgcaacgga cccggcggtg cgggcggcgc tgcagagcca   8880
gccgtccggc cttaactcca cggacgactg gcgccaggtc atggaccgca tcatgtcgct   8940
gactgcgcgc aatcctgacg cgttccggca gcagccgcag gccaaccggc tctccgcaat   9000
tctggaagcg gtggtcccgg cgcgcgcaaa ccccacgcac gagaaggtgc tggcgatcgt   9060
aaacgcgctg gccgaaaaca gggccatccg gcccgacgaa gccggcctgg tctacgacgc   9120
gctgcttcag cgcgtggctc gttacaacag cggcaacgtg cagaccaacc tggaccggct   9180
ggtgggggat gtgcgcgagg ccgtggcgca gcgtgagcgc gcgcagcagc agggcaacct   9240
gggctccatg gttgcactaa acgccttcct gagtacacag cccgccaacg tgccgcgggg   9300
acaggaggac tacaccaact ttgtgagcgc actgcggcta atggtgactg agacaccgca   9360
aagtgaggtg taccagtctg ggccagacta tttttttccag accagtagac aaggcctgca   9420
gaccgtaaac ctgagccagg ctttcaaaaa cttgcagggg ctgtgggggg tgcgggctcc   9480
cacaggcgac cgcgcgaccg tgtctagctt gctgacgccc aactcgcgcc tgttgctgct   9540
gctaatagcg cccttcacgg acagtggcag cgtgtcccgg gacacatacc taggtcactt   9600
gctgacactg taccgcgagg ccataggtca ggcgcatgtg gacgagcata ctttccagga   9660
gattacaagt gtcagccgcg cgctggggca ggaggacacg ggcagcctgg aggcaaccct   9720
aaactacctg ctgaccaacc ggcggcagaa gatcccctcg ttgcacagtt taaacagcga   9780
ggaggagcgc attttgcgct acgtgcagca gagcgtgagc cttaacctga tgcgcgacgg   9840
ggtaacgccc agcgtggcgc tggacatgac cgcgcgcaac atggaaccgg gcatgtatgc   9900
ctcaaaccgg ccgtttatca accgcctaat ggactacttg catcgcgcgg ccgccgtgaa   9960
ccccgagtat ttcaccaatg ccatcttgaa cccgcactgg ctaccgcccc ctggtttcta  10020
caccggggga ttcgaggtgc ccgagggtaa cgatggattc ctctgggacg acatagacga  10080
cagcgtgttt tccccgcaac cgcagaccct gctagagttg caacagcgcg agcaggcaga  10140
ggcggcgctg cgaaaggaaa gcttccgcag gccaagcagc ttgtccgatc taggcgctgc  10200
ggccccgcgg tcagatgcta gtagcccatt tccaagcttg atagggtctc ttaccagcac  10260
tcgcaccacc cgcccgcgcc tgctgggcga ggaggagtac ctaaacaact cgctgctgca  10320
gccgcagcgc gaaaaaaacc tgcctccggc atttcccaac aacgggatag agagcctagt  10380
ggacaagatg agtagatgga agacgtacgc gcaggagcac agggacgtgc caggcccgcg  10440
cccgcccacc cgtcgtcaaa ggcacgaccg tcagcggggt ctggtgtggg aggacgatga  10500
ctcggcagac gacagcagcg tcctggattt gggagggagt ggcaacccgt ttgcgcacct  10560
tcgccccagg ctggggagaa tgttttaaaa aaaaaaaagc atgatgcaaa ataaaaaact  10620
caccaaggcc atggcaccga gcgttggttt tcttgtattc cccttagtat gcggcgcgcg  10680
gcgatgtatg aggaaggtcc tcctccctcc tacgagagtg tggtgagcgc ggcgccagtg  10740
gcggcggcgc tgggttctcc cttcgatgct cccctggacc cgccgtttgt gcctccgcgg  10800
tacctgcggc ctaccggggg gagaaacagc atccgttact ctgagttggc accectattc  10860
```

-continued

```
gacaccaccc gtgtgtacct ggtggacaac aagtcaacgg atgtggcatc cctgaactac  10920
cagaacgacc acagcaactt tctgaccacg gtcattcaaa acaatgacta cagcccgggg  10980
gaggcaagca cacagaccat caatcttgac gaccggtcgc actggggcgg cgacctgaaa  11040
accatcctgc ataccaacat gccaaatgtg aacgagttca tgtttaccaa taagtttaag  11100
gcgcgggtga tggtgtcgcg cttgcctact aaggacaatc aggtggagct gaaatacgag  11160
tgggtggagt tcacgctgcc cgagggcaac tactccgaga ccatgaccat agaccttatg  11220
aacaacgcga tcgtggagca ctacttgaaa gtgggcagac agaacggggt tctggaaagc  11280
gacatcgggg taaagtttga cacccgcaac ttcagactgg ggtttgaccc cgtcactggt  11340
cttgtcatgc ctggggtata tacaaacgaa gccttccatc cagacatcat tttgctgcca  11400
ggatgcgggg tggacttcac ccacagccgc ctgagcaact tgttgggcat ccgcaagcgg  11460
caacccttcc aggagggctt taggatcacc tacgatgatc tggagggtgg taacattccc  11520
gcactgttgg atgtggacgc ctaccaggcg agcttgaaag atgacaccga acagggcggg  11580
ggtggcgcag gcggcagcaa cagcagtggc agcggcgcgg aagagaactc caacgcggca  11640
gccgcggcaa tgcagccggt ggaggacatg aacgatcatg ccattcgcgg cgacaccttt  11700
gccacacggg ctgaggagaa gcgcgctgag gccgaagcag cggccgaagc tgccgccccc  11760
gctgcgcaac ccgaggtcga gaagcctcag aagaaaccgg tgatcaaacc cctgacagag  11820
gacagcaaga aacgcagtta caacctaata agcaatgaca gcaccttcac ccagtaccgc  11880
agctggtacc ttgcatacaa ctacggcgac cctcagaccg gaatccgctc atggaccctg  11940
ctttgcactc ctgacgtaac ctgcggctcg gagcaggtct actggtcgtt gccagacatg  12000
atgcaagacc ccgtgacctt ccgctccacg cgccagatca gcaactttcc ggtggtgggc  12060
gccgagctgt tgcccgtgca ctccaagagc ttctacaacg accaggccgt ctactcccaa  12120
ctcatccgcc agtttacctc tctgacccac gtgttcaatc gctttcccga gaaccagatt  12180
ttggcgcgcc cgccagcccc caccatcacc accgtcagtg aaaacgttcc tgctctcaca  12240
gatcacggga cgctaccgct gcgcaacagc atcggaggag tccagcgagt gaccattact  12300
gacgccagac gccgcacctg cccctacgtt tacaaggccc tgggcatagt ctcgccgcgc  12360
gtcctatcga gccgcacttt ttgagcaagc atgtccatcc ttatatcgcc cagcaataac  12420
acaggctggg gcctgcgctt cccaagcaag atgtttggcg gggccaagaa gcgctccgac  12480
caacacccag tgcgcgtgcg cgggcactac cgcgcgccct ggggcgcgca caaacgcggc  12540
cgcactgggc gcaccaccgt cgatgacgcc atcgacgcgg tggtggagga ggcgcgcaac  12600
tacacgccca cgccgccacc agtgtccaca gtggacgcgg ccattcagac cgtggtgcgc  12660
ggagcccggc gctatgctaa aatgaagaga cggcggaggc gcgtagcacg tcgccaccgc  12720
cgccgacccg gcactgccgc ccaacgcgcg gcggcggccc tgcttaaccg cgcacgtcgc  12780
accggccgac gggcggccat gcgggccgct cgaaggctgg ccgcgggtat tgtcactgtg  12840
ccccccaggt ccaggcgacg agcggccgcc gcagcagccg cggccattag tgctatgact  12900
cagggtcgca ggggcaacgt gtattgggtg cgcgactcgg ttagcggcct gcgcgtgccc  12960
gtgcgcaccc gcccccccgcg caactagatt gcaagaaaaa actacttaga ctcgtactgt  13020
tgtatgtatc cagcggcggc ggcgcgcaac gaagctatgt ccaagcgcaa aatcaaagaa  13080
gagatgctcc aggtcatcgc gccggagatc tatggccccc cgaagaagga agagcaggat  13140
tacaagcccc gaaagctaaa gcgggtcaaa aagaaaaaga aagatgatga tgatgaactt  13200
gacgacgagg tggaactgct gcacgctacc gcgcccaggc gacgggtaca gtggaaaggt  13260
```

cgacgcgtaa aacgtgtttt gcgacccggc accaccgtag tctttacgcc cggtgagcgc 13320
tccacccgca cctacaagcg cgtgtatgat gaggtgtacg gcgacgagga cctgcttgag 13380
caggccaacg agcgcctcgg ggagtttgcc tacggaaagc ggcataagga catgctggcg 13440
ttgccgctgg acgagggcaa cccaacacct agcctaaagc ccgtaacact gcagcaggtg 13500
ctgcccgcgc ttgcaccgtc cgaagaaaag cgcggcctaa agcgcgagtc tggtgacttg 13560
gcacccaccg tgcagctgat ggtacccaag cgccagcgac tggaagatgt cttggaaaaa 13620
atgaccgtgg aacctgggct ggagcccgag gtccgcgtgc ggccaatcaa gcaggtggcg 13680
ccgggactgg gcgtgcagac cgtggacgtt cagataccca ctaccagtag caccagtatt 13740
gccaccgcca cagagggcat ggagacacaa acgtccccgg ttgcctcagc ggtggcggat 13800
gccgcggtgc aggcggtcgc tgcggccgcg tccaagacct ctacggaggt gcaaacggac 13860
ccgtggatgt ttcgcgtttc agccccccgg cgcccgcgcg gttcgaggaa gtacggcgcc 13920
gccagcgcgc tactgcccga atatgcccta catccttcca ttgcgcctac ccccggctat 13980
cgtggctaca cctaccgccc cagaagacga gcaactaccc gacgccgaac caccactgga 14040
acccgccgcc gccgtcgccg tcgccagccc gtgctggccc cgatttccgt gcgcagggtg 14100
gctcgcgaag gaggcaggac cctggtgctg ccaacagcgc gctaccaccc cagcatcgtt 14160
taaaagccgg tctttgtggt tcttgcagat atggccctca cctgccgcct ccgtttcccg 14220
gtgccgggat tccgaggaag aatgcaccgt aggaggggca tggccggcta cggcctgacg 14280
ggcggcatgc gtcgtgcgca ccaccggcgg cggcgcgcgt cgcaccgtcg catgcgcggc 14340
ggtatcctgc ccctccttat tccactgatc gccgcggcga ttggcgccgt gcccggaatt 14400
gcatccgtgg ccttgcaggc gcagagacac tgattaaaaa caagttgcat gtggaaaaat 14460
caaaataaaa agtctggact ctcacgctcg cttggtcctg taactatttt gtagaatgga 14520
agacatcaac tttgcgtctc tggccccgcg acacggctcg cgcccgttca tgggaaactg 14580
gcaagatatc ggcaccagca atatgagcgg tggcgccttc agctggggct cgctgtggag 14640
cggcattaaa aatttcggtt ccaccgttaa gaactatggc agcaaggcct ggaacagcag 14700
cacaggccag atgctgaggg ataagttgaa agagcaaaat ttccaacaaa aggtggtaga 14760
tggcctggcc tctggcatta gcggggtggt ggacctggcc aaccaggcag tgcaaaataa 14820
gattaacagt aagcttgatc cccgccctcc cgtagaggag cctccaccgg ccgtggagac 14880
agtgtctcca gaggggcgtg gcgaaaagcg tccgcgcccc gacagggaag aaactctggt 14940
gacgcaaata gacgagcctc cctcgtacga ggaggcacta aagcaaggcc tgcccaccac 15000
ccgtcccatc gcgcccatgg ctaccggagt gctgggccag cacacacccg taacgctgga 15060
cctgcctccc cccgccgaca cccagcagaa acctgtgctg ccaggcccga ccgccgttgt 15120
tgtaacccgt cctagccgcg cgtccctgcg ccgcgccgcc agcggtccgc gatcgttgcg 15180
gcccgtagcc agtggcaact ggcaaagcac actgaacagc atcgtgggtc tgggggtgca 15240
atccctgaag cgccgacgat gcttctgaat agctaacgtg tcgtatgtgt gtcatgtatg 15300
cgtccatgtc gccgccagag gagctgctga gccgccgcgc gcccgctttc caagatggct 15360
accccttcga tgatgccgca gtggtcttac atgcacatct cgggccagga cgcctcggag 15420
tacctgagcc ccgggctggt gcagtttgcc cgcgccaccg agacgtactt cagcctgaat 15480
aacaagttta gaaaccccac ggtggcgcct acgcacgacg tgaccacaga ccggtcccag 15540
cgtttgacgc tgcggttcat ccctgtggac cgtgaggata ctgcgtactc gtacaaggcg 15600
cggttcaccc tagctgtggg tgataaccgt gtgctggaca tggcttccac gtactttgac 15660

-continued

```
atccgcggcg tgctggacag gggccctact tttaagccct actctggcac tgcctacaac  15720
gccctggctc ccaagggtgc cccaaatcct tgcgaatggg atgaagctgc tactgctctt  15780
gaaataaacc tagaagaaga ggacgatgac aacgaagacg aagtagacga gcaagctgag  15840
cagcaaaaaa ctcacgtatt tgggcaggcg ccttattctg gtataaatat tacaaaggag  15900
ggtattcaaa taggtgtcga aggtcaaaca cctaaatatg ccgataaaac atttcaacct  15960
gaacctcaaa taggagaatc tcagtggtac gaaactgaaa ttaatcatgc agctgggaga  16020
gtccttaaaa agactacccc aatgaaacca tgttacggtt catatgcaaa acccacaaat  16080
gaaaatggag ggcaaggcat tcttgtaaag caacaaaatg gaaagctaga aagtcaagtg  16140
gaaatgcaat tttctcaac tactgaggcg accgcaggca atggtgataa cttgactcct  16200
aaagtggtat tgtacagtga agatgtagat atagaaaccc cagacactca tatttcttac  16260
atgcccacta ttaaggaagg taactcacga gaactaatgg gccaacaatc tatgcccaac  16320
aggcctaatt acattgcttt tagggacaat tttattggtc taatgtatta caacagcacg  16380
ggtaatatgg gtgttctggc gggccaagca tcgcagttga atgctgttgt agatttgcaa  16440
gacagaaaca cagagctttc ataccagctt ttgcttgatt ccattggtga tagaaccagg  16500
tacttttcta tgtggaatca ggctgttgac agctatgatc cagatgttag aattattgaa  16560
aatcatggaa ctgaagatga acttccaaat tactgctttc cactgggagg tgtgattaat  16620
acagagactc ttaccaaggt aaaacctaaa acaggtcagg aaaatggatg ggaaaaagat  16680
gctacagaat tttcagataa aaatgaaata agagttggaa ataattttgc catggaaatc  16740
aatctaaatg ccaacctgtg gagaaatttc ctgtactcca acatagcgct gtatttgccc  16800
gacaagctaa agtacagtcc ttccaacgta aaaatttctg ataacccaaa cacctacgac  16860
tacatgaaca agcgagtggt ggctcccggg ttagtggact gctacattaa ccttggagca  16920
cgctggtccc ttgactatat ggacaacgtc aacccattta accaccaccg caatgctggc  16980
ctgcgctacc gctcaatgtt gctgggcaat ggtcgctatg tgcccttcca catccaggtg  17040
cctcagaagt tctttgccat taaaaacctc cttctcctgc cgggctcata cacctacgag  17100
tggaacttca ggaaggatgt taacatggtt ctgcagagct ccctaggaaa tgacctaagg  17160
gttgacggag ccagcattaa gtttgatagc atttgccttt acgccacctt cttccccatg  17220
gcccacaaca ccgcctccac gcttgaggcc atgcttagaa acgacaccaa cgaccagtcc  17280
tttaacgact atctctccgc cgccaacatg ctctacccta tacccgccaa cgctaccaac  17340
gtgcccatat ccatcccctc ccgcaactgg gcggctttcc gcggctgggc cttcacgcgc  17400
cttaagacta aggaaacccc atcactgggc tcgggctacg acccttatta cacctactct  17460
ggctctatac cctacctaga tggaaccttt tacctcaacc acacctttaa gaaggtggcc  17520
attacctttg actcttctgt cagctggcct ggcaatgacc gcctgcttac ccccaacgag  17580
tttgaaatta agcgctcagt tgacggggag ggttacaacg ttgcccagtg taacatgacc  17640
aaagactggt tcctggtaca aatgctagct aactacaaca ttggctacca gggcttctat  17700
atcccagaga gctacaagga ccgcatgtac tccttcttta gaaacttcca gcccatgagc  17760
cgtcaggtgg tggatgatac taaatacaag gactaccaac aggtgggcat cctacaccaa  17820
cacaacaact ctggatttgt tggctacctt gcccccacca tgcgcgaagg acaggcctac  17880
cctgctaact tcccctatcc gcttataggc aagaccgcag ttgacagcat tacccagaaa  17940
aagtttcttt gcgatcgcac cctttggcgc atcccattct ccagtaactt tatgtccatg  18000
ggcgcactca cagacctggg ccaaaacctt ctctacgcca actccgccca cgcgctagac  18060
```

-continued

```
atgacttttg aggtggatcc catggacgag cccacccttc tttatgtttt gtttgaagtc  18120
tttgacgtgg tccgtgtgca ccggccgcac cgcggcgtca tcgaaaccgt gtacctgcgc  18180
acgcccttct cggccggcaa cgccacaaca taaagaagca agcaacatca acaacagctg  18240
ccgccatggg ctccagtgag caggaactga aagccattgt caaagatctt ggttgtgggc  18300
catatttttt gggcacctat gacaagcgct ttccaggctt tgtttctcca cacaagctcg  18360
cctgcgccat agtcaatacg gccggtcgcg agactggggg cgtacactgg atggcctttg  18420
cctggaaccc gcactcaaaa acatgctacc tctttgagcc ctttggcttt tctgaccagc  18480
gactcaagca ggtttaccag tttgagtacg agtcactcct gcgccgtagc gccattgctt  18540
cttcccccga ccgctgtata acgctggaaa agtccaccca aagcgtacag gggcccaact  18600
cggccgcctg tggactattc tgctgcatgt ttctccacgc ctttgccaac tggccccaaa  18660
ctcccatgga tcacaacccc accatgaacc ttattaccgg ggtacccaac tccatgctca  18720
acagtcccca ggtacagccc accctgcgtc gcaaccagga acagctctac agcttcctgg  18780
agcgccactc gccctacttc cgcagccaca gtgcgcagat taggagcgcc acttcttttt  18840
gtcacttgaa aaacatgtaa aaataatgta ctagagacac tttcaataaa ggcaaatgct  18900
tttatttgta cactctcggg tgattattta cccccaccct tgccgtctgc gccgtttaaa  18960
aatcaaaggg gttctgccgc gcatcgctat gcgccactgg cagggacacg ttgcgatact  19020
ggtgtttagt gctccactta aactcaggca caaccatccg cggcagctcg gtgaagtttt  19080
cactccacag gctgcgcacc atcaccaacg cgtttagcag gtcgggcgcc gatatcttga  19140
agtcgcagtt ggggcctccg ccctgcgcgc gcgagttgcg atacacaggg ttgcagcact  19200
ggaacactat cagcgccggg tggtgcacgc tggccagcac gctcttgtcg gagatcagat  19260
ccgcgtccag gtcctccgcg ttgctcaggg cgaacggagt caactttggt agctgccttc  19320
ccaaaaaggg cgcgtgccca ggctttgagt tgcactcgca ccgtagtggc atcaaaaggt  19380
gaccgtgccc ggtctgggcg ttaggataca gcgcctgcat aaaagccttg atctgcttaa  19440
aagccacctg agcctttgcg ccttcagaga agaacatgcc gcaagacttg ccggaaaact  19500
gattggccgg acaggccgcg tcgtgcacgc agcaccttgc gtcggtgttg gagatctgca  19560
ccacatttcg gccccaccgg ttcttcacga tcttggcctt gctagactgc tccttcagcg  19620
cgcgctgccc gttttcgctc gtcacatcca tttcaatcac gtgctcctta tttatcataa  19680
tgcttccgtg tagacactta agctcgcctt cgatctcagc gcagcggtgc agccacaacg  19740
cgcagcccgt gggctcgtga tgcttgtagg tcacctctgc aaacgactgc aggtacgcct  19800
gcaggaatcg ccccatcatc gtcacaaagg tcttgttgct ggtgaaggtc agctgcaacc  19860
cgcggtgctc ctcgttcagc caggtcttgc atacggccgc cagagcttcc acttggtcag  19920
gcagtagttt gaagttcgcc tttagatcgt tatccacgtg gtacttgtcc atcagcgcgc  19980
gcgcagcctc catgcccttc tcccacgcag acacgatcgg cacactcagc gggttcatca  20040
ccgtaatttc actttccgct tcgctgggct cttcctcttc ctcttgcgtc cgcataccac  20100
gcgccactgg gtcgtcttca ttcagccgcc gcactgtgcg cttacctcct ttgccatgct  20160
tgattagcac cggtgggttg ctgaaaccca ccatttgtag cgccacatct tctctttctt  20220
cctcgctgtc cacgattacc tctggtgatg gcgggcgctc gggcttggga gaagggcgct  20280
tctttttctt cttgggcgca atggccaaat ccgccgccga ggtcgatggc cgcgggctgg  20340
gtgtgcgcgg caccagcgcg tcttgtgatg agtcttcctc gtcctcggac tcgatacgcc  20400
gcctcatccg ctttttgggg ggcgcccggg gaggcggcgg cgacggggac ggggacgaca  20460
```

cgtcctccat ggttggggga cgtcgcgccg caccgcgtcc gcgctcgggg gtggtttcgc 20520
gctgctcctc ttcccgactg gccatttcct tctcctatag gcagaaaaag atcatggagt 20580
cagtcgagaa gaaggacagc ctaaccgccc cctctgagtt cgccaccacc gcctccaccg 20640
atgccgccaa cgcgcctacc accttccccg tcgaggcacc cccgcttgag gaggaggaag 20700
tgattatcga gcaggaccca ggttttgtaa gcgaagacga cgaggaccgc tcagtaccaa 20760
cagaggataa aaagcaagac caggacaacg cagaggcaaa cgaggaacaa gtcgggcggg 20820
gggacgaaag gcatggcgac tacctagatg tgggagacga cgtgctgttg aagcatctgc 20880
agcgccagtg cgccattatc tgcgacgcgt tgcaagagcg cagcgatgtg cccctcgcca 20940
tagcggatgt cagccttgcc tacgaacgcc acctattctc accgcgcgta ccccccaaac 21000
gccaagaaaa cggcacatgc gagcccaacc cgcgcctcaa cttctacccc gtatttgccg 21060
tgccagaggt gcttgccacc tatcacatct ttttccaaaa ctgcaagata cccctatcct 21120
gccgtgccaa ccgcagccga gcggacaagc agctggcctt gcggcagggc gctgtcatac 21180
ctgatatcgc ctcgctcaac gaagtgccaa aaatctttga gggtcttgga cgcgacgaga 21240
agcgcgcggc aaacgctctg caacaggaaa acagcgaaaa tgaaagtcac tctggagtgt 21300
tggtggaact cgagggtgac aacgcgcgcc tagccgtact aaaacgcagc atcgaggtca 21360
cccactttgc ctacccggca cttaacctac cccccaaggt catgagcaca gtcatgagtg 21420
agctgatcgt gcgccgtgcg cagcccctgg agagggatgc aaatttgcaa gaacaaacag 21480
aggagggcct acccgcagtt ggcgacgagc agctagcgcg ctggcttcaa acgcgcgagc 21540
ctgccgactt ggaggagcga cgcaaactaa tgatggccgc agtgctcgtt accgtggagc 21600
ttgagtgcat gcagcggttc tttgctgacc cggagatgca gcgcaagcta gaggaaacat 21660
tgcactacac ctttcgacag ggctacgtac gccaggcctg caagatctcc aacgtggagc 21720
tctgcaacct ggtctcctac cttggaattt tgcacgaaaa ccgccttggg caaaacgtgc 21780
ttcattccac gctcaagggc gaggcgcgcc gcgactacgt ccgcgactgc gtttacttat 21840
ttctatgcta cacctggcag acggccatgg gcgtttggca gcagtgcttg gaggagtgca 21900
acctcaagga gctgcagaaa ctgctaaagc aaaacttgaa ggacctatgg acggccttca 21960
acgagcgctc cgtggccgcg cacctggcgg acatcatttt ccccgaacgc ctgcttaaaa 22020
ccctgcaaca gggtctgcca gacttcacca gtcaaagcat gttgcagaac tttaggaact 22080
ttatcctaga gcgctcagga atcttgcccg ccacctgctg tgcacttcct agcgactttg 22140
tgcccattaa gtaccgcgaa tgccctccgc cgctttgggg ccactgctac cttctgcagc 22200
tagccaacta ccttgcctac cactctgaca taatggaaga cgtgagcggt gacggtctac 22260
tggagtgtca ctgtcgctgc aacctatgca ccccgcaccg ctccctggtt tgcaattcgc 22320
agctgcttaa cgaaagtcaa attatcggta cctttgagct gcagggtccc tcgcctgacg 22380
aaaagtccgc ggctccgggg ttgaaactca ctccggggct gtggacgtcg gcttaccttc 22440
gcaaatttgt acctgaggac taccacgccc acgagattag gttctacgaa gaccaatccc 22500
gcccgccaaa tgcggagctt accgcctgcg tcattaccca gggccacatt cttggccaat 22560
tgcaagccat caacaaagcc cgccaagagt ttctgctacg aaagggacgg ggggtttact 22620
tggaccccca gtccggcgag gagctcaacc caatcccccc gccgccgcag ccctatcagc 22680
agcagccgcg ggcccttgct tcccaggatg gcacccaaaa agaagctgca gctgccgccg 22740
ccacccacgg acgaggagga atactgggac agtcaggcag aggaggtttt ggacgaggag 22800
gaggaggaca tgatggaaga ctgggagagc ctagacgagg aagcttccga ggtcgaagag 22860

-continued

```
gtgtcagacg aaacaccgtc accctcggtc gcattcccct cgccggcgcc ccagaaatcg  22920
gcaaccggtt ccagcatggc tacaacctcc gctcctcagg cgccgccggc actgcccgtt  22980
cgccgaccca accgtagatg ggacaccact ggaaccaggg ccggtaagtc caagcagccg  23040
ccgccgttag cccaagagca acaacagcgc caaggctacc gctcatggcg cgggcacaag  23100
aacgccatag ttgcttgctt gcaagactgt gggggcaaca tctccttcgc ccgccgcttt  23160
cttctctacc atcacggcgt ggccttcccc cgtaacatcc tgcattacta ccgtcatctc  23220
tacagcccat actgcaccgg cggcagcggc agcggcagca acagcagcgg ccacacagaa  23280
gcaaaggcga ccggatagca agactctgac aaagcccaag aaatccacag cggcggcagc  23340
agcaggagga ggagcgctgc gtctggcgcc caacgaaccc gtatcgaccc gcgagcttag  23400
aaacaggatt tttcccactc tgtatgctat atttcaacag agcaggggcc aagaacaaga  23460
gctgaaaata aaaaacaggt ctctgcgatc cctcacccgc agctgcctgt atcacaaaag  23520
cgaagatcag cttcggcgca cgctggaaga cgcggaggct ctcttcagta aatactgcgc  23580
gctgactctt aaggactagt ttcgcgccct ttctcaaatt taagcgcgaa aactacgtca  23640
tctccagcgg ccacacccgg cgccagcacc tgtcgtcagc gccattatga gcaaggaaat  23700
tcccacgccc tacatgtgga gttaccagcc acaaatggga cttgcggctg gagctgccca  23760
agactactca acccgaataa actacatgag cgcgggaccc cacatgatat cccgggtcaa  23820
cggaatccgc gcccaccgaa accgaattct cttggaacag gcggctatta ccaccacacc  23880
tcgtaataac cttaatcccc gtagttggcc cgctgccctg gtgtaccagg aaagtcccgc  23940
tcccaccact gtggtacttc ccagagacgc ccaggccgaa gttcagatga ctaactcagg  24000
ggcgcagctt gcgggcggct ttcgtcacag ggtgcggtcg cccgggcagg gtataactca  24060
cctgacaatc agagggcgag gtattcagct caacgacgag tcggtgagct cctcgcttgg  24120
tctccgtccg gacgggacat ttcagatcgg cggcgccggc cgtccttcat tcacgcctcg  24180
tcaggcaatc ctaactctgc agacctcgtc ctctgagccg cgctctggag gcattggaac  24240
tctgcaattt attgaggagt ttgtgccatc ggtctacttt aaccccttct cgggacctcc  24300
cggccactat ccggatcaat ttattcctaa ctttgacgcg gtaaaggact cggcggacgg  24360
ctacgactga atgttaagtg gagaggcaga gcaactgcgc ctgaaacacc tggtccactg  24420
tcgccgccac aagtgctttg cccgcgactc cggtgagttt tgctactttg aattgcccga  24480
ggatcatatc gagggcccgg cgcacggcgt ccggcttacc gcccagggag agcttgcccg  24540
tagcctgatt cgggagttta cccagcgccc cctgctagtt gagcgggaca ggggaccctg  24600
tgttctcact gtgatttgca actgtcctaa ccttggatta catcaagatc ctctagttaa  24660
ttaacagctt gcatgcctgc aggtcgacgg atcgggagat ctcggccgca tattaagtgc  24720
attgttctcg ataccgctaa gtgcattgtt ctcgttagct cgatggacaa gtgcattgtt  24780
ctcttgctga aagctcgatg gacaagtgca ttgttctctt gctgaaagct cgatggacaa  24840
gtgcattgtt ctcttgctga aagctcagta cccgggagta ccctcgaccg ccggagtata  24900
aatagaggcg cttcgtctac ggagcgacaa ttcaattcaa acaagcaaag tgaacacgtc  24960
gctaagcgaa agctaagcaa ataaacaagc gcagctgaac aagctaaaca atctgcagta  25020
aagtgcaagt taaagtgaat caattaaaag taaccagcaa ccaagtaaat caactgcaac  25080
tactgaaatc tgccaagaag taattattga atacaagaag agaactctga atactttcaa  25140
caagttaccg agaaagaaga actcacacac agctagcgtt taaacttaag cttcaccatg  25200
gtggggccct gcatgctgct gctgctgctg ctgctgggcc tgaggctaca gctctccctg  25260
```

-continued

```
ggcatcatcc tagttgagga ggagaacccg gacttctgga accgcgaggc agccgaggcc  25320
ctgggtgccg ccaagaagct gcagcctgca cagacagccg ccaagaacct catcatcttc  25380
ctgggcgatg gggtgggggt gtctacggtg acagctgcca ggatcctaaa agggcagaag  25440
aaggacaaac tggggcctga gataccccctg gccatggacc gcttcccata tgtggctctg  25500
tccaagacat acaatgtaga caaacatgtg ccagacagtg gagccacagc cacggcctac  25560
ctgtgcgggg tcaagggcaa cttccagacc attggcttga gtgcagccgc ccgctttaac  25620
cagtgcaaca cgacacgcgg caacgaggtc atctccgtga tgaatcgggc caagaaagca  25680
gggaagtcag tgggagtggt aaccaccaca cgagtgcagc acgcctcgcc agccggcacc  25740
tacgcccaca cggtgaaccg caactggtac tcggacgccg acgtgcctgc ctcggcccgc  25800
caggaggggt gccaggacat cgctacgcag ctcatctcca acatggacat tgacgtgatc  25860
ctaggtgggg gccgaaagta catgtttcgc atgggaaccc cagaccctga gtacccagat  25920
gactacagcc aaggtgggac caggctggac gggaagaatc tggtgcagga atggctggcg  25980
aagcaccagg gtgcccggta cgtgtggaac cgcactgagc tcatgcgggc ttccctggac  26040
ccgtctgtgg cccatctcat gggtctcttt gagcctggag acatgaaata cgagatccac  26100
cgagactcca cactggaccc ctccctgatg gagatgacag aggctgccct gcgcctgctg  26160
agcaggaacc cccgcggctt cttcctcttc gtggagggtg gtcgcatcga ccatggtcat  26220
catgaaagca gggcttaccg ggcactgact gagacgatca tgttcgacga cgccattgag  26280
agggcgggcc agctcaccag cgaggaggac acgctgagcc tcgtcactgc cgaccactcc  26340
cacgtcttct ccttcggagg ctgccccctg cgagggggct ccatcttcgg gctggcccct  26400
ggcaaggccc gggacaggaa ggcctacacg gtcctcctat acggaaacgg tccaggctat  26460
gtgctcaagg acggcgcccg gccggatgtt accgagagcg agagcgggag ccccgagtat  26520
cggcagcagt cagcagtgcc cctggacgaa gagacccacg caggcgagga cgtggcggtg  26580
ttcgcgcgcg gcccgcaggc gcacctggtt cacggcgtgc aggagcagac cttcatagcg  26640
cacgtcatgg ccttcgccgc ctgcctggag ccctacaccg cctgcgacct ggcgcccccc  26700
gccggcacca ccgacgccgc gcacccgggg cggtccgtgg tccccgcgtt gcttcctctg  26760
ctggccggga ccctgctgct gctggagacg gccactgctc cctgagtgtc ccgtccctgg  26820
ggctcctgct tccccatccc ggagttctcc tgctccccgc ctcctgtcgt cctgcctggc  26880
ctccagcccg agtcgtcatc cccggagtcc ctatacagag gtcctgccat ggaaccttcc  26940
cctccccgtg cgctctgggg actgagccca tgacaccaaa cctgcccctt ggctgctctc  27000
ggactcccta ccccaacccc agggacagat ctggccagat ttgtaaaaca aatagatttt  27060
aggcccaaag attatttaaa gcattgcctg gaacgcagtg agtttttgtt agaaaagaga  27120
ataattcaaa gtggcattgc tttgcttctt atgttaattt ggtacagacc tgtggctgag  27180
tttgctcaaa gtattcagag cagaattgtg gagtggaaag agagattgga caaagagttt  27240
agtttgtcag tgtatcaaaa aatgaagttt aatgtggcta tgggaattgg agttttagat  27300
tggctaagaa acagtgatga tgatgatgaa gacagccagg aaaatgctga taaaaatgaa  27360
gatggtgggg agaagaacat ggaagactca gggcatgaaa caggcattga ttcacagtcc  27420
caaggctcat ttcaggcccc tcagtcctca cagtctgttc atgatcataa tcagccatac  27480
cacatttgta gaggttttac ttgctttaaa aaacctccca cacctccccc tgaacctgaa  27540
acataaaatg aatgcaattg ttgttgttaa cttgtttatt gcagcttata atggttacaa  27600
ataaagcaat agcatcacaa atttcacaaa taaagcattt ttttcactgc attctagttg  27660
```

-continued tggtttgtcc aaactcatca atgtatctta tcatgtctgg atccccagga agctcctctg 27720
tgtcctcata aaccctaacc tcctctactt gagaggacat tccaatcata ggctgcccat 27780
ccaccctctg tgtcctcctg ttaattaggt cacttaacaa aaaggaaatt gggtaggggt 27840
ttttcacaga ccgctttcta agggtaattt taaaatatct gggaagtccc ttccactgct 27900
gtgttccaga agtgttggta aacagcccac aaatgtcaac agcagaaaca tacaagctgt 27960
cagctttgca caagggccca acaccctgct catcaagaag cactgtggtt gctgtgttag 28020
taatgtgcaa aacaggaggc acattttccc cacctgtgta ggttccaaaa tatctagtgt 28080
tttcattttt acttggatca ggaacccagc actccactgg ataagcatta tccttatcca 28140
aaacagcctt gtggtcagtg ttcatctgct gactgtcaac tgtagcattt tttggggtta 28200
cagtttgagc aggatatttg gtcctgtagt ttgctaacac accctgcagc tccaaaggtt 28260
ccccaccaac agcaaaaaaa tgaaaatttg acccttgaat gggttttcca gcaccatttt 28320
catgagtttt ttgtgtccct gaatgcaagt ttaacatagc agttacccca ataacctcag 28380
ttttaacagt aacagcttcc cacatcaaaa tatttccaca ggttaagtcc tcatttaaat 28440
taggcaaagg aattccactt cccactgcct tgcttccgtc tcccattcaa acttttatca 28500
actgacatta ttctaagtaa aatcctcttc attatgttgt cagcaatcca ttgcttgaag 28560
gcctggctcc ccagaacccc tcgactggta tgtcttctcc tagaatactc cagaagaaaa 28620
ggagtgtatg aagatagtga ctgcacatta aaatgactga aaccatagta aattaggatg 28680
agattctggg cagataaaca gacagctggc taggatcatt tttttatgcc ttggacttct 28740
ttggcaatct gttgaagcct gacattcctc agaataatgt tttaaagccc aacaataaga 28800
ccctgtagca catataataa gtactgcagt tttgaagtag tgataagcat aaatgatatt 28860
ttgatatatt tattataact gtaatgagat gtgtacatat ctgtgacttc ataggtactg 28920
attgtactac tgtgattttt ttgcctactt tcaaaatgaa aaggaatgct taatttcagt 28980
tagaggttag taaagacaaa taggtaattt tcttctccag tgaagagcat ggcgcccctt 29040
gctattcatg gacgcttgct taaagacttg tacacaggct tgctttgtat caacctatga 29100
cttcccctta cagccgatga taggttttta tttgcacctc cttcgtgtac aaagacagtt 29160
ttggtggcta cgccatcatt aaactcatta ttatcatgct taagcctata gatgtatcca 29220
gttcttctgt tacataattg aagctgtagt gaattgtcta tcttaaactg catcgctaac 29280
tgactacatt tcacacttca tttgcttcca acatagacta accttcttgg atgtccacta 29340
ttatttgaac ttttgagatt ttttttccta tttctaatat cttaaaattt cagaagactt 29400
aaagttttgc aactacaggg ctccatatag acatctagct tgaatttata cactttcttt 29460
cattgatgtc cctggactaa aaaatgttaa atatttctaa ccgctgtact taaagtccat 29520
tacaaacgaa gactactgtt gttaagttga ataggcatct tatatatttt tcaccggtgc 29580
aataaataac ttctattccc ttctaacatc tgcttgcgtt gcactgagag tacactattg 29640
attagcaata ggttcgtgat tacagccctt ctataattaa ttgttaggtt aacatattat 29700
tcataaaata ttattttatt aatttttact tgatttgcta ctggatgctt agaaatagct 29760
atgagtatat tggtagaacc agtacttata ttttattaca tttttacatt tcataaaatt 29820
taagtgatat aaaaatcctg aggaagtatg ccacaaaagt ggtctcagtg gaaatttaaa 29880
tatgttaaca tttattttta aaatgtagcg tgaaatagac aactttaaaa gctcagctta 29940
aaaaaaaaac tcaaggaagc tgaacttgac tttttaaagc actgaagtgc aatatttaat 30000
gtaggtcaac atgtttaaat gggaaaattt ttttcctaat tacagccaaa tccctagctg 30060

-continued

```
taattaactt aaaatttgta tactatttca caacagagtc agcatatacc actttcttat  30120
aaaattagaa agatctaaaa ttttagagct tatttggtga aacaggcata ttgctacatc  30180
tttgtttata aattataatg tgcctttaga gcccaataac agataacaag attttgaaaa  30240
ttcaggtgaa ttagagttat cagagggaat gttaatacac tctattcaaa tactatatga  30300
gtaagacatt taaaatagga aacaatactt tatatattaa aaaaaattaa tcttccagtc  30360
gatttaatcc actttatgaa ttcatttaaa tcgatttaaa ttcgaattaa ttaactagag  30420
tacccgggga tcttattccc tttaactaat aaaaaaaaat aataaagcat cacttactta  30480
aaatcagtta gcaaatttct gtccagttta ttcagcagca cctccttgcc ctcctcccag  30540
ctctggtatt gcagcttcct cctggctgca aactttctcc acaatctaaa tggaatgtca  30600
gtttcctcct gttcctgtcc atccgcaccc actatcttca tgttgttgca gatgaagcgc  30660
gcaagaccgt ctgaagatac cttcaacccc gtgtatccat atgacacgga aaccggtcct  30720
ccaactgtgc cttttcttac tcctcccttt gtatccccca atgggtttca agagagtccc  30780
cctggggtac tctctttgcg cctatccgaa cctctagtta cctccaatgg catgcttgcg  30840
ctcaaaatgg gcaacggcct ctctctggac gaggccggca accttacctc ccaaaatgta  30900
accactgtga gcccacctct caaaaaaacc aagtcaaaca taaacctgga aatatctgca  30960
cccctcacag ttacctcaga agccctaact gtggctgccg ccgcacctct aatggtcgcg  31020
ggcaacacac tcaccatgca atcacaggcc ccgctaaccg tgcacgactc caaacttagc  31080
attgccaccc aaggacccct cacagtgtca gaaggaaagc tagccctgca aacatcaggc  31140
cccctcacca ccaccgatag cagtaccctt actatcactg cctcaccccc tctaactact  31200
gccactggta gcttgggcat tgacttgaaa gagcccattt atacacaaaa tggaaaacta  31260
ggactaaagt acggggctcc tttgcatgta acagacgacc taaacacttt gaccgtagca  31320
actggtccag gtgtgactat taataatact tccttgcaaa ctaaagttac tggagccttg  31380
ggttttgatt cacaaggcaa tatgcaactt aatgtagcag gaggactaag gattgattct  31440
caaaacagac gccttatact tgatgttagt tatccgtttg atgctcaaaa ccaactaaat  31500
ctaagactag gacagggccc tctttttata aactcagccc acaacttgga tattaactac  31560
aacaaaggcc tttacttgtt tacagcttca aacaattcca aaaagcttga ggttaaccta  31620
agcactgcca aggggttgat gtttgacgct acagccatag ccattaatgc aggagatggg  31680
cttgaatttg gttcacctaa tgcaccaaac acaaatcccc tcaaaacaaa aattggccat  31740
ggcctagaat ttgattcaaa caaggctatg gttcctaaac taggaactgg ccttagtttt  31800
gacagcacag gtgccattac agtaggaaac aaaaataatg ataagctaac tttgtggacc  31860
acaccagctc catctcctaa ctgtagacta aatgcagaga aagatgctaa actcactttg  31920
gtcttaacaa aatgtggcag tcaaatactt gctacagttt cagttttggc tgttaaaggc  31980
agtttggctc caatatctgg aacagttcaa agtgctcatc ttattataag atttgacgaa  32040
aatggagtgc tactaaacaa ttccttcctg gacccagaat attggaactt tagaaatgga  32100
gatcttactg aaggcacagc ctatacaaac gctgttggat ttatgcctaa cctatcagct  32160
tatccaaaat ctcacggtaa aactgccaaa agtaacattg tcagtcaagt ttacttaaac  32220
ggagacaaaa ctaaacctgt aacactaacc attacactaa acggtacaca ggaaacagga  32280
gacacaactc caagtgcata ctctatgtca ttttcatggg actggtctgg ccacaactac  32340
attaatgaaa tatttgccac atcctcttac acttttttcat acattgccca agaataaaga  32400
atcgtttgtg ttatgtttca acgtgtttat ttttcaattg cagaaaattt caagtcattt  32460
```

-continued ttcattcagt agtatagccc caccaccaca tagcttatac agatcaccgt accttaatca 32520
aactcacaga accctagtat tcaacctgcc acctccctcc caacacacag agtacacagt 32580
cctttctccc cggctggcct taaaaagcat catatcatgg gtaacagaca tattcttagg 32640
tgttatattc cacacggttt cctgtcgagc caaacgctca tcagtgatat taataaactc 32700
cccgggcagc tcacttaagt tcatgtcgct gtccagctgc tgagccacag gctgctgtcc 32760
aacttgcggt tgcttaacgg gcggcgaagg agaagtccac gcctacatgg gggtagagtc 32820
ataatcgtgc atcaggatag ggcggtggtg ctgcagcagc gcgcgaataa actgctgccg 32880
ccgccgctcc gtcctgcagg aatacaacat ggcagtggtc tcctcagcga tgattcgcac 32940
cgcccgcagc ataaggcgcc ttgtcctccg ggcacagcag cgcaccctga tctcacttaa 33000
atcagcacag taactgcagc acagcaccac aatattgttc aaaatcccac agtgcaaggc 33060
gctgtatcca aagctcatgg cggggaccac agaacccacg tggccatcat accacaagcg 33120
caggtagatt aagtggcgac ccctcataaa cacgctggac ataaacatta cctcttttgg 33180
catgttgtaa ttcaccacct cccggtacca tataaacctc tgattaaaca tggcgccatc 33240
caccaccatc ctaaaccagc tggccaaaac ctgcccgccg gctatacact gcagggaacc 33300
gggactggaa caatgacagt ggagagccca ggactcgtaa ccatggatca tcatgctcgt 33360
catgatatca atgttggcac aacacaggca cacgtgcata cacttcctca ggattacaag 33420
ctcctcccgc gttagaacca tatcccaggg aacaacccat tcctgaatca gcgtaaatcc 33480
cacactgcag ggaagacctc gcacgtaact cacgttgtgc attgtcaaag tgttacattc 33540
gggcagcagc ggatgatcct ccagtatggt agcgcgggtt tctgtctcaa aaggaggtag 33600
acgatcccta ctgtacggag tgcgccgaga caaccgagat cgtgttggtc gtagtgtcat 33660
gccaaatgga acgccggacg tagtcatatt tcctgaagca aaaccaggtg cgggcgtgac 33720
aaacagatct gcgtctccgg tctcgccgct tagatcgctc tgtgtagtag ttgtagtata 33780
tccactctct caaagcatcc aggcgccccc tggcttcggg ttctatgtaa actccttcat 33840
gcgccgctgc cctgataaca tccaccaccg cagaataagc cacacccagc caacctacac 33900
attcgttctg cgagtcacac acgggaggag cgggaagagc tggaagaacc atgttttttt 33960
ttttattcca aaagattatc caaaacctca aaatgaagat ctattaagtg aacgcgctcc 34020
cctccggtgg cgtggtcaaa ctctacagcc aaagaacaga taatggcatt tgtaagatgt 34080
tgcacaatgg cttccaaaag gcaaacggcc ctcacgtcca agtggacgta aaggctaaac 34140
ccttcagggt gaatctcctc tataaacatt ccagcacctt caaccatgcc caaataattc 34200
tcatctcgcc accttctcaa tatatctcta agcaaatccc gaatattaag tccggccatt 34260
gtaaaaatct gctccagagc gccctccacc ttcagcctca agcagcgaat catgattgca 34320
aaaattcagg ttcctcacag acctgtataa gattcaaaag cggaacatta acaaaaatac 34380
cgcgatcccg taggtccctt cgcagggcca gctgaacata atcgtgcagg tctgcacgga 34440
ccagcgcggc cacttccccg ccaggaacct tgacaaaaga acccacactg attatgacac 34500
gcatactcgg agctatgcta accagcgtag ccccgatgta agctttgttg catgggcggc 34560
gatataaaat gcaaggtgct gctcaaaaaa tcaggcaaag cctcgcgcaa aaaagaaagc 34620
acatcgtagt catgctcatg cagataaagg caggtaagct ccggaaccac cacagaaaaa 34680
gacaccattt ttctctcaaa catgtctgcg ggtttctgca taaacacaaa ataaaataac 34740
aaaaaaacat ttaaacatta gaagcctgtc ttacaacagg aaaaacaacc cttataagca 34800
taagacggac tacggccatg ccggcgtgac cgtaaaaaaa ctggtcaccg tgattaaaaa 34860

-continued

```
gcaccaccga cagctcctcg gtcatgtccg gagtcataat gtaagactcg gtaaacacat  34920
caggttgatt catcggtcag tgctaaaaag cgaccgaaat agcccggggg aatacatacc  34980
cgcaggcgta gagacaacat tacagccccc ataggaggta taacaaaatt aataggagag  35040
aaaaacacat aaacacctga aaaaccctcc tgcctaggca aaatagcacc ctcccgctcc  35100
agaacaacat acagcgcttc acagcggcag cctaacagtc agccttacca gtaaaaaaga  35160
aaacctatta aaaaaacacc actcgacacg gcaccagctc aatcagtcac agtgtaaaaa  35220
agggccaagt gcagagcgag tatatatagg actaaaaaat gacgtaacgg ttaaagtcca  35280
caaaaaacac ccagaaaacc gcacgcgaac ctacgcccag aaacgaaagc caaaaaaccc  35340
acaacttcct caaatcgtca cttccgtttt cccacgttac gtaacttccc attttaagaa  35400
aactacaatt cccaacacat acaagttact ccgccctaaa acctacgtca cccgccccgt  35460
tcccacgccc cgcgccacgt cacaaactcc accccctcat tatcatattg gcttcaatcc  35520
aaaataaggt atattattga tgatggccgg ccgaattgaa tcaggggata acgcaggaaa  35580
gaacatgtga gcaaaaggcc agcaaaaggc caggaaccgt aaaaaggccg cgttgctggc  35640
gtttttccat aggctccgcc cccctgacga gcatcacaaa aatcgacgct caagtcagag  35700
gtggcgaaac ccgacaggac tataaagata ccaggcgttt ccccctggaa gctccctcgt  35760
gcgctctcct gttccgaccc tgccgcttac cggatacctg tccgcctttc tcccttcggg  35820
aagcgtggcg ctttctcata gctcacgctg taggtatctc agttcggtgt aggtcgttcg  35880
ctccaagctg ggctgtgtgc acgaaccccc cgttcagccc gaccgctgcg ccttatccgg  35940
taactatcgt cttgagtcca acccggtaag acacgactta tcgccactgg cagcagccac  36000
tggtaacagg attagcagag cgaggtatgt aggcggtgct acagagttct tgaagtggtg  36060
gcctaactac ggctacacta gaaggacagt atttggtatc tgcgctctgc tgaagccagt  36120
taccttcgga aaaagagttg gtagctcttg atccggcaaa caaaccaccg ctggtagcgg  36180
tggttttttt gtttgcaagc agcagattac gcgcagaaaa aaaggatctc aagaagatcc  36240
tttgatcttt tctacggggt ctgacgctca gtggaacgaa aactcacgtt aagggatttt  36300
ggtcatgaga ttatcaaaaa ggatcttcac ctagatcctt ttaaattaaa aatgaagttt  36360
taaatcaatc taaagtatat atgagtaaac ttggtctgac agttaccaat gcttaatcag  36420
tgaggcacct atctcagcga tctgtctatt tcgttcatcc atagttgcct gactccccgt  36480
cgtgtagata actacgatac gggagggctt accatctggc cccagtgctg caatgatacc  36540
gcgagaccca cgctcaccgg ctccagattt atcagcaata aaccagccag ccggaagggc  36600
cgagcgcaga agtggtcctg caactttatc cgcctccatc cagtctatta attgttgccg  36660
ggaagctaga gtaagtagtt cgccagttaa tagtttgcgc aacgttgttg ccattgctac  36720
aggcatcgtg gtgtcacgct cgtcgtttgg tatggcttca ttcagctccg gttcccaacg  36780
atcaaggcga gttacatgat cccccatgtt gtgcaaaaaa gcggttagct ccttcggtcc  36840
tccgatcgtt gtcagaagta agttggccgc agtgttatca ctcatggtta tggcagcact  36900
gcataattct cttactgtca tgccatccgt aagatgcttt tctgtgactg gtgagtactc  36960
aaccaagtca ttctgagaat agtgtatgcg gcgaccgagt tgctcttgcc cggcgtcaat  37020
acgggataat accgcgccac atagcagaac tttaaaagtg ctcatcattg gaaaacgttc  37080
ttcggggcga aaactctcaa ggatcttacc gctgttgaga tccagttcga tgtaacccac  37140
tcgtgcaccc aactgatctt cagcatcttt tactttcacc agcgtttctg ggtgagcaaa  37200
aacaggaagg caaaatgccg caaaaaaggg aataagggcg acacggaaat gttgaatact  37260
```

-continued catactcttc ctttttcaat attattgaag catttatcag ggttattgtc tcatgagcgg 37320
atacatattt gaatgtattt agaaaaataa acaaataggg gttccgcgca catttccccg 37380
aaaagtgcca c 37391

<210> SEQ ID NO 16

<400> SEQUENCE: 16

000

<210> SEQ ID NO 17
<211> LENGTH: 671
<212> TYPE: PRT
<213> ORGANISM: Homo sapiens

<400> SEQUENCE: 17

Met Ala Leu Ser Val Asn Asp Cys Ala Arg Leu Thr Gly Gln Ser Val
1 5 10 15

Pro Thr Met Glu His Phe Leu Pro Leu Arg Asn Ile Trp Asn Arg Val
20 25 30

Arg Asp Phe Pro Arg Ala Ser Thr Thr Ala Ala Gly Ile Thr Trp Met
35 40 45

Ser Arg Tyr Ile Tyr Gly Tyr His Arg Leu Met Leu Glu Asp Leu Ala
50 55 60

Pro Gly Ala Pro Ala Thr Leu Arg Trp Pro Leu Tyr Arg Gln Pro Pro
65 70 75 80

Pro His Phe Leu Val Gly Tyr Gln Tyr Leu Val Arg Thr Cys Asn Asp
85 90 95

Tyr Val Phe Asp Ser Arg Ala Tyr Ser Arg Leu Arg Tyr Thr Glu Leu
100 105 110

Ser Gln Pro Gly His Gln Thr Val Asn Trp Ser Val Met Ala Asn Cys
115 120 125

Thr Tyr Thr Ile Asn Thr Gly Ala Tyr His Arg Phe Val Asp Met Asp
130 135 140

Asp Phe Gln Ser Thr Leu Thr Gln Val Gln Gln Ala Ile Leu Ala Glu
145 150 155 160

Arg Val Val Ala Asp Leu Ala Leu Leu Gln Pro Met Arg Gly Phe Gly
165 170 175

Val Thr Arg Met Gly Gly Arg Gly Arg His Leu Arg Pro Asn Ser Ala
180 185 190

Ala Ala Val Ala Ile Asp Ala Arg Asp Ala Gly Gln Glu Glu Gly Glu
195 200 205

Glu Glu Val Pro Val Glu Arg Leu Met Gln Asp Tyr Tyr Lys Asp Leu
210 215 220

Arg Arg Cys Gln Asn Glu Ala Trp Gly Met Ala Asp Arg Leu Arg Ile
225 230 235 240

Gln Gln Ala Gly Pro Lys Asp Met Val Leu Leu Ser Thr Ile Arg Arg
245 250 255

Leu Lys Thr Ala Tyr Phe Asn Tyr Ile Ile Ser Ser Thr Ser Ala Arg
260 265 270

Asn Asn Pro Asp Arg His Pro Leu Pro Pro Ala Thr Val Leu Ser Leu
275 280 285

Pro Cys Asp Cys Asp Trp Leu Asp Ala Phe Leu Glu Arg Phe Ser Asp
290 295 300

Pro Val Asp Ala Asp Ser Leu Arg Ser Leu Gly Gly Gly Val Pro Thr
305 310 315 320

```
Gln Gln Leu Leu Arg Cys Ile Val Ser Ala Val Ser Leu Pro His Gly
            325                 330                 335

Ser Pro Pro Pro Thr His Asn Arg Asp Met Thr Gly Gly Val Phe Gln
        340                 345                 350

Leu Arg Pro Arg Glu Asn Gly Arg Ala Val Thr Glu Thr Met Arg Arg
    355                 360                 365

Arg Arg Gly Glu Met Ile Glu Arg Phe Val Asp Arg Leu Pro Val Arg
    370                 375                 380

Arg Arg Arg Arg Arg Val Pro Pro Pro Pro Pro Pro Pro Glu Glu Glu
385                 390                 395                 400

Glu Glu Gly Glu Ala Leu Met Glu Glu Glu Ile Glu Glu Glu Glu Ala
                405                 410                 415

Pro Val Ala Phe Glu Arg Glu Val Arg Asp Thr Val Ala Glu Leu Ile
            420                 425                 430

Arg Leu Leu Glu Glu Glu Leu Thr Val Ser Ala Arg Asn Ser Gln Phe
        435                 440                 445

Phe Asn Phe Ala Val Asp Phe Tyr Glu Ala Met Glu Arg Leu Glu Ala
    450                 455                 460

Leu Gly Asp Ile Asn Glu Ser Thr Leu Arg Arg Trp Val Met Tyr Phe
465                 470                 475                 480

Phe Val Ala Glu His Thr Ala Thr Thr Leu Asn Tyr Leu Phe Gln Arg
                485                 490                 495

Leu Arg Asn Tyr Ala Val Phe Ala Arg His Val Glu Leu Asn Leu Ala
            500                 505                 510

Gln Val Val Met Arg Ala Arg Asp Ala Glu Gly Gly Val Val Tyr Ser
        515                 520                 525

Arg Val Trp Asn Glu Gly Gly Leu Asn Ala Phe Ser Gln Leu Met Ala
    530                 535                 540

Arg Ile Ser Asn Asp Leu Ala Ala Thr Val Glu Arg Ala Gly Arg Gly
545                 550                 555                 560

Asp Leu Gln Glu Glu Glu Ile Glu Gln Phe Met Ala Glu Ile Ala Tyr
                565                 570                 575

Gln Asp Asn Ser Gly Asp Val Gln Glu Ile Leu Arg Gln Ala Ala Val
            580                 585                 590

Asn Asp Thr Glu Ile Asp Ser Val Glu Leu Ser Phe Arg Phe Lys Leu
        595                 600                 605

Thr Gly Pro Val Val Phe Thr Gln Arg Arg Gln Ile Gln Glu Ile Asn
    610                 615                 620

Arg Arg Val Val Ala Phe Ala Ser Asn Leu Arg Ala Gln His Gln Leu
625                 630                 635                 640

Leu Pro Ala Arg Gly Ala Asp Val Pro Leu Pro Pro Leu Pro Ala Gly
                645                 650                 655

Pro Glu Pro Pro Leu Pro Pro Gly Ala Arg Pro Arg His Arg Phe
            660                 665                 670


<210> SEQ ID NO 18
<211> LENGTH: 322
<212> TYPE: PRT
<213> ORGANISM: Homo sapiens

<400> SEQUENCE: 18

Val Phe Gln Leu Arg Pro Arg Glu Asn Gly Arg Ala Val Thr Glu Thr
1               5                   10                  15

Met Arg Arg Arg Arg Gly Glu Met Ile Glu Arg Phe Val Asp Arg Leu
            20                  25                  30
```

Pro Val Arg Arg Arg Arg Arg Arg Val Pro Pro Pro Pro Pro Pro Pro
35 40 45

Glu Glu Glu Glu Glu Gly Glu Ala Leu Met Glu Glu Glu Ile Glu Glu
50 55 60

Glu Glu Ala Pro Val Ala Phe Glu Arg Glu Val Arg Asp Thr Val Ala
65 70 75 80

Glu Leu Ile Arg Leu Leu Glu Glu Glu Leu Thr Val Ser Ala Arg Asn
85 90 95

Ser Gln Phe Phe Asn Phe Ala Val Asp Phe Tyr Glu Ala Met Glu Arg
100 105 110

Leu Glu Ala Leu Gly Asp Ile Asn Glu Ser Thr Leu Arg Arg Trp Val
115 120 125

Met Tyr Phe Phe Val Ala Glu His Thr Ala Thr Thr Leu Asn Tyr Leu
130 135 140

Phe Gln Arg Leu Arg Asn Tyr Ala Val Phe Ala Arg His Val Glu Leu
145 150 155 160

Asn Leu Ala Gln Val Val Met Arg Ala Arg Asp Ala Glu Gly Gly Val
165 170 175

Val Tyr Ser Arg Val Trp Asn Glu Gly Gly Leu Asn Ala Phe Ser Gln
180 185 190

Leu Met Ala Arg Ile Ser Asn Asp Leu Ala Ala Thr Val Glu Arg Ala
195 200 205

Gly Arg Gly Asp Leu Gln Glu Glu Glu Ile Glu Gln Phe Met Ala Glu
210 215 220

Ile Ala Tyr Gln Asp Asn Ser Gly Asp Val Gln Glu Ile Leu Arg Gln
225 230 235 240

Ala Ala Val Asn Asp Thr Glu Ile Asp Ser Val Glu Leu Ser Phe Arg
245 250 255

Phe Lys Leu Thr Gly Pro Val Val Phe Thr Gln Arg Arg Gln Ile Gln
260 265 270

Glu Ile Asn Arg Arg Val Val Ala Phe Ala Ser Asn Leu Arg Ala Gln
275 280 285

His Gln Leu Leu Pro Ala Arg Gly Ala Asp Val Pro Leu Pro Pro Leu
290 295 300

Pro Ala Gly Pro Glu Pro Pro Leu Pro Pro Gly Ala Arg Pro Arg His
305 310 315 320

Arg Phe

<210> SEQ ID NO 19
<211> LENGTH: 671
<212> TYPE: PRT
<213> ORGANISM: Homo sapiens

<400> SEQUENCE: 19

Met Ala Leu Ser Val Asn Asp Cys Ala Arg Leu Thr Gly Gln Ser Val
1 5 10 15

Pro Thr Met Glu His Phe Leu Pro Leu Arg Asn Ile Trp Asn Arg Val
20 25 30

Arg Asp Phe Pro Arg Ala Ser Thr Thr Ala Ala Gly Ile Thr Trp Met
35 40 45

Ser Arg Tyr Ile Tyr Gly Tyr His Arg Leu Met Leu Glu Asp Leu Ala
50 55 60

Pro Gly Ala Pro Ala Thr Leu Arg Trp Pro Leu Tyr Arg Gln Pro Pro
65 70 75 80

-continued

```
Pro His Phe Leu Val Gly Tyr Gln Tyr Leu Val Arg Thr Cys Asn Asp
                85                  90                  95

Tyr Val Phe Asp Ser Arg Ala Tyr Ser Arg Leu Arg Tyr Thr Glu Leu
            100                 105                 110

Ser Gln Pro Gly His Gln Thr Val Asn Trp Ser Val Met Ala Asn Cys
        115                 120                 125

Thr Tyr Thr Ile Asn Thr Gly Ala Tyr His Arg Phe Val Asp Met Asp
    130                 135                 140

Asp Phe Gln Ser Thr Leu Thr Gln Val Gln Gln Ala Ile Leu Ala Glu
145                 150                 155                 160

Arg Val Val Ala Asp Leu Ala Leu Leu Gln Pro Met Arg Gly Phe Gly
                165                 170                 175

Val Thr Arg Met Gly Gly Arg Gly Arg His Leu Arg Pro Asn Ser Ala
            180                 185                 190

Ala Ala Ala Ala Ile Asp Ala Arg Asp Ala Gly Gln Glu Glu Gly Glu
        195                 200                 205

Glu Glu Val Pro Val Glu Arg Leu Met Gln Asp Tyr Tyr Lys Asp Leu
    210                 215                 220

Arg Arg Cys Gln Asn Glu Ala Trp Gly Met Ala Asp Arg Leu Arg Ile
225                 230                 235                 240

Gln Gln Ala Gly Pro Lys Asp Met Val Leu Leu Ser Thr Ile Arg Arg
                245                 250                 255

Leu Lys Thr Ala Tyr Phe Asn Tyr Ile Ile Ser Ser Thr Ser Ala Arg
            260                 265                 270

Asn Asn Pro Asp Arg Arg Pro Leu Pro Pro Ala Thr Val Leu Ser Leu
        275                 280                 285

Pro Cys Asp Cys Asp Trp Leu Asp Ala Phe Leu Glu Arg Phe Ser Asp
    290                 295                 300

Pro Val Asp Ala Asp Ser Leu Arg Ser Leu Gly Gly Gly Val Pro Thr
305                 310                 315                 320

Gln Gln Leu Leu Arg Cys Ile Val Ser Ala Val Ser Leu Pro His Gly
                325                 330                 335

Ser Pro Pro Pro Thr His Asn Arg Asp Met Thr Gly Gly Val Phe Gln
            340                 345                 350

Leu Arg Pro Arg Glu Asn Gly Arg Ala Val Thr Glu Thr Met Arg Arg
        355                 360                 365

Arg Arg Gly Glu Met Ile Glu Arg Phe Val Asp Arg Leu Pro Val Arg
    370                 375                 380

Arg Arg Arg Arg Arg Val Pro Pro Pro Pro Pro Pro Pro Glu Glu Glu
385                 390                 395                 400

Glu Gly Glu Ala Leu Met Glu Glu Glu Ile Glu Glu Glu Glu Glu Ala
                405                 410                 415

Pro Val Ala Phe Glu Arg Glu Val Arg Asp Thr Val Ala Glu Leu Ile
            420                 425                 430

Arg Leu Leu Glu Glu Glu Leu Thr Val Ser Ala Arg Asn Ser Gln Phe
        435                 440                 445

Phe Asn Phe Ala Val Asp Phe Tyr Glu Ala Met Glu Arg Leu Glu Ala
    450                 455                 460

Leu Gly Asp Ile Asn Glu Ser Thr Leu Arg Arg Trp Val Met Tyr Phe
465                 470                 475                 480

Phe Val Ala Glu His Thr Ala Thr Thr Leu Asn Tyr Leu Phe Gln Arg
                485                 490                 495

Leu Arg Asn Tyr Ala Val Phe Ala Arg His Val Glu Leu Asn Leu Ala
            500                 505                 510
```

-continued

```
Gln Val Val Met Arg Ala Arg Asp Ala Glu Gly Gly Val Val Tyr Ser
        515                 520                 525

Arg Val Trp Asn Glu Gly Gly Leu Asn Ala Phe Ser Gln Leu Met Ala
    530                 535                 540

Arg Ile Ser Asn Asp Leu Ala Ala Thr Val Glu Arg Ala Gly Arg Gly
545                 550                 555                 560

Asp Leu Gln Glu Glu Glu Ile Glu Gln Phe Met Ala Glu Ile Ala Tyr
                565                 570                 575

Gln Asp Asn Ser Gly Asp Val Gln Glu Ile Leu Arg Gln Ala Ala Val
            580                 585                 590

Asn Asp Thr Glu Ile Asp Ser Val Glu Leu Ser Phe Arg Leu Lys Leu
        595                 600                 605

Thr Gly Pro Val Val Phe Thr Gln Arg Arg Gln Ile Gln Glu Ile Asn
    610                 615                 620

Arg Arg Val Val Ala Phe Ala Ser Asn Leu Arg Ala Gln His Gln Leu
625                 630                 635                 640

Leu Pro Ala Arg Gly Ala Asp Val Pro Leu Pro Pro Leu Pro Ala Gly
                645                 650                 655

Pro Glu Pro Pro Leu Pro Pro Gly Ala Arg Pro Arg His Arg Phe
            660                 665                 670


<210> SEQ ID NO 20
<211> LENGTH: 322
<212> TYPE: PRT
<213> ORGANISM: Homo sapiens

<400> SEQUENCE: 20

Val Phe Gln Leu Arg Pro Arg Glu Asn Gly Arg Ala Val Thr Glu Thr
1               5                   10                  15

Met Arg Arg Arg Arg Gly Glu Met Ile Glu Arg Phe Val Asp Arg Leu
            20                  25                  30

Pro Val Arg Arg Arg Arg Arg Arg Val Pro Pro Pro Pro Pro Pro Pro
        35                  40                  45

Glu Glu Glu Glu Gly Glu Ala Leu Met Glu Glu Glu Ile Glu Glu Glu
    50                  55                  60

Glu Glu Ala Pro Val Ala Phe Glu Arg Glu Val Arg Asp Thr Val Ala
65                  70                  75                  80

Glu Leu Ile Arg Leu Leu Glu Glu Glu Leu Thr Val Ser Ala Arg Asn
                85                  90                  95

Ser Gln Phe Phe Asn Phe Ala Val Asp Phe Tyr Glu Ala Met Glu Arg
            100                 105                 110

Leu Glu Ala Leu Gly Asp Ile Asn Glu Ser Thr Leu Arg Arg Trp Val
        115                 120                 125

Met Tyr Phe Phe Val Ala Glu His Thr Ala Thr Thr Leu Asn Tyr Leu
    130                 135                 140

Phe Gln Arg Leu Arg Asn Tyr Ala Val Phe Ala Arg His Val Glu Leu
145                 150                 155                 160

Asn Leu Ala Gln Val Val Met Arg Ala Arg Asp Ala Glu Gly Gly Val
                165                 170                 175

Val Tyr Ser Arg Val Trp Asn Glu Gly Gly Leu Asn Ala Phe Ser Gln
            180                 185                 190

Leu Met Ala Arg Ile Ser Asn Asp Leu Ala Ala Thr Val Glu Arg Ala
        195                 200                 205

Gly Arg Gly Asp Leu Gln Glu Glu Glu Ile Glu Gln Phe Met Ala Glu
    210                 215                 220
```

```
Ile Ala Tyr Gln Asp Asn Ser Gly Asp Val Gln Glu Ile Leu Arg Gln
225                 230                 235                 240

Ala Ala Val Asn Asp Thr Glu Ile Asp Ser Val Glu Leu Ser Phe Arg
                245                 250                 255

Leu Lys Leu Thr Gly Pro Val Val Phe Thr Gln Arg Arg Gln Ile Gln
            260                 265                 270

Glu Ile Asn Arg Arg Val Val Ala Phe Ala Ser Asn Leu Arg Ala Gln
        275                 280                 285

His Gln Leu Leu Pro Ala Arg Gly Ala Asp Val Pro Leu Pro Pro Leu
    290                 295                 300

Pro Ala Gly Pro Glu Pro Pro Leu Pro Pro Gly Ala Arg Pro Arg His
305                 310                 315                 320

Arg Phe


<210> SEQ ID NO 21
<211> LENGTH: 12
<212> TYPE: DNA
<213> ORGANISM: Artificial Sequence
<220> FEATURE:
<223> OTHER INFORMATION: Synthetic

<400> SEQUENCE: 21

catcatcaat aa                                                           12


<210> SEQ ID NO 22
<211> LENGTH: 12
<212> TYPE: DNA
<213> ORGANISM: Artificial Sequence
<220> FEATURE:
<223> OTHER INFORMATION: Synthetic

<400> SEQUENCE: 22

gtagtagtta tt                                                           12


<210> SEQ ID NO 23
<211> LENGTH: 15
<212> TYPE: DNA
<213> ORGANISM: Artificial Sequence
<220> FEATURE:
<223> OTHER INFORMATION: Synthetic

<400> SEQUENCE: 23

taacatcatc aataa                                                        15


<210> SEQ ID NO 24
<211> LENGTH: 17
<212> TYPE: DNA
<213> ORGANISM: Artificial Sequence
<220> FEATURE:
<223> OTHER INFORMATION: Synthetic

<400> SEQUENCE: 24

taattgtagt agttatt                                                      17


<210> SEQ ID NO 25
<211> LENGTH: 13
<212> TYPE: DNA
<213> ORGANISM: Artificial Sequence
<220> FEATURE:
<223> OTHER INFORMATION: Synthetic

<400> SEQUENCE: 25

ccatcatcaa taa                                                          13
```

<210> SEQ ID NO 26
<211> LENGTH: 17
<212> TYPE: DNA
<213> ORGANISM: Artificial Sequence
<220> FEATURE:
<223> OTHER INFORMATION: Synthetic

<400> SEQUENCE: 26
ggccggtagt agttatt 17

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
gacgaggccg gcctggtc 18

<210> SEQ ID NO 28
<211> LENGTH: 18
<212> TYPE: DNA
<213> ORGANISM: Artificial Sequence
<220> FEATURE:
<223> OTHER INFORMATION: Synthetic

<400> SEQUENCE: 28
ggcatggccg gccacggc 18

<210> SEQ ID NO 29
<211> LENGTH: 18
<212> TYPE: DNA
<213> ORGANISM: Artificial Sequence
<220> FEATURE:
<223> OTHER INFORMATION: Synthetic

<400> SEQUENCE: 29
gacgaagccg gcctggtc 18

<210> SEQ ID NO 30
<211> LENGTH: 18
<212> TYPE: DNA
<213> ORGANISM: Artificial Sequence
<220> FEATURE:
<223> OTHER INFORMATION: Synthetic

<400> SEQUENCE: 30
ggcatggccg gctacggc 18

<210> SEQ ID NO 31
<211> LENGTH: 13
<212> TYPE: DNA
<213> ORGANISM: Artificial Sequence
<220> FEATURE:
<223> OTHER INFORMATION: Synthetic

<400> SEQUENCE: 31
ccatcatcaa taa 13

<210> SEQ ID NO 32
<211> LENGTH: 17
<212> TYPE: DNA
<213> ORGANISM: Artificial Sequence
<220> FEATURE:
<223> OTHER INFORMATION: Synthetic -continued

```
<400> SEQUENCE: 32

ggccggtagt agttatt                                              17


<210> SEQ ID NO 33
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: n is a, c, g, or t

<400> SEQUENCE: 33

nnnnnggccg gtagtagtta tt                                        22


<210> SEQ ID NO 34
<211> LENGTH: 13
<212> TYPE: DNA
<213> ORGANISM: Artificial Sequence
<220> FEATURE:
<223> OTHER INFORMATION: Synthetic

<400> SEQUENCE: 34

ggtagtagtt att                                                  13
```